United States Patent
Brondyk et al.

(10) Patent No.: US 12,378,308 B2
(45) Date of Patent: *Aug. 5, 2025

(54) ANTI-NGF ANTIBODIES AND USES THEREOF

(71) Applicant: INVETX, INC., Boston, MA (US)

(72) Inventors: William Brondyk, Boston, MA (US); Jordan Willis, Boston, MA (US); Leila Sevigny, Boston, MA (US)

(73) Assignee: INVETX, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,296

(22) Filed: Jan. 23, 2024

(65) Prior Publication Data

US 2024/0199727 A1    Jun. 20, 2024

Related U.S. Application Data

(63) Continuation of application No. 18/348,173, filed on Jul. 6, 2023, which is a continuation of application No. PCT/US2022/080428, filed on Nov. 23, 2022.

(60) Provisional application No. 63/383,173, filed on Nov. 10, 2022, provisional application No. 63/282,590, filed on Nov. 23, 2021.

(51) Int. Cl.
*C07K 16/22* (2006.01)

(52) U.S. Cl.
CPC ........... *C07K 16/22* (2013.01); *C07K 2317/24* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| 2010/0011197 A1 | 5/2010 | Pons et al. |
| 2010/0111970 A1 | 5/2010 | Pons et al. |
| 2022/0153832 A1* | 5/2022 | Jahchan ................ C07K 16/28 |

FOREIGN PATENT DOCUMENTS

| WO | 2012/012750 A1 | 1/2012 |
| WO | 2020/092554 A1 | 5/2020 |

OTHER PUBLICATIONS

NASA retrieved Jul. 8, 2024 from the Internet at <URL: https://universe.nasa.gov/stars/basics/>). (Year: 2024).*
Rudikoff et al. Proc. Natl. Acad. Sci. 1982. 79: 1979-1983 (Year: 1982).*
Bedouelle et al. Fees J. Jan. 2006;273(1):34-46. (Year: 2006).*
Vajdos et al. J Mol Biol. Jul. 5, 2002;320(2):415-28. (Year: 2002).*
International Search Report and Written Opinion issued May 8, 2023 in Int'l Application No. PCT/US22/80428.

* cited by examiner

*Primary Examiner* — Zachary S Skelding
*Assistant Examiner* — Brianna K Swartwout
(74) *Attorney, Agent, or Firm* — Duane Morris LLP; Thomas J. Kowalski

(57) ABSTRACT

The invention provides novel anti-NGF proteins, antibodies, and NGF-binding fragments thereof which inhibit association of NGF with TrkA and/or p75 and are suitable for administration to a canine or feline subject. The invention also provides novel compositions and methods of treating pain or eliciting an analgesic effect in a canine or feline subject, comprising administering an effective amount of an anti-NGF protein, antibody or fragment thereof. The methods and compositions are used to treat or prevent NGF-related disorders.

27 Claims, 55 Drawing Sheets

Specification includes a Sequence Listing.

| SEQ ID NO: | Clone Name | FR1H | CDR1H | FR2H | CDR2H |
|---|---|---|---|---|---|
| 1 | 2166 | QVQLKESGPGLVQPSQTLSLTCTVS | GLSLTSNS | VSWIRQPPGKGLEWMGV | IWSNGGT |
| 3 | SC-42_006 | EVQLVESGGDLVQPAGSLRLSCVAS | GLSLNSNS | MSWVRQAPEKGLQLVAT | IWSNGGT |
| 5 | SC-42_007 | EVQLVESGGDLVAPSQSLSITCTVS | GLSLTSNA | ISWVRQPPGRGLEWLGT | IWSNGGT |
| 7 | SC-42_008 | EVQLVESGGDLVKPEGSLRLSCVVS | GLELTSNS | MSWVRQAPGKGLQWVGV | LWSNGGT |
| 9 | SC-42_010 | EVQLVESGGDLVAPSQSLSITCTVS | GLSLTSNA | MSWVRQAPGKGLEWLGV | IWSNGGT |
| 11 | SC-42_011 | EVQLVESGGGELVKPGGSLRLSCVAS | GLSLTENS | ISWVRQPPGRGLENLGV | IWSNGGT |
| 13 | SC-42_023 | EVQLVESGGGELVKPGGSLRLSCVAS | GLSLTSNS | MSWIRQAFGKGLQWVAT | IWSNGGT |
| 15 | SC-42_024 | EVQLVESGGGELVKPGGSLRLSCVAS | GLSLNSNS | MSWIRQAPGKGLQWVAT | IWSNGGT |
| 17 | SC-42_025 | EVQLVESGGGELVKPGGSLRLSCVAS | GLSLTSNS | MSWIRQAPGKGLQWVAT | IWSNGGT |
| 19 | SC-42_026 | EVQLVESGGGELVKPGGSLRLSCVAS | GLALTSNS | MSWIRQAPGKGLQWVAT | IWSNGGT |
| 21 | SC-42_027 | EVQLVESGGGELVKPGGSLRLSCVAS | GLELTSNS | MSWIRQAPGKGLQWVAT | IWSNGGT |
| 23 | SC-42_028 | EVQLVESGGGELVKPGGSLRLSCVAS | NLSLTSNS | MSWIRQAPGKGLQWVAT | IWSNGGT |
| 25 | SC-42_029 | EVQLVESGGGELVKPGGSLRLSCVAS | GLSLTSNS | MSWIRQAPGKGLQWVAT | IWSNGGT |
| 27 | SC-42_030 | EVQLVESGGGELVKPGGSLRLSCVAS | GLSLTTNS | MSWIRQAPGKGLQWVAT | IWSNGGT |
| 29 | SC-42_031 | EVQLVESGGGELVKPGGSLRLSCVAS | GLSLTSNS | MSWIRQAPGKGLQWVAT | IWSNGGT |
| 31 | SC-42_032 | EVQLVESGGGELVKPGGSLRLSCVAS | GLALTSNS | MSWIRQAPGKGLQWVAT | IWSNGGT |
| 33 | SC-42_033 | EVQLVESGGGELVKPGGSLRLSCVAS | GLALTSNS | MSWIRQAPGKGLQWVAT | IWSNGGT |
| 35 | SC-42_034 | EVQLVESGGGELVKPGGSLRLSCVAS | GLALTSNS | MSWIRQAPGKGLQWVAT | IWSNGGT |
| 37 | SC-42_035 | EVQLVESGGGELVKPGGSLRLSCVAS | NLSLTSNS | MSWIRQAPGKGLQWVAT | IWSNGGT |
| 39 | SC-42_036 | EVQLVESGGGELVKPGGSLRLSCVAS | GLSLNSNS | MSWIRQAPGKGLQWVAT | IWSNGGT |
| 41 | SC-42_037 | EVQLVESGGGELVKPGGSLRLSCVAS | GLELTSNS | MSWIRQAPGKGLQWVAT | IWSNGGT |
| 43 | SC-42_038 | EVQLVESGGGELVKPGGSLRLSCVAS | GLSLTSNS | MSWIRQAPGKGLQWVAT | IWSNGGT |
| 45 | SC-42_040 | EVQLVESGGGELVKPGGSLRLSCVAS | GLSLTSHS | MSWIRQAPGKGLQWVAT | IWSNGGT |
| 47 | SC-42_041 | EVQLVESGGGELVKPGGSLRLSCVAS | GLSLTTNS | MSWIRQAPGKGLQWVAT | IWSNGGT |

FIG. 1A

| SEQ ID NO: | Clone Name | FR1H | CDR1H | FR2H | CDR2H |
|---|---|---|---|---|---|
| 49 | SC-42_042 | EVQLVESGGGELVKPGGSLRLSCVAS | GLSLTSNS | MSWIRQAPGKGLQWVAT | IWSNGGT |
| 51 | SC-42_043 | EVQLVESGGGELVKPGGSLRLSCVAS | GLALTSNS | MSWIRQAPGKGLQWVAT | IWSNGGT |
| 53 | SC-42_044 | EVQLVESGGGELVKPGGSLRLSCVAS | GLALTSNS | MSWIRQAPGKGLQWVAT | IWSNGGT |
| 55 | SC-42_045 | EVQLVESGGGELVKPGGSLRLSCVAS | GLELTSNS | MSWIRQAPGKGLQWVAT | IWSNGGT |
| 57 | SC-42_046 | EVQLVESGGGELVKPGGSLRLSCVAS | GLSLTSNS | MSWIRQAPGKGLQWVAT | IWSNGGT |
| 59 | SC-42_047 | EVQLVESGGGELVKPGGSLRLSCVAS | NLSLTSNS | MSWIRQAPGKGLQWVAT | IWSNGGT |
| 61 | SC-42_048 | EVQLVESGGGELVKPGGSLRLSCVAS | GLSLTSHS | MSWIRQAPGKGLQWVAT | IWSNGGT |
| 63 | SC-42_049 | EVQLVESGGGELVKPGGSLRLSCVAS | GLALTSNS | MSWIRQAPGKGLQWVAT | IWSNGGT |
| 65 | SC-42_050 | EVQLVESGGGELVKPGGSLRLSCVAS | GLSLTTNS | MSWIRQAPGKGLQWVAT | IWSNGGT |
| 67 | SC-42_051 | EVQLVESGGGELVKPGGSLRLSCVAS | GLSLTSHS | MSWIRQAPGKGLQWVAT | IWSNGGT |
| 69 | SC-42_052 | EVQLVESGGGELVKPGGSLRLSCVAS | GLELTSNS | MSWIRQAPGKGLQWVAT | IWSNGGT |
| 71 | SC-42_053 | EVQLVESGGGELVKPGGSLRLSCVAS | GLSLNSNS | MSWIRQAPGKGLQWVAT | IWSNGGT |
| 73 | SC-42_054 | EVQLVESGGGELVKPGGSLRLSCVAS | GLSLTTNS | MSWIRQAPGKGLQWVAT | IWSNGGT |
| 75 | SC-42_055 | EVQLVESGGGELVKPGGSLRLSCVAS | GLSLTSHS | MSWIRQAPGKGLQWVAT | IWSNGGT |
| 77 | SC-42_057 | EVQLVESGGGELVKPGGSLRLSCVAS | GLSLTSHS | MSWIRQAPGKGLQWVAT | IWSNGGT |
| 79 | SC-42_058 | EVQLVESGGGELVKPGGSLRLSCVAS | GLSLTSNS | MSWIRQAPGKGLQWVAT | IWSNGGT |
| 81 | SC-42_059 | EVQLVESGGGELVKPGGSLRLSCVAS | NLSLTSNS | MSWIRQAPGKGLQWVAT | IWSNGGT |
| 83 | SC-42_060 | EVQLVESGGGELVKPGGSLRLSCVAS | GLALTSNS | MSWIRQAPGKGLQWVAT | IWSNGGT |
| 85 | SC-42_061 | EVQLVESGGGELVKPGGSLRLSCVAS | GLSLTSNS | MSWIRQAPGKGLQWVAT | IWSNGGT |
| 87 | SC-42_062 | EVQLVESGGGELVKPGGSLRLSCVAS | GLALTSNS | MSWIRQAPGKGLQWVAT | IWSNGGT |
| 89 | SC-42_063 | EVQLVESGGGELVKPGGSLRLSCVAS | GLSLNSNS | MSWIRQAPGKGLQWVAT | IWSNGGT |
| 91 | SC-42_064 | EVQLVESGGGELVKPGGSLRLSCVAS | GLSLTSHS | MSWIRQAPGKGLQWVAT | IWSNGGT |
| 93 | SC-42_065 | EVQLVESGGGELVKPGGSLRLSCVAS | GLSLTSHS | MSWIRQAPGKGLQWVAT | IWSNGGT |
| 95 | SC-42_066 | EVQLVESGGGELVKPGGSLRLSCVAS | GLSLTSHS | MSWIRQAPGKGLQWVAT | IWSNGGT |

FIG. 1A Cont'd

| SEQ ID NO: | Clone Name | FR1H | CDR1H | FR2H | CDR2H |
|---|---|---|---|---|---|
| 97 | SC-42_067 | EVQLVESGGGELVKPGGSLRLSCVAS | GLSLTSNS | MSWIRQAPGKGLQWVAT | IWSNGGT |
| 99 | SC-42_068 | EVQLVESGGGELVKPGGSLRLSCVAS | GLSLTSHS | MSWIRQAPGKGLQWVAT | IWSNGGT |
| 101 | SC-42_069 | EVQLVESGGGELVKPGGSLRLSCVAS | GLSLTTNS | MSWIRQAPGKGLQWVAT | IWSNGGT |
| 103 | SC-42_070 | EVQLVESGGGELVKPGGSLRLSCVAS | GLSLTSNS | MSWIRQAPGKGLQWVAT | IWSNGGT |
| 105 | SC-42_071 | EVQLVESGGGDLVKPEGSLRLSCVVS | GLSLTSGS | MSWVRQAPGKGLQWVGV | IYSNGGT |
| 107 | SC-42_072 | EVQLVESGGGDLVQPGGSLRLSCVVS | GLDLTSNS | MSWVRQAPGKGLQWVTV | IWSNGGS |
| 109 | SC-42_073 | EVQLVESGGGDLVKPAGSLRLSCVAS | ALSLTSNS | MSWVRQAPGKGLQLVAT | IWSNGGT |
| 111 | SC-42_075 | EVQLVESGGGDLVQPAGSLRLSCVVS | GLSLTSQS | MSWVRQAPGKGLQLVAI | IWSNGGT |
| 113 | SC-42_077 | EVQLVESGGGDLVQPGGSLRLSCVVS | GLSLTTNS | MSWVRQAPGKGLQWVTT | IWSNGGT |
| 115 | SC-42_079 | EVQLVESGGGDLVKPGGSLSLSCVAS | GLSVTSNS | MDWVRQAPGKGLQWLST | IWSNGGT |
| 117 | SC-42_080 | EVQLVESGGGDLVKPEGSLSLSCVVS | GLSLTSSS | MSWVRQAPGKGLEWVAT | IWSNGGT |
| 119 | SC-42_081 | EVQLVESGGGDLVKPEGSLRLTCVVS | GLSMTSNS | MSWVRQAPGKGLQWVAT | IWSNGGT |
| 121 | SC-42_082 | EVQLVESGGGDLVAPSQSLSITCTVS | GLSLTSHS | ISWVRQAPGKGLQWVAT | IWSNGGT |
| 123 | SC-42_083 | EVQLVESGGGDLVKPEGSLRLSCVVS | GLSLTSNG | MSWVRQAPGKGLEWVAT | IWSNGGT |
| 125 | SC-42_084 | EVQLVESGGGDLVKPEGSLRLSCVVS | GLSLTSHS | MSWVRQAPGKGLQWVAT | IWSNGGT |
| 127 | SC-42_085 | EVQLVESGGGDLVKPGGSLRLSCVVS | GLELTSNS | MSWVRQAPGKGLQWVGT | IWSNGGT |
| 129 | SC-42_088 | EVQLVESGGGDLVKPAGSLRLSCVAS | GLSLTSNS | MSWVRQAPEKGLQLVAT | IWSNGGT |
| 131 | SC-42_089 | EVQLVESGGGDLVKPAGSLRLSCVAS | GLSLTSHS | MSWVRQAPGKGLQLVAT | IWSNGGT |
| 133 | SC-42_090 | EVQLVESGGGDLVKPGGSLRLSCVAS | GLSFTSNS | MSWVRQAPGKGLQLVAT | IWSNGGT |
| 135 | SC-42_091 | EVQLVESGGGDLVKPGGSLSLSCVAS | GLSLTSHS | MDWVRQAPGKGLQWLST | IWSNGGT |
| 137 | SC-42_101 | EVQLVESGGGDLVAPSQSLSITCTVS | GMSLTSNS | ISWVRQPPGRGLEWLGT | IWSNGGT |
| 207 | SC-42_101R | EVQLVESGGGDLVAPSQSLSITCTVS | GMSLTSNS | ISWVRQPPGRGLEWLGT | IWSNRGT |
| 139 | SC-42_102 | EVQLVESGGGDLVKPAGSLRLSCVAS | GLGLTSNS | MSWVRQAPEKGLQLVAV | IWSNGGT |

FIG. 1A Cont'd

| SEQ ID NO: | Clone Name | FR3H | CDR3H | FR4 |
|---|---|---|---|---|
| 1 | 2166 | DYNSAIESRLSINRDTSKSQVFLKMNSLQPEDTAMYFC | ASIYYYDADYLHWYFDF | WGPGTMVTVSS |
| 3 | SC-42_006 | QYTDAVKGRFTISRDNAKNTVYLQMNSLRAEDTAMYYC | ATIYYYDADYLHWYFDF | WGQGTLVTVSS |
| 5 | SC-42_007 | SYTDAVKGRFTISRDNAKNTLYLQMNSLRTEDTARYYC | ASIYYYDADYLHWYFDM | WGQGTLVTVSS |
| 7 | SC-42_008 | DYTDAVKGRFTISRDNAKNTLYLQMNSLRTEDTARYYC | ASIYYYDADYLHWYFDY | WGQGTLVTVSS |
| 9 | SC-42_010 | DYTDAVKGRFTISRDNAKNTLYLQMNSLRTEDTARYYC | ASIYYYDADYLHWYFDF | WGPGTLVTISS |
| 11 | SC-42_011 | SYNSAVKGRFTISRDNAKNTLYLQMNSLRTEDTAVYYC | ASIYYYDADYLHFYFDF | WGQGTLVTISS |
| 13 | SC-42_023 | DYTDAVKGRFTISRDNVKNSLYLQMNSLRAEDTAVYYC | ASIYFYDADYLHWYFDL | WGQGTLVTVSS |
| 15 | SC-42_024 | DYTDAVKGRFTISRDNVKNSLYLQMNSLRAEDTAVYYC | ASIYFFDADYLHWYFDF | WGQGTLVTVSS |
| 17 | SC-42_025 | DYTDAVKGRFTISRDNVKNSLYLQMNSLRAEDTAVYYC | ADIYYYDADYLHWYFDF | WGQGTLVTVSS |
| 19 | SC-42_026 | DYTDAVKGRFTISRDNVKNSLYLQMNSLRAEDTAVYYC | ASIYYYDADYLHWYFDF | WGQGTLVTVSS |
| 21 | SC-42_027 | DYTDAVKGRFTISRDNVKNSLYLQMNSLRAEDTAVYYC | ANIYYYDADYLHWYFDF | WGQGTLVTVSS |
| 23 | SC-42_028 | DYTDAVKGRFTISRDNVKNSLYLQMNSLRAEDTAVYYC | ASIYYYDADYLHWYFDM | WGQGTLVTVSS |
| 25 | SC-42_029 | DYTDAVKGRFTISRDNVKNSLYLQMNSLRAEDTAVYYC | ASIYYYDADYLHWYFDF | WGQGTLVTVSS |
| 27 | SC-42_030 | DYTDAVKGRFTISRDNVKNSLYLQMNSLRAEDTAVYYC | ANIYYYDADYLHWYFDF | WGQGTLVTVSS |
| 29 | SC-42_031 | DYTDAVKGRFTISRDNVKNSLYLQMNSLRAEDTAVYYC | ASIYYYDADYLHWYFDI | WGQGTLVTVSS |
| 31 | SC-42_032 | DYTDAVKGRFTISRDNVKNSLYLQMNSLRAEDTAVYYC | AEIYYYDADYLHWYFDF | WGQGTLVTVSS |
| 33 | SC-42_033 | DYTDAVKGRFTISRDNVKNSLYLQMNSLRAEDTAVYYC | ASIYYYDADYLHWYFDF | WGQGTLVTVSS |
| 35 | SC-42_034 | DYTDAVKGRFTISRDNVKNSLYLQMNSLRAEDTAVYYC | AQIYYYDADYLHWYFDF | WGQGTLVTVSS |
| 37 | SC-42_035 | DYTDAVKGRFTISRDNVKNSLYLQMNSLRAEDTAVYYC | ASIYYYDADYLHWYFDF | WGQGTLVTVSS |
| 39 | SC-42_036 | DYTDAVKGRFTISRDNVKNSLYLQMNSLRAEDTAVYYC | ASIYYYDADYLHWYFDI | WGQGTLVTVSS |
| 41 | SC-42_037 | DYTDAVKGRFTISRDNVKNSLYLQMNSLRAEDTAVYYC | ASIYYYDADYLHWYFDF | WGQGTLVTVSS |
| 43 | SC-42_038 | DYTDAVKGRFTISRDNVKNSLYLQMNSLRAEDTAVYYC | ASIYYYDADYLHWYFDW | WGQGTLVTVSS |
| 45 | SC-42_040 | DYTDAVKGRFTISRDNVKNSLYLQMNSLRAEDTAVYYC | ASIYYYDADYLHWYFDF | WGQGTLVTVSS |
| 47 | SC-42_041 | DYTDAVKGRFTISRDNVKNSLYLQMNSLRAEDTAVYYC | AQIYYYDADYLHWYFDF | WGQGTLVTVSS |

FIG. 1B

| SEQ ID NO: | Clone Name | FR3H | CDR3H | FR4 |
|---|---|---|---|---|
| 49 | SC-42_042 | DYTDAVKGRFTISRDNVKNSLYLQMNSLRAEDTAVYYC | ASIYYYDADYLHWYFDF | WGQGTLVTVSS |
| 51 | SC-42_043 | DYTDAVKGRFTISRDNVKNSLYLQMNSLRAEDTAVYYC | ADIYYYDADYLHWYFDF | WGQGTLVTVSS |
| 53 | SC-42_044 | DYTDAVKGRFTISRDNVKNSLYLQMNSLRAEDTAVYYC | ANIYYYDADYLHWYFDF | WGQGTLVTVSS |
| 54 | SC-42_045 | DYTDAVKGRFTISRDNVKNSLYLQMNSLRAEDTAVYYC | ASIYYYDADYLHWYFDE | WGQGTLVTVSS |
| 55 | SC-42_046 | DYTDAVKGRFTISRDNVKNSLYLQMNSLRAEDTAVYYC | ASIYYYDADYLHFYFDF | WGQGTLVTVSS |
| 59 | SC-42_047 | DYTDAVKGRFTISRDNVKNSLYLQMNSLRAEDTAVYYC | ASIYYYEADYLHWYFDE | WGQGTLVTVSS |
| 61 | SC-42_048 | DYTDAVKGRFTISRDNVKNSLYLQMNSLRAEDTAVYYC | ANIYYYDADYLHWYFDF | WGQGTLVTVSS |
| 63 | SC-42_049 | DYTDAVKGRFTISRDNVKNSLYLQMNSLRAEDTAVYYC | ASIYYYDADYLHWYFDI | WGQGTLVTVSS |
| 65 | SC-42_050 | DYTDAVKGRFTISRDNVKNSLYLQMNSLRAEDTAVYYC | ASIYYYEADYLHWYFDF | WGQGTLVTVSS |
| 67 | SC-42_051 | DYTDAVKGRFTISRDNVKNSLYLQMNSLRAEDTAVYYC | ASIYYYDADYLHFYFDF | WGQGTLVTVSS |
| 69 | SC-42_052 | DYTDAVKGRFTISRDNVKNSLYLQMNSLRAEDTAVYYC | AQIYYYDADYLHWYFDF | WGQGTLVTVSS |
| 71 | SC-42_053 | DYTDAVKGRFTISRDNVKNSLYLQMNSLRAEDTAVYYC | ASIYYYDADYLHWYFDF | WGQGTLVTVSS |
| 73 | SC-42_054 | DYTDAVKGRFTISRDNVKNSLYLQMNSLRAEDTAVYYC | ASIYYYDADYLHWYFDF | WGQGTLVTVSS |
| 75 | SC-42_055 | DYTDAVKGRFTISRDNVKNSLYLQMNSLRAEDTAVYYC | ASIYYYDADYLHWYFDL | WGQGTLVTVSS |
| 77 | SC-42_057 | DYTDAVKGRFTISRDNVKNSLYLQMNSLRAEDTAVYYC | ASIYYYDADYLHFYFDF | WGQGTLVTVSS |
| 79 | SC-42_058 | DYTDAVKGRFTISRDNVKNSLYLQMNSLRAEDTAVYYC | ASIYYYDADYLHWYFDL | WGQGTLVTVSS |
| 81 | SC-42_059 | DYTDAVKGRFTISRDNVKNSLYLQMNSLRAEDTAVYYC | ASIYYYDADYLHFYFDF | WGQGTLVTVSS |
| 83 | SC-42_060 | DYTDAVKGRFTISRDNVKNSLYLQMNSLRAEDTAVYYC | ANIYYYDADYLHWYFDF | WGQGTLVTVSS |
| 85 | SC-42_061 | DYTDAVKGRFTISRDNVKNSLYLQMNSLRAEDTAVYYC | ASIYYYDADYLHWYFDI | WGQGTLVTVSS |
| 87 | SC-42_062 | DYTDAVKGRFTISRDNVKNSLYLQMNSLRAEDTAVYYC | ADIYYYDADYLHWYFDF | WGQGTLVTVSS |
| 89 | SC-42_063 | DYTDAVKGRFTISRDNVKNSLYLQMNSLRAEDTAVYYC | ANIYYYDADYLHWYFDF | WGQGTLVTVSS |
| 91 | SC-42_064 | DYTDAVKGRFTISRDNVKNSLYLQMNSLRAEDTAVYYC | AKIYYYDADYLHWYFDF | WGQGTLVTVSS |
| 93 | SC-42_065 | DYTDAVKGRFTISRDNVKNSLYLQMNSLRAEDTAVYYC | ASIYYYDADYLHWYFDF | WGQGTLVTVSS |
| 95 | SC-42_066 | DYTDAVKGRFTISRDNVKNSLYLQMNSLRAEDTAVYYC | ASIYYYEADYLHWYFDF | WGQGTLVTVSS |

FIG. 1B Cont'd

| SEQ ID NO: | Clone Name | FR3H | CDR3H | FR4 |
|---|---|---|---|---|
| 97 | SC-42_067 | DYTDAVKGRFTISRDNVKNSLYLQMNSLRAEDTAVYYC | ASIYFYDADYLHWYFDE | WGQGTLVTVSS |
| 99 | SC-42_068 | DYTDAVKGRFTISRDNVKNSLYLQMNSLRAEDTAVYYC | ANIYYYDADYLHWYFDE | WGQGTLVTVSS |
| 101 | SC-42_069 | DYTDAVKGRFTISRDNVKNSLYLQMNSLRAEDTAVYYC | ASIYYYDADYLHWYFDL | WGQGTLVTVSS |
| 103 | SC-42_070 | DYTDAVKGRFTISRDNVKNSLYLQMNSLRAEDTAVYYC | ASIYYYDADYLHFYFDE | WGQGTLVTVSS |
| 105 | SC-42_071 | DYTDAVKGRFTISRDNAKNTVYLQMNSLRTEDTAVYYC | ASIYYYDAYYLHWYYDF | WGQGTLVTVSS |
| 107 | SC-42_072 | DYTDAVKGRFTISRDNAKNTVYLQMNSLRTEDTAVYYC | ASIYYYDADYLHWYFDF | WGQGTLVTVSS |
| 109 | SC-42_073 | DYADAVKGRFTISRDNAKNTVYLQMNSLRAEDTAMYYC | ASIYYYDADYLHWYFQF | WGQGTLVTVSS |
| 111 | SC-42_075 | DYTDAVKGRFTISRDNAKNTVYLQMNSLRAEDTAVYYC | ASIYYYDADYLHWYWDF | WGQGTLVTVSS |
| 113 | SC-42_077 | DYTDAVKGRFTISRDNAKNTVYLQMNSLRAEDTAMYYC | ASIYYYDADYLHWYFDM | WGQGTLVTVSS |
| 115 | SC-42_079 | DYADAVKGRFTISRDNAKNTVYLQMNSLRTEDTAVYYC | AQIYYYDADYLHWYFDE | WGQGTLVTVSS |
| 117 | SC-42_080 | DYNDAVKGRFTISRDNAKNTLYLKMNSLRTEDTAVYYC | AKIYYYDADYLHWYFDE | WGQGTLVTVSS |
| 119 | SC-42_081 | DYTDAVKGRFTISRDNAKNTLYLYLQMNSLRTEDTARYYC | ASIYYYDADYLWYFDE | WGQGTLVTVSS |
| 121 | SC-42_082 | DYTSAVKGRFTISRDNAKNTVYLQMNSLRTEDTAVYYC | ASIYYYDSDYLHWYFDE | WGQGTLVTVSS |
| 123 | SC-42_083 | DYTDAVKGRFTISKDNSKSQVFLKMNSLQVFLKMNSLQTDDTARYYC | ASIYYYEADYLHWYFDE | WGQGTLVTVSS |
| 125 | SC-42_084 | DYTDAVKGRFTISRDNSNAKNTVYLQMNSLQTEDTAVYYC | ASIYYYDADYLHWYIDF | WGQGTLVTVSS |
| 127 | SC-42_085 | DYTDAVKGRFTISRDNAKNTVYLQMNSLQTEDTAVYYC | ASIYYYDADYLHWYFDL | WGQGTLVTVSS |
| 129 | SC-42_088 | DYTDAVKGRFTISRDNAKNTVYLQMNSLRAEDTGMYYC | ASIYYYDADYLHWYFDE | WGQGTLVTVSS |
| 131 | SC-42_089 | DYTDAVKGRFTISRDNAKNTVYLQMNSLRAEDTAMYYC | ASIYYYDADYLHWYFDE | WGQGTLVTVSS |
| 133 | SC-42_090 | DYTDAVKGRFTISRDNAKNTVYLQMNSLRAEDTAMYYC | ASIWYYDADYLHWYFDE | WGQGTLVTVSS |
| 135 | SC-42_091 | QYADAVKGRFTISRDNAKNTVYLQMNSLRAEDTAMYYC | AQIYYYDADYLHWYLDE | WGQGTLVTVSS |
| 137 | SC-42_101 | DYTDAVKGRFTISRDNAKNTVYLQMNSLRAEDTAMYYC | AQIYYYDADYLHWYFDE | WGQGTLVTVSS |
| 207 | SC-42_101R | DYTDAVKGRFTISRDNAKNTVYLQMNSLRAEDTAMYYC | AKIYYYDADYLHWYFDE | WGQGTLVTVSS |
| 139 | SC-42_102 | QYADAVKGRFTISRDNAKNTVYLQMNSLRAEDTAMYYC | AKIYYYDADYLHWYFDE | WGQGTLVTVSS |

FIG. 1B Cont'd

| SEQ ID NO: | Clone Name | FR1L | CDR1L | FR2L | CDR2L |
|---|---|---|---|---|---|
| 2 | 2166 | DIQMTQSPASLSASLGETVSIECLAS | EGISNS | LAWYQLKPGKSPQFLIY | ATS |
| 4 | SC-42_006 | EIVMTQSPASLSLSQEEKVTITCRAS | EGISNN | LAWYQQKPGQAPKLLIY | ATN |
| 6 | SC-42_007 | EIVMTQSPASLSLSVEEKVTITCRAS | EGISNN | LAWYQQKPGQAPKLLIY | ATS |
| 8 | SC-42_008 | EIVMTQSPASLSLSQEDKVTITCRAS | EGISNN | VAWYQQKPGQAPKLLIY | ATS |
| 10 | SC-42_010 | EIVMTQSPASLSLSQEDKVTITCRAS | EGISSS | LAWYQQKPGQAPKLLIY | ATS |
| 12 | SC-42_011 | EIVMTQSPASLSLSQEDKVTITCRAS | EGINNS | LAWYQQKPGQAPKLLIY | ATQ |
| 14 | SC-42_023 | EIVMTQSPASLSLSQGEKVTITCRAS | EGISNN | LAWYQQKPGQAPKLLIY | ATS |
| 16 | SC-42_024 | EIVMTQSPASLSLSQGEKVTITCRAS | EGISNN | LAWYQQKPGQAPKLLIY | ATS |
| 18 | SC-42_025 | EIVMTQSPASLSLSQGEKVTITCRAS | EGISNN | LAWYQQKPGQAPKLLIY | ATS |
| 20 | SC-42_026 | EIVMTQSPASLSLSQGEKVTITCRAS | EGISNN | LAWYQQKPGQAPKLLIY | ATS |
| 22 | SC-42_027 | EIVMTQSPASLSLSQGEKVTITCRAS | EGISNN | LAWYQQKPGQAPKLLIY | ATS |
| 24 | SC-42_028 | EIVMTQSPASLSLSQGEKVTITCRAS | EGISNN | LAWYQQKPGQAPKLLIY | ATS |
| 26 | SC-42_029 | EIVMTQSPASLSLSQGEKVTITCRAS | EGISNN | LAWYQQKPGQAPKLLIY | ATS |
| 28 | SC-42_030 | EIVMTQSPASLSLSQGEKVTITCRAS | EGISNN | LAWYQQKPGQAPKLLIY | ATS |
| 30 | SC-42_031 | EIVMTQSPASLSLSQGEKVTITCRAS | EGISNN | LAWYQQKPGQAPKLLIY | ATS |
| 32 | SC-42_032 | EIVMTQSPASLSLSQGEKVTITCRAS | EGISNN | LAWYQQKPGQAPKLLIY | ATS |
| 34 | SC-42_033 | EIVMTQSPASLSLSQGEKVTITCRAS | EGISNN | LAWYQQKPGQAPKLLIY | ATS |
| 36 | SC-42_034 | EIVMTQSPASLSLSQGEKVTITCRAS | EGISNN | LAWYQQKPGQAPKLLIY | ATS |
| 38 | SC-42_035 | EIVMTQSPASLSLSQGEKVTITCRAS | EGISNN | LAWYQQKPGQAPKLLIY | ATS |
| 40 | SC-42_036 | EIVMTQSPASLSLSQEDKVTITCRAS | EGISNN | LAWYQQKPGQAPKLLIY | ATS |
| 42 | SC-42_037 | EIVMTQSPASLSLSQEDKVTITCRAS | EGISNN | LAWYQQKPGQAPKLLIY | ATS |
| 44 | SC-42_038 | EIVMTQSPASLSLSQEDKVTITCRAS | EGISNN | LAWYQQKPGQAPKLLIY | ATS |
| 46 | SC-42_040 | EIVMTQSPASLSLSQEDKVTITCRAS | EGISNN | LAWYQQKPGQAPKLLIY | ATS |
| 48 | SC-42_041 | EIVMTQSPASLSLSQEDKVTITCRAS | EGISNN | LAWYQQKPGQAPKLLIY | ATS |

FIG. 2A

| SEQ ID NO: | Clone Name | FR1L | CDR1L | FR2L | CDR2L |
|---|---|---|---|---|---|
| 50 | SC-42_042 | EIVMTQSPASLSLSQEDKVTITCRAS | EGISNN | LAWYQQKPGQAPKLLIY | ATS |
| 52 | SC-42_043 | EIVMTQSPASLSLSQEDKVTITCRAS | EGISNN | LAWYQQKPGQAPKLLIY | ATS |
| 54 | SC-42_044 | EIVMTQSPASLSLSQEDKVTITCRAS | EGISNN | LAWYQQKPGQAPKLLIY | ATS |
| 56 | SC-42_045 | EIVMTQSPASLSLSQEDKVTITCRAS | EGISNN | LAWYQQKPGQAPKLLIY | ATS |
| 58 | SC-42_046 | EIVMTQSPASLSLSQEDKVTITCRAS | EGISNN | LAWYQQKPGQAPKLLIY | ATD |
| 60 | SC-42_047 | EIVMTQSPASLSLSQEDKVTITCRAS | EGISNN | LAWYQQKPGQAPKLLIY | ATD |
| 62 | SC-42_048 | EIVMTQSPASLSLSQEDKVTITCRAS | EGISNN | LAWYQQKPGQAPKLLIY | ATD |
| 64 | SC-42_049 | EIVMTQSPASLSLSQEDKVTITCRAS | EGISNN | LAWYQQKPGQAPKLLIY | ATD |
| 66 | SC-42_050 | EIVMTQSPASLSLSQEDKVTITCRAS | EGISNN | LAWYQQKPGQAPKLLIY | ATD |
| 68 | SC-42_051 | EIVMTQSPASLSLSQEDKVTITCRAS | EGISNN | LAWYQQKPGQAPKLLIY | ATS |
| 70 | SC-42_052 | EIVMTQSPASLSLSQEDKVTITCRAS | EGISNN | LAWYQQKPGQAPKLLIY | ATS |
| 72 | SC-42_053 | EIVMTQSPASLSLSQEDKVTITCRAS | EGISNN | LAWYQQKPGQAPKLLIY | ATS |
| 74 | SC-42_054 | EIVMTQSPASLSASQEEKVTITCRAS | EGISNN | LAWYQQKPGQAPKLLIY | ATS |
| 76 | SC-42_055 | EIVMTQSPASLSASQEEKVTITCRAS | EGISNN | LAWYQQKPGQAPKLLIY | ATS |
| 78 | SC-42_057 | EIVMTQSPASLSASQEEKVTITCRAS | EGISNN | LAWYQQKPGQAPKLLIY | ATS |
| 80 | SC-42_058 | EIVMTQSPASLSASQEEKVTITCRAS | EGISNN | LAWYQQKPGQAPKLLIY | ATS |
| 82 | SC-42_059 | EIVMTQSPASLSASQEEKVTITCRAS | EGISNN | LAWYQQKPGQAPKLLIY | ATD |
| 84 | SC-42_060 | EIVMTQSPASLSASQEEKVTITCRAS | EGISNN | LAWYQQKPGQAPKLLIY | ATD |
| 86 | SC-42_061 | EIVMTQSPASLSASQEEKVTITCRAS | EGISNN | LAWYQQKPGQAPKLLIY | ATD |
| 88 | SC-42_062 | EIVMTQSPASLSASQEEKVTITCRAS | EGISNN | LAWYQQKPGQAPKLLIY | ATD |
| 90 | SC-42_063 | EIVMTQSPASLSLSQEDKVTITCRAS | EGISNN | LAWYQQKPGQAPKLLIY | ATD |
| 92 | SC-42_064 | EIVMTQSPASLSASQEEKVTITCRAS | EGISNN | LAWYQQKPGQAPKLLIY | ATD |
| 94 | SC-42_065 | EIVMTQSPASLSASQEEKVTITCRAS | EGISNN | LAWYQQKPGQAPKLLIY | ATD |
| 96 | SC-42_066 | EIVMTQSPASLSLSQEDKVTITCRAS | EGISNN | LAWYQQKPGQAPKLLIY | ATS |

FIG. 2A Cont'd

| SEQ ID NO: | Clone Name | FR1L | CDR1L | FR2L | CDR2L |
|---|---|---|---|---|---|
| 98 | SC-42_067 | EIVMTQSPASLSLSQEDKVTITCRAS | EGISNN | LAWYQQKPGQAPKLLIY | ATS |
| 100 | SC-42_068 | EIVMTQSPASLSLSQEDKVTITCRAS | EGISNN | LAWYQQKPGQAPKLLIY | ATS |
| 102 | SC-42_069 | EIVMTQSPASLSLSQEDKVTITCRAS | EGISNN | LAWYQQKPGQAPKLLIY | ATS |
| 104 | SC-42_070 | EIVMTQSPASLSLSQEDKVTITCRAS | EGISNN | LAWYQQKPGQAPKLLIY | ATS |
| 106 | SC-42_071 | EIVMTQSPASLSLSQGEKVTITCRAS | EGISNN | LAWYQQKPGQAPKLLIY | ATS |
| 108 | SC-42_072 | EIVMTQSPASLSLSQEEKVTITCRAS | EGISNN | LAWYQQKPGQAPKLLIY | AAS |
| 110 | SC-42_073 | EIVMTQSPASLSASQEEKVTITCRAS | EGIQNS | LAWYQQKPGQAPKLLIY | ATN |
| 112 | SC-42_075 | EIVMTQSPASLSLSQEEKVTITCRAS | EGISNA | LAWYQQKPGKAPKLLIY | ATE |
| 114 | SC-42_077 | EIVMTQSPASLSASQEEKVTITCRAS | EGIGNS | LAWYQQKPGQAPKLLIY | ATE |
| 116 | SC-42_079 | EIVMTQSPASLSLSQEEKVTITCRAS | EGIGNS | LAWYQQKPGQAPKLLIY | ATS |
| 118 | SC-42_080 | EIVMTQSPASLSLSQEEKVTITCRAS | DGISNS | LAWYQQKPGQAPKLLIY | ATQ |
| 120 | SC-42_081 | EIVMTQSPASLSASQEEKVTITCRAS | EAISNS | LAWYQQKPGQAPKLLIY | ASS |
| 122 | SC-42_082 | EIVMTQSPASLSLSQEKVTITCRAS | EGISNG | LAWYQQKPGQAPKLLIY | ATS |
| 124 | SC-42_083 | EIVMTQSPASLSLSQEKVTITCRAS | EGISSS | LAWYQQKPGQAPKLLIY | ATA |
| 126 | SC-42_084 | EIVMTQSPASLSLSQEDKVTITCRAS | EGISNN | LAWYQQKPGQAPKLLIY | ATS |
| 128 | SC-42_085 | EIVMTQSPASLSLSQGEKVTITCRAS | DGISNS | LAWYQQKPGQAPKLLIY | ATS |
| 130 | SC-42_088 | EIVMTQSPASLSLSQGEKVTITCRAS | EAISNS | LAWYQQKPGQAPKLLIY | ATT |
| 132 | SC-42_089 | EIVMTQSPASLSLSQGEKVTITCRAS | KGISNS | LAWYQQKPGQAPKLLIY | ATS |
| 134 | SC-42_090 | EIVMTQSPASLSLSQGEKVTITCRAS | EGISNT | LAWYQQKPGQAPKLLIY | ATE |
| 136 | SC-42_091 | EIVMTQSPASLSLSQGEKVTITCRAS | ENISNS | LAWYQQKPGQAPKLLIH | ATS |
| 138 | SC-42_101 | EIVMTQSPASLSLSQGEKVTITCRAS | EGISNN | LAWYQQKPGQAPKLLIY | ATS |
| 140 | SC-42_102 | EIVMTQSPASLSLSQGEKVTITCRAS | EGISNN | LAWYQQKPGQAPKLLIY | ATS |

FIG. 2A Cont'd

| SEQ ID NO: | Clone Name | FR3L | CDR3L | FR4L |
|---|---|---|---|---|
| 2 | 2166 | SLQDGVPSRFSGSGSGTQYSLKISGMQPEDEGVYYC | QQGYKFPLT | FGSGTKLKIK |
| 4 | SC-42_006 | SLATGVPSRFSGSGSGTDFSLTISSLEPEDVAVYYC | QQGYKFPLT | FGQGTKVEIK |
| 6 | SC-42_007 | SLATGVPSRFSGSGSGTDFTLTISSLQPEDFATYYC | QQGWKFPLT | FGQGTKVEIK |
| 8 | SC-42_008 | ELATGVPSRFSGSGSGTDFSLTISSLEPEDVAVYYC | QQGYKFPMT | FGQGTKVEIK |
| 10 | SC-42_010 | QLATGVPSRFSGSGSGTDFSFTISSLEPEDVAVYYC | QQGYKWPLT | FGQGTKVEIK |
| 12 | SC-42_011 | SLATGVPSRFSGSGSGTDFSLTISSLEPEDVAVYYC | QQGFKFPLT | FGQGTKVEIK |
| 14 | SC-42_023 | ELATGVPSRFSGSGSGTDFSFTISSLEPEDVATYYC | QQGYKFPLT | FGQGTKVEIK |
| 16 | SC-42_024 | ELATGVPSRFSGSGSGTDFSFTISSLEPEDVATYYC | QQGYKWPLT | FGQGTKVEIK |
| 18 | SC-42_025 | ELATGVPSRFSGSGSGTDFSFTISSLEPEDVATYYC | QQGYKWPLT | FGQGTKVEIK |
| 20 | SC-42_026 | ELATGVPSRFSGSGSGTDFSFTISSLEPEDVATYYC | QQGYKFPLT | FGQGTKVEIK |
| 22 | SC-42_027 | ELATGVPSRFSGSGSGTDFSFTISSLEPEDVATYYC | QQGYKWPLT | FGQGTKVEIK |
| 24 | SC-42_028 | ELATGVPSRFSGSGSGTDFSFTISSLEPEDVATYYC | QQGYKWPLT | FGQGTKVEIK |
| 26 | SC-42_029 | ELATGVPSRFSGSGSGTDFSFTISSLEPEDVATYYC | QQGYKFPLT | FGQGTKVEIK |
| 28 | SC-42_030 | ELATGVPSRFSGSGSGTDFSFTISSLEPEDVATYYC | QQGYKFPLT | FGQGTKVEIK |
| 30 | SC-42_031 | ELATGVPSRFSGSGSGTDFSFTISSLEPEDVATYYC | QQGYKFPLT | FGQGTKVEIK |
| 32 | SC-42_032 | ELATGVPSRFSGSGSGTDFSFTISSLEPEDVATYYC | QQGYKFPLT | FGQGTKVEIK |
| 34 | SC-42_033 | ELATGVPSRFSGSGSGTDFSFTISSLEPEDVATYYC | QQGYKFPLT | FGQGTKVEIK |
| 36 | SC-42_034 | ELATGVPSRFSGSGSGTDFSFTISSLEPEDVATYYC | QQGYKFPLT | FGQGTKVEIK |
| 38 | SC-42_035 | ELATGVPSRFSGSGSGTDFSFTISSLEPEDVATYYC | QQGYKFPLT | FGQGTKVEIK |
| 40 | SC-42_036 | ELATGVPSRFSGSGSGTDFSFTISSLEPEDVATYYC | QQGYKFPLT | FGQGTKVEIK |
| 42 | SC-42_037 | ELATGVPSRFSGSGSGTDFSFTISSLEPEDVATYYC | QQGYKFPLT | FGQGTKVEIK |
| 44 | SC-42_038 | ELATGVPSRFSGSGSGTDFSFTISSLEPEDVATYYC | QQGYKFPLT | FGQGTKVEIK |
| 46 | SC-42_040 | QLATGVPSRFSGSGSGTDFSFTISSLEPEDVATYYC | QQGYKWPLT | FGQGTKVEIK |
| 48 | SC-42_041 | QLATGVPSRFSGSGSGTDFSFTISSLEPEDVATYYC | QQGYKFPLT | FGQGTKVEIK |

FIG. 2B

| SEQ ID NO: | Clone Name | FR3L | CDR3L | FR4L |
|---|---|---|---|---|
| 50 | SC-42_042 | QLATGVPSRFSGSGSGTDFSFTISSLEPEDVATYYC | QQGYKWPLT | FGQGTKVEIK |
| 52 | SC-42_043 | QLATGVPSRFSGSGSGTDFSFTISSLEPEDVATYYC | QQGYKWPLT | FGQGTKVEIK |
| 54 | SC-42_044 | QLATGVPSRFSGSGSGTDFSFTISSLEPEDVATYYC | QQGYKWPLT | FGQGTKVEIK |
| 56 | SC-42_045 | QLATGVPSRFSGSGSGTDFSFTISSLEPEDVATYYC | QQGYKWPLT | FGQGTKVEIK |
| 58 | SC-42_046 | SLATGVPSRFSGSGSGTDFSFTISSLEPEDVATYYC | QQGYKWPLT | FGQGTKVEIK |
| 60 | SC-42_047 | SLATGVPSRFSGSGSGTDFSFTISSLEPEDVATYYC | QQGYKWPLT | FGQGTKVEIK |
| 62 | SC-42_048 | SLATGVPSRFSGSGSGTDFSFTISSLEPEDVATYYC | QQGYKWPLT | FGQGTKVEIK |
| 64 | SC-42_049 | SLATGVPSRFSGSGSGTDFSFTISSLEPEDVATYYC | QQGYKWPLT | FGQGTKVEIK |
| 66 | SC-42_050 | SLATGVPSRFSGSGSGTDFSFTISSLEPEDVATYYC | QQGYKWPLT | FGQGTKVEIK |
| 68 | SC-42_051 | SLATGVPSRFSGSGSGTDFSFTISSLEPEDVATYYC | QQGYKWPLT | FGQGTKVEIK |
| 70 | SC-42_052 | ELATGVPSRFSGSGSGTDFSFTISSLQPEDVAVYYC | QQGYKWPLT | FGQGTKVEIK |
| 72 | SC-42_053 | ELATGVPSRFSGSGSGTDFSFTISSLQPEDVAVYYC | QQGYKWPLT | FGQGTKVEIK |
| 74 | SC-42_054 | ELATGVPSRFSGSGSGTDFSFTISSLQPEDVAVYYC | QQGYKWPLT | FGQGTKVEIK |
| 76 | SC-42_055 | ELATGVPSRFSGSGSGTDFSFTISSLQPEDVAVYYC | QQGYKWPLT | FGQGTKVEIK |
| 78 | SC-42_057 | ELATGVPSRFSGSGSGTDFSFTISSLQPEDVAVYYC | QQGYKWPLT | FGQGTKVEIK |
| 80 | SC-42_058 | ELATGVPSRFSGSGSGTDFSFTISSLQPEDVAVYYC | QQGYKWPLT | FGQGTKVEIK |
| 82 | SC-42_059 | ELATGVPSRFSGSGSGTDFSFTISSLQPEDVAVYYC | QQGYKWPLT | FGQGTKVEIK |
| 84 | SC-42_060 | SLATGVPSRFSGSGSGTDFSFTISSLQPEDVAVYYC | QQGYKWPLT | FGQGTKVEIK |
| 86 | SC-42_061 | SLATGVPSRFSGSGSGTDFSFTISSLQPEDVAVYYC | QQGYKWPLT | FGQGTKVEIK |
| 88 | SC-42_062 | SLATGVPSRFSGSGSGTDFSFTISSLQPEDVAVYYC | QQGYKWPLT | FGQGTKVEIK |
| 90 | SC-42_063 | SLATGVPSRFSGSGSGTDFSFTISSLQPEDVAVYYC | QQGYKWPLT | FGQGTKVEIK |
| 92 | SC-42_064 | SLATGVPSRFSGSGSGTDFSFTISSLQPEDVAVYYC | QQGYKWPLT | FGQGTKVEIK |
| 94 | SC-42_065 | SLATGVPSRFSGSGSGTDFSFTISSLQPEDVAVYYC | QQGYKWPLT | FGQGTKVEIK |
| 96 | SC-42_066 | ELATGVPSRFSGSGSGTDFTLTISSLQPEDFATYYC | QQGYKWPLT | FGQGTKVEIK |

FIG. 2B Cont'd

| SEQ ID NO: | Clone Name | FR3L | CDR3L | FR4L |
|---|---|---|---|---|
| 98 | SC-42_067 | ELATGVPSRFSGSGSGTDFTLTISSLQPEDFATYYC | QQGYKWPLT | FGQGTKVEIK |
| 100 | SC-42_068 | ELATGVPSRFSGSGSGTDFTLTISSLQPEDFATYYC | QQGYKWPLT | FGQGTKVEIK |
| 102 | SC-42_069 | ELATGVPSRFSGSGSGTDFTLTISSLQPEDFATYYC | QQGYKWPLT | FGQGTKVELK |
| 104 | SC-42_070 | ELATGVPSRFSGSGSGTDFTLTISSLQPEDFATYYC | QQGYKWPLT | FGAGTKVELK |
| 106 | SC-42_071 | SMATGVPSRFSGSGSGTDFSFTISSLEPEDVATYYC | QQGYKFPLT | FGAGTKVELK |
| 108 | SC-42_072 | SLQTGVPSRFSGSGSGTDFSFTISSLEPEDVATYYC | QHGYKFPLT | FGAGTKVELK |
| 110 | SC-42_073 | SLATGVPSRFSGSGSGTDFTLTISSLQPEDFATYYC | QQGHKFPLT | FGAGTKVELK |
| 112 | SC-42_075 | SLATGVPSRFSGSGSGTDFSFTISSLEPEDVATYYC | QQGFKFPLT | FGQGTKVELK |
| 114 | SC-42_077 | SLARGVPSRFSGSGSGTDFSFTISSLEPEDVAVYYC | QQGYKWPLT | FGQGTKVELK |
| 116 | SC-42_079 | QLATGVPSRFSGSGSGTDFSFTISSLEPEDVAVYYC | QQGHKFPLT | FGAGTKVELK |
| 118 | SC-42_080 | SLARGVPSRFSGSGSGTDFSLTISSLEPEDVATYYC | QQGYKWPLT | FGAGTKVELK |
| 120 | SC-42_081 | SLATGVPSRFSGSGSGTDFSFTISSLEPEDVATYYC | QQGWKFPLT | FGAGTKVELK |
| 122 | SC-42_082 | ELATGVPSRFSGSGSGTDFSFTISSLEPEDVATYYC | QQGYKFPLT | FGQGTKVEIK |
| 124 | SC-42_083 | SLATGVPSRFSGSGSGTDFSFTISSLEPEDVATYYC | QQGYKWPLT | FGQGTKVEIK |
| 126 | SC-42_084 | KLATGVPSRFSGSGSGTDFSFTISSLEPEDVATYYC | QQGYKWPLT | FGQGTKVEIK |
| 128 | SC-42_085 | ELATGVPSRFSGSGSGTDFSFTISSLEPEDVATYYC | QQGYKWPLT | FGQGTKVEIK |
| 130 | SC-42_088 | SLATGVPSRFSGSGSGTDFSFTISSLEPEDVATYYC | QQGYKWPLT | FGQGTKVEIK |
| 132 | SC-42_089 | ELATGVPSRFSGSGSGTDFSFTISSLEPEDVAVYYC | QQGYKFPLT | FGQGTKVEIK |
| 134 | SC-42_090 | SLATGVPSRFSGSGSGTDFTLTISSLQPEDFATYYC | QQGFKFPLT | FGQGTKVEIK |
| 136 | SC-42_091 | TLATGVPSRFSGSGSGTDFSLTISSLEPEDVATYYC | QQGYKWPLT | FGQGTKVEIK |
| 138 | SC-42_101 | SLQTGVPSRFSGSGSGTDFSFTISSLEPEDVATYYC | QQGYQFPLT | FGQGTKVEIK |
| 140 | SC-42_102 | ALATGVPSRFSGSGSGTDFTLTISSLQPEDFATYYC | QQGYKFPLT | FGQGTKVEIK |

FIG. 2B Cont'd

Heavy chain
QVQLKESGPGLVQPSQTLSLTCTVSGLSLTSNSVSWIRQPPGKGLEWMGVIWSNGGTDYNSAIESRLSINRDTSKSQ
VFLKMNSLQPEDTAMYFCASIYYYDADYLHWYFDFWGPGTMVTVSSASTTAPSVFPLAPSCGSTSGSTVALACLVSG
YFPEPVTVSWNSGSLTSGVHTFPSVLQSSGLYSLSSMVTVPSSRWPSETFTCNVAHPASKTKVDKPVPKRENGRVPR
PPDCPCPKCPAPEAAGGPSVFIFPPKPKDTLLIARTPEVTCVVVDLDPEDPEVQISWFVDGKQMQTAKTQPREEQFNGT
YRVVSVLPIGHQDWLKGKQFTCKVNNKALPSPIERTISKARGQAHQPSVVLPPSREELSKNTVSLTCLIKDFFPPD
IDVEWQSNGQQEPESKYRTTPPQLDEDGSYFLYSKLSVDKSRWQRGDTFICAVMHEALHNHYTQESLSHSPG Light chain
DIQMTQSPASLSASLGETVSIECLASEGISNSLAWYQLKPGKSPQFLIYATSSLQDGVPSRFSGSGSGTQYSLKISG
MQPEDEGVYYCQQGYKEPLTFGSGTKLLKIKRNDAQPAVLFQPSPDQLHTGSASVVCLLNSFYPKDINVKWKVDGV
IQDTGIQESVTEQDKDSTYSLSSTLTMSSTEYLSHELYSCEIHKSLPSTLIKSFQRSECQRVD

FIG. 4

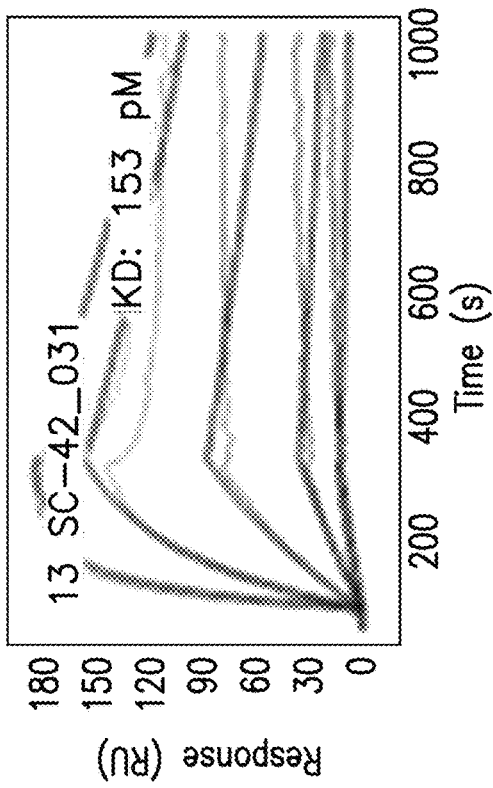
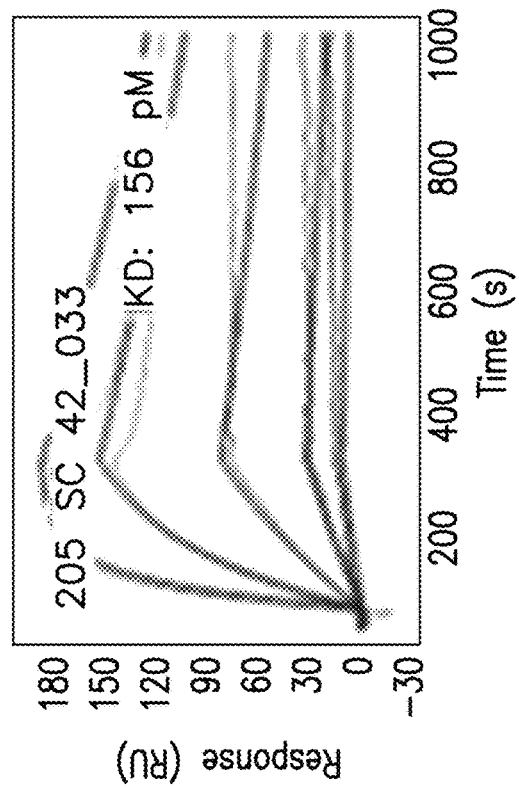
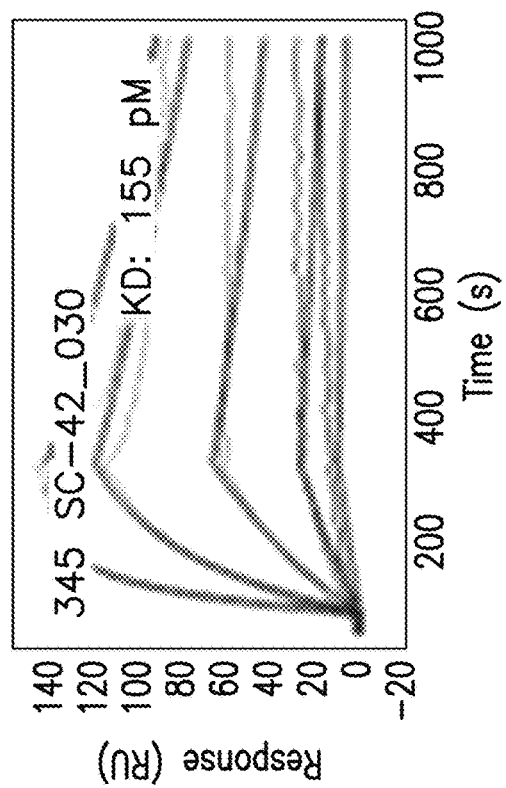
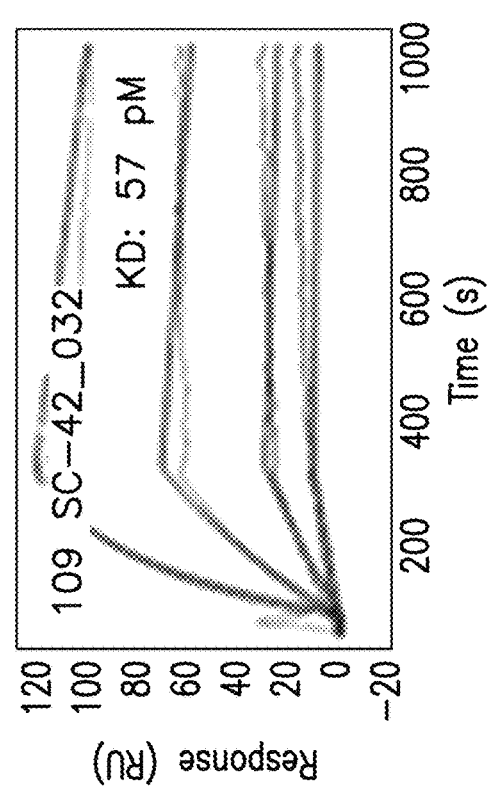
FIG. 10 Cont'd

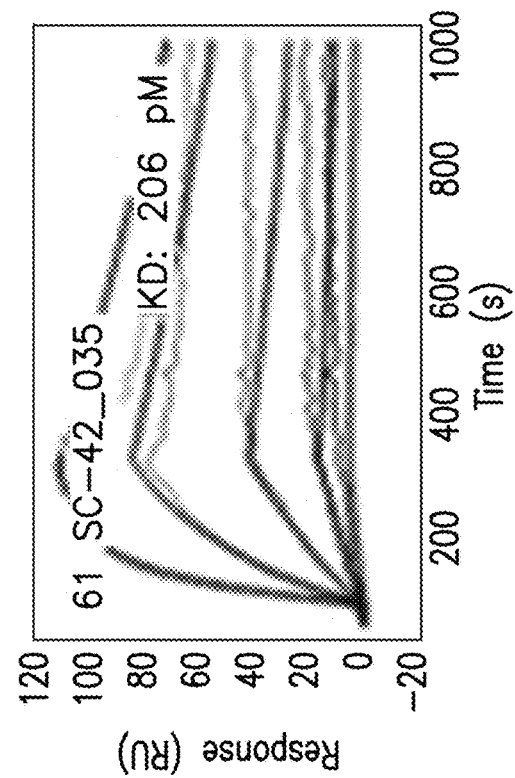
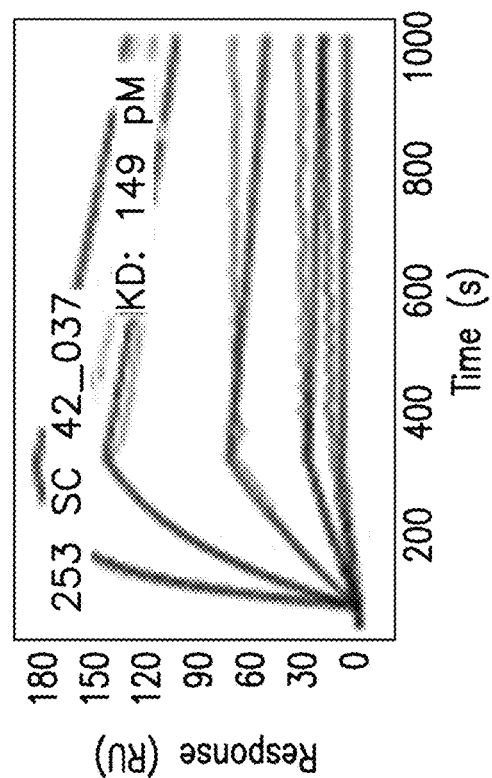
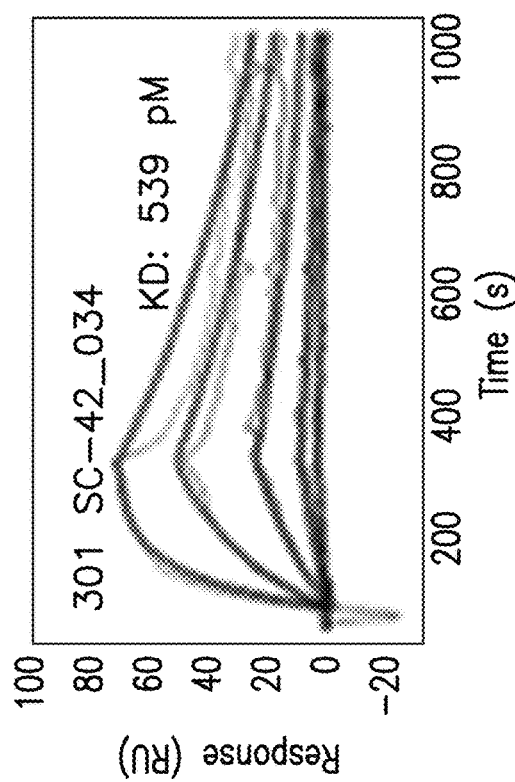
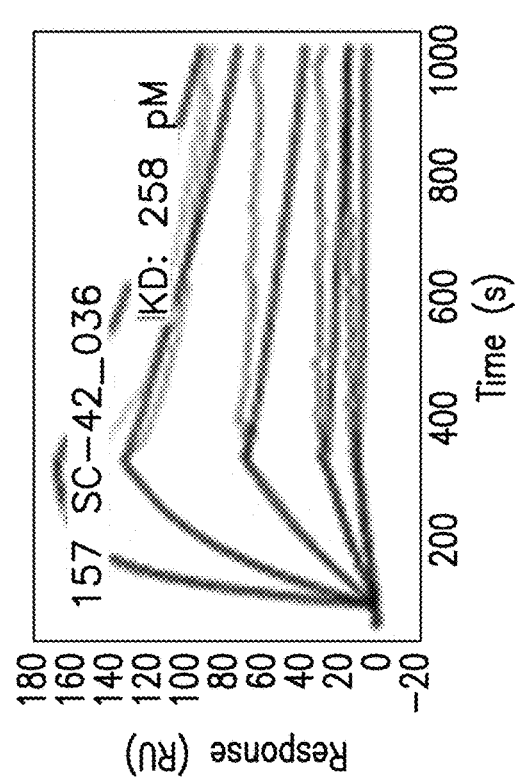
FIG. 10 Cont'd

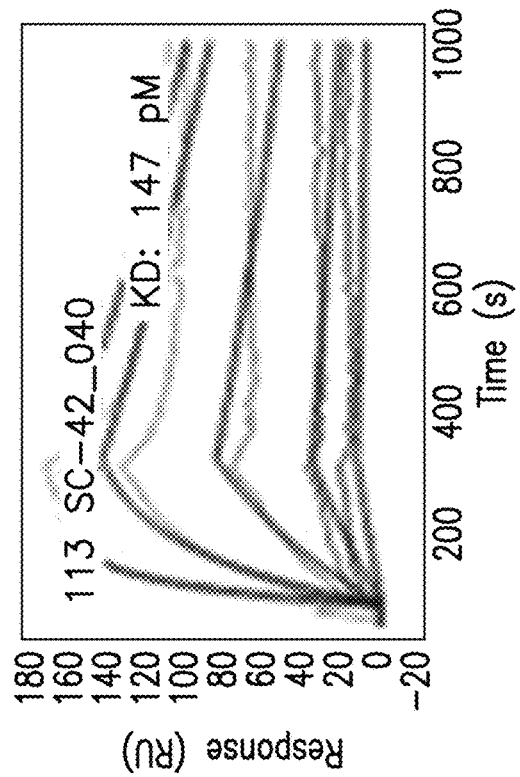
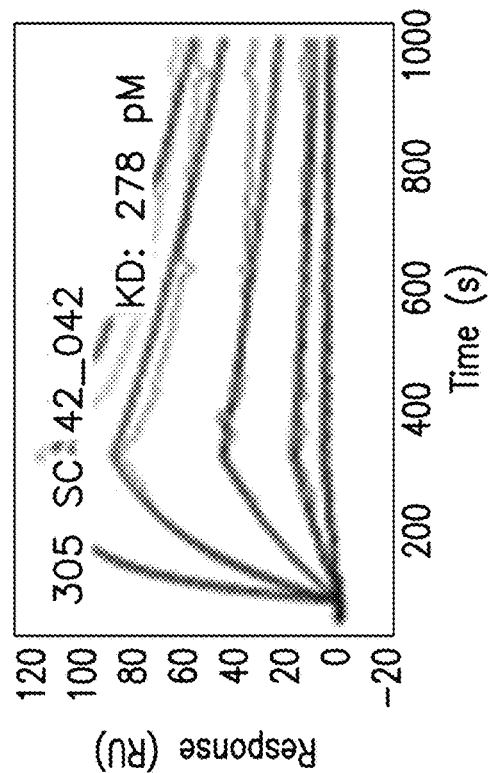
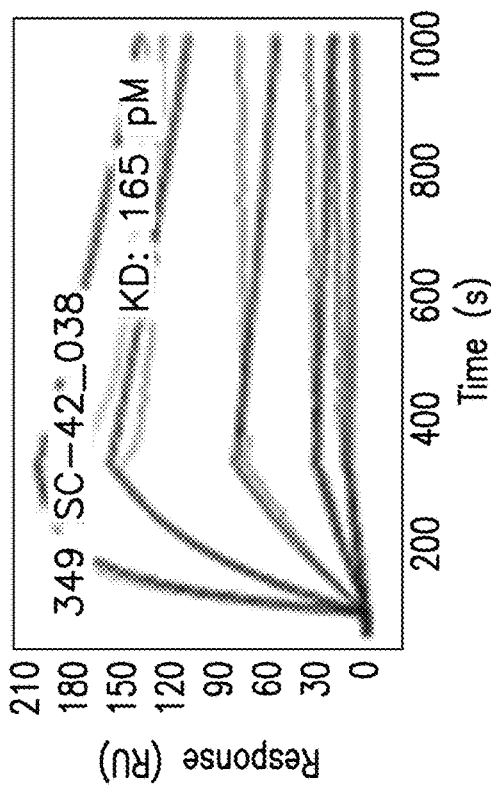
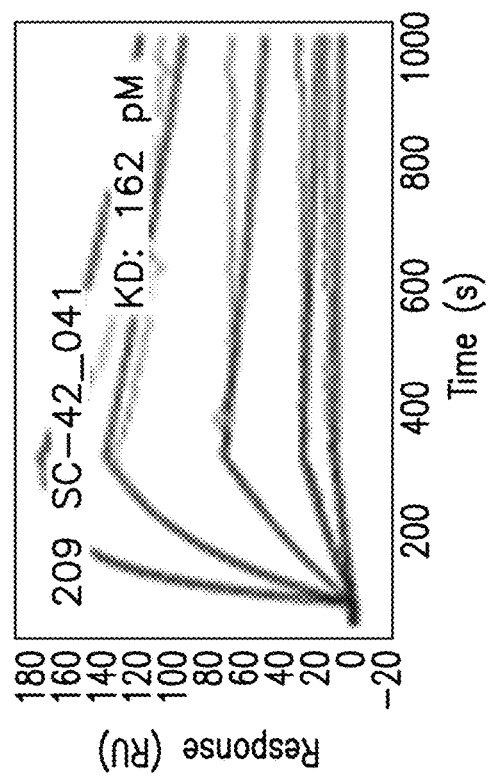
FIG. 10 Cont'd

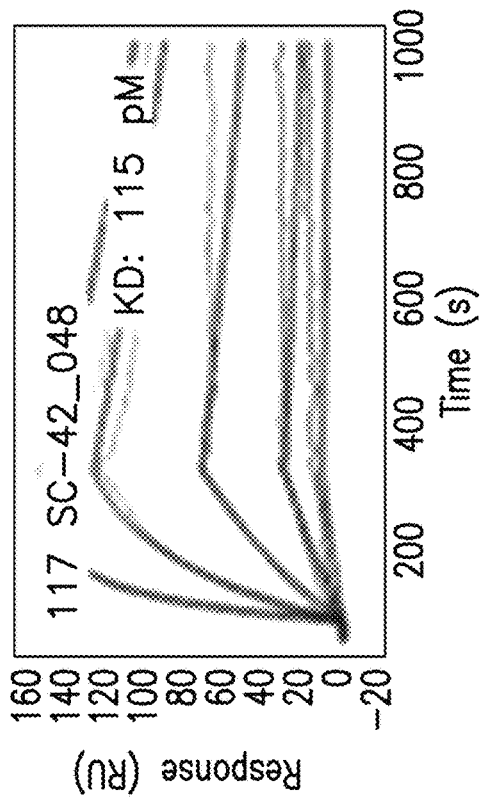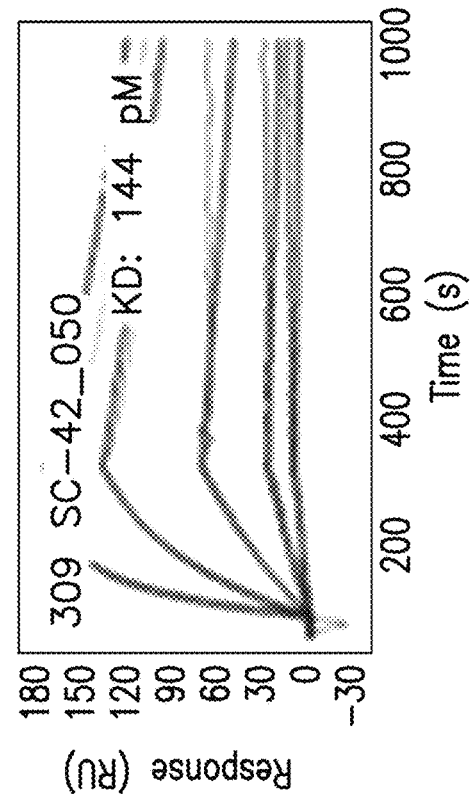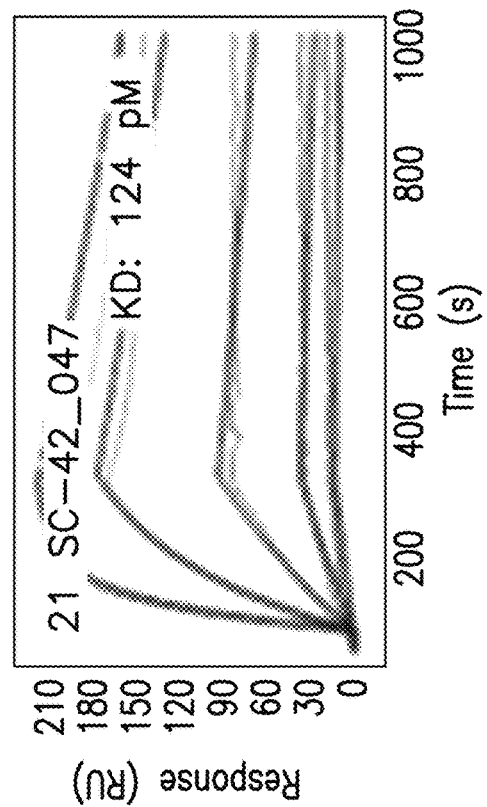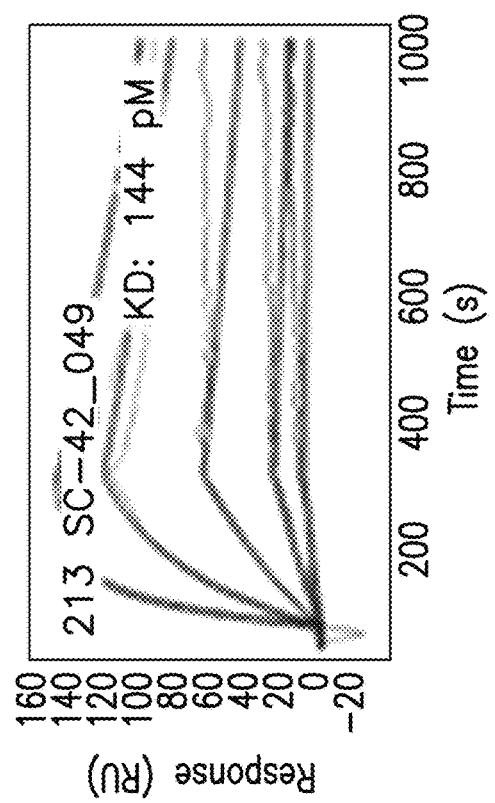
FIG. 10 Cont'd

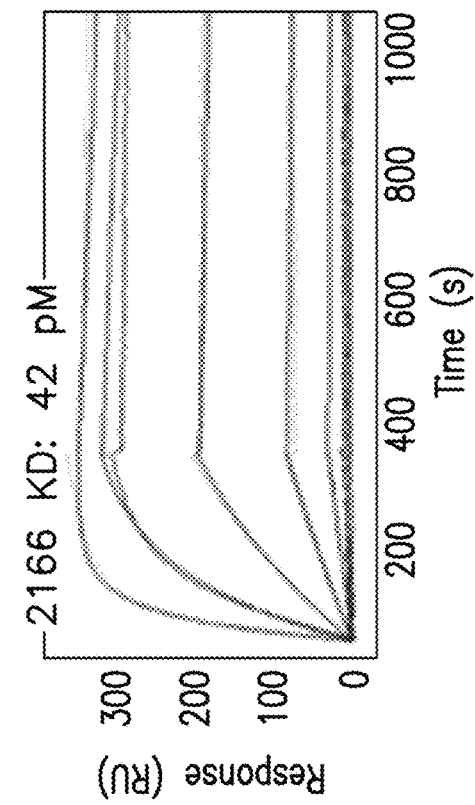
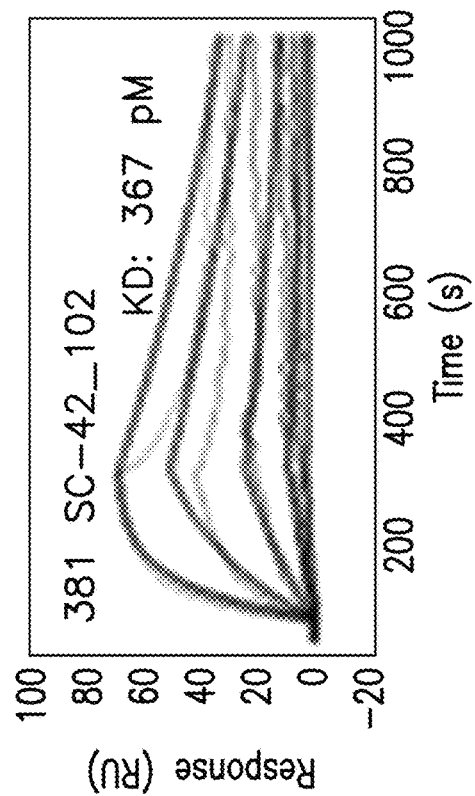
FIG. 10 Cont'd

Heavy Chain Variable Domain
DVQLVESGGDLVKPGGSLRLTCVASGLSLTSSSMSWVRQAPGKGLQWVSTIYSNGGTYYTDSVKGRFTISKDN
AENTLYLQMNNLKTEDTATYYCASIYYYDADYLHWYFDFWGQGALVTVSS Light Chain Variable Domain
EIQMTQSPTSLSASVGDRVTITCRASEGISNNLSWYQQTPGKAPKLLIYATSNLHSGVPSRFSGSGSGTDFTL
TISSLQPEDFATYYCQQGYKWPLTFGGGTKLEIT

FIG. 15

| SEQ ID NO: | Clone Name | FR1H | CDR1H | FR2H | CDR2H |
|---|---|---|---|---|---|
| 141 | 101 | DVQLVESGGGDLVKPGGSLRLTCVAS | GLSLTSSS | MSWVRQAPGKGLQWVST | IYSNGGT |
| 184 | AHF17591 | DVQLVESGGGDLVKPGGSLRLTCVAS | GLSLTSSS | MVWVRQAPGKGLQWVST | IYSNRGT |
| 185 | AHF17593 | DVQLVESGGGDLVKPGGSLRLTCVAS | GLSLTSSS | MVWVRQAPGKGLQWVST | IYSNRGT |
| 186 | AHF17594 | DVQLVESGGGDLVKPGGSLRLTCVAS | GLSLTSSS | MVWVRQAPGKGLQWVST | IYSNGGT |
| 187 | AHF17601 | DVQLVESGGGDLVKPGGSLRLTCVAS | GLSLTSSS | MVWVRQAPGKGLQWVST | IYSNRGT |
| 188 | AHF17602 | DVQLVESGGGDLVKPGGSLRLTCVAS | GLSLTSSS | MVWVRQAPGKGLQWVST | IYSNGGT |
| 189 | AHF17603 | DVQLVESGGGDLVKPGGSLRLTCVAS | GLSLTSSS | MVWVRQAPGKGLQWVST | IYSNRGT |
| 190 | AHF17605 | DVQLVESGGGDLVKPGGSLRLTCVAS | GLSLTSSS | MVWVRQAPGKGLQWVST | IYSNGGT |
| 198 | SC-184_76 | DVQLVESGGGDLVKPGGSLRLTCVAS | GLSLTSDS | MSWVRQAPGKGLQWVST | LWSNRGT |
| 200 | SC-184_102 | DVQLVESGGGDLVKPGGSLRLTCVAS | GLSLTSNS | MSWVRQAPGKGLQWVST | IWSNRGT |
| 202 | SC-184_110 | DVQLVESGGGDLVKPGGSLRLTCVAS | GLSLTSAS | MSWVRQAPGKGLQWVST | IYSNGGT |
| 204 | SC-184_76-Arg | DVQLVESGGGDLVKPGGSLRLTCVAS | GLSLTSDS | MSWVRQAPGKGLQWVST | LWSNRGT |
| 205 | SC-184_102-Arg | DVQLVESGGGDLVKPGGSLRLTCVAS | GLSLTSNS | MSWVRQAPGKGLQWVST | IWSNRGT |
| 206 | SC-184_110-Arg | DVQLVESGGGDLVKPGGSLRLTCVAS | GLSLTSAS | MSWVRQAPGKGLQWVST | IYSNRGT |

FIG. 17A

| SEQ ID NO: | Clone Name | FR3H | CDR3H | FR4 |
|---|---|---|---|---|
| 141 | 101 | YYTDSVKGRFTISKDNAENTLYLQMNNLKTEDTATYYC | ASIYYYDADYLHWYFDF | WGQGALVTVSS |
| 184 | AHF17591 | YYTDSVKGRFTISKDNAENTLYLQMNNLKTEDTATYYC | ASIYYYDADYLHWYFDF | WGQGALVTVSS |
| 185 | AHF17593 | YYTDSVKGRFTISKDNAENTLYLQMNNLKTEDTATYYC | AQIYYYDADYLHWYFDF | WGQGALVTVSS |
| 186 | AHF17594 | YYTDSVKGRFTISKDNAENTLYLQMNNLKTEDTATYYC | ASIYYYDADYLHWYFDF | WGQGALVTVSS |
| 187 | AHF17601 | YYTDSVKGRFTISKDNAENTLYLQMNNLKTEDTATYYC | AQIYYYDADYLHWYFDE | WGQGALVTVSS |
| 188 | AHF17602 | YYTDSVKGRFTISKDNAENTLYLQMNNLKTEDTATYYC | ASIYYYDADYLHWYFDE | WGQGALVTVSS |
| 189 | AHF17603 | YYTDSVKGRFTISKDNAENTLYLQMNNLKTEDTATYYC | ASIYYYDADYLHWYFDE | WGQGALVTVSS |
| 190 | AHF17605 | YYTDSVKGRFTISKDNAENTLYLQMNNLKTEDTATYYC | AQIYYYDADYLHWYFDE | WGQGALVTVSS |
| 198 | SC-184_76 | YYTDSVKGRFTISKDNAENTLYLQMNNLKTEDTATYYC | ASIYYYEADYLHWYFDF | WGQGALVTVSS |
| 200 | SC-184_102 | YYTDSVKGRFTISKDNAENTLYLQMNNLKTEDTATYYC | ASIYYYEAEYLHWYFDF | WGQGALVTVSS |
| 202 | SC-184_110 | YYTDSVKGRFTISKDNAENTLYLQMNNLKTEDTATYYC | ASIYYYEADYLHWYFDF | WGQGALVTVSS |
| 204 | SC-184_76-Arg | YYTDSVKGRFTISKDNAENTLYLQMNNLKTEDTATYYC | ASIYYEADYLHWYFDF | WGQGALVTVSS |
| 205 | SC-184_102-Arg | YYTDSVKGRFTISKDNAENTLYLQMNNLKTEDTATYYC | ASIYYYEAEYLHWYFDF | WGQGALVTVSS |
| 206 | SC-184_110-Arg | YYTDSVKGRFTISKDNAENTLYLQMNNLKTEDTATYYC | ASIYYYEAEYLHWYFDF | WGQGALVTVSS |

FIG. 17A Cont'd

| SEQ ID NO: | Clone Name | FR1L | CDR1L | FR2L | CDR2L |
|---|---|---|---|---|---|
| 142 | 101 | EIQMTQSPTSLSASVGDRVTITCRAS | EGISNN | LSWYQQTPGKAPKLLIY | ATS |
| 191 | AHF17591 | EIQMTQSPTSLSASVGDRVTITCRAS | EGIANN | LSWYQQTPGKAPKLLIY | ATS |
| 192 | AHF17592 | EIQMTQSPTSLSASVGDRVTITCRAS | EGISNN | LSWYQQTPGKAPKLLIY | ATS |
| 193 | AHF17593 | EIQMTQSPTSLSASVGDRVTITCRAS | EGIANN | LSWYQQTPGKAPKLLIY | ATS |
| 194 | AHF17595 | EIQMTQSPTSLSASVGDRVTITCRAS | EGIQNN | LSWYQQTPGKAPKLLIY | ATS |
| 195 | AHF17597 | EIQMTQSPTSLSASVGDRVTITCRAS | EGIQNN | LSWYQQTPGKAPKLLIY | ATS |
| 196 | AHF17602 | EIQMTQSPTSLSASVGDRVTITCRAS | EGIANN | LSWYQQTPGKAPKLLIY | ATS |
| 197 | AHF17607 | EIQMTQSPTSLSASVGDRVTITCRAS | EGISNN | LSWYQQTPGKAPKLLIY | ATS |
| 199 | SC-184_76 | EIQMTQSPTSLSASVGDRVTITCRAS | EGIANN | LSWYQQTPGKAPKLLIY | ATS |
| 201 | SC-184_102 | EIQMTQSPTSLSASVGDRVTITCRAS | KGISNN | LSWYQQTPGKAPKLLIY | AQS |
| 203 | SC-184_110 | EIQMTQSPTSLSASVGDRVTITCRAS | EGISKN | LSWYQQTPGKAPKLLIY | ATD |
| 199 | SC-184_76-Arg | EIQMTQSPTSLSASVGDRVTITCRAS | EGIANN | LSWYQQTPGKAPKLLIY | ATS |
| 201 | SC-184_102-Arg | EIQMTQSPTSLSASVGDRVTITCRAS | KGISNN | LSWYQQTPGKAPKLLIY | AQS |
| 203 | SC-184_110-Arg | EIQMTQSPTSLSASVGDRVTITCRAS | EGISKN | LSWYQQTPGKAPKLLIY | ATD |

FIG. 17B

| SEQ ID NO: | Clone Name | FR3L | CDR3L | FR4L |
|---|---|---|---|---|
| 142 | 101 | NLHSGVPSRFSGSGSGTDFTLTISSLQPEDFATYYC | QQGYKWPLT | FGGGTKLEIT |
| 191 | AHF17591 | ILHSGVPSRFSGSGSGTDFTLTISSLQPEDFATYYC | QQGYKWPLT | FGGGTKLEIT |
| 192 | AHF17592 | VLHSGVPSRFSGSGSGTDFTLTISSLQPEDFATYYC | QQGYKWPLT | FGGGTKLEIT |
| 193 | AHF17593 | VLHSGVPSRFSGSGSGTDFTLTISSLQPEDFATYYC | QQGYKWPLT | FGGGTKLEIT |
| 194 | AHF17595 | NLHSGVPSRFSGSGSGTDFTLTISSLQPEDFATYYC | QQGYKWPLT | FGGGTKLEIT |
| 195 | AHF17597 | ILHSGVPSRFSGSGSGTDFTLTISSLQPEDFATYYC | QQGYKWPLT | FGGGTKLEIT |
| 196 | AHF17602 | NLHSGVPSRFSGSGSGTDFTLTISSLQPEDFATYYC | QQGYKWPLT | FGGGTKLEIT |
| 197 | AHF17607 | ILHSGVPSRFSGSGSGTDFTLTISSLQPEDFATYYC | QQGYKWPLT | FGGGTKLEIT |
| 199 | SC-184_76 | NLHSGVPSRFSGSGSGTDFTLTISSLQPEDFATYYC | QQGFKWPLT | FGGGTKLEIT |
| 201 | SC-184_102 | NLHSGVPSRFSGSGSGTDFTLTISSLQPEDFATYYC | QQGWKWPLT | FGGGTKLEIT |
| 203 | SC-184_110 | NLHSGVPSRFSGSGSGTDFTLTISSLQPEDFATYYC | QQGFKWPLT | FGGGTKLEIT |
| 199 | SC-184_76-Arg | NLHSGVPSRFSGSGSGTDFTLTISSLQPEDFATYYC | QQGYKWPLT | FGGGTKLEIT |
| 201 | SC-184_102-Arg | NLHSGVPSRFSGSGSGTDFTLTISSLQPEDFATYYC | QQGYKWPLT | FGGGTKLEIT |
| 203 | SC-184_110-Arg | NLHSGVPSRFSGSGSGTDFTLTISSLQPEDFATYYC | QQGWKWPLT | FGGGTKLEIT |

FIG. 17B Cont'd

ANTI-NGF ANTIBODIES AND USES THEREOF

RELATED APPLICATIONS AND INCORPORATION BY REFERENCE

This application is a continuation of U.S. application Ser. No. 18/348,173 filed Jul. 6, 2023, issued as U.S. Pat. No. 12,110,322, which is a continuation of International Application No. PCT/US2022/080428 filed Nov. 23, 2022 and published as International Publication No. WO 2023/097275 on Jun. 1, 2023 and which claims priority to U.S. provisional application Ser. No. 63/282,590, filed Nov. 23, 2021, and U.S. provisional application Ser. No. 63/383,173, filed Nov. 10, 2022, each incorporated by reference herein in its entirety.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which is being submitted in .XML format via Patent Center and is hereby incorporated by reference in its entirety. Said .XML copy, created on Nov. 22, 2022, and amended on Oct. 9, 2024 and on Nov. 12, 2024, is named Replacement Y9432-03003.xml and is 515,773 517,501 bytes in size.

FIELD OF THE INVENTION

The invention provides novel anti-NGF proteins, antibodies, and NGF-binding fragments thereof which inhibit association of NGF with TrkA and/or p75 and are suitable for administration to a canine or feline subject. The invention also provides novel compositions and methods of treating pain or eliciting an analgesic effect in a canine or feline subject, comprising administering an effective amount of an anti-NGF protein, antibody or fragment thereof. The methods and compositions are used to treat or prevent NGF-related disorders.

BACKGROUND OF THE INVENTION

Nerve growth factor (NGF) is critical in the development and maintenance of peripheral sympathetic and embryonic sensory neurons and of basal forebrain cholinergic neurons. NGF upregulates expression of neuropeptides in sensory neurons and its activity is mediated through two different membrane-bound receptors. Several neurotropins (NTs) including NGF bind to a low-affinity receptor identified as p75. NGF selectively binds to, and displays a high affinity for the high affinity neurotrophin receptor TrkA.

Upon neurotrophin binding, TrkA undergoes autophosphorylation as well as phosphorylates members of the MAPK pathway. The presence of this kinase leads to cell differentiation and may play a role in specifying sensory neuron subtypes.

NGF plays a role in several diseases and disorders, including but not limited to pain associated with a broad range of diseases and disorders, such as pain associated with cancers, neuropathic pain, and neurogenic pain. Due to the involvement of NGF in a wide range of pain-related diseases and disorders, there is a need in the art for compositions and methods useful for preventing or treating diseases and disorders associated with NGF, particularly those associated with pain, including in canines, felines and other animals. Particularly preferred anti-NGF compositions are those having minimal or minimized adverse reactions, such as inflammation when administered to a subject.

Citation or identification of any document in this application is not an admission that such document is available as prior art to the present invention.

SUMMARY OF THE INVENTION

The invention provides novel anti-NGF binding protein for treatment or amelioration of NGF-related disorders, particularly adapted for use in dogs and cats but not limited thereby.

The invention provides binding proteins that specifically binds to NGF. In certain embodiments, the binding proteins are optimized for administration to a canine. In certain embodiments, the binding proteins are optimized for administration to a feline.

In an aspect, the invention provides binding proteins designed or adapted to bind NGF in the manner of an antibody, i.e. by one or more complementarity determining regions (CDRs). CDRs can be identified by the international ImMunoGeneTics (IMGT) information system. Accordingly, in certain embodiments, the anti-NGF binding protein comprises an antigen binding portion that comprises one or more of (a) a heavy chain complementarity determining region 1 (VH-CDR1) comprising the amino acid sequence $X_1X_2X_3X_4X_5X_6X_7X_8$ (SEQ ID NO:146), wherein $X_1$ comprises A, G, or N, $X_2$ comprises L or M, $X_3$ comprises A, D, E, or S, $X_4$ comprises F, I, L, M, or V, $X_5$ comprises N or T, $X_6$ comprises E, S, or T, $X_7$ comprises G, H, N, S, or Q, and $X_8$ comprises A or S; (b) a heavy chain complementarity determining region 2 (VH-CDR2) comprising the amino acid sequence $X_1X_2SNX_5GT$ (SEQ ID NO:215), wherein $X_1$ comprises I or L, $X_2$ comprises W or Y, and $X_5$ comprises G or R; (c) a heavy chain complementarity determining region 3 (VH-CDR3) comprising the amino acid sequence $AX_2IX_4X_5YX_7X_8X_9YLX_{12}X_{13}YX_{15}X_{16}X_{17}$ (SEQ ID NO:148), wherein $X_2$ comprises D, E, K, N, Q, S, or T, $X_4$ comprises W or Y, $X_5$ comprises F, H, W, or Y, $X_7$ comprises D or E, $X_8$ comprises A or S, $X_9$ comprises D or Y, $X_{12}$ comprises H or Y, $X_{13}$ comprises F or W, $X_{15}$ comprises F, I, L, W, or Y, $X_{16}$ comprises D or Q, and $X_{17}$ comprises F, I, L, M, W, or Y; (d) a light chain complementarity determining region 1 (VL-CDR1) comprising the amino acid sequence $X_1X_2IX_4X_5X_6$ (SEQ ID NO: 149), wherein $X_1$ comprises D, E, or K, $X_2$ comprises A, G, or N, $X_4$ comprises G, N, Q or S, $X_5$ comprises N or S, $X_6$ comprises A, G, N, S or T; (e) a light chain complementarity determining region 2 (VL-CDR2) comprising the amino acid sequence $AX_2X_3$ (SEQ ID NO:150), wherein $X_2$ comprises A, S, or T, $X_3$ comprises A, D, E, N, Q, S, or T; and (f) a light chain complementarity determining region 3 (VL-CDR3) comprising the amino acid sequence $QX_2GX_4X_5X_6PX_8T$ (SEQ ID NO:151), wherein $X_2$ comprises H or Q, $X_4$ comprises F, H, W, or Y, $X_5$ comprises K or Q, $X_6$ comprises F or W, and $X_8$ comprises L or M.

In certain embodiments, the anti-NGF binding protein comprises an antigen binding portion which comprises (a) a heavy chain complementarity determining region 1 (VH-CDR1) comprising the amino acid sequence $X_1X_2X_3X_4X_5X_6X_7X_8$ (SEQ ID NO:152), wherein $X_1$ comprises A or G, $X_2$ comprises L or M, $X_3$ comprises E or S, $X_4$ comprises F or L, $X_5$ comprises N or T, $X_6$ comprises E, S, or T, $X_7$ comprises H, N, or S, and $X_8$ comprises A or S; (b) a heavy chain complementarity determining region 2 (VH-CDR2) comprising the amino acid sequence $X_1WSNX_5GT$ (SEQ ID NO:381), wherein $X_1$ comprises I or L, $X_5$ comprises G or R; (c) a heavy chain complementarity determining region 3 (VH-CDR3) comprising the amino acid sequence $AX_2IYYYX_7ADYLHX_{13}$ $YX_{15}DX_{17}$ (SEQ ID NO:382), wherein $X_2$ comprises N, Q, S, or T, $X_7$ comprises D or E, $X_{13}$ comprises F or W, $X_{15}$ comprises F, I, L, W, or Y, and $X_{17}$ comprises F, I, L, or M; (d) a light chain complementarity determining region 1 (VL-CDR1) comprising the amino acid sequence $X_1GIX_4X_5X_6$ (SEQ ID NO: 155), wherein $X_1$ comprises D or E, $X_4$ comprises N, Q, or S, $X_5$ comprises N or S, $X_6$ comprises G, N, S or T; (e) a light chain complementarity determining region 2 (VL-CDR2) comprising the amino acid sequence $ATX_3$ (SEQ ID NO:156), wherein $X_3$ comprises D, E, N, Q, or S; and (f) a light chain complementarity determining region 3 (VL-CDR3) comprising the amino acid sequence $QQGX_4X_5X_6PX_8T$ (SEQ ID NO:383), wherein $X_4$ comprises F, H, W, or Y, $X_5$ comprises K or Q, $X_6$ comprises F or W, and $X_8$ comprises L or M.

In certain embodiments, the anti-NGF binding protein comprises a heavy chain CDR1 set forth in FIG. 1. In certain embodiments, the anti-NGF binding protein comprises a heavy chain CDR2 set forth in FIG. 1. In certain embodiments, the anti-NGF binding protein comprises a heavy chain CDR3 set forth in FIG. 1. In certain embodiments, the anti-NGF binding protein comprises a light chain CDR1 set forth in FIG. 2. In certain embodiments, the anti-NGF binding protein comprises a light chain CDR2 set forth in FIG. 2. In certain embodiments, the anti-NGF binding protein comprises a light chain CDR3 set forth in FIG. 2.

In certain embodiments, the anti-NGF binding protein comprises heavy chain CDRs of a heavy chain variable domain set forth in FIG. 1.

In certain embodiments, the anti-NGF binding protein comprises a heavy chain variable domain ($V_H$) at least 80%, at least 85%, at least 90%, at least 93%, at least 95%, at least 98%, or identical to a $V_H$ domain set forth in FIG. 1.

In certain embodiments, the anti-NGF binding protein comprises light chain CDRs of a light chain variable domain set forth in FIG. 2.

In certain embodiments, the anti-NGF binding protein comprises a light chain variable domain ($V_L$) at least 80%, at least 85%, at least 90%, at least 93%, at least 95%, at least 98%, or identical to a light chain variable domain set forth in FIG. 2.

In certain embodiments, the anti-NGF binding protein comprises $V_H$ and $V_L$ from an Fv set forth in FIG. 1 and FIG. 2.

In FIG. 1 and FIG. 2, CDRs are identified by the IMGT system. Alternatively, CDRs can be identified according to the Kabat numbering system or the Chothia numbering system. Accordingly, in certain embodiments, the anti-NGF binding protein comprises an antigen binding portion that comprises one or more of VH-CDR1, VH-CDR2, VH-CDR3, VL-CDR1, VL-CDR2, and VL-CDR3 according to the Kabat or Chothia numbering system as further set forth herein.

In paring of $V_H$ and $V_L$ domains described herein, any $V_H$ domain can be used with any $V_L$ domain. Similarly, the CDRs of any $V_H$ domain can be used with the CDRs of any $V_L$ domain. In an embodiment, an antibody of the invention comprises $V_H$ CDRs of SEQ ID NO:137 (SC-42_101) and $V_L$ CDRs of SEQ ID NO:3 (SC-42_006). In an embodiment which comprises the amino acid arginine at position 55 in VH-CDR2, an antibody of the invention comprises $V_H$ CDRs of SEQ ID NO:207 (SC-42_101R) and $V_L$ CDRs of SEQ ID NO:3 (SC-42_006).

In certain embodiments, an antibody of the invention incorporate $V_H$ and $V_L$ domains that were selected together, i.e. identified in the same clone. $V_H$ and $V_L$ clones selected together are identified as having the same clone name in FIG. 1 as in FIG. 2. Similarly, the CDRs of a $V_H$ domain identified by clone name in FIG. 1 can be used with the CDRs of the $V_L$ domain identified by the same clone name in FIG. 2. The paired $V_H$ and $V_L$ domains can further comprise conservative substitutions, such as but not limited to conservative variation observed at specific positions of $V_H$ CDRs and $V_L$ CDRs, positions adjacent to $V_H$ and $V_L$ CDRs and positions of the $V_H$ domains and $V_L$ domains set forth herein.

In certain embodiments, an antibody of the invention comprises $V_H$ and $V_L$ CDRs of clone 2166, SC-42_006, SC-42_007, SC-42_008, SC-42_010, SC-42_011, SC-42_023, SC-42_032, SC-42_045, SC-42_047, SC-42_048, SC-42_052, SC-42_070, SC-42_073, SC-42_077, SC-42_082, SC-42_090, or SC-42_101 (FIG. 1 and FIG. 2).

In certain embodiments, an antibody of the invention comprises $V_H$ and $V_L$ domains at least 80%, at least 85%, at least 90%, at least 93%, at least 95%, at least 98%, or identical to those of clone 2166, SC-42_006, SC-42_007, SC-42_008, SC-42_010, SC-42_011, SC-42_023, SC-42_032, SC-42_045, SC-42_047, SC-42_048, SC-42_052, SC-42_070, SC-42_073, SC-42_077, SC-42_082, SC-42_090, or SC-42_101.

In certain embodiments, a felinized anti-NGF binding protein comprises (a) a heavy chain complementarity determining region 1 (VH-CDR1) comprising the amino acid sequence $X_1LX_3X_4X_5X_6X_7X_8MX_{10}$ (SEQ ID NO:208), wherein $X_1$ comprises A, G, L, N, or Q, $X_3$ comprises A, D, E, G, H, I, M, S, T, or Y, $X_4$ comprises L, M, or V, $X_5$ comprises A, M, N, R, S, T, or V, $X_6$ comprises A, E, G, H, K, R, S, or T, $X_7$ comprises A, D, H, I, N, Q, S, T, or Y, $X_8$ comprises A or S, and $X_{10}$ comprises S or V; (b) a heavy chain complementarity determining region 2 (VH-CDR2) comprising the amino acid sequence $X_1X_2X_3X_4X_5GTX_8YX_{10}DX_{12}VX_{14}$ (SEQ ID NO:209), wherein $X_1$ comprises I or L, $X_2$ comprises W or Y; $X_3$ comprises A, P, or S, $X_4$ comprises D, E, N, Q, R, or S, $X_5$ comprises G, R, or Y, $X_8$ comprises D or Y, $X_{10}$ comprises D, E, H, S, or T, $X_{12}$ comprises D or S, and $X_{14}$ comprises D, E, or K; (c) a heavy chain complementarity determining region 3 (VH-CDR3) comprising the amino acid sequence $X_1X_2X_3X_4X_5X_6X_7X_8X_9X_{10}LX_{12}X_{13}X_{14}FX_{16}X_{17}$ (SEQ ID NO:210), wherein $X_1$ comprises A, D, E, K, N, Q, S, or T, $X_2$ comprises A, D, E, G, H, I, K, L, M, N, P, Q, R, S, T, V, or Y, $X_3$ comprises I, L, W, or Y, $X_4$ comprises F, T, W, or Y, $X_5$ comprises F, H, or Y, $X_6$ comprises H or Y, $X_7$ comprises D or E, $X_8$ comprises A, S, or V, $X_9$ comprises D, E, H, K, N, Q, or Y, $X_{10}$ comprises F, H, or Y, $X_{12}$ comprises H or Y, $X_{13}$ comprises F or W, $X_{14}$ comprises D, I, L, W, or Y, $X_{16}$ comprises D or Q, and $X_{17}$ comprises E, F, H, I, L, M, N, P, W, or Y; (d) a light chain complementarity determining region 1 (VL-CDR1) comprising the amino acid sequence $X_1ASX_4X_5X_6X_7X_8XLX_{11}$ (SEQ ID NO:211), wherein $X_1$ comprises F or R, $X_4$ comprises E, K, or N, $X_5$ comprises A, or G, $X_6$ comprises I, L, or V, $X_7$ comprises A, D, G, L, P, Q, S, V, or Y, $X_8$ comprises K, Q, N, S, or Y, $X_9$ comprises A, D, E, F, G, H, K, L, N, Q, R, S or T, and $X_{11}$ comprises A, G, or S; (e) a light chain complementarity determining region 2 (VL-CDR2) comprising the amino acid sequence $AX_2X_3X_4X_5X_6X_7$ (SEQ ID NO:212), wherein $X_2$ comprises A, D, L, Q, S, T, V, or Y, $X_3$ comprises D, E, K, N, Q, or S, $X_4$ comprises H, I, K, L, M, N, or V; $X_8$ comprises H or L, $X_6$ comprises H, I, L, or M, and $X_7$ comprises D, E, N, S, or T; and (f) a light chain complementarity determining region 3 (VL-CDR3) comprising the amino acid sequence $QQX_3X_4X_5X_6X_7X_8T$ (SEQ ID NO:213), wherein $X_3$ comprises G or Y, $X_4$ comprises D, F, G, H, K, L, R, S, T, V, W, or Y, $X_5$ comprises E, K, Q, R, or S, $X_6$ comprises I, F, T, or W, $X_7$ comprises E or P, and $X_8$ comprises L, M, or W.

In certain embodiments, the anti-NGF binding protein comprises a heavy chain CDR1 set forth in FIG. 17A. In certain embodiments, the anti-NGF binding protein comprises a heavy chain CDR2 set forth in FIG. 17A. In certain embodiments, the anti-NGF binding protein comprises a heavy chain CDR3 set forth in FIG. 17A. In certain embodiments, the anti-NGF binding protein comprises a light chain CDR1 set forth in FIG. 17B. In certain embodiments, the anti-NGF binding protein comprises a light chain CDR2 set forth in FIG. 17B. In certain embodiments, the anti-NGF binding protein comprises a light chain CDR3 set forth in FIG. 17B.

In certain embodiments, the anti-NGF binding protein comprises heavy chain CDRs of a heavy chain variable domain set forth in FIG. 17A.

In certain embodiments, the anti-NGF binding protein comprises a heavy chain variable domain ($V_H$) at least 80%, at least 85%, at least 90%, at least 93%, at least 95%, at least 98%, or identical to a $V_H$ domain set forth in FIG. 17A.

In certain embodiments, the anti-NGF binding protein comprises light chain CDRs of a light chain variable domain set forth in FIG. 17B.

In certain embodiments, the anti-NGF binding protein comprises a light chain variable domain ($V_L$) at least 80%, at least 85%, at least 90%, at least 93%, at least 95%, at least 98%, or identical to a light chain variable domain set forth in FIG. 17B.

The $V_H$ CDRs set forth in FIG. 17A can be used with the $V_L$ CDRs set forth in FIG. 17B in any combination. The $V_H$ domains set forth in FIG. 17A can be used with the $V_L$ domains set forth in FIG. 17B in any combination. Table 11 and Table 12 provide exemplary combinations.

In certain embodiments, the anti-NGF binding protein comprises $V_H$ and $V_L$ from an Fv whose $V_H$ is set forth in FIG. 17A and $V_L$ set forth in FIG. 17B.

In FIG. 17, CDRs are identified by the IMGT system. Alternatively, CDRs can be identified according to the Kabat numbering system or the Chothia numbering system. Accordingly, in certain embodiments, the anti-NGF binding protein comprises an antigen binding portion that comprises one or more of VH-CDR1, VH-CDR2, VH-CDR3, VL-CDR1, VL-CDR2, and VL-CDR3 according to the Kabat or Chothia or IMGT numbering system as further set forth herein.

In certain embodiments, the anti-NGF binding protein comprises CDRs as described above, with the further limitation that each of the CDRs comprises no more than one or two amino acid differences as compared to specific antibody heavy and light chains described herein, for example, CDRs of the heavy and light chains whose sequences are set forth in FIG. 1, FIG. 2, FIG. 17A, and FIG. 17B, which are of similar sequence and bind to NGF with high affinity. In certain embodiments, the anti-NGF binding protein comprise CDRs of a $V_H$ and $V_L$ disclosed herein.

In certain embodiments, the anti-NGF protein comprises no more than one or two amino acid differences per CDR as compared to specificcaninized antibody heavy and light chains described herein, for example, CDRs of the heavy and light chains set forth in FIG. 1 and FIG. 2 which are of similar sequence and bind to NGF with the highest affinity. Such antibodies include antibodies which comprise no more than two (2) changes per VH-CDR, i.e. 2, 1 or no changes per CDR as compared to SEQ ID NO: 1, SEQ ID NO:3, SEQ ID NO:5, SEQ ID NO:7, SEQ ID NO:9, SEQ ID NO:11, SEQ ID NO: 13, SEQ ID NO:31, SEQ ID NO:55, SEQ ID NO:61, SEQ ID NO:69, SEQ ID NO:77, SEQ ID NO: 103, SEQ ID NO: 109, SEQ ID NO: 113, SEQ ID NO: 121, SEQ ID NO: 133, SEQ ID NO: 137, or SEQ ID NO: 141 and no more than two (2) changes per VL-CDR, i.e. 2, 1 or no changes per CDR as compared to SEQ ID NO:2, SEQ ID NO:4, SEQ ID NO:6, SEQ ID NO: 8, SEQ ID NO: 10, SEQ ID NO: 12, SEQ ID NO: 14, SEQ ID NO:32, SEQ ID NO:56, SEQ ID NO: 62, SEQ ID NO:70, SEQ ID NO:78, SEQ ID NO: 104, SEQ ID NO:110, SEQ ID NO:114, SEQ ID NO:122, SEQ ID NO:134, SEQ ID NO:138, or SEQ ID NO:142.

In certain embodiments, the anti-NGF protein comprises no more than one or two amino acid differences per CDR as compared to specificfelinized antibody heavy and light chains described herein, for example, CDRs of the heavy and light chains set forth in FIG. 17A and FIG. 17B which are of similar sequence and bind to NGF with the highest affinity. Such antibodies include antibodies which comprise no more than two (2) changes per VH-CDR, i.e. 2, 1 or no changes per CDR as compared to SEQ ID NO:141, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 198, SEQ ID NO:200, SEQ ID NO:202, SEQ ID NO:204, SEQ ID NO:205, or SEQ ID NO:206 and no more than two (2) changes per VL-CDR, i.e. 2, 1 or no changes per CDR as compared to SEQ ID NO: 142, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 199, SEQ ID NO:201, or SEQ ID NO:203.

Mutations and combinations thereof, within CDRs and among CDRs, including allowed mutations and advantageous mutations are evident from the sequence datasets shown in FIG. 1 and FIG. 2, and FIG. 17A and FIG. 17B. For example, by comparing sequence variability or lack thereof at various CDR positions in the datasets as a whole, one can observe CDR locations at which particular amino acids are beneficial for binding. Similarly, by comparing sequence variability among $V_H$ chains or among $V_L$ chains from the same germline, one can observe CDR locations at which amino acid changes may be cooperative. The dataset further allows on to identify CDR positions that are likely to be critical for binding.

Certain antibodies disclosed herein were selected from canine or feline libraries on the basis of CDR sequence similarity to other anti-NGF antibodies. Accordingly both CDRs and FRs are canine-like or feline-like and there will be observed some degree of uniformity among antibody heavy and light chains resulting from the same germline sequence. It is understood that such uniformity is not a necessity but a consequence of the caninization and felinization methods employed. It is also understood that a substantial degree of sequence variability is allowed or can be introduced into FRs that is not detrimental to antigen binding. In certain embodiments, the anti-NGF protein comprises a heavy chain framework (FR1H+FR2H+FR3HH) at least 75%, or at least 80%, or at least 85%, or at least 90%, or at least 93%, or at least 95% identical to a heavy chain set forth in FIG. 1. In certain embodiments, the anti-NGF protein comprises a heavy chain framework (FR1H+FR2H+FR3H+FR4H) at least 75%, or at least 80%, or at least 85%, or at least 90%, or at least 93%, or at least 95% identical to SEQ ID NO:1, SEQ ID NO:3, SEQ ID NO:5, SEQ ID NO:7, SEQ ID NO:9, SEQ ID NO: 11, SEQ ID NO: 13, SEQ ID NO:31, SEQ ID NO:55, SEQ ID NO:61, SEQ ID NO:69, SEQ ID NO: 77, SEQ ID NO: 103, SEQ ID NO: 109, SEQ ID NO: 113, SEQ ID NO: 121, SEQ ID NO: 133, SEQ ID NO: 137, or SEQ ID NO: 141.

In certain embodiments, the anti-NGF protein comprises a heavy chain framework (FR1H+FR2H+FR3HH) at least 75%, or at least 80%, or at least 85%, or at least 90%, or at least 93%, or at least 95% identical to a heavy chain set forth in FIG. 17A. In certain embodiments, the anti-NGF protein comprises a heavy chain framework (FR1H+FR2H+FR3H+FR4H) at least 75%, or at least 80%, or at least 85%, or at least 90%, or at least 93%, or at least 95% identical to SEQ ID NO: 141, SEQ ID NO:184, SEQ ID NO: 185, SEQ ID NO: 186, SEQ ID NO:187, SEQ ID NO: 188, SEQ ID NO: 189, SEQ ID NO: 190, SEQ ID NO: 198, SEQ ID NO:200, SEQ ID NO:202, SEQ ID NO:204, SEQ ID NO:205, or SEQ ID NO:206.

In certain embodiments, the anti-NGF protein comprises a light chain framework (FR1+FR2+FR3+FR4) at least 75%, or at least 80%, or at least 85%, or at least 90%, or at least 93%, or at least 95% identical to a light chain set forth in FIG. 2. In certain embodiments, the anti-NGF protein comprises a light chain framework (FR1L+FR2L+FR3L+FR4L) at least 75%, or at least 80%, or at least 85%, or at least 90%, or at least 93%, or at least 95% identical to SEQ ID NO: 2, SEQ ID NO:4, SEQ ID NO:6, SEQ ID NO:8, SEQ ID NO: 10, SEQ ID NO: 12, SEQ ID NO: 14, SEQ ID NO:32, SEQ ID NO:56, SEQ ID NO:62, SEQ ID NO: 70, SEQ ID NO: 78, SEQ ID NO: 104, SEQ ID NO:110, SEQ ID NO:114, SEQ ID NO: 122, SEQ ID NO: 134, SEQ ID NO: 138, or SEQ ID NO: 142.

In certain embodiments, the anti-NGF protein comprises a light chain framework (FR1+FR2+FR3+FR4) at least 75%, or at least 80%, or at least 85%, or at least 90%, or at least 93%, or at least 95% identical to a light chain set forth in FIG. 17B. In certain embodiments, the anti-NGF protein comprises a light chain framework (FR1L+FR2L+FR3L+FR4L) at least 75%, or at least 80%, or at least 85%, or at least 90%, or at least 93%, or at least 95% identical to SEQ ID NO: 142, SEQ ID NO:191, SEQ ID NO:192, SEQ ID NO:193, SEQ ID NO:194, SEQ ID NO: 195, SEQ ID NO:196, SEQ ID NO: 197, SEQ ID NO: 199, SEQ ID NO:201, or SEQ ID NO: 203.

For a discussion of naturally conserved networks of amino acids that support antibody V(H) and V(L) function, see, e.g., Wang et al., Conserved amino acid networks involved in antibody variable domain interactions. Proteins 2009 July; 76 (1): 99-114. Wang identifies conserved and non-conserved amino acid pairs in antibody $V_H$ and $V_L$ domains, the $V_H$-$C_H$1 variable-constant domain interface, as well as in camelid $V_{HH}$ domains, which have evolved to lack interactions with $V_L$ and $C_H$1. In certain embodiments, mutations are introduces to optimize biopharmaceutical and biophysical properties, such as efficacy, safety, and manufacturability, and stability of therapeutic antibodies. See, e.g. Douillard et al., Optimization of an Antibody Light Chain Framework Enhances Expression, Biophysical Properties and Pharmacokinetics. Antibodies (Basel) 2019 Sep. 6; 8 (3): 46.

In certain embodiments, the invention provides an isolated, recombinant NGF-binding protein wherein the variable heavy chain comprises an amino acid sequence having at least about 85%, 86%, 87%, 88%, 89%, 90%, 91%, 92%, 93%, 94%, 95%, 96%, 97%, 98%, 99%, or 100% identity to a heavy chain variable domain set forth in FIG. 1. In certain embodiments, the heavy chain variable domain comprises an amino acid sequence having at least about 85%, 86%, 87%, 88%, 89%, 90%, 91%, 92%, 93%, 94%, 95%, 96%, 97%, 98%, 99%, or 100% identity to SEQ ID NO: 13, SEQ ID NO:31, SEQ ID NO:55, SEQ ID NO:61, SEQ ID NO:69, SEQ ID NO:77, SEQ ID NO: 103, SEQ ID NO:109, SEQ ID NO:113, SEQ ID NO: 121, SEQ ID NO: 133, or SEQ ID NO: 137.

In certain embodiments, the invention provides an isolated, recombinant NGF-binding protein wherein the variable light chain comprises an amino acid sequence having at least about 85%, 86%, 87%, 88%, 89%, 90%, 91%, 92%, 93%, 94%, 95%, 96%, 97%, 98%, 99%, or 100% identity to a light chain variable domain set forth in FIG. 2. In certain embodiments, the light chain variable domain comprises an amino acid sequence having at least about 85%, 86%, 87%, 88%, 89%, 90%, 91%, 92%, 93%, 94%, 95%, 96%, 97%, 98%, 99%, or 100% identity to SEQ ID NO: 14, SEQ ID NO:32, SEQ ID NO:56, SEQ ID NO:62, SEQ ID NO: 70, SEQ ID NO: 78, SEQ ID NO: 104, SEQ ID NO:110, SEQ ID NO:114, SEQ ID NO:122, SEQ ID NO:134, or SEQ ID NO: 138.

In another aspect, the invention provides a nucleic acid that encodes an anti-NGF protein of the invention. In another aspect, the invention provides a vector which comprises a nucleic acid that encodes an anti-NGF protein of the invention.

In another aspect, the invention provides a cell which comprises a nucleic acid of vector or the invention or expresses an anti-NGF protein of the invention.

The anti-NGF binding proteins, such as but not limited to antibodies and antibody fragments, specifically bind NGF which inhibits the association of NGF with TrkA and further inhibits the association of NGF with p75. In certain embodiments, these novel anti-NGF binding proteins are suitable for detecting NGF, and for treating pain and pain-associated disorders and conditions, e.g., pain associated with inflammation, cancer, specific pain and inflammation associated disorders, especially pain-associated disorders associated with elevated NGF levels, and may be administered alone or in association with another active agent, such as but not limited to another biologic, an NSAID or opioid analgesic.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

FIG. 1A-1B shows an alignment of amino acid sequences of exemplary $V_H$ heavy chain variable domains of the invention. The aligned variable domains are divided in two parts: part (A) shows the N-terminal end and part (B) shows the C-terminal end. For alignment purposes frameworks (FRs) and complementarity determining regions (CDRs) are identified according to the IMGT system. CDRs and FRs may be mapped according to other systems disclosed herein.

FIG. 2A-2B shows an alignment of amino acid sequences of exemplary $V_\kappa$ light chain variable domains of the invention. The aligned variable domains are divided in two parts: part (A) shows the N-terminal end and part (B) shows the C-terminal end. For alignment purposes frameworks (FRs) and complementarity determining regions (CDRs) are identified according to the IMGT system. CDRs and FRs may be mapped according to other systems disclosed herein. Each of the $V_L$ domains is suitable for paring with any one of the $V_H$ domains depicted in FIG. 1. Together with FIG. 1, the Clone Names indicate a selection of exemplary $V_H$-$V_L$ pairs that were tested for binding.

FIG. 4 depicts heavy chain (SEQ ID NO:144) and light chain (SEQ ID NO:145) amino acid sequences of chimeric 2166 antibody. Two residue changes ("AA," underlined and in bold font) were made in the Fc to eliminate effector activity. The changes are analogous to the "LALA" mutation described for human IgG1 Fc. The chimeric 2166 antibody comprises a canine IgGB heavy chain constant region and kappa light chain constant region.

FIG. 15 depicts the VI (SEQ ID NO:141) and $V_L$ (SEQ ID NO:142) amino acid sequence of a felinized anti-NGF antibody.

FIG. 17A-17B shows alignments of amino acid sequences of exemplary felinized and affinity matured felinized $V_H$ heavy chain variable domains (A) and $V_\kappa$ light chain variable domains (B) of the invention. For alignment purposes frameworks (FRs) and complementarity determining regions (CDRs) are identified according to the IMGT system. CDRs and FRs may be mapped according to other systems disclosed herein. See, e.g., Table 4 and CDRs defined using a combination of Kabat and IMGT methodology.

Figure 3:
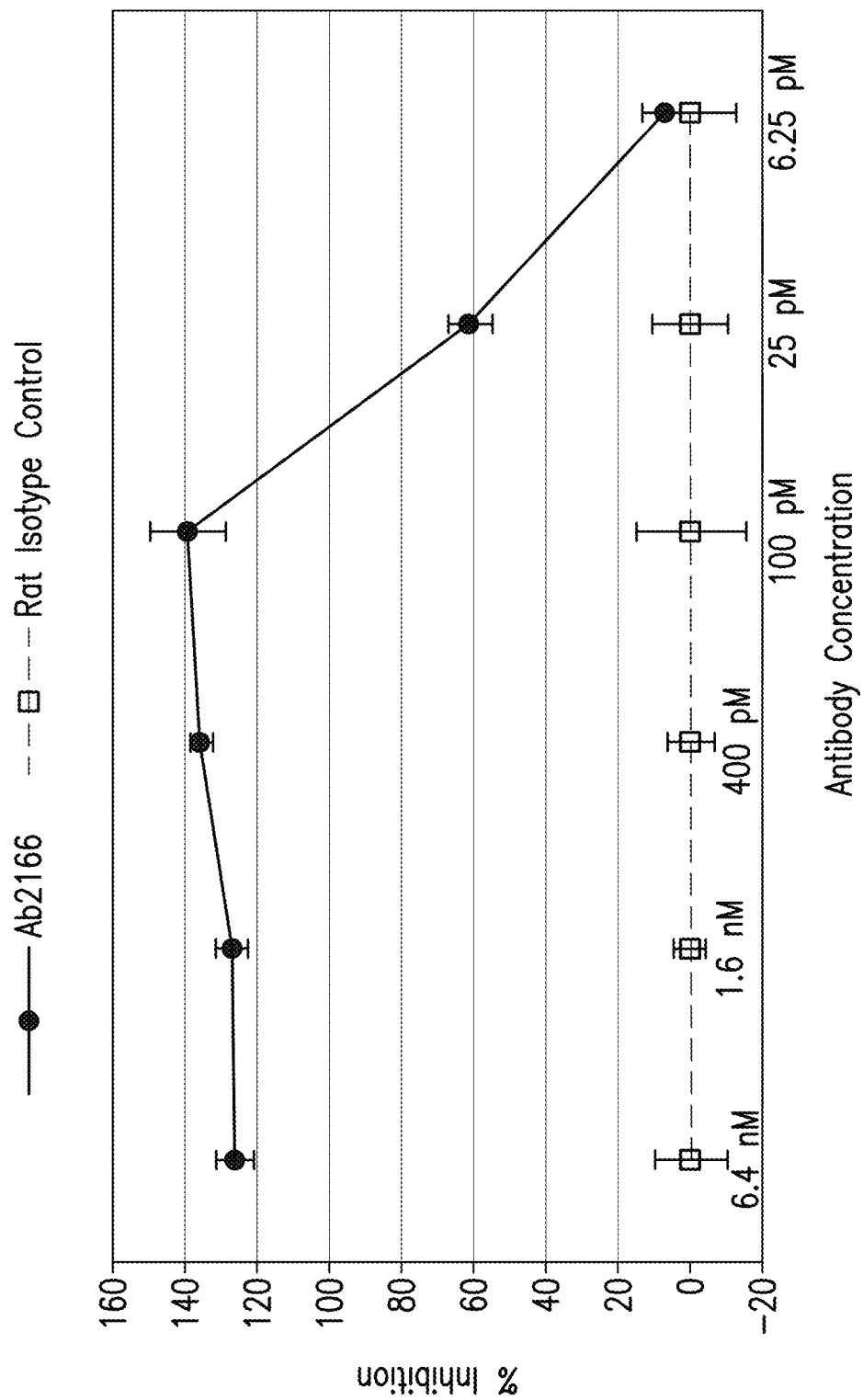
FIG. 3 depicts inhibition of proliferation of TF-1 cells.

The following detailed description, given by way of example, but not intended to limit the invention solely to the specific embodiments described, may best be understood in conjunction with the accompanying drawings.

DETAILED DESCRIPTION OF THE INVENTION

According to certain exemplary embodiments of the present invention, the NGF binding protein is an anti-NGF antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-NGF antibody (or antigen-binding portion thereof) may be identical to the canine germline sequences, or may be naturally or artificially modified. An amino acid consensus sequence may be defined based on a side-by-side analysis of two or more CDRs.

Antibody residues that have a substantial impact on affinity and specificity of binding to target antigen are primarily located in CDRs. Kabat et al. compiled and aligned immunoglobulin heavy and light chain sequences and were the first to propose a standardized numbering scheme for the variable regions of immunoglobulins identifying conserved and hypervariable regions and residues. (Kabat E A et al., 1979, Sequences of Immunoglobulin Chains: Tabulation and Analysis of Amino Acid Sequences of Precursors, V-regions, C-regions, J-Chain and BP-Microglobulins, Department of Health, Education, and Welfare, Public Health Service, National Institutes of Health). While the Kabat system is a widely adopted standard for numbering antibody residues, the hypervariable regions defined by Kabat do not exactly match with the structural aspects of antigen-binding loops. Chothia and Lesk developed a structure-based numbering scheme by aligning crystal structures of antibody variable regions and classified CDR loops in a small number of "canonical" classes (Chothia C, et al., 1987, Canonical structures for the hypervariable regions of immunoglobulins. J. Mol. Biol. 196:901-17. doi: 10.1016/0022-2836 (87) 90412-8). An advantage of the Chothia numbering scheme is that topologically aligned residues from different antibodies are localized at the same position number and the Chothia CDR definition corresponds in most antibody sequences to the structural antigen-binding loop. Lefranc introduced a new system based on germ-line sequences intended to standardize numbering for all proteins of the immunoglobulin superfamily, including T cell receptor chains. (Giudicelli V et al., 1997, IMGT, the international ImMunoGeneTics database. Nucleic Acids Res. 25:206-11), which was then extended to entire variable domains (Lefranc M-P et al., 2003, IMGT unique numbering for immunoglobulin and T cell receptor variable domains and Ig superfamily V-like domains. Dev Comp Immunol. 27:55-77. doi: 10.1016/S0145-305X (02) 00039-3). Additional numbering systems have been proposed to align unconventional frameworks (Abhinandan K R et al., 2008, Analysis and improvements to Kabat and structurally correct numbering of antibody variable domains. Mol Immunol. 45:3832-9. doi: 10.1016/j.molimm.2008.05.022) and to subdivide variable chain sequences into multiple fragments including structurally invariant "cores" (Gelfand et al., 1998, Algorithmic determination of core positions in the $V_L$ and $V_H$ domains of immunoglobulin molecules. J Comput Biol. (1998) 5:467-77). In certain embodiments of the invention, CDR residues are identified according to such a standard system as set forth above. In certain embodiments, antibodies of the invention are identified by all or a subset of Kabat CDR residues of the antibody sequences set forth herein. In certain embodiments, antibodies of the invention are identified by all or a subset of Chothia CDR residues of the antibody sequences set forth herein. In certain embodiments, antibodies of the invention are identified by all or a subset of IMGT CDR residues of the antibody sequences set forth herein. In certain embodiments, antibodies of the invention are identified by CDR residues defined by two or more systems, comprising e.g., but not limited to, all or a subset of residues of VH-CDR1 according to Kabat, all or a subset of residues of VH-CDR2 according to Chothia, all or a subset of residues of VH-CDR3 according to Kabat, all or a subset of residues of VL-CDR1 according to Kabat, all or a subset of residues of VL-CDR2 according to IMGT, and all or a subset of residues of VL-CDR3 according to Chothia. Table 1 shows the correspondence of FRs and CDRs for the antibody sequences shown in FIGS. 1 and 2.

TABLE 1

| | CDR amino acids | | | | | | |
|---|---|---|---|---|---|---|---|
| | VH-FR1 | VH-CDR1 | VH-FR2 | VH-CDR2 | VH-FR3 | VH-CDR3 | VH-FR4 |
| IMGT | 1-25 | 26-33 | 34-50 | 51-57 | 58-95 | 96-112 | 113-123 |
| Kabat | 1-30 | 31-35 | 36-49 | 50-65 | 66-97 | 98-112 | 113-123 |
| Chothia | 1-25 | 26-32 | 33-51 | 52-56 | 57-97 | 98-112 | 113-123 |
| | VL-FR1 | VL-CDR1 | VL-FR2 | VL-CDR2 | VL-FR3 | VL-CDR3 | VL-FR4 |
| IMGT | 1-26 | 27-32 | 33-49 | 50-52 | 53-88 | 89-97 | 98-107 |
| Kabat | 1-23 | 24-34 | 35-49 | 50-56 | 57-88 | 89-97 | 98-107 |
| Chothia | 1-25 | 26-32 | 33-49 | 50-52 | 53-90 | 91-96 | 97-107 |

Identifying CDRs according to Kabat, in certain embodiments, a caninized anti-NGF binding protein comprises an antigen binding portion that comprises one or more of (a) a heavy chain complementarity determining region 1 (VH-CDR1) comprising the amino acid sequence $X_1X_2X_3X_4X_5$ (SEQ ID NO:158), wherein $X_1$ comprises E, S, or T, $X_2$ comprises G, H, N, S, or Q, $X_3$ comprises A or S; and $X_4$ comprises I, M, or V, and $X_5$ comprises D or S; (b) a heavy chain complementarity determining region 2 (VH-CDR2) comprising the amino acid sequence $X_1X_2X_3SNX_6GTX_9YX_{11}X_{12}AX_{14}X_{15}X_{16}$ (SEQ ID NO:159), wherein $X_1$ comprises V, L, M, or T, $X_2$ comprises I or L, $X_3$ comprises W or Y, $X_6$ comprises G or R, $X_9$ comprises D, Q, or S, $X_{11}$ comprises A, N, or T, $X_{12}$ comprises D or S, $X_{14}$ comprises I or V, $X_{15}$ comprises E or K, and $X_{16}$ comprises G or S; (c) a heavy chain complementarity determining region 3 (VH-CDR3) comprising the amino acid sequence $IX_2X_3YX_5X_6X_7YLX_{10}X_{11}YX_{13}X_{14}X_{15}$, (SEQ ID NO:160), wherein $X_2$ comprises W or Y, $X_3$ comprises F, H, W, or Y, $X_5$ comprises D or E, $X_6$ comprises A or S, $X_7$ comprises D or Y, $X_{10}$ comprises H or Y, $X_{11}$ comprises F or W, $X_{13}$ comprises F, I, L, W, or Y, $X_{14}$ comprises D or Q, and $X_{15}$ comprises F, I, L, M, W, or Y; (d) a light chain complementarity determining region 1 (VL-CDR1) comprising the amino acid sequence $X_1ASX_4X_5IX_7X_8X_9X_{10}X_{11}$ (SEQ ID NO:161), wherein $X_1$ comprises L or R, $X_4$ comprises D, E, or K, $X_5$ comprises A, G, or N, $X_7$ comprises G, N, Q or S, $X_8$ comprises N or S, $X_9$ comprises A, G, N, S or T, $X_{10}$ comprises L or V, and $X_{11}$ comprises A or N; (e) a light chain complementarity determining region 2 (VL-CDR2) comprising the amino acid sequence $AX_2X_3X_4X_5X_6X_7$ (SEQ ID NO: 162), wherein $X_2$ comprises A, S, or T, $X_3$ comprises A, D, E, N, Q, S, or T, $X_4$ comprises A, E, K, L, N, Q, S, or T, $X_5$ comprises L, M, or N, $X_6$ comprises A or Q, and $X_7$ comprises G, D, R, S, or T; and (f) a light chain complementarity determining region 3 (VL-CDR3) comprising the amino acid sequence $X_1X_2GX_4X_5X_6PX_8T$ (SEQ ID NO:163), wherein $X_1$ comprises H, M Q, or R, $X_2$ comprises H, N, Q, or S, $X_4$ comprises F, H, W, or Y, $X_5$ comprises K or Q, $X_6$ comprises F or W, and $X_8$ comprises L or M.

In certain embodiments, the caninized anti-NGF binding protein comprises an antigen binding portion which comprises (a) a heavy chain complementarity determining region 1 ($V_H$-CDR1) comprising the amino acid sequence $X_1X_2X_3X_4S$ (SEQ ID NO:164), wherein $X_1$ comprises E, S or T, $X_2$ comprises H or N, $X_3$ comprises A or S, $X_4$ comprises I or M, (b) a heavy chain complementarity determining region 2 (VH-CDR2) comprising the amino acid sequence $TIWSNX_6GTDYX_{11}X_{12}AVKG$ (SEQ ID NO:165), wherein $X_6$ comprises G or R, $X_{11}$ comprises A or T, and $X_{12}$ comprises D or S; (c) a heavy chain complementarity determining region 3 (VH-CDR3) comprising the amino acid sequence $IYYYX_5ADYLX_{10}X_{11}YX_{13}DX_{15}$ (SEQ ID NO:166), wherein $X_5$ comprises D or E, $X_{10}$ comprises H or Y, $X_{11}$ comprises F or W, $X_{13}$ comprises F, I, L, W, or Y, and $X_{15}$ comprises F, I, L, or M; (d) a light chain complementarity determining region 1 (VL-CDR1) comprising the amino acid sequence $RASEGIX_7X_8X_9X_{10}A$ (SEQ ID NO:167), wherein $X_7$ comprises N, Q, or S, $X_8$ comprises N or S, $X_9$ comprises G, N, S or T, and $X_{10}$ comprises L or V; (e) a light chain complementarity determining region 2 (VL-CDR2) comprising the amino acid sequence $ATX_3X_4LX_6X_7$ (SEQ ID NO: 168), wherein $X_3$ comprises A, D, E, N, Q, or S, $X_4$ comprises E, K, Q, or S, $X_6$ comprises A or Q, and $X_7$ comprises R or T; and (f) a light chain complementarity determining region 3 (VL-CDR3) comprising the amino acid sequence $QQGX_4X_5X_6PLT$ (SEQ ID NO:169), wherein $X_4$ comprises F, H, W, or Y, $X_5$ comprises K or Q, and $X_6$ comprises F or W.

Identifying CDRs according to Chothia, in certain embodiments, the anti-NGF binding protein comprises an antigen binding portion that comprises one or more of (a) a heavy chain complementarity determining region 1 (VH-CDR1) comprising the amino acid sequence $X_1X_2X_3X_4X_5X_6X_7$ (SEQ ID NO:170), wherein $X_1$ comprises A, G, or N, $X_2$ comprises L or M, $X_3$ comprises A, D, E, or S, $X_4$ comprises F, I, L, M, or V, $X_5$ comprises N or T, $X_6$ comprises E, S, or T, and $X_7$ comprises G, H, N, S, or Q; (b) a heavy chain complementarity determining region 2 (VH-CDR2) comprising the amino acid sequence $X_1SNX_4G$ (SEQ ID NO:171), wherein $X_1$ comprises W or Y and $X_4$ comprises G or R; (c) a heavy chain complementarity determining region 3 (VH-CDR3) comprising the amino acid sequence $IX_2X_3YX_5X_6X_7YLX_{10}X_{11}YX_{13}X_{14}X_{15}$, (SEQ ID NO: 172), wherein $X_2$ comprises W or Y, $X_3$ comprises F, H, W, or Y, $X_5$ comprises D or E, $X_6$ comprises A or S, $X_7$ comprises D or Y, $X_{10}$ comprises H or Y, $X_{11}$ comprises F or W, $X_{13}$ comprises F, I, L, W, or Y, $X_{14}$ comprises D or Q, and $X_{15}$ comprises F, I, L, M, W, or Y; (d) a light chain complementarity determining region 1 (VL-CDR1) comprising the amino acid sequence $SX_2X_3IX_5X_6X_7$ (SEQ ID NO: 173), wherein $X_2$ comprises D, E, or K, $X_3$ comprises A, G, or N, $X_5$ comprises G, N, Q or S, $X_6$ comprises N or S, $X_7$ comprises A, G, N, S or T; (e) a light chain complementarity determining region 2 (VL-CDR2) comprising the amino acid sequence $AX_2X_3$ (SEQ ID NO:174), wherein $X_2$ comprises A, S, or T, and $X_3$ comprises A, D, E, N, Q, S, or T; and (f) a light chain complementarity determining region 3 (VL-CDR3) comprising the amino acid sequence $GX_2X_3X_4PX_6$ (SEQ ID NO: 175), wherein $X_2$ comprises F, H, W, or Y, $X_3$ comprises K or Q, $X_4$ comprises F or W, and $X_6$ comprises L or M.

In certain embodiments, the anti-NGF binding protein comprises an antigen binding portion which comprises (a) a heavy chain complementarity determining region 1 (VH-CDR1) comprising the amino acid sequence $X_1X_2X_3X_4X_5X_6X_7$ (SEQ ID NO:176), wherein $X_1$ comprises A, G, or N, $X_2$ comprises L or M, $X_3$ comprises A, E, or S, $X_4$ comprises F or L, $X_5$ comprises N or T, $X_6$ comprises E, S or T, and $X_7$ comprises H, N, or S; (b) a heavy chain complementarity determining region 2 (VH-CDR2) comprising the amino acid sequence $WSNX_4G$ (SEQ ID NO: 177), wherein $X_4$ comprises G or R; (c) a heavy chain complementarity determining region 3 (VH-CDR3) comprising the amino acid sequence $IYX_3YX_5ADYLX_{10}X_{11}YX_{13}DX_{15}$ (SEQ ID NO: 178), wherein $X_3$ comprises For Y, $X_5$ comprises D or E, $X_{10}$ comprises H or Y, $X_{11}$ comprises F or W, $X_{13}$ comprises F, I, L, W, or Y, and $X_{15}$ comprises F, I, L, M, W, or Y; (d) a light chain complementarity determining region 1 (VL-CDR1) comprising the amino acid sequence $SX_2GIXX6X_7$ (SEQ ID NO:179), wherein $X_2$ comprises D or E, $X_5$ comprises N, Q, or S, $X_6$ comprises N or S, and $X_7$ comprises G, N, S, or T; (e) a light chain complementarity determining region 2 (VL-CDR2) comprising the amino acid sequence $ATX_3$ (SEQ ID NO:180), wherein $X_3$ comprises D, E, N, Q, or S; and (f) a light chain complementarity determining region 3 (VL-CDR3) comprising the amino acid sequence $GX_2X_3X_4PX_6$ (SEQ ID NO:181), wherein $X_2$ comprises F, H, W, or Y, $X_3$ comprises K or Q, $X_4$ comprises F or W, and $X_6$ comprises L or M.

In another aspect, the invention provides a binding protein suitable for use in a mammal, for example, but without limitation, a feline. In certain embodiments, a felinized anti-NGF binding protein comprises (a) a heavy chain complementarity determining region 1 ($V_H$-CDR1) comprising the amino acid sequence $X_1LX_3X_4X_5X_6X_7X_8MX_{10}$ (SEQ ID NO:208), wherein $X_1$ comprises A, G, L, N, or Q, $X_3$ comprises A, D, E, G, H, I, M, S, T, or Y, $X_4$ comprises L, M, or V, $X_5$ comprises A, M, N, R, S, T, or V, $X_6$ comprises A, E, G, H, K, R, S, or T, $X_7$ comprises A, D, H, I, N, Q, S, T, or Y, $X_8$ comprises A or S, and $X_{10}$ comprises S or V; (b) a heavy chain complementarity determining region 2 (VH-CDR2) comprising the amino acid sequence $X_1X_2X_3X_4X_5GTX_8YX_{10}DX_{12}VX_{14}$ (SEQ ID NO:209), wherein $X_1$ comprises I or L, $X_2$ comprises W or Y; $X_3$ comprises A, P, or S, $X_4$ comprises D, E, N, Q, R, or S, $X_5$ comprises G, R, or Y, $X_8$ comprises D or Y, $X_{10}$ comprises D, E, H, S, or T, $X_{12}$ comprises D or S, and $X_{14}$ comprises D, E, or K; (c) a heavy chain complementarity determining region 3 (VH-CDR3) comprising the amino acid sequence $X_1X_2X_3X_4X_5X_6X_7X_8X_9X_{10}LX_{12}X_{13}X_{14}FX_{16}X_{17}$ (SEQ ID NO:210), wherein $X_1$ comprises A, D, E, K, N, Q, S, or T, $X_2$ comprises A, D, E, G, H, I, K, L, M, N, P, Q, R, S, T, V, or Y, $X_3$ comprises I, L, W, or Y, $X_4$ comprises F, T, W, or Y, $X_5$ comprises F, H, or Y, $X_6$ comprises H or Y, $X_7$ comprises D or E, $X_8$ comprises A, S, or V, $X_9$ comprises D, E, H, K, N, Q, or Y, $X_{10}$ comprises F, H, or Y, $X_{12}$ comprises H or Y, $X_{13}$ comprises F or W, $X_{14}$ comprises D, I, L, W, or Y, $X_{16}$ comprises D or Q, and $X_{17}$ comprises E, F, H, I, L, M, N, P, W, or Y; (d) a light chain complementarity determining region 1 (VL-CDR1) comprising the amino acid sequence $X_1ASX_4X_5X_6X_7X_8X_9LX_{11}$ (SEQ ID NO:211), wherein $X_1$ comprises F or R, $X_4$ comprises E, K, or N, $X_5$ comprises A, or G, $X_6$ comprises I, L, or V, $X_7$ comprises A, D, G, L, P, Q, S, V, or Y, $X_8$ comprises K, Q, N, S, or Y, $X_9$ comprises A, D, E, F, G, H, K, L, N, Q, R, S or T, and $X_{11}$ comprises A, G, or S; (e) a light chain complementarity determining region 2 (VL-CDR2) comprising the amino acid sequence $AX_2X_3X_4X_5X_6X_7$ (SEQ ID NO:212), wherein $X_2$ comprises A, D, L, Q, S, T, V, or Y, $X_3$ comprises D, E, K, N, Q, or S, $X_4$ comprises H, I, K, L, M, N, or V; $X_8$ comprises H or L, $X_6$ comprises H, I, L, or M, and $X_7$ comprises D, E, N, S, or T; (f) a light chain complementarity determining region 3 (VL-CDR3) comprising the amino acid sequence $QQX_3X_4X_5X_6X_7X_8T$ (SEQ ID NO:213), wherein $X_3$ comprises G or Y, $X_4$ comprises D, F, G, H, K, L, R, S, T, V, W, or Y, $X_5$ comprises E, K, Q, R, or S, $X_6$ comprises I, F, T, or W, $X_7$ comprises E or P, and $X_8$ comprises L, M, or W.

In certain embodiments, the anti-NGF binding protein comprises: VH-CDR1 comprises $GLSLTSX_7SMX_{10}$ (SEQ ID NO:214), wherein $X_7$ comprises A, D, or N, and $X_{10}$ comprises S or V; VH-CDR2 comprises $X_1X_2SNX_5GT$ (SEQ ID NO:215), wherein $X_1$ comprises I or L, $X_2$ comprises W or Y, and $X_5$ comprises G or R; VH-CDR3 comprises $ASIYYYX_7AX_9YLHWYFDX_{12}$ (SEQ ID NO:216), wherein $X_7$ comprises D or E, $X_9$ comprises D or E, and $X_{12}$ comprises E or F; VL-CDR1 comprises $RASX_4GIX_7X_8NLS$ (SEQ ID NO:217), wherein $X_4$ comprises E or K, $X_7$ comprises A, Q, or S, $X_8$ comprises K or N; VL-CDR2 comprises $AX_2X_3X_4LHS$ (SEQ ID NO:218), wherein $X_2$ comprises Q or T, $X_3$ comprises D or S, and $X_4$ comprises I, N, or V; and VL-CDR3 comprises $QQGX_4KWPLT$ (SEQ ID NO:219), wherein $X_4$ comprises F, W, or Y.

In certain embodiments, the anti-NGF binding protein comprises one or more (i.e. one, two, three, four, five, or all six) CDRs of felinized antibody 101 disclosed herein. In certain embodiments, the anti-NGF binding protein comprises one or more (i.e. one, two, three, four, five, or all six) CDRs of an affinity matured felinized antibody disclosed herein. In certain embodiments, the anti-NGF binding protein comprises CDRs from one or more of felinized antibody 101 and the affinity matured variants provided herein. In certain embodiments, the anti-NGF binding protein comprises $V_H$ CDRs set forth in FIG. 17A. In certain embodiments, the anti-NGF binding protein comprises $V_L$ CDRs set forth in FIG. 17B. In certain embodiments, the anti-NGF binding protein comprises $V_H$ CDRs of an antibody $V_H$ domain set forth in FIG. 17A. In certain embodiments, the anti-NGF binding protein comprise $V_L$ CDRs of an antibody $V_L$ domain set forth in FIG. 17B.

According to the invention, in certain embodiments, the anti-NGF binding protein comprises an amino acid of a felinized antibody 101 variant disclosed herein, for example one or more of the following amino acids in $V_H$: S28H, T30N, T30R, S31H, S35V, Y52W, S53P, G55R, G55Y, Y58D, T60D, T60E, T60H, T60S, S62D, K64D, K64E, S97H, S97K, S97M, S97N, S97Q, S97T, Y99F, Y101H, D104E, D104K, D104N, D104Q, F112E, D112H, F112N, F112P; and/or in $V_L$: R24F, S30A, S30L, S30P, S30Q, S30V, S30Y, N31Q, S34A, S34G, N53H, N53I, N53K, N53L, N53M, N53V, L54H, H55I, H55L, H55M, S56D, S56E, S56N, S56T. In certain embodiments, the anti-NGF binding protein does not comprise one or more of the above-listed amino aicd variants. For example, in certain embodiments, the anti-NGF binding protein does not comprise arginine of G55R. Amino acid positions are indicated by residue and number in felinized antibody 101, e.g., S28H indicates H at the position corresponding to S28 of $V_H$ or antibody 101. The aforementioned positions include CDR and framework amino acid residues.

In certain embodiments, the anti-NGF binding protein comprises one or more of the following amino acids in $V_H$: S35V, G55R, S97Q, F112E; and/or in $V_L$: S30A, S30Q, N53I, N53V. Pairings of VH and VL chains comprising the above-described sequence variation demonstrate compatibility of the VH and VL mutations and interchangeability of the VH and VL domains comprising the mutations.

In certain embodiments, the binding proteins comprise a canine or a caninized antibody. In certain embodiments, the binding proteins comprise a feline or a felinized antibody.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parentheses indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10:6487-6500 (1982); Wang A. et al., Science 224:1431-1433; Dalbadie-McFarland G. et al., Proc. Natl. Acad. Sci. U.S.A. 79:6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

The invention provides recombinant antibodies designed or modified to minimize antigenicity in canines and felines. In certain embodiments, the antibodies are further modified to remove T cell epitopes.

As used herein, the term "canine" includes all domestic dogs, *Canis lupus familiaris* or *Canis familiaris*, unless otherwise indicated.

As used herein, the term "feline" refers to any member of the Felidae family. Domestic cats, pure-bred and/or mongrel companion cats, and wild or feral cats are all felines.

As used herein the term "canine framework" or "feline framework" refers to the amino acid sequence of the heavy chain and light chain of a canine antibody other than the hypervariable region residues defined herein as CDR residues. With regard to a caninized antibody, in certain embodiments, canine CDRs are identified in canine antibody heavy and light chains variable domain sequences that closely match CDRs of NGF-binding antibodies originating in other species. In certain embodiments, native canine CDRs are replaced with the corresponding foreign CDRs (e.g., those from a rat or a mouse antibody) in both chains. With regard to a felinized antibody, in certain embodiments, feline CDRs are identified in feline antibody heavy and light chains variable domain sequences that closely match CDRs of NGF-binding antibodies originating in other species. In certain embodiments, native feline CDRs are replaced with the corresponding foreign CDRs (e.g., those from a rat or a mouse antibody) in both chains. Optionally the heavy and/or light chains of the caninized or felinized antibody may contain some mutated or foreign non-CDR residues, e.g., framework amino acid residues that vary among germline antibody sequence or mutations that preserve the conformation of the foreign CDRs within the antibody.

Five major isotypes (IgA, IgG, IgM, IgD, IgE) and two forms of light chain (K and 2) are present in dogs. In the dog, there are four subtypes for IgG, which are IgGA, IgGB, IgGC, and IgGD (Bergeron etal al, 2014, *Comparative functional characterization of canine IgG subclasses*. Veterinary Immunology and Immunopathology. 157:31-41). For the cat, there are three subtypes of IgG which are IgG1a, IgG1b, and IgG2 (Streitzel et al. 2014, *In vitro functional characterization of feline IgGs*. Vet Immunol Immunopathol 158, 214-223, doi.org/10.1016/j.vetimm.2014.01.012).

The invention provides caninized and felinized antibodies engineered to modulate one or more effector functions or circulation half-life. Hinge and constant domains of an antibody engage host receptors or complement protein to mediate effector functions and regulate antibody circulation. In certain embodiments, one or more effector functions is enhanced. In certain embodiments, one or more effector funtions is reduced or eliminated. In certain embodiments, antibodies of the invention comprise modifications to modulate antibody-dependent cytotoxicity (ADCC) and/or complement-dependent cytotoxicity (CDC). A non-limiting example involves engineering of canine IgGB constant region residues Met242 and/or Leu243 to reduce effector function. In certain embodiments, a IgGB constant region of the invention comprises M242A and L243A substitution. In certain embodiments, the second constant domain ($C_H2$) and/or the third constant domain ($C_H3$) comprises mutations and combinations of mutations from wild-type designed to modulate binding to FcRn (neonatal Fc) receptor. In canine constant regions, such mutations include, without limitation substitutions of Ala426, for example A426Y or A426H, substitutions of Thr286, for example T286L or T286Y, substitutions of Tyr436, for example Y436H, and combinations of such mutations including but not limited to A426Y+T286L, A426Y +Y436H, A426H+T286L, and A426H+T286Y. In certain embodiments a chimeric or caninized antibody of the invention comprises a substitution at amino acid Asn434, such as but not limited to N434H. In feline constant regions, such mutations include, without limitation substitutions of Ser428, including but not limited to S428Y or S428L, substitutions of Gln311, including but not limited to Q311V, substitutions of Leu309, including but not limited to L309V, substitutions of Thr286, including but not limited to T286E, substitutions of Glu380, including but not limited to E380T, and combinations of such mutations including but not limited to S428Y+Q311V, S428Y +L309V, S428Y+Q311V+T286E, S428Y+Q311V+E380T, and S428Y+L309V+E380T. In certain embodiments a chimeric or felinized antibody of the invention comprises a substitution at amino acid Ser428 and/or Ser434 including but not limited to S428L and/or S434H.

The term "antibody," as used herein, includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. As used herein, the term "specifically binds" or "binds specifically" means that an NGF binding protein of the invention reacts or associates more frequently, more rapidly, with greater duration and/or with greater affinity with NGF than it does with alternative antigens. For example, NGF binding protein binds to NGF with materially greater affinity (e.g., at least 2-fold or 5-fold or 10-fold or 20-fold or 50-fold or 100-fold or 500-fold or 1000-fold or 10,000-fold or greater) than it does to other proteins or peptides. In certain embodiments, the NGF-binding proteins binds to NGF with an equilibrium dissociation constant $K_D$ for the epitope or target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. It will be recognized by one of skill that an antibody that specifically binds to a target (e.g., NGF) from one species may also specifically bind to orthologs of NGF.

Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

In certain embodiments, an antigen-binding fragment of an antibody comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$, (x) $V_L$-$C_H3$; (xi) $V_L$-$C_H1$-$C_H2$; (xii) $V_L$-$CH_1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "diabody (Db)" refers to a bivalent antibody fragment constructed by gene fusion (for example, P. Holliger et al., Proc. Natl. Acad. Sci. USA 90:6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The term "Kd" as used herein, refers to the dissociation constant of an antibody-antigen interaction. The dissociation constant, Kd, and the association constant, Ka, are quantitative measures of affinity. At equilibrium, free antigen (Ag) and free antibody (Ab) are in equilibrium with antigen-antibody complex (Ag-Ab), and the rate constants, ka and kd, quantitate the rates of the individual reactions. At equilibrium, ka [Ab][Ag]–kd [Ag-Ab]. The dissociation constant, Kd, is given by: Kd=kd/ka–[Ag][Ab]/[Ag-Ab]. Kd has units of concentration, most typically M, mM, nM, pM, etc. When comparing antibody affinities expressed as Kd, having greater affinity for NGF is indicated by a lower value. The association constant, Ka, is given by: Ka=ka/kd= [Ag-Ab]/[Ag][Ab]. Ka has units of inverse concentration, most typically $M^{-1}$, $mM^{-1}$, $nM^{-1}$, $pM^{-1}$, etc. As used herein, the term "avidity" refers to the strength of the antigen-antibody binding taking valency into account.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

The anti-NGF proteins described herein, including antibodies or fragments thereof, are useful for ameliorating, or reducing the symptoms of, or treating, or preventing, diseases and disorders associated with NGF. The anti-NGF proteins or fragments, as well as combinations with other agent, are to be administered in a therapeutically effective amount to subjects in need of treatment of diseases and disorders associated with NGF in the form of a pharmaceutical composition as described herein In certain embodiments the method comprises ameliorating, or reducing the symptoms of, or treating, or preventing pain in a subject. In certain embodiments, the anti-NGF proteins, antibodies, or fragments thereof inhibit the association of NGF with TrkA and/or p75, for example administered alone or in conjunction with a second agent and are used to treat, ameliorate, reduce the symptoms of, or prevent inflammatory pain, post-operative incision pain, complex, cancer pain (including but not limited to primary or metastatic bone cancer pain), fracture pain, osteoporotic fracture pain, pain from osteoporosis, pain resulting from burn, and other nociceptic pain.

In certain embodiments the antibody compositions and methods are used for ameliorating, or reducing the symptoms of, or treating, or preventing pain of osteoarthritis (OA). OA is a slowly progressive degenerative joint disease characterized by whole-joint structural changes including articular cartilage, synovium, subchondral bone and periarticular components, leading to pain and loss of joint function. Chronic pain and OA are common in dogs and cats. 20-30% of dogs are affected clinically and have signs of OA. Up to 40% of all cats being affected clinically, with 90% of all cats over 12 years of age have signs of OA.

In dogs the most common site of OA is the hip, followed by stifle (knee), shoulder and carpus. In cats hip, stifle, carpus or spine are most commonly affected.

The anti-NGF proteins, antibodies or antibody fragments, are optionally administered in combination with one or more active agents including other analgesic agents. Such active agents include analgesic, anti-histamine, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include, without limitation, 2-arylpropionic acids, aceclofenac, acemetacin, acetylsalicylic acid (Aspirin), alclofenac, alminoprofen, amoxiprin, ampyrone, arylalkanoic acids, azapropazone, benorylate/benorilate, benoxaprofen, bromfenac, carprofen, celecoxib, choline magnesium salicylate, clofezone, COX-2 inhibitors, dexibuprofen, dexketoprofen, diclofenac, diflunisal, droxicam, ethenzamide, etodolac, etoricoxib, faislamine, fenamic acids, fenbufen, fenoprofen, flufenamic acid, flunoxaprofen, flurbiprofen, ibuprofen, ibuproxam, indometacin, indoprofen, kebuzone, ketoprofen, ketorolac, lomoxicam, loxoprofen, lumiracoxib, magnesium salicylate, meclofenamic acid, mefenamic acid, meloxicam, metamizole, methyl salicylate, mofebutazone, nabumetone, naproxen, n-arylanthranilic acids, nerve growth factor (NGF), oxametacin, oxaprozin, oxicams, oxyphenbutazone, parecoxib, phenazone, phenylbutazone, phenylbutazone, piroxicam, pirprofen, profens, proglumetacin, pyrazolidine derivatives, rofecoxib, salicyl salicylate, salicylamide, salicylates, sulfinpyrazone, sulindac, suprofen, tenoxicam, tiaprofenic acid, tolfenamic acid, tolmetin, and valdecoxib.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Antibiotics include but are not limited to amikacin, aminoglycosides, amoxicillin, ampicillin, ansamycins, arsphenamine, azithromycin, azlocillin, aztreonam, bacitracin, carbacephem, carbapenems, carbenicillin, cefaclor, cefadroxil, cefalexin, cefalothin, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalosporins, chloramphenicol, cilastatin, ciprofloxacin, clarithromycin, clindamycin, cloxacillin, colistin, co-trimoxazole, dalfopristin, demeclocycline, dicloxacillin, dirithromycin, doripenem, doxycycline, enoxacin, ertapenem, erythromycin, ethambutol, flucloxacillin, fosfomycin, furazolidone, fusidic acid, gatifloxacin, geldanamycin, gentamicin, glycopeptides, herbimycin, imipenem, isoniazid, kanamycin, levofloxacin, lincomycin, linezolid, lomefloxacin, loracarbef, macrolides, mafenide, meropenem, meticillin, metronidazole, mezlocillin, minocycline, monobactams, moxifloxacin, mupirocin, nafcillin, neomycin, netilmicin, nitrofurantoin, norfloxacin, ofloxacin, oxacillin, oxytetracycline, paromomycin, penicillin, penicillins, piperacillin, platensimycin, polymyxin B, polypeptides, prontosil, pyrazinamide, quinolones, quinupristin, rifampicin, rifampin, roxithromycin, spectinomycin, streptomycin, sulfacetamide, sulfamethizole, sulfanilimide, sulfasalazine, sulfisoxazole, sulfonamides, teicoplanin, telithromycin, tetracycline, tetracyclines, ticarcillin, tinidazole, tobramycin, trimethoprim, trimethoprim-sulfamethoxazole, troleandomycin, trovafloxacin, and vancomycin.

Active agents also include aldosterone, beclometasone, betamethasone, corticosteroids, cortisol, cortisone acetate, deoxycorticosterone acetate, dexamethasone, fludrocortisone acetate, glucocorticoids, hydrocortisone, methylprednisolone, prednisolone, prednisone, steroids, and triamcinolone. Any suitable combination of these active agents is also contemplated.

The most common form of current treatment for OA and pain related to OA is NSAIDs (which are also anti-pain medications). NSAIDs are not always sufficiently effective, typically need to be administered daily and none are approved for long-term use in cats in the US. Additionally, there are safety and tolerability concerns with the use of NSAIDS in both dogs and cats, especially with long-term treatment. NSAIDs are not recommended to be co-administered with anti-NGF mAbs for long periods.

In certain embodiments, treatment comprises coadministration of dietary supplements containing Omega-3 fatty acids, microlactin, and/or glucosamine/chondroitin as an aid to joint health. Adequan (polysulfated glycosaminoglycan) is an FDA-approved disease modifying drug that inhibits cartilage loss and may also be co-administered.

Formulations and Methods of Administration

For in vivo use, a therapeutic agent as described herein is generally incorporated into a pharmaceutical composition prior to administration. Within such compositions, one or more therapeutic compounds as described herein are present as active ingredient(s) (i.e., are present at levels sufficient to provide a statistically significant effect on the symptoms of cystic fibrosis, as measured using a representative assay). A pharmaceutical composition comprises one or more such compounds in combination with any pharmaceutically acceptable carrier(s) known to those skilled in the art to be suitable for the particular mode of administration. In addition, other pharmaceutically active ingredients (including other therapeutic agents) may, but need not, be present within the composition.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15:167-277 (1981); Langer, Chem. Tech. 12:98-105 (1982); U.S. Pat. No. 3,773,919; EP Patent Application No. 58,481; Sidman et al., Biopolymers 22:547-556 (1983); EP: 133,988).

A preferred route of administration in both canines and felines is by subcutaneous injection usually into the skin at the base of the neck. In certain embodiments, the anti-NGF protein is packaged in an integrated delivery system such as a pen or prefilled syringe for subcutaneous administration. Ghil et al. describes administration of the adalimumab biosimilar, SB5, via prefilled syringe (PFS) and autoinjector (AI) pen based on injection site pain, patient preference, and safety in rheumatoid arthritis (RA) (See Ghil et al., Usability and safety of SB5 (an adalimumab biosimilar) prefilled syringe and autoinjector in patients with rheumatoid arthritis. Curr Med Res Opin 2019 March; 35 (3): 497-502.) Compositions of the invention are similarly administered to canines, felines, and other mammals.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

In certain embodiments, the present therapeutic agent may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of the present invention can be determined by comparing their in vitro activity, and in vivo activity in animal models. In certain embodiments, a useful dose is from about 0.1 mg/kg to about 5 mg/kg or from about 0.5 mg/kg to about 2 mg/kg. Methods for the extrapolation of effective dosages in humans and animals of different sizes are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Generation and characterization of rat antibody 2166 that binds to canine NGF.

Lewis rats were immunized with human NGF (R&D Systems, 256-GF-100/CF) on a weekly basis for eight weeks. The titers were measured in a flow cytometry assay using human NGF-coated beads. Beads were conjugated with human NGF (R&D Systems, 256-GF-100/CF) and incubated with different dilutions of serum (1:100, 1:500, 1:2500) for 30 minutes. Beads were washed and binding was detected by using a fluorescently labeled anti-rat IgG secondary antibody. Fluorescence was measured using the Intellicyt iQue Screener Plus. Titers were measured at a 1:2500 dilution for all three rats and they were ~100-fold greater than the values of normal Lewis rat serum.

Lymph nodes (brachial, axillary, inguinal, popliteal and sciatic) and bone marrow from femur, tibia and pelvis were collected from rats with significant NGF titers. Cells from both tissues were isolated and enriched for plasma cells using flow cytometry. Enriched plasma cell suspension was injected into AbCellera's microfluidic screening devices with either 91,000 or 153,000 individual nanoliter-volume reaction chambers. Single cells secreting NGF-specific antibodies were identified and isolated using a bead-based assay. Beads coated with anti-rat IgG antibody were flowed onto microfluidic screening devices and incubated with single antibody-secreting cells. The IgG secreted by plasma cells were captured on beads using the constant region. Binding to secreted IgG immobilized onto beads was subsequently assessed using fluorescently labeled human NGF antigen. Positive hits were identified using machine vision and recovered using automated robotics-based protocols. Approximately 269,000 individual B cells were screened in the NGF binding assay and 592 cells expressed antibodies recognized NGF. From these positive cells, 190 unique antibody sequences were identified. Eighty-eight antibodies were selected from the 190 antibodies based on the diversity of the clonotypes.

Single cell polymerase chain reaction and custom molecular biology protocols generated NGS sequencing libraries (MiSeq, Illumina) using automated workstations (Bravo, Agilent). Sequencing data were analyzed using a custom bioinformatics pipeline to yield paired heavy and light chain sequences for each recovered antibody-secreting cell (Jones et al., 2020, bioRxiv 2020.09.30.318972. doi: 10.1101/2020.09.30.318972). The amino acid sequences of the heavy and light variable domains of rat antibody 2166 are shown in FIG. 1 and FIG. 2 respectively and the CDRs are indicated. The variable (V (D) J) region of each antibody chain was synthesized and inserted into mammalian expression plasmids using a custom, automated high-throughput cloning pipeline.

The expression vectors were transfected into Expi293-F cells (Gibco, ThermoFisher Scientific) in 24 deep well plates using the manufacturer's recommended protocol. Four days post-transfection, the conditioned medium was purified with protein A beads and the antibody was eluted by the addition of 100 mM glycine, pH 2.0 and neutralized to pH 7.0 by the addition of 1 M Tris-HCL, pH 8.0. The neutralized antibodies were buffer exchanged into PBS, pH 7.2.

The analytics for the purified antibodies included CE-SDS (denaturing capillary sodium dodecyl sulfate gel electrophoresis) and DSF (differential scanning fluorimetry). The CE-SDS was used to determine the purity of the purified antibodies and was completed by using the LabChip GXII Touch instrument (Perkin Elmer). Two microliters of antibody solution at a concentration of 350 µg/mL in PBS was mixed with a non-reducing denaturing buffer solution (Perkin Elmer) and incubated at 70° C. for 10 minutes. Separation and detection were performed using the HT Antibody Analysis 200 assay setting on the LabChip instrument (Perkin Elmer). The fluorescence data was analyzed using the LabChip GX Reviewer Software (Perkin Elmer), with percent purity. The percent purity of the rat monoclonal antibody 2166 was 96%.

The melting point (Tm) of antibodies was assessed by differential scanning fluorimetry (DSF) using the SYPRO™ Orange fluorescence probe (5000× concentrated solution, Thermo Fisher Scientific). 6 µL of mAb solution at 350 µg/mL in PBS was mixed with 6 µL of a 19× concentrated SYPRO™ Orange solution diluted in PBS. Thermal unfolding as assessed by a change in fluorescence was measured on a Bio-Rad C1000 Touch Thermal Cycler instrument (Bio-Rad Laboratories) using a CFX96 Real-Time System reader head (Bio-Rad Laboratories). The wavelengths for excitation and emission were 450-490 nm and 560-580 nm, respectively. The fluorescence signal was measured at a starting temperature of 25° C. and increased to 95° C. in 0.5° C./min increments. Data was analyzed and melting curves integrated using the Bio-Rad CFX Maestro software (v1.1). The Tm was defined as the local minimum taken from the derivative of the melting curve. The Tm of the rat antibody 2166 was 66.5° C.

A binding assay was completed to confirm binding of the antibodies to NGF (R&D Systems, 256-GF-100/CF). In addition, the specificity of the antibodies was determined by testing the binding of the antibodies to NT-3 and BDNF which are closely related proteins. Unique antibody sequences were confirmed to bind the screening target using a multiplexed bead assay on a high throughput flow cytometer. Different optically encoded beads were conjugated to either human NGF (R&D Systems, 256-GF-100/CF), NT-3 (R&D Systems, 267-N3-025/CF) or BDNF (R&D Systems, 248-BDB-050/CF). Purified antibodies were incubated with the multiplexed beads at different antibody concentrations for 30 minutes at room temperature. Beads were washed and binding was detected by using a fluorescently labelled secondary antibody. Fluorescence was measured using high throughput plate-based flow cytometry on an Intellicyt® iQue Screener Plus.

Median fluorescence intensity of each antibody was normalized over the median fluorescence intensity of the appropriate isotype control for individual bead types. Antibody values greater than 10-fold over isotype were considered as binders.

Antibody 2166 bound to NGF greater than 59-fold higher than background levels and the binding of this antibody to NT-3 and BDNF was at background levels.

A functional assay with TF-1 cells was used to determine if the binding of the 2166 antibody to canine NGF blocks the ability of canine NGF to induce signaling with human TrkA which is the high affinity receptor for NGF (Chevalier et al., 1994. Blood, 83:1479). For these studies, canine NGF (Genbank NP_001181879.1) was used for the NGF source. Canine NGF with a strep-tag (Trp-Ser-His-Pro-Gln-Phe-Glu-Lys (SEQ ID NO:220)) at the C-terminus was stably expressed in Dmel-2 cells and purified using StrepTactinXT chromatography followed by a polishing step with Superdex 200 16/600 chromatography. The proliferation of TF-1 cells can be stimulated by different growth factors such as GM-CSF and NGF. TF-1 cells (ATCC-CRL2003) were cultured in RPMI-1640 media containing 10% fetal bovine serum, 100 U/mL Penicillin, 100 µg/ml Streptomycin and 2 ng/mL recombinant human GM-CSF. Cells were maintained between $3 \times 10^4$ and $5 \times 10^5$ viable cells/mL and passaged every 48 hours. Each condition was run in triplicate wells. Cells were collected and counted. Cells were resuspended in media without GM-CSF at $1.75 \times 10^5$ cells/ml and incubated in a flask in a humidified 37° C., 5% CO2 incubator for 4 hours. During the incubation, NGF/antibody mixtures were prepared in media as 2× media solutions in full media without GM-CSF and with 10 ng/mL canine NGF. Antibodies were added to the appropriate 2× media solutions and the NGF/antibody solutions were incubated for at least 1 hour at room temperature before being added to the cells. Cells were then collected and resuspended in appropriate media volume to achieve a $0.5 \times 10^6$ cells/ml suspension in media without GM-CSF. 50 µl of the cell suspension was added per well in a 96-well plate, to which 50 µl of the 2×NGF/antibody media was added per well to the cell plate. Cells were incubated in a humidified 37° C., 5% CO2 incubator for 48 hours, then 20 µl of Aqueous One solution Reagent (Promega) was added per well. Cells were incubated for further 4 hours in a humidified 37° C., 5% CO2 incubator and then absorbance was read at 490 nm on a BioTek Synergy/neO2. Data was analyzed by subtracting the blank well from all measured values. Percent inhibition was calculated using the following formula: % inhibition=100×[1−(X−MIN)/(MAX−MIN)], where X=signal at a given concentration, MAX=0% inhibition=Canine NGF only and MIN=100% inhibition=No NGF control. The average of the triplicates for each condition was calculated. The proliferation data for rat antibody 2166 and the isotype rat antibody control are shown in FIG. 3. The data demonstrates that the rat antibody 2166 effectively blocks NGF from binding to TrkA.

The VH domain of antibody 2166 was fused with the canine IgGB constant domains (Tang et al. 2001. Vet. Immunol. Immunopathol. 80:259) and the VL domain of antibody 2166 was fused to the canine kappa constant domain to generate a canine chimeric antibody (FIG. 4). Two residue changes (AA) were made in the Fc (underlined and in bold font) to eliminate effector activity and these changes are analogous to the "LALA" mutation described for human IgG1 Fc (Tamm & Schmidt, 1997. Int. Rev. Immunol. 16:57). These two constructs were subcloned into pcDNA3.4 (ThermoFisher Scientific) and co-transfected with the Expi293 system (ThermoFisher Scientific) and purified with HiTrap Protein A HP chromatography. The purity of the antibody as measured by SDS/PAGE was >95% and by SEC (size exclusion chromatography) the antibody was 98% monomeric.

Figure 5:
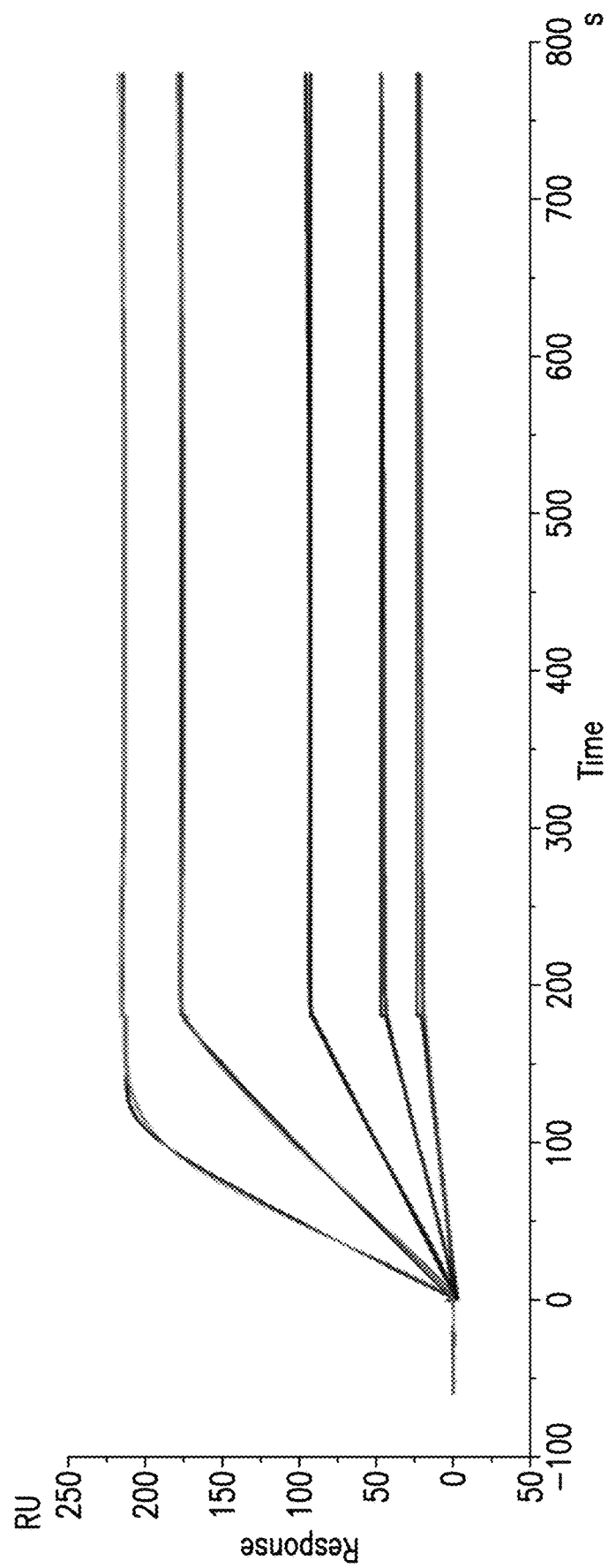
FIG. 5 is a sensorgram for canine 2166 chimeric antibody binding to canine NGF. The NGF concentrations were 0.78, 1.56, 3.12, 6.25, and 12.5 nM.

The affinity of the canine 2166 chimeric antibody for canine NGF was measured by SPR (surface plasmon resonance). For these studies, canine NGF (Genbank NP_001181879.1) was generated by fusing the C-terminus with the Flag tag (DYKDDDDK) (SEQ ID NO:221), expressing the canine NGF construct with baculovirus technology and then purifying the NGF with Anti-DYKDDDDK (SEQ ID NO:221) G1 affinity chromatography. The binding kinetics of canine 2166 chimeric antibody to canine NGF was measured with a Biacore T200 instrument. The format of the assay was to capture the Fc of 2166 antibody onto a protein A sensor chip and use canine NGF as the analyte. The running buffer was HBS-EP buffer (10 mM HEPES, pH 7.4, 150 mM NaCl, 3 mM EDTA, 0.005% tween 20) and the instrument temperature was set at 25° C. The flow rate was 40 µl/min and the five analyte concentrations tested in duplicate ranged from 0.78 nM to 12.5 nM. The binding signals were corrected for the blank and the resulting sensorgram (FIG. 5) was used to determine the rate constants ($k_a$ and $k_d$) and binding affinity ($K_D$) using a one-to-one binding model with the BIAEVAL software. Under these binding conditions, the binding kinetics for canine 2166 chimeric antibody were $k_a$ (1/Ms)=1.2E+7, $k_d$ (1/s)=3.5E-6, and $K_D$=3E-13. The measured affinity ($K_D$) of this antibody exceeds the sensitivity of the Biacore instrument but from these data it is estimated to be at least 50 pM.

The ability of canine 2166 chimeric antibody to block canine NGF from binding to the canine NGF receptors (TrkA and p75) was measured in an SPR assay on a Biacore T200. The format of the assay was to capture the NGF receptor on a sensor chip and flow over either canine NGF only, NGF mixed with canine 2166 chimeric antibody, or canine 2166 chimeric antibody only.

The NGF receptors used in the assay consist of the extracellular domains of canine p75 (XP_038340439.1) and canine TrkA (XP_038398906.1) fused to the human IgG1 Fc (UniProtKB P01857) with a 2× Gly-Gly-Gly-Ser (SEQ ID NO:377) linker between the receptor and the Fc. The fusion proteins were expressed in CHO cells and purified with protein A chromatography. For this assay, the proteins p75-Fc and Trk-Fc were captured onto a human anti-Fc sensor chip.

NGF only, canine 2166 chimeric antibody only and canine 2166 chimeric antibody-NGF mixture (at a 2:1 molar ratio) were the analytes. The seven concentrations of NGF in NGF only condition ranged from 0.78 nM to 50 nM. The concentrations of canine NGF in the canine 2166 chimeric antibody-NGF mixture was 50 nM, 25 nM and 12.5 nM. Lastly, the four concentrations of canine 2166 chimeric antibody alone condition ranged from 12.5 nM to 100 nM. The instrument temperature and flow rate were set at 25° C. and 40 µL/min, respectively.

Figure 6:
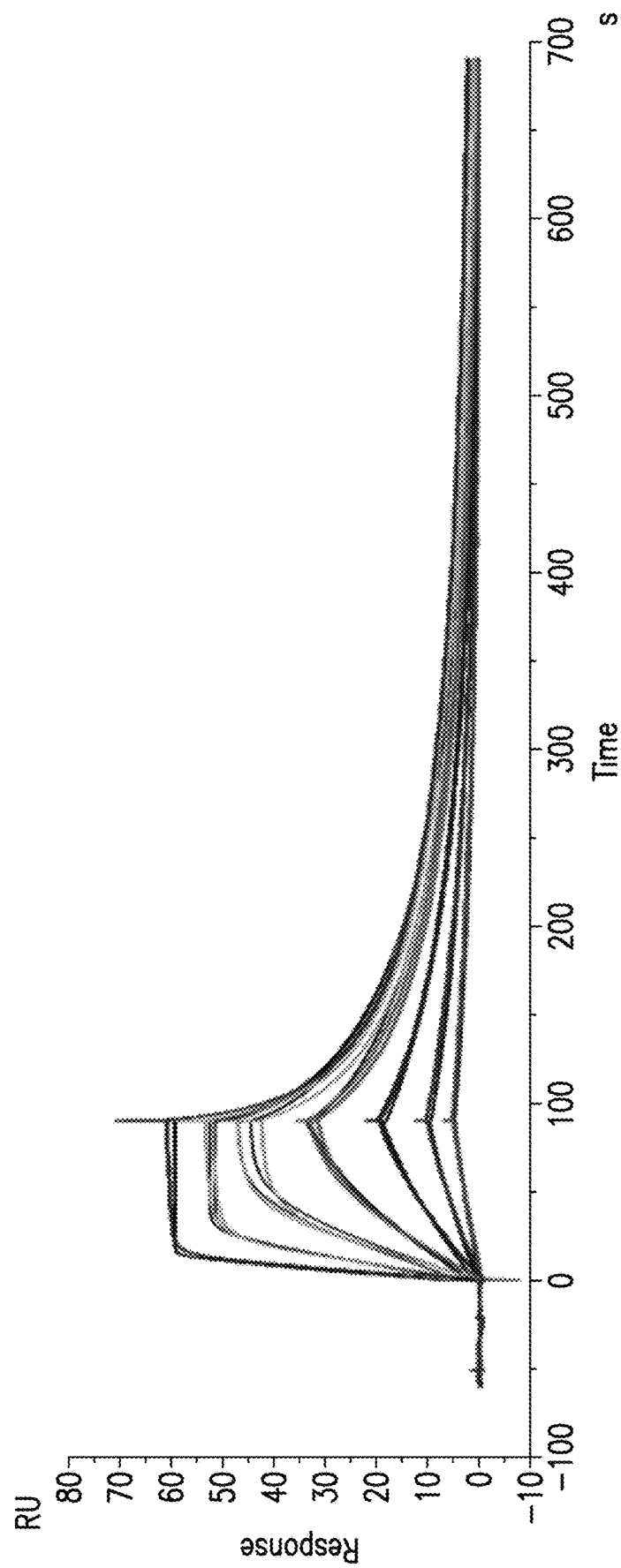
FIG. 6 is a sensorgram for canine NGF only binding to canine p75-Fc. The NGF concentrations were 0.78, 1.56, 3.12, 6.25, 12.5, 25, and 50 nM.
Figure 7:
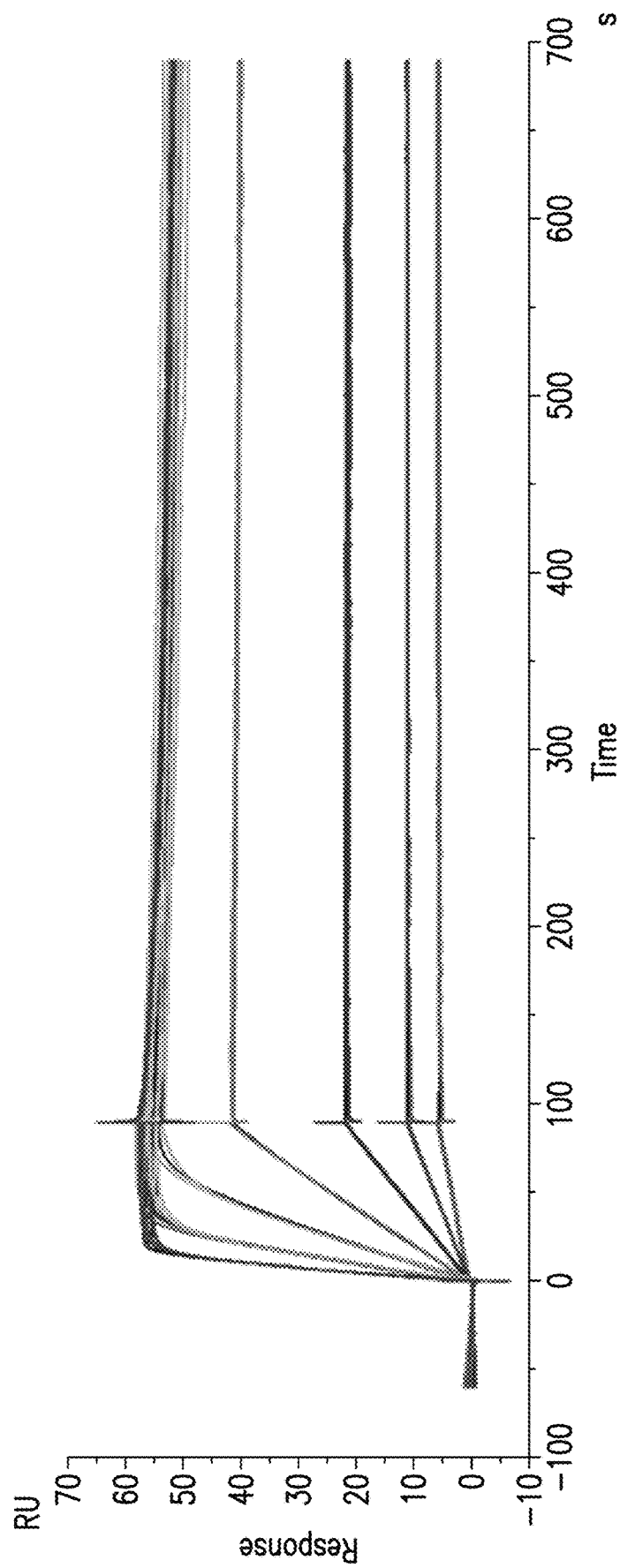
FIG. 7 is a sensorgram for canine NGF only binding to canine TrkA-Fc. The NGF concentrations were 0.78, 1.56, 3.12, 6.25, 12.5, 25, and 50 nM.
Figure 8:
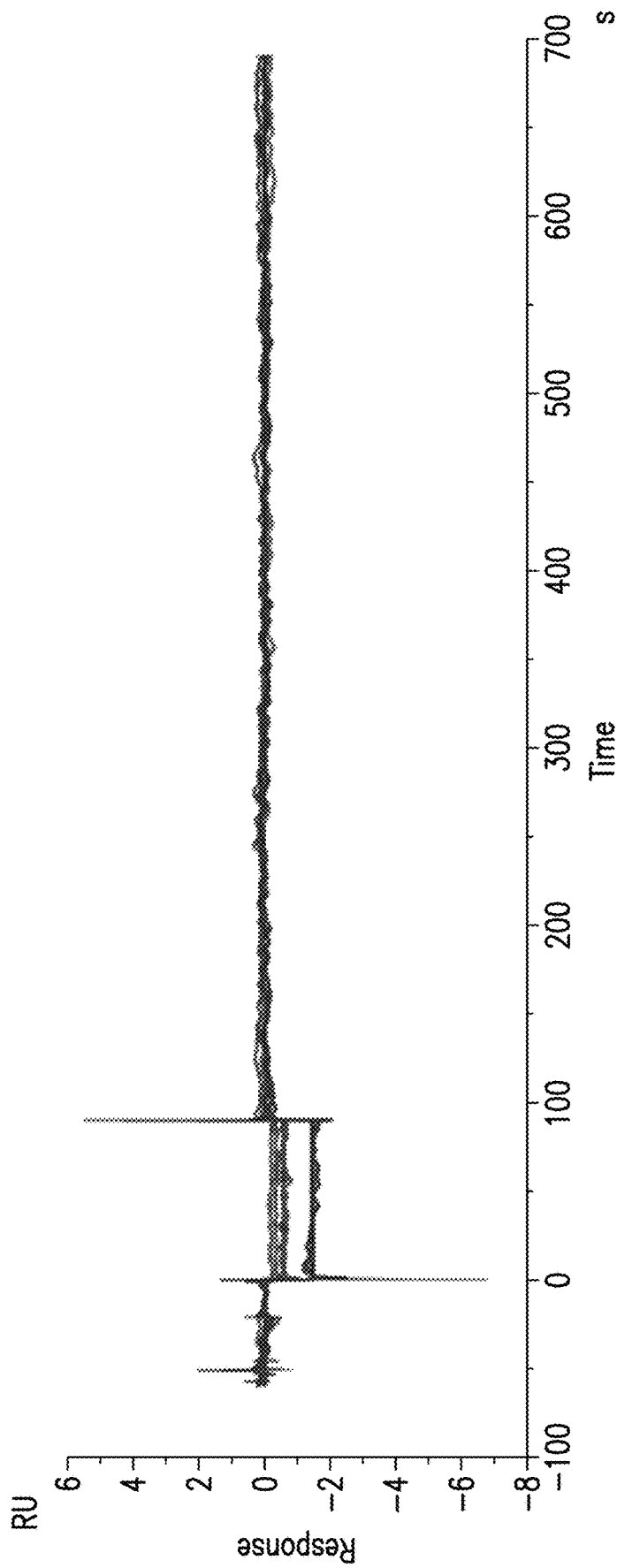
FIG. 8 is a sensorgram for canine 2166 chimeric antibody-NGF mixture binding to canine p75-Fc. The NGF concentrations were 12.5, 25, and 50 nM.
Figure 9:
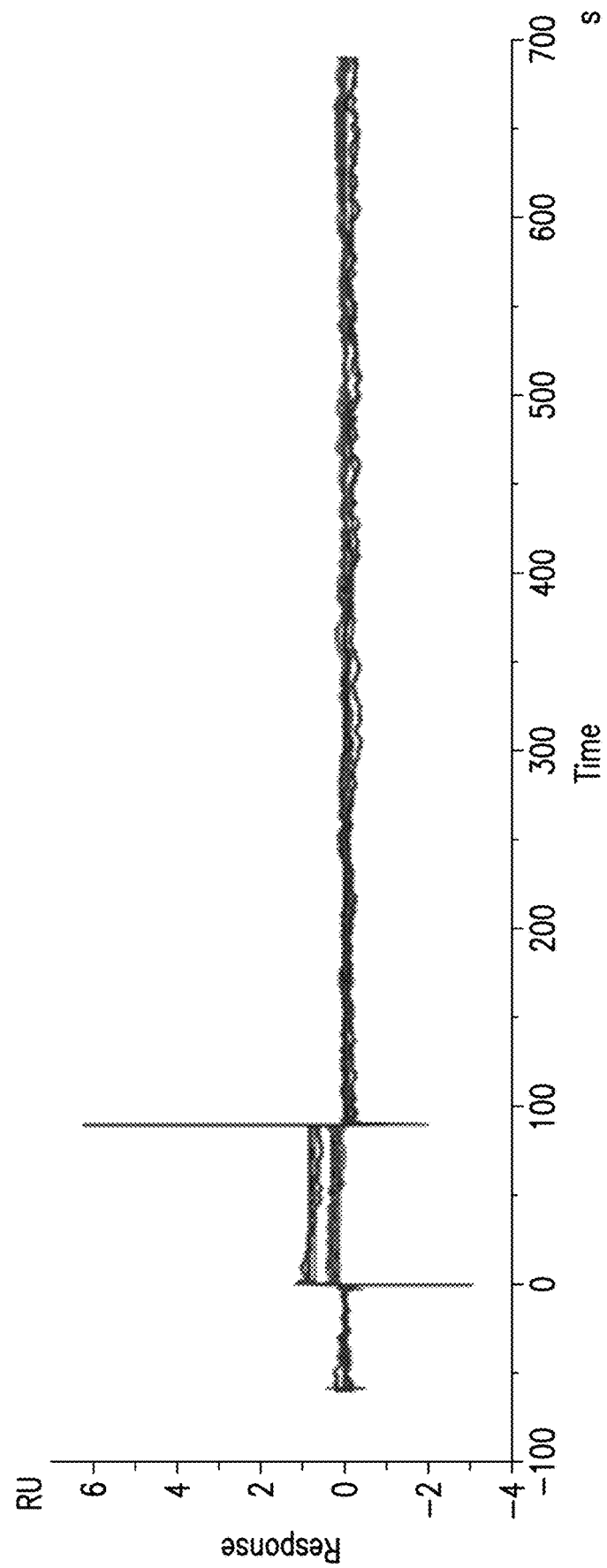
FIG. 9 is a sensorgram for canine 2166 chimeric antibody-NGF mixture binding to canine TrkA-Fc. The NGF concentrations were 12.5, 25, and 50 nM.

The binding signals were corrected for the reference, and the resulting sensorgrams were used to determine the rate constants ($k_a$ and $k_d$) and binding affinity ($K_D$) using a one-to-one binding model with the BIAEVAL software. The sensorgrams (FIGS. 5, 6, 7, 8) represent the NGF only condition and the canine 2166 chimeric antibody-NGF mixture for both the p75-Fc and TrkA-Fc receptors. Under these binding conditions, the binding kinetics for canine NGF only to canine p75 in a dimer format were $k_a$ (1/Ms)=1.2E+10, $k_d$ (1/s)=45, and $K_D$=3.7E-9 (FIG. 6). The binding kinetics for canine NGF only to canine TrkA in a dimer format were $k_a$ (1/Ms)=1.3E+7, $k_d$ (1/s)=1.7E-4, and $K_D$=1.3E-11 (FIG. 7). No binding to the canine NGF receptors was observed with the canine 2166 chimeric antibody only condition (data not shown). As evidenced by the sensorgrams (FIGS. 8 and 9), canine 2166 chimeric antibody effectively blocks canine NGF binding to canine TrkA and p75.

Example 2

Caninization of Rat 2166 Antibody

A canine antibody database was generated by performing NGS (next generation sequencing) on canine PBMCs (peripheral blood mononuclear cells). This database contains the sequences from $5.0 \times 10^6$ VH domains, $3.7 \times 10^6$ VK domains and $2.6 \times 10^6$ VL domains. The HCDR 1, 2 and LCDR 1, 2, 3 sequences from the 2166 parental antibody were used in an algorithm to identify the closest canine CDR sequences and their linked framework sequences in the canine antibody database. These linked framework sequences were included in the scFv phage display library along with the closest framework germline sequences and the linked framework sequences with 1 to 3 residues reverted back to the closest germline. A proprietary algorithm was used to identify a set of CDR sequences that are similar to the original 2166 CDRs and closer in identity to the germline and expressed CDR sequences. These CDRs and framework sequences were used to generate a scFv antibody phage display library with a theoretical complexity of $3 \times 10^{12}$. Antibody phage selections were completed with canine NGF for four rounds and with each round the stringency was increased by reducing the antigen concentration and increasing the number of washes. Specifically, 96-multi well plates were coated with 200 pmol of NGF for the first round, 100 pmol for the second round and 50 pmol for the third and fourth rounds. The number of washes with PBS-tween 20 (0.01%) after the selection were six for the first round, seven for the second round, eight for the third round and nine for the fourth round. The output scFv clones from the third and fourth rounds were sequenced and unique clones were reformatted into IgGs and screened for binding to canine NGF by SPR. The sequences and the binding kinetics to canine NGF of the top 69 caninized clones along with parental clone 2166 are shown in FIGS. 1 and 2 and Table 2.

TABLE 2

| Binding to canine NGF | | | |
|---|---|---|---|
| Clone | ka | kd | KD |
| 2166 | 2.38E+06 | 1.00E−05 | 4.20E−12 |
| SC-42_006 | 2.22E+06 | 1.75E−04 | 7.88E−11 |
| SC-42_007 | 1.32E+06 | 1.38E−04 | 1.05E−10 |
| SC-42_008 | 1.96E+06 | 9.40E−05 | 4.79E−11 |
| SC-42_010 | 2.06E+06 | 8.55E−05 | 4.16E−11 |
| SC-42_011 | 1.27E+06 | 7.28E−05 | 5.75E−11 |
| SC-42_023 | 4.19E+06 | 4.66E−04 | 1.11E−10 |
| SC-42_024 | 3.63E+06 | 5.22E−04 | 1.44E−10 |
| SC-42_025 | 3.90E+06 | 5.88E−04 | 1.51E−10 |
| SC-42_026 | 4.26E+06 | 9.20E−04 | 2.16E−10 |
| SC-42_027 | 3.43E+06 | 6.51E−04 | 1.90E−10 |
| SC-42_028 | 3.19E+06 | 4.96E−04 | 1.56E−10 |
| SC-42_029 | 4.09E+06 | 5.44E−04 | 1.33E−10 |
| SC-42_030 | 4.10E+06 | 6.34E−04 | 1.55E−10 |
| SC-42_031 | 4.23E+06 | 6.46E−04 | 1.53E−10 |
| SC-42_032 | 4.61E+06 | 2.64E−04 | 5.73E−11 |
| SC-42_033 | 3.73E+06 | 5.81E−04 | 1.56E−10 |
| SC-42_034 | 2.81E+06 | 1.51E−03 | 5.39E−10 |
| SC-42_035 | 3.02E+06 | 6.24E−04 | 2.06E−10 |
| SC-42_036 | 3.40E+06 | 8.77E−04 | 2.58E−10 |
| SC-42_037 | 3.25E+06 | 4.82E−04 | 1.49E−10 |
| SC-42_038 | 3.21E+06 | 5.30E−04 | 1.65E−10 |
| SC-42_040 | 4.82E+06 | 7.09E−04 | 1.47E−10 |
| SC-42_041 | 3.42E+06 | 5.55E−04 | 1.62E−10 |
| SC-42_042 | 3.51E+06 | 9.76E−04 | 2.78E−10 |
| SC-42_043 | 2.79E+06 | 7.13E−04 | 2.55E−10 |
| SC-42_044 | 3.12E+06 | 4.53E−04 | 1.45E−10 |
| SC-42_045 | 3.34E+06 | 4.12E−04 | 1.23E−10 |

TABLE 2-continued

Binding to canine NGF

| Clone | ka | kd | KD |
|---|---|---|---|
| SC-42_046 | 3.45E+06 | 4.89E-04 | 1.42E-10 |
| SC-42_047 | 3.55E+06 | 4.41E-04 | 1.24E-10 |
| SC-42_048 | 4.25E+06 | 4.89E-04 | 1.15E-10 |
| SC-42_049 | 3.80E+06 | 5.49E-04 | 1.44E-10 |
| SC-42_050 | 3.49E+06 | 5.02E-04 | 1.44E-10 |
| SC-42_051 | 3.27E+06 | 6.09E-04 | 1.86E-10 |
| SC-42_052 | 3.35E+06 | 4.13E-04 | 1.23E-10 |
| SC-42_053 | 3.41E+06 | 4.71E-04 | 1.38E-10 |
| SC-42_054 | 3.32E+06 | 5.91E-04 | 1.78E-10 |
| SC-42_055 | 4.23E+06 | 7.73E-04 | 1.83E-10 |
| SC-42_057 | 3.73E+06 | 5.53E-04 | 1.48E-10 |
| SC-42_058 | 3.31E+06 | 5.88E-04 | 1.78E-10 |
| SC-42_059 | 3.20E+06 | 6.38E-04 | 2.00E-10 |
| SC-42_060 | 3.87E+06 | 5.85E-04 | 1.51E-10 |
| SC-42_061 | 3.16E+06 | 4.94E-04 | 1.56E-10 |
| SC-42_062 | 3.27E+06 | 6.36E-04 | 1.95E-10 |
| SC-42_063 | 3.57E+06 | 8.52E-04 | 2.39E-10 |
| SC-42_064 | 2.43E+06 | 6.51E-04 | 2.68E-10 |
| SC-42_065 | 3.47E+06 | 5.95E-04 | 1.71E-10 |
| SC-42_066 | 3.16E+06 | 5.21E-04 | 1.65E-10 |
| SC-42_067 | 3.57E+06 | 7.02E-04 | 1.97E-10 |
| SC-42_068 | 3.59E+06 | 4.87E-04 | 1.36E-10 |
| SC-42_069 | 2.39E+06 | 4.67E-04 | 1.96E-10 |
| SC-42_070 | 4.70E+06 | 5.43E-04 | 1.15E-10 |
| SC-42_071 | 1.45E+06 | 6.89E-04 | 4.74E-10 |
| SC-42_072 | 3.98E+06 | 7.86E-04 | 1.98E-10 |
| SC-42_073 | 5.83E+06 | 5.46E-04 | 9.37E-11 |
| SC-42_075 | 4.54E+06 | 1.55E-03 | 3.42E-10 |
| SC-42_077 | 3.35E+06 | 2.91E-04 | 8.71E-11 |
| SC-42_079 | 3.53E+06 | 8.49E-04 | 2.40E-10 |
| SC-42_080 | 3.31E+06 | 4.46E-04 | 1.35E-10 |
| SC-42_081 | 3.41E+06 | 2.17E-03 | 6.35E-10 |
| SC-42_082 | 3.45E+06 | 2.52E-04 | 7.29E-11 |
| SC-42_083 | 4.17E+06 | 6.23E-04 | 1.49E-10 |
| SC-42_084 | 3.60E+06 | 4.73E-04 | 1.32E-10 |
| SC-42_085 | 4.28E+06 | 8.34E-04 | 1.95E-10 |
| SC-42_088 | 3.39E+06 | 1.06E-03 | 3.11E-10 |
| SC-42_089 | 4.26E+06 | 7.74E-04 | 1.82E-10 |
| SC-42_090 | 1.91E+06 | 1.52E-04 | 7.99E-11 |
| SC-42_091 | 1.00E+04 | 1.00E-04 | 1.00E-08 |
| SC-42_101 | 3.41E+06 | 3.80E-04 | 1.11E-10 |
| SC-42_102 | 2.91E+06 | 1.07E-03 | 3.67E-10 |

Figure 10:
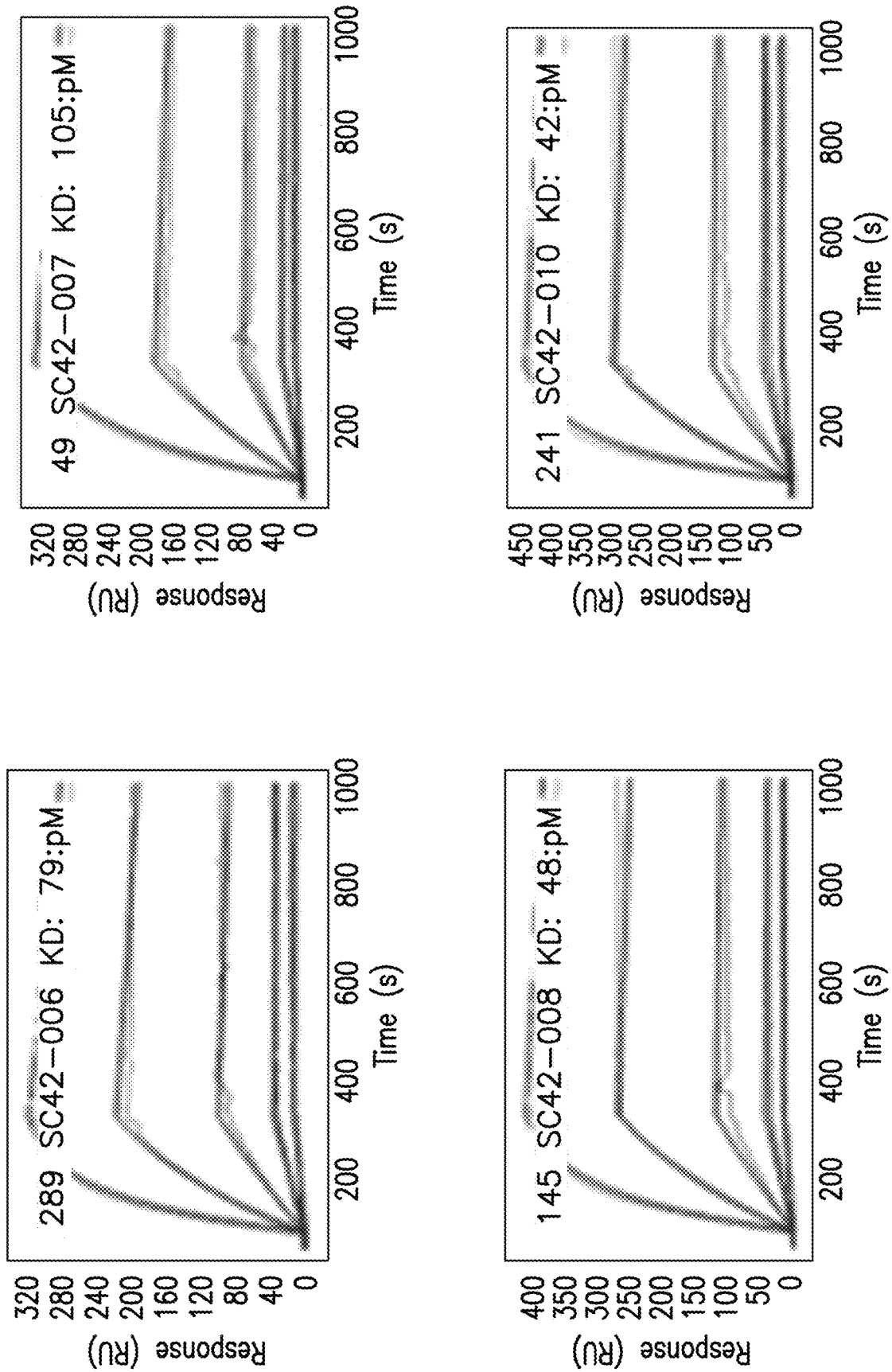
FIG. 10 shows sensorgrams of parental clone 2166 and 69 caninized clones binding to canine NGF. The NGF concentrations were 0.23, 0.69, 2.06, 6.17, and 18.52 nM
Figure 10:
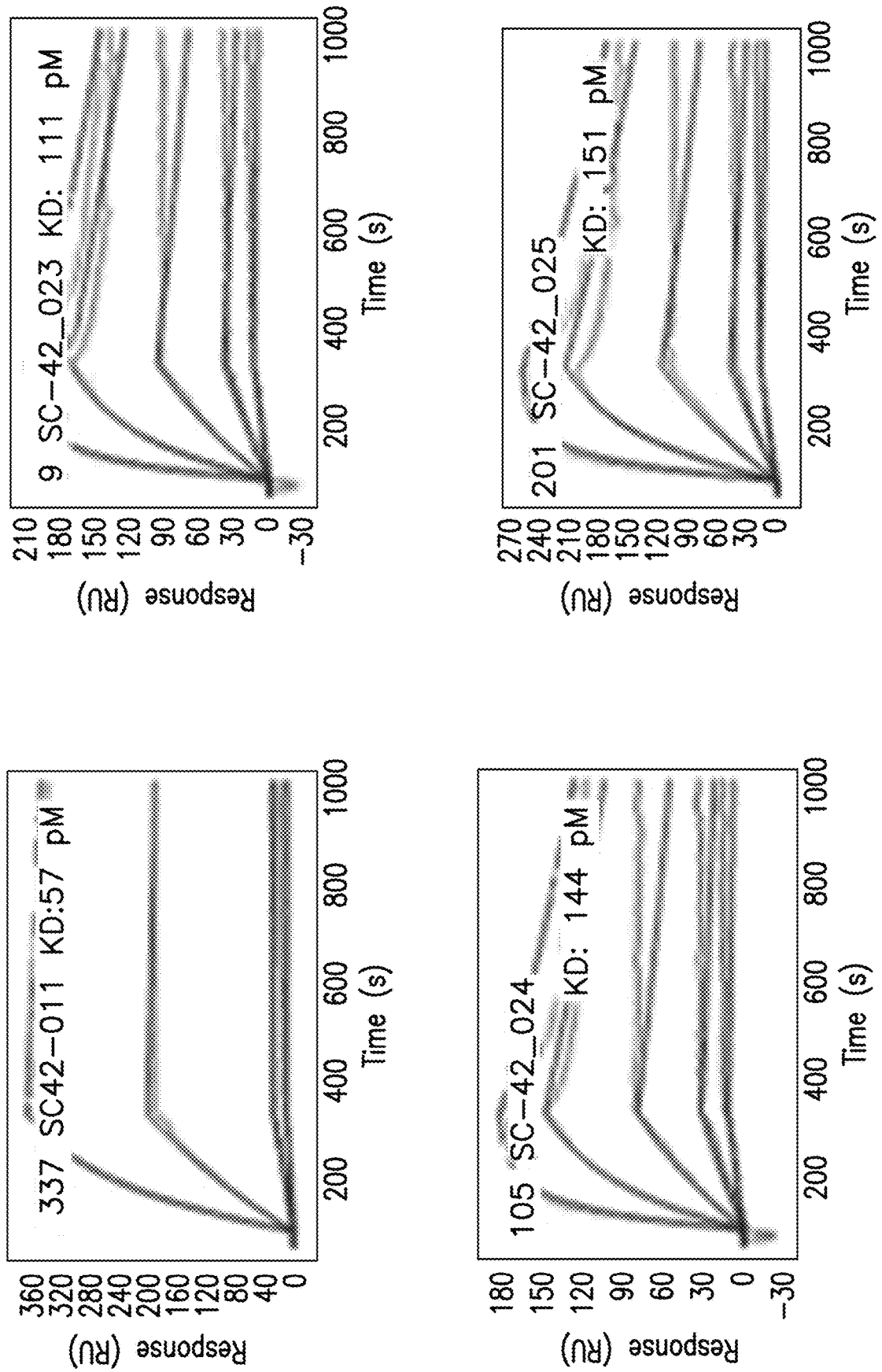
Figure 10:
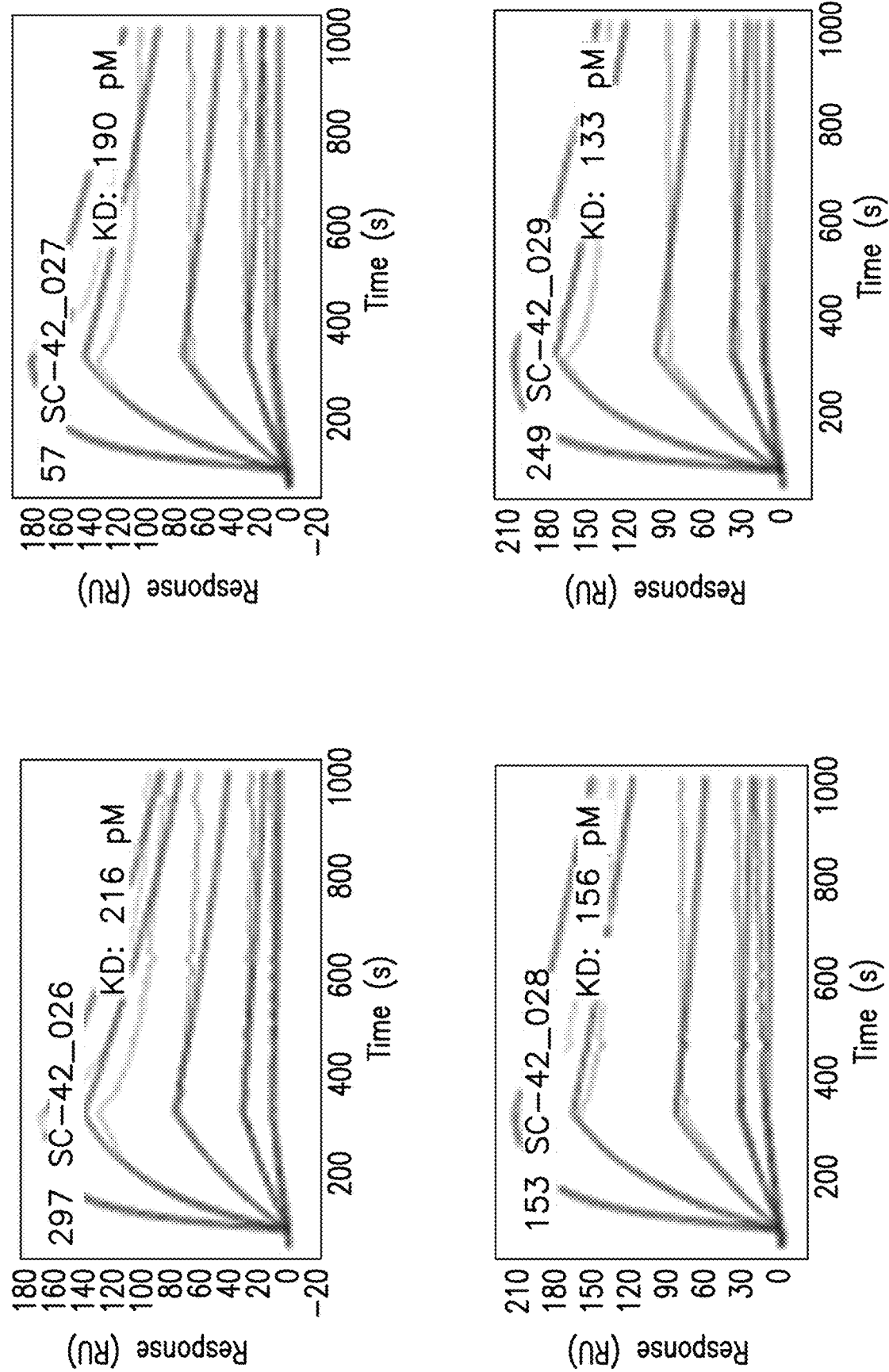
Figure 10:
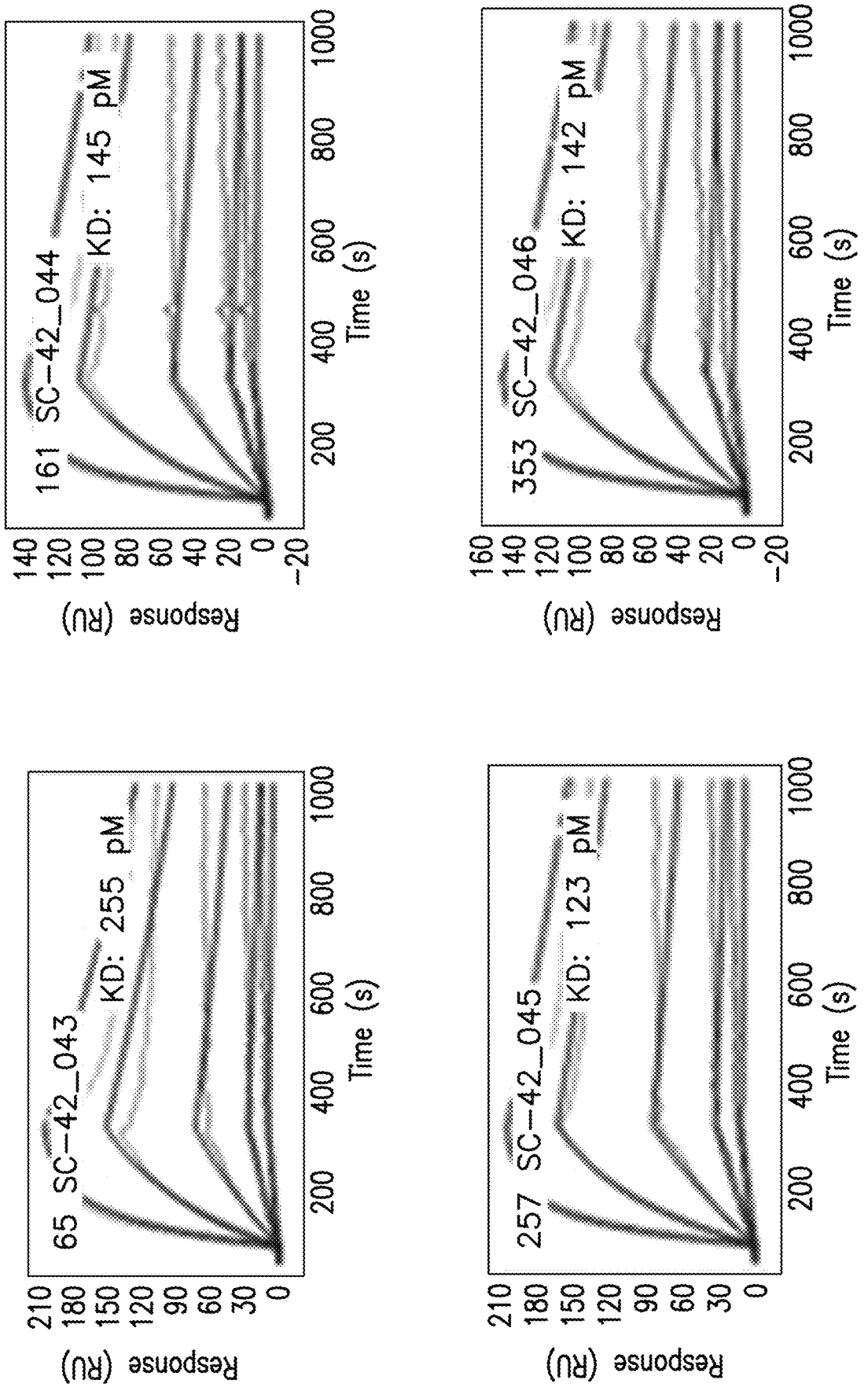
Figure 10:
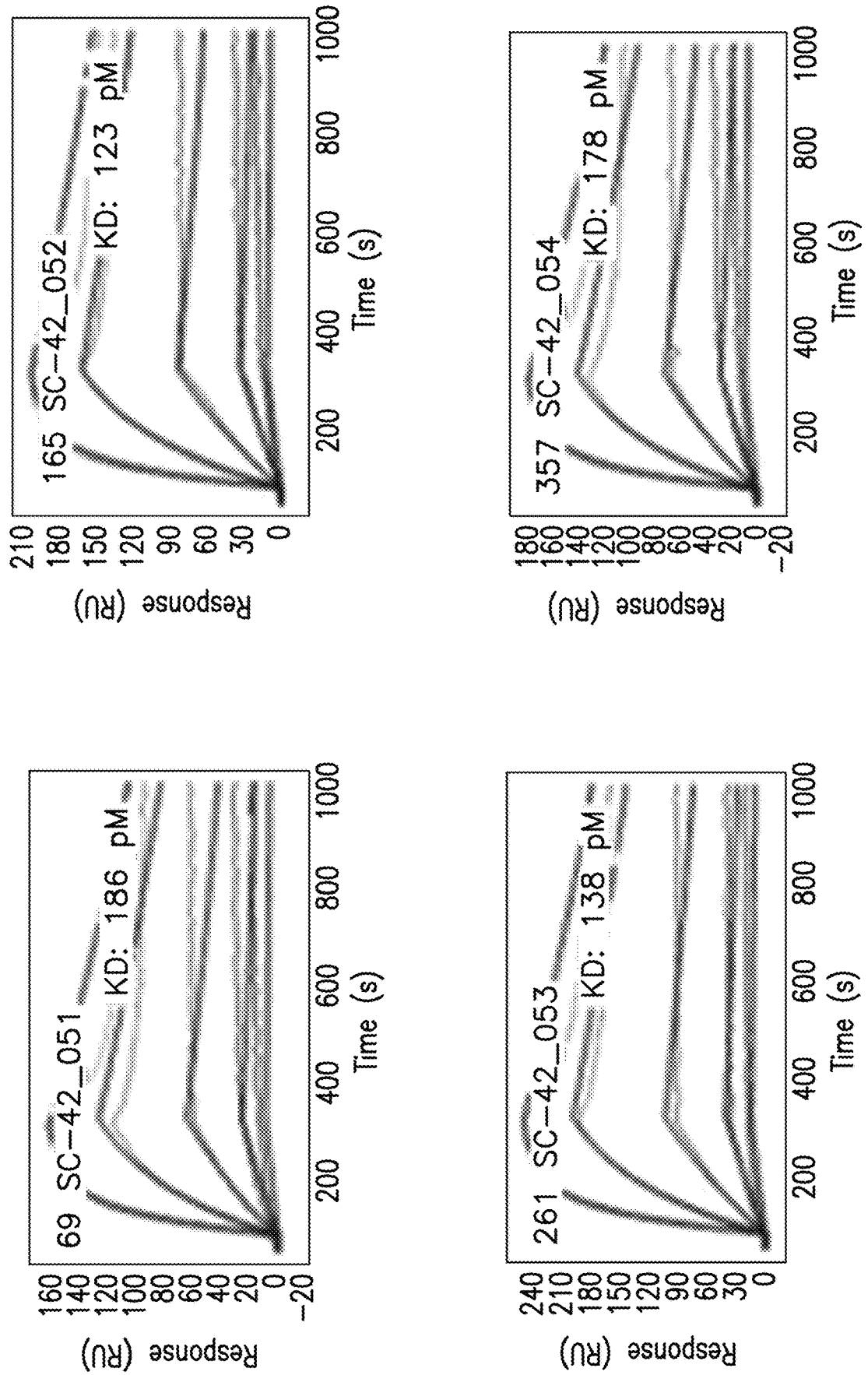
Figure 10:
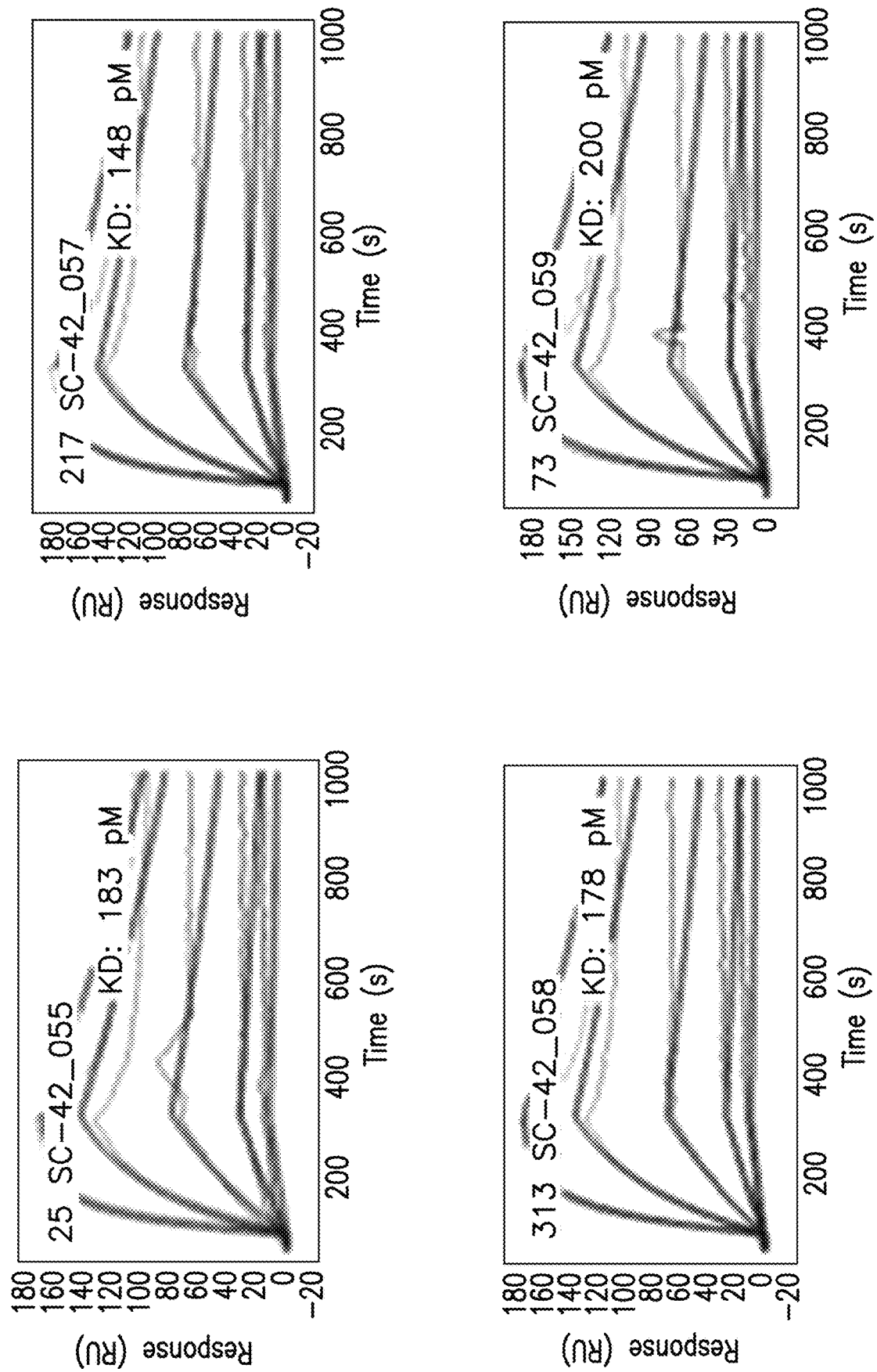
Figure 10:
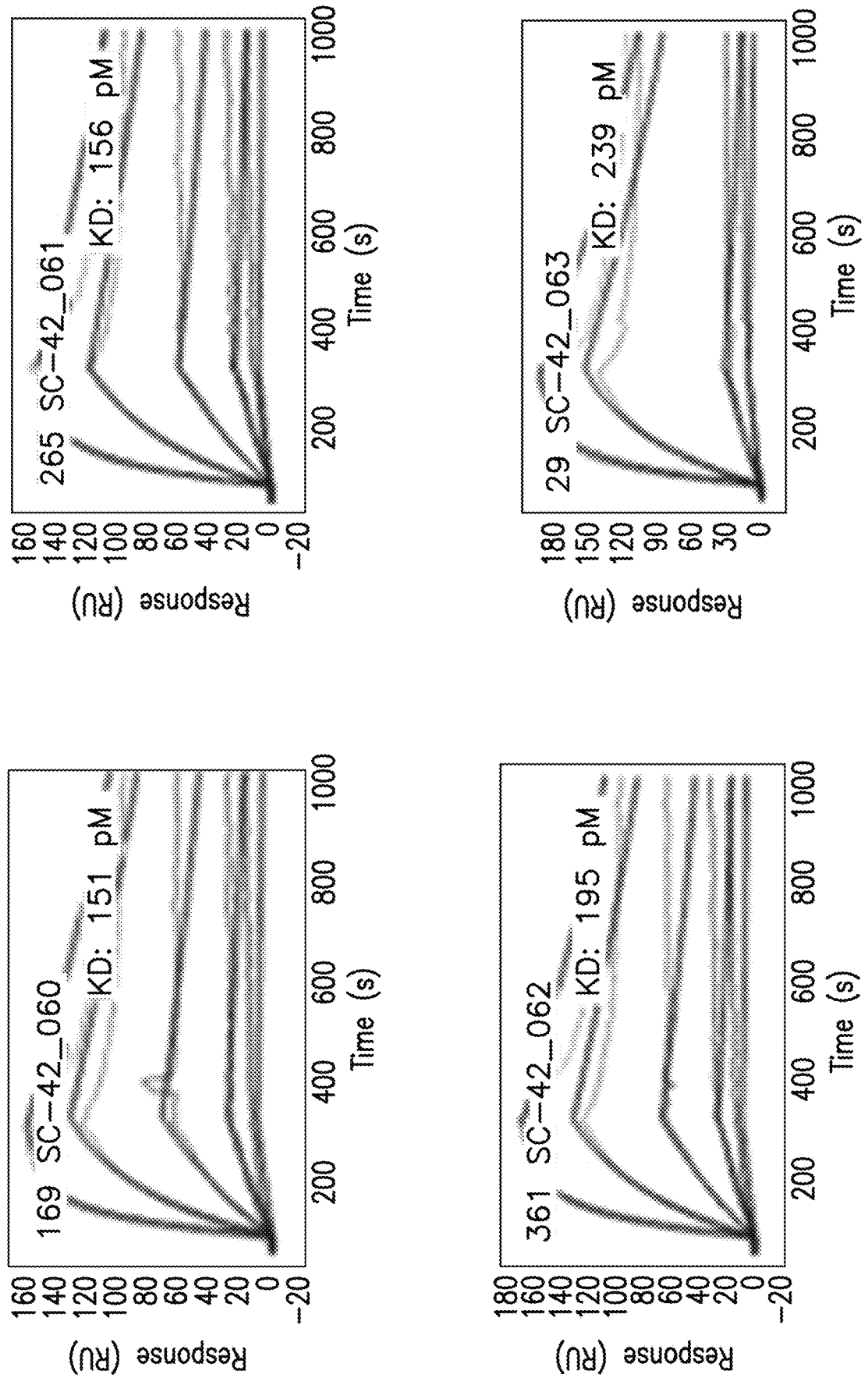
Figure 10:
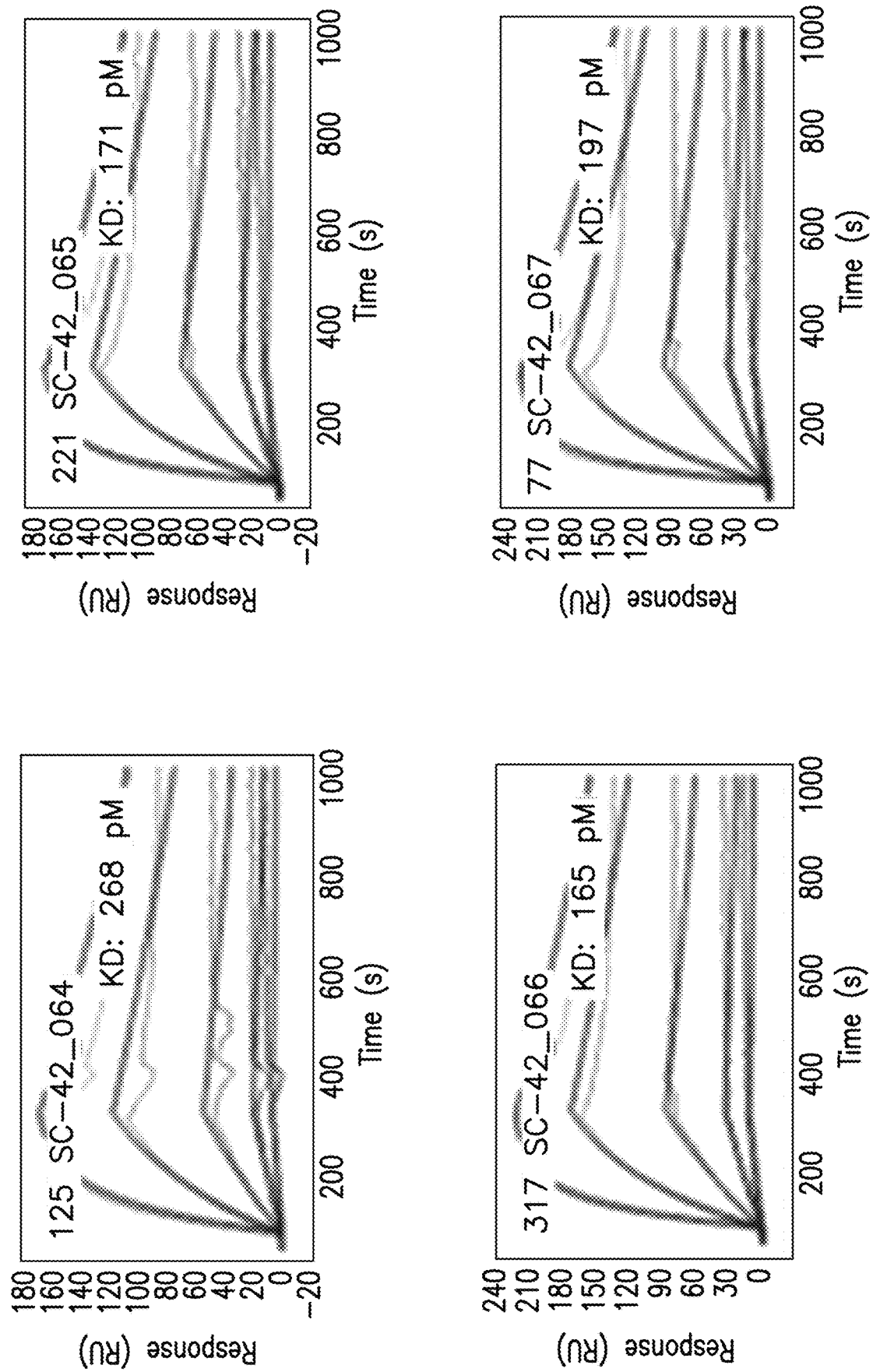
Figure 10:
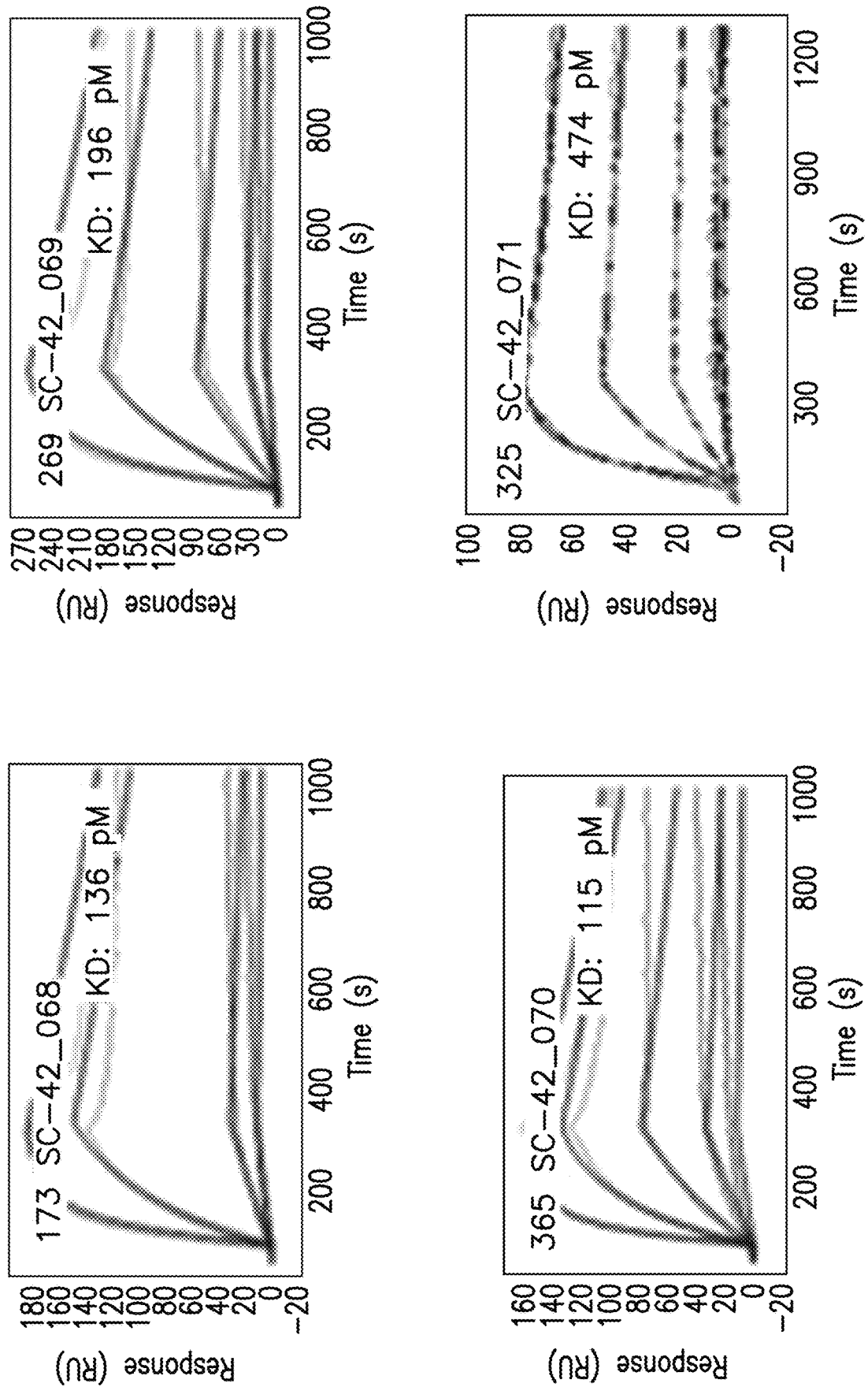
Figure 10:
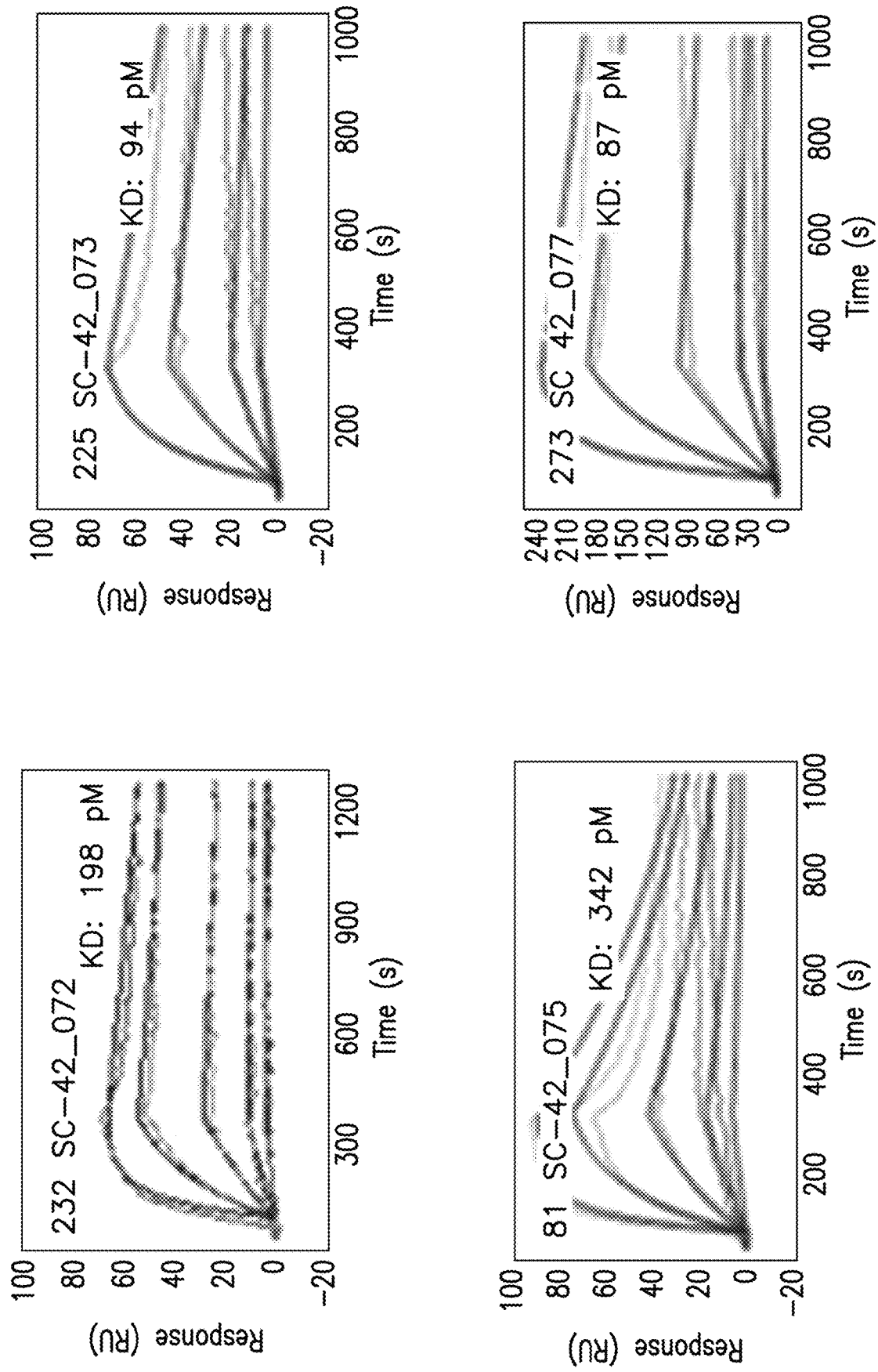
Figure 10:
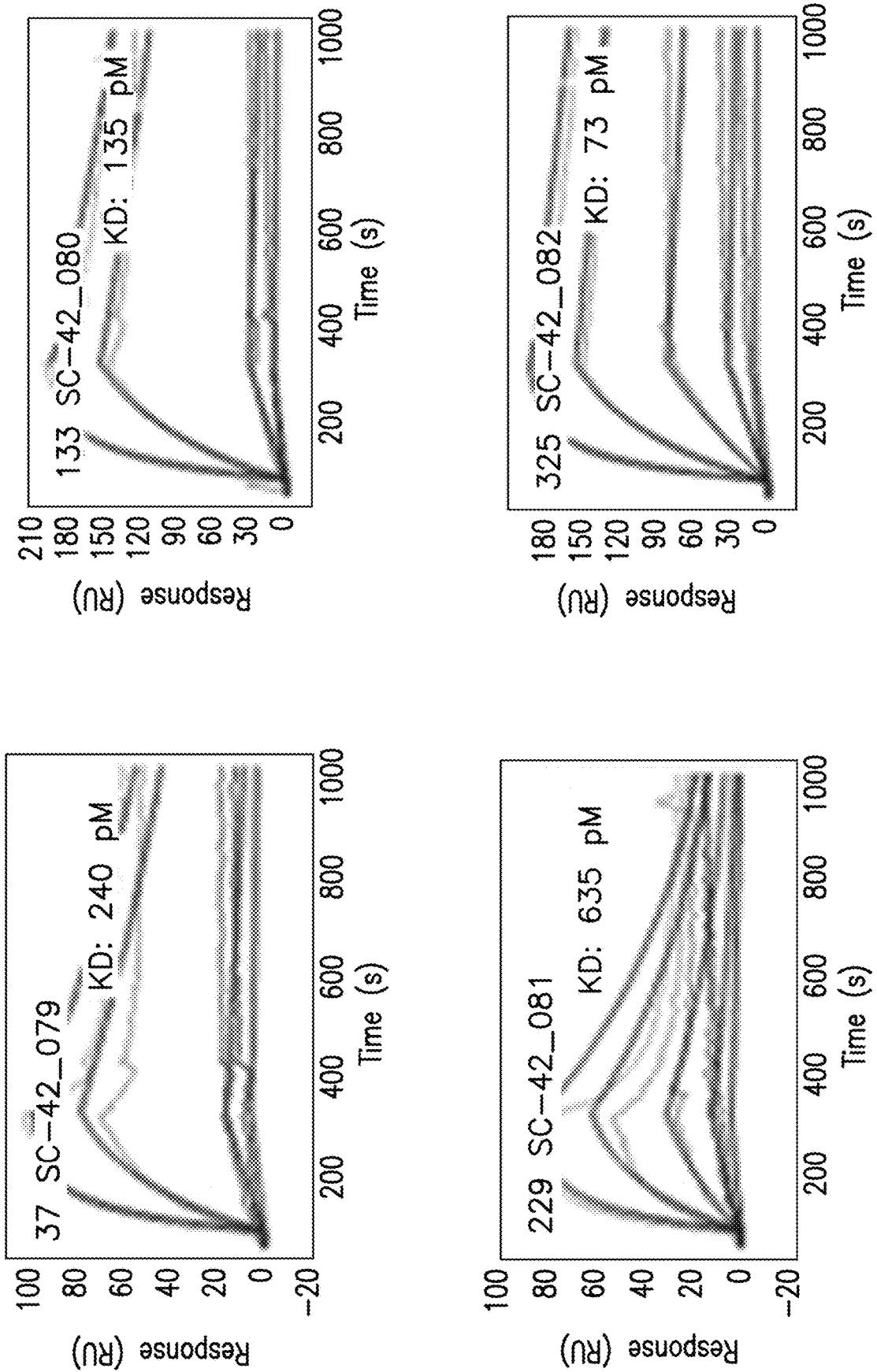
Figure 10:
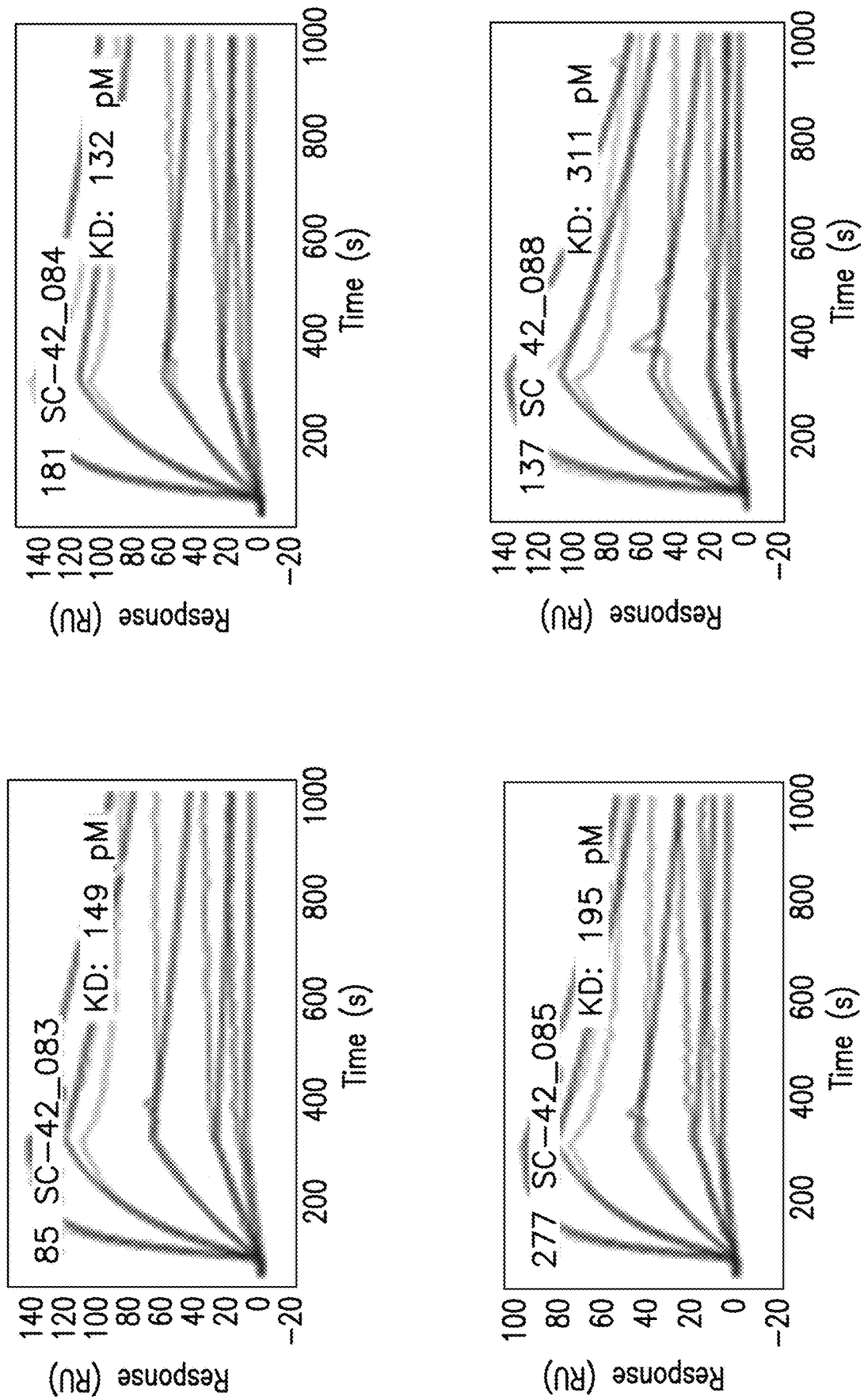
Figure 10:
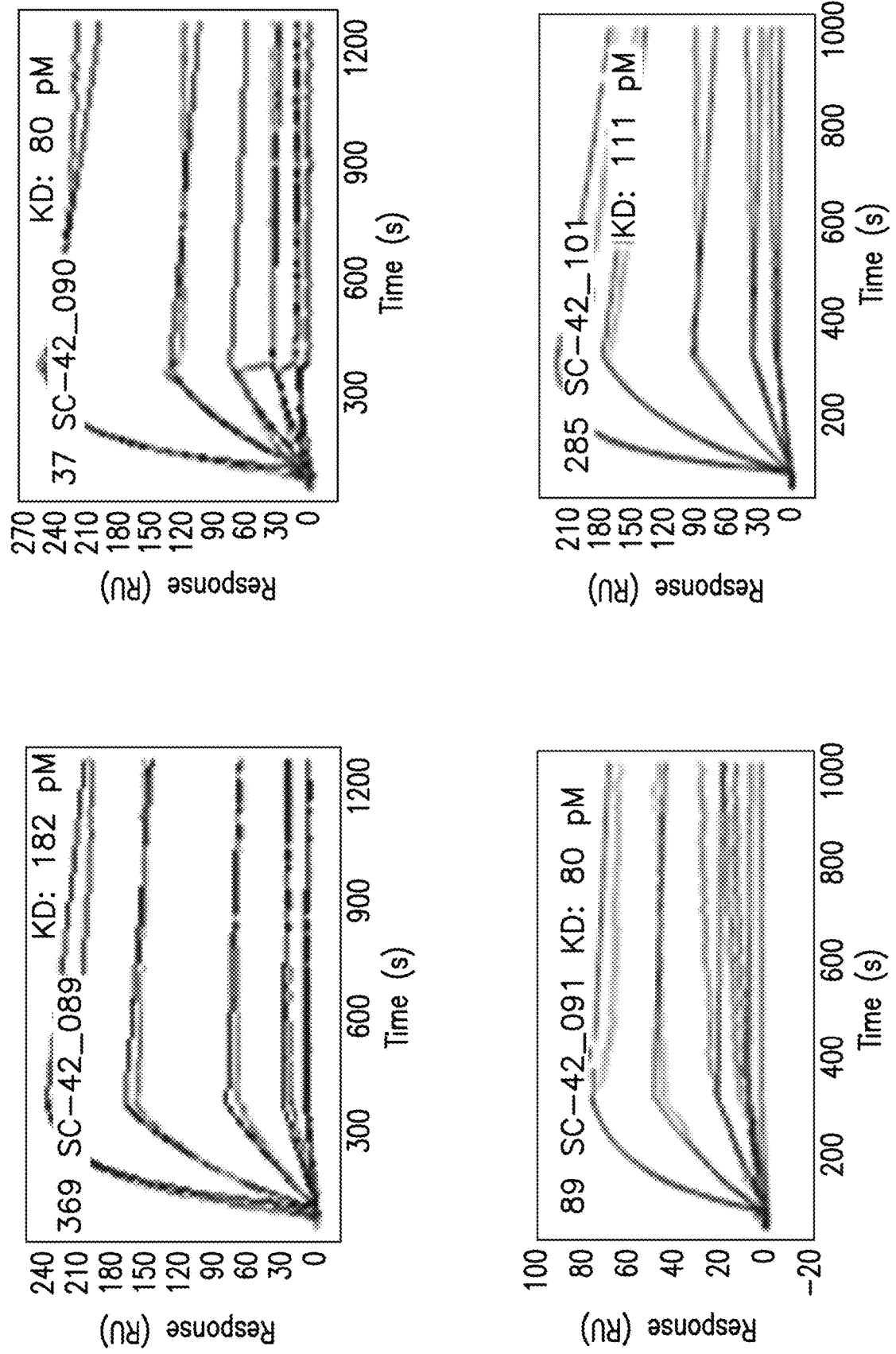

Sensorgrams for all 69 clones are in FIG. 10. The SPR was completed by amine coupling the antibody (~5 µg/ml) to the HC30M sensor chip by EDC/NHS activation, followed by ethanolamine HCL quenching. The canine NGF (Genbank NP_001181879.1) used as the analyte for the SPR analyses was the same preparation described in Example 1 for the canine NGF tagged at the C-terminus with the Flag tag (DYKDDDDK) (SEQ ID NO:221).

Figure 11:
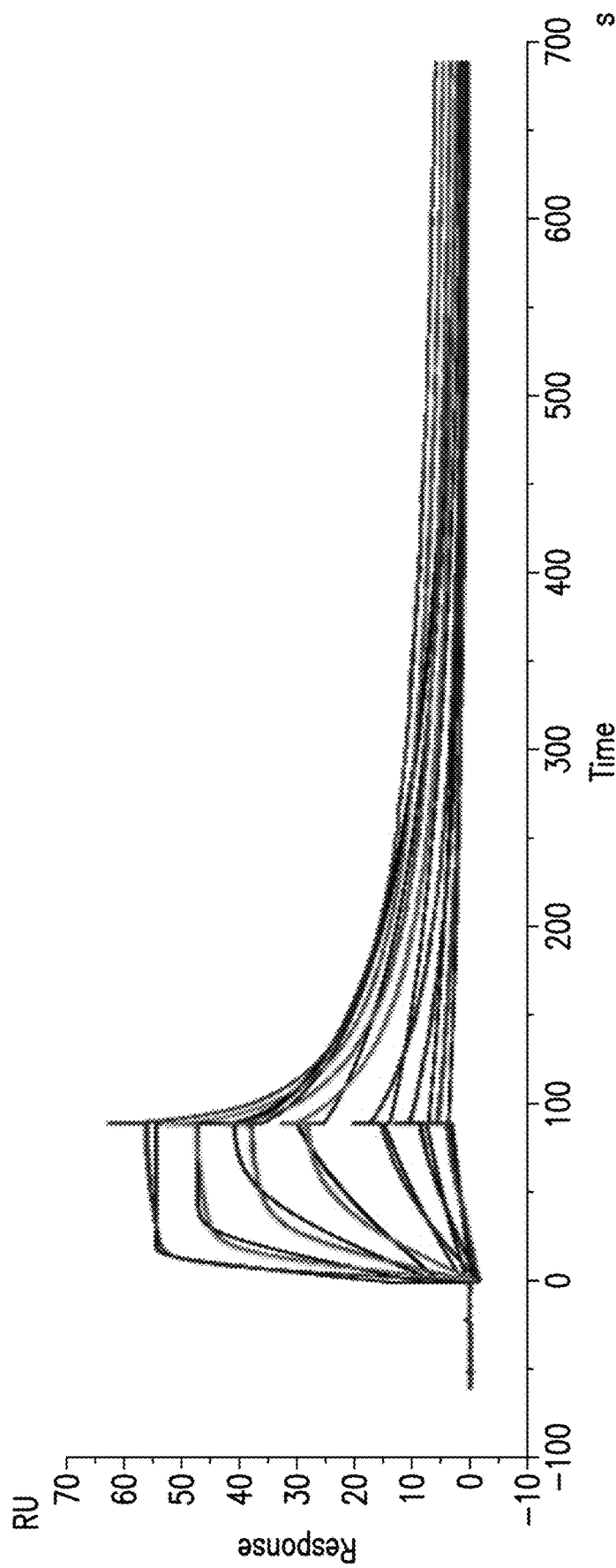
FIG. 11 is a sensorgram for canine NGF only binding to canine p75-Fc. The NGF concentrations 0.78, 1.56, 3.12, 6.25, 12.5, 25, and 50 nM.
Figure 12:
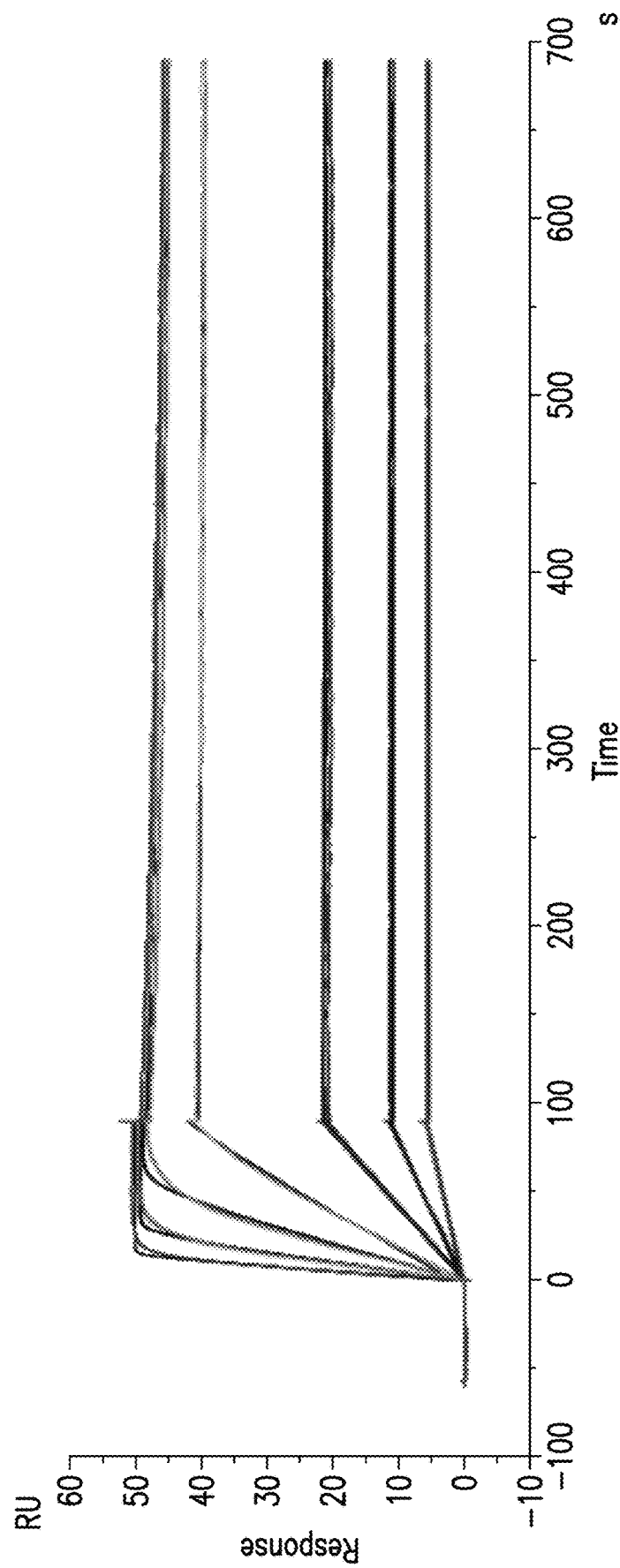
FIG. 12 is a sensorgram for canine NGF only binding to canine TrkA-Fc. The NGF concentrations 0.78, 1.56, 3.12, 6.25, 12.5, 25, and 50 nM.
Figure 13:
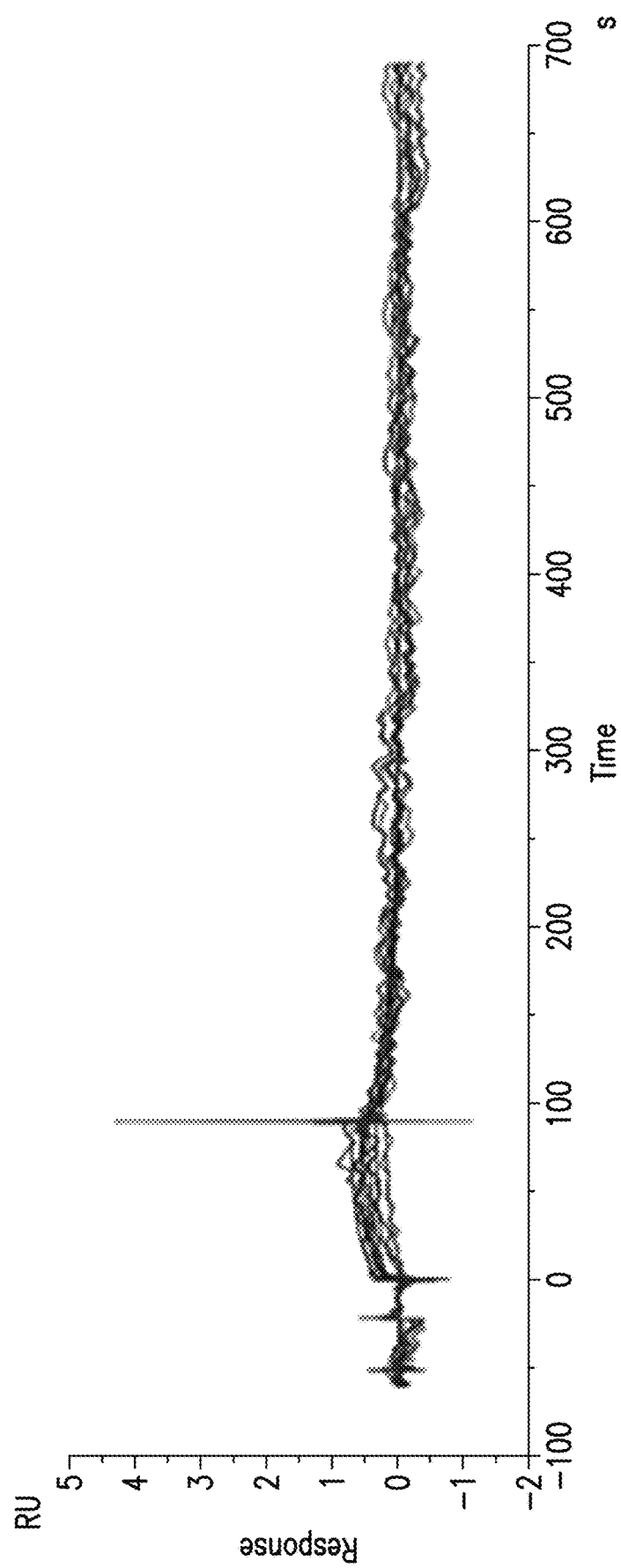
FIG. 13 is a sensorgram for caninized SC42_101 antibody-NGF mixture binding to canine p75-Fc. The NGF concentrations were 12.5, 25, and 50 nM.
Figure 14:
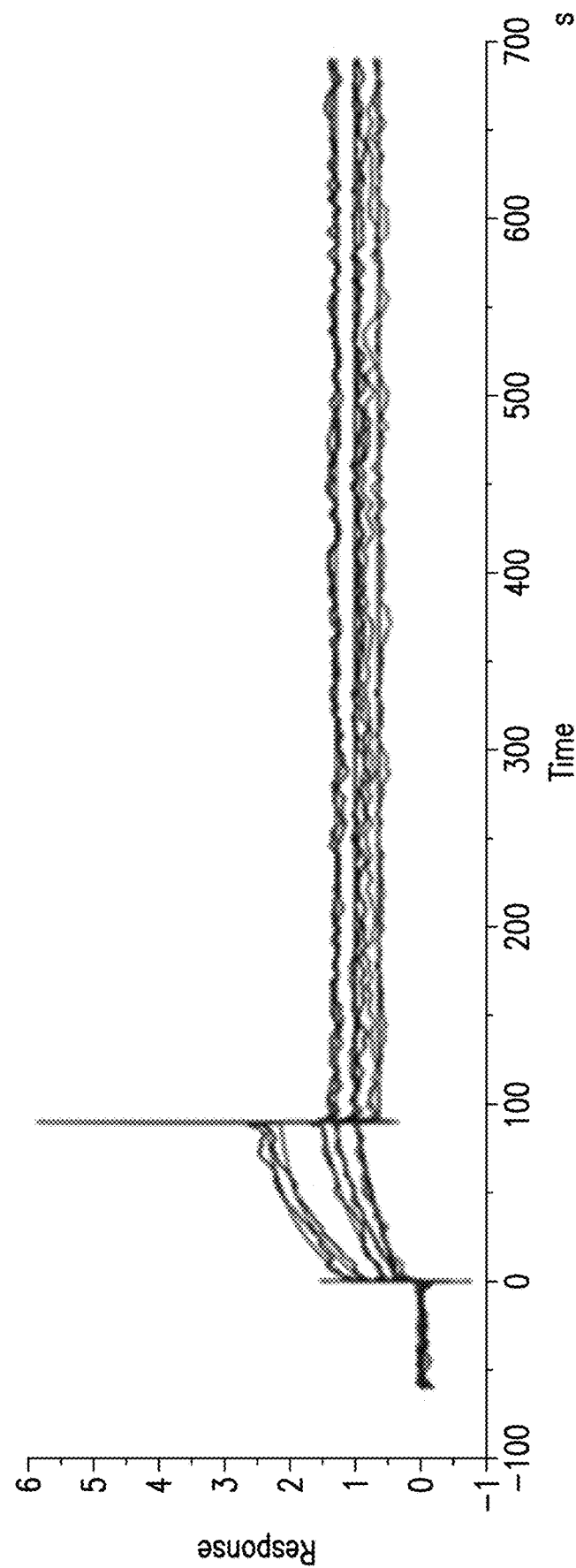
FIG. 14 is a sensorgram for caninized SC42_101 antibody-NGF mixture binding to canine TrkA-Fc. The NGF concentrations were 12.5, 25, and 50 nM.
Figure 16:
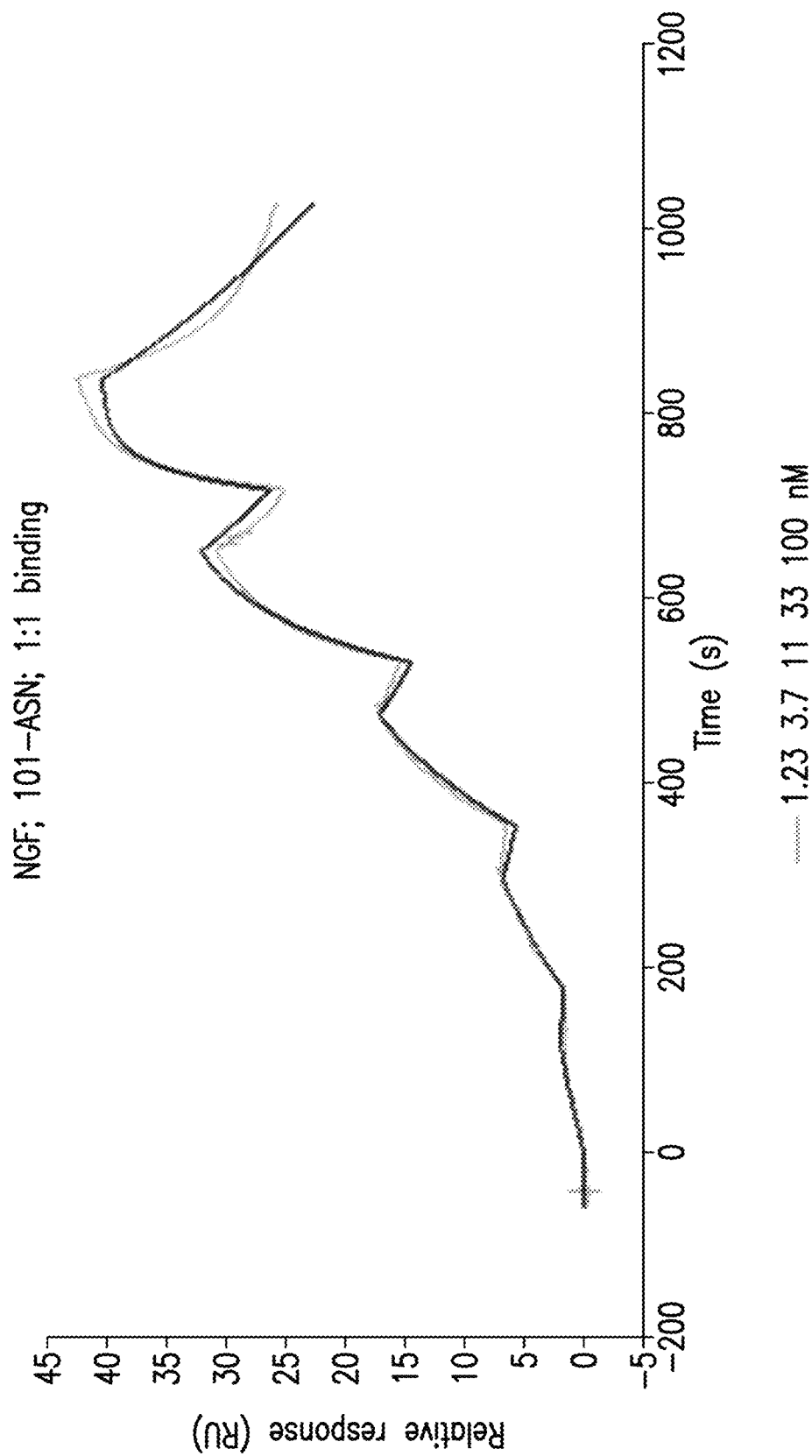
FIG. 16 is a sensorgram for felinized clone 101 binding to NGF. The NGF concentrations were 1.23, 3.7, 11, 33, and 100 nM.
Figure 18A:
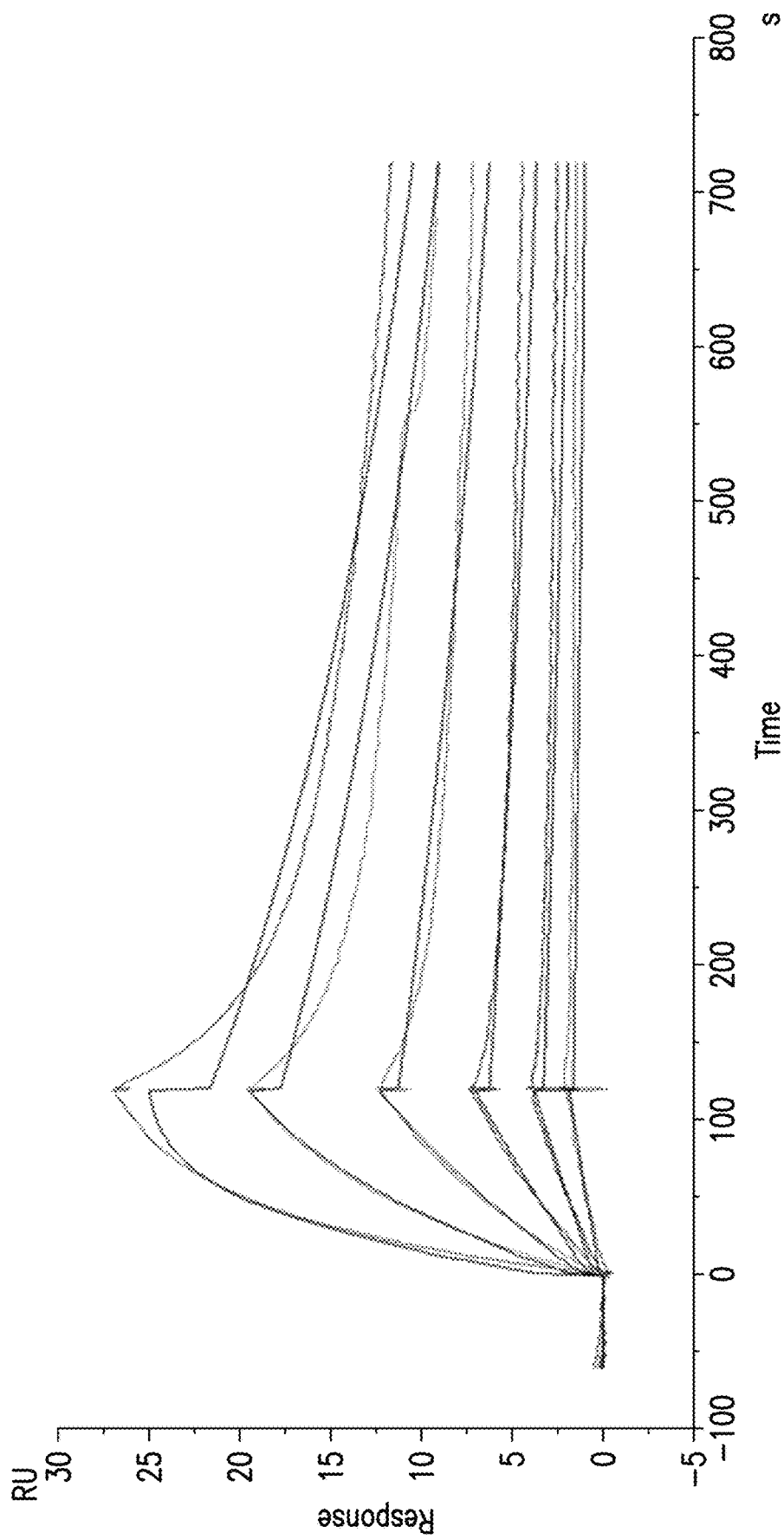
FIG. 18A-18H shows sensorgrams for affinity-matured feline antibodies: (A) clone 101; (B) AHF17602; (C) SC-184_76; (D) SC-184_76-Arg; (E) SC-102; (F) SC-184_102-Arg; (G) SC-110; (H) SC-184_110-Arg. The NGF concentrations were 50, 25, 12.5, 6.25, 3.125, and 1.56 nM.
Figure 18B:
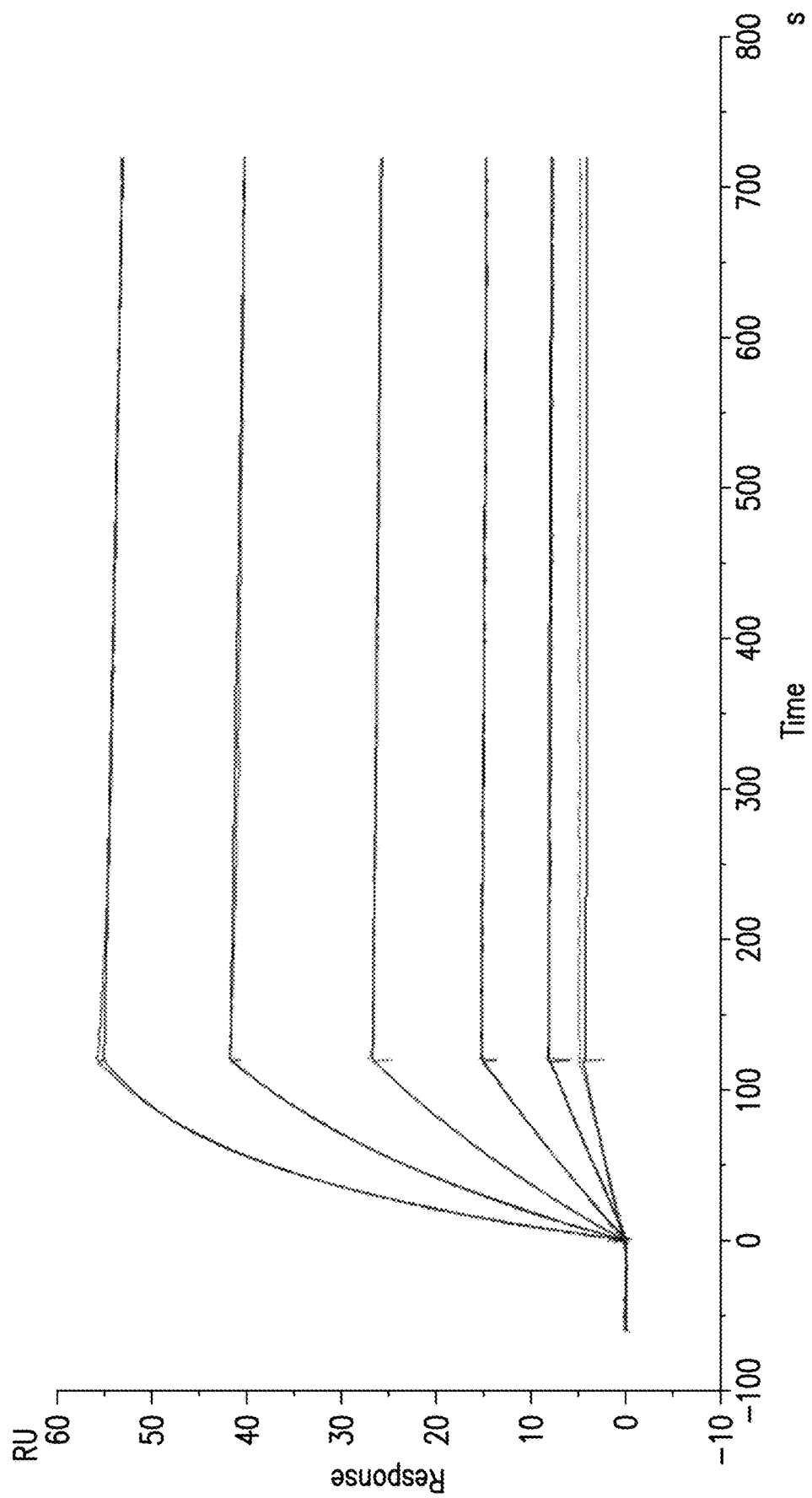
Figure 18C:
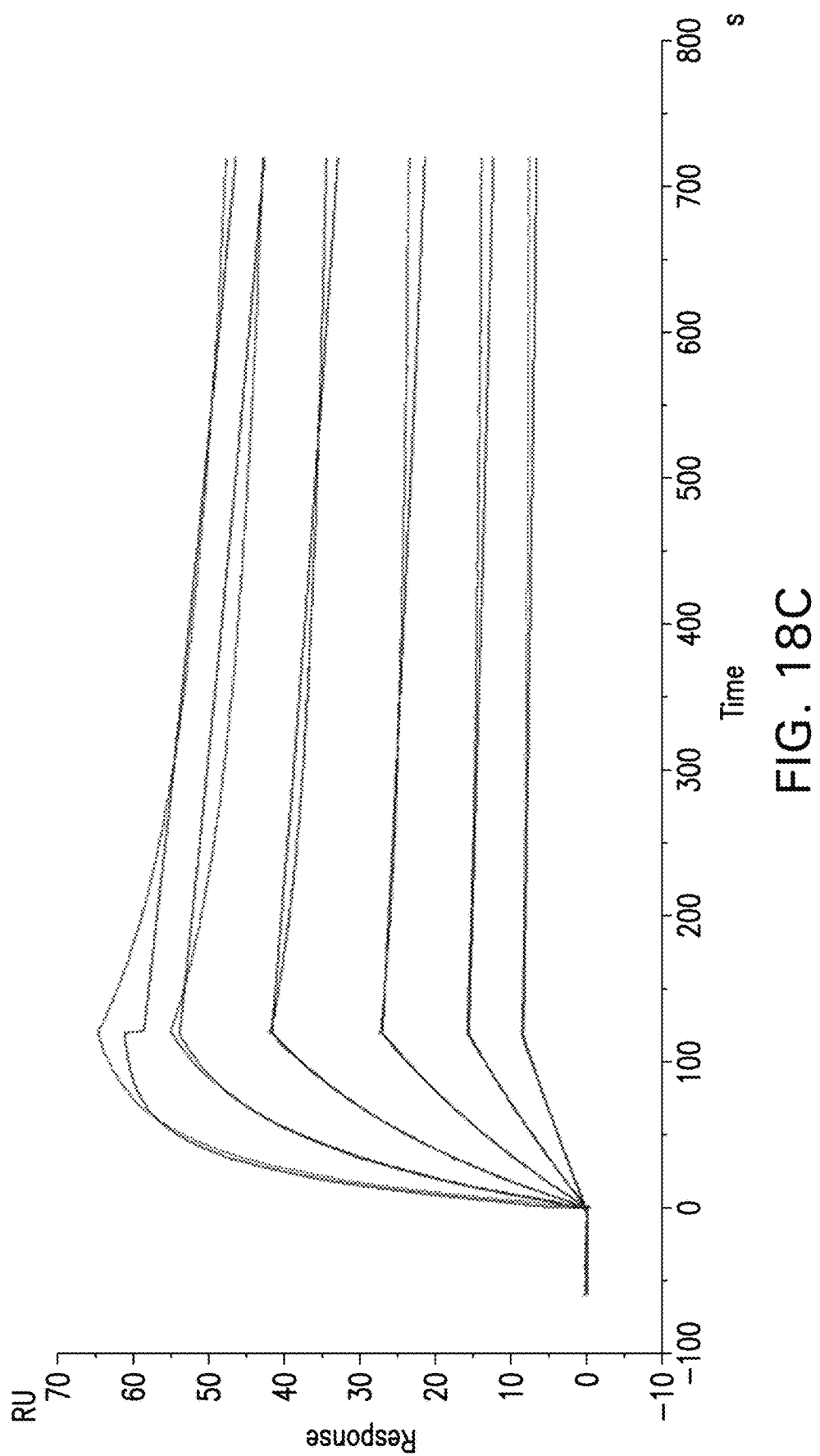
Figure 18D:
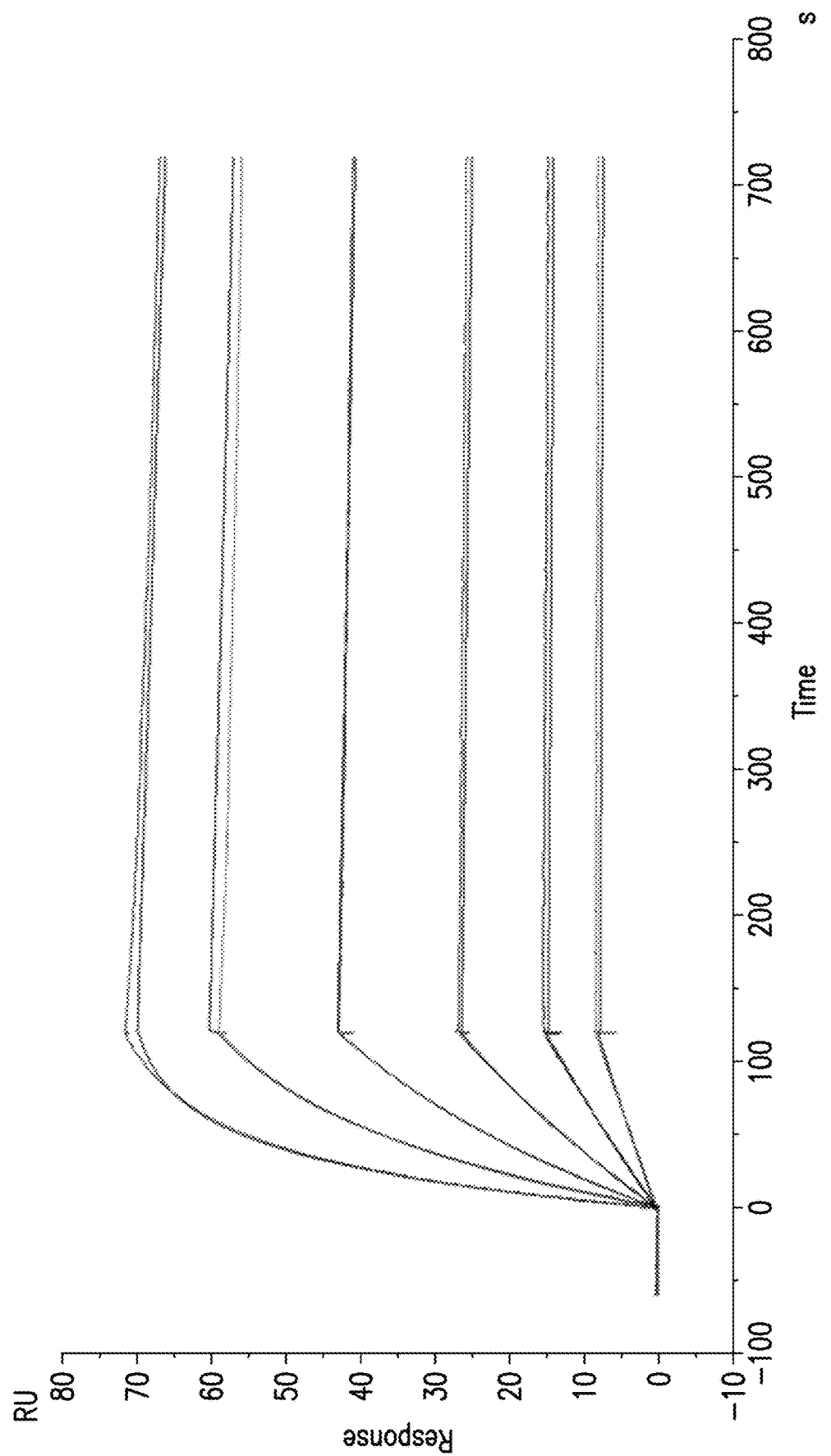
Figure 18E:
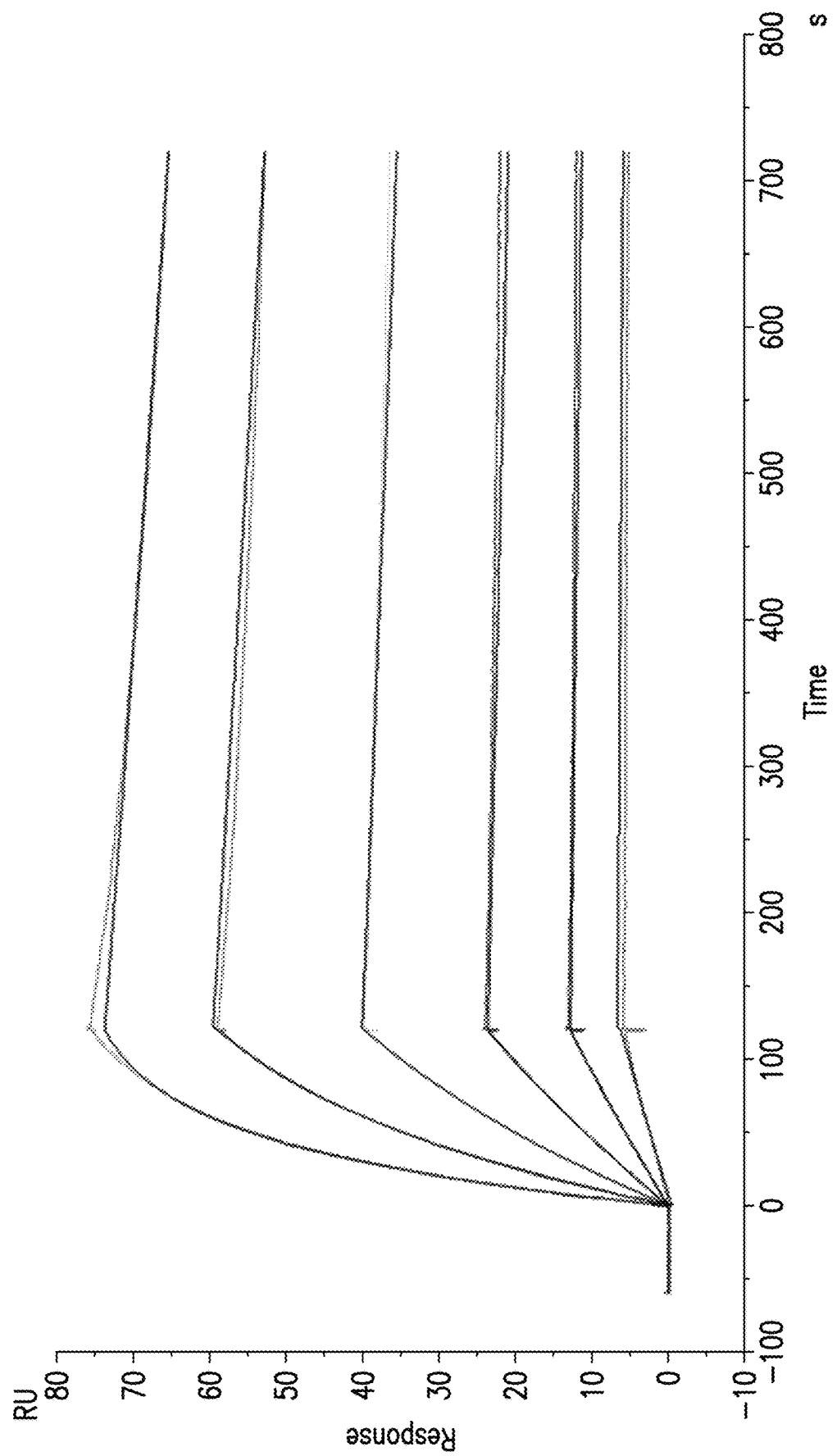
Figure 18F:
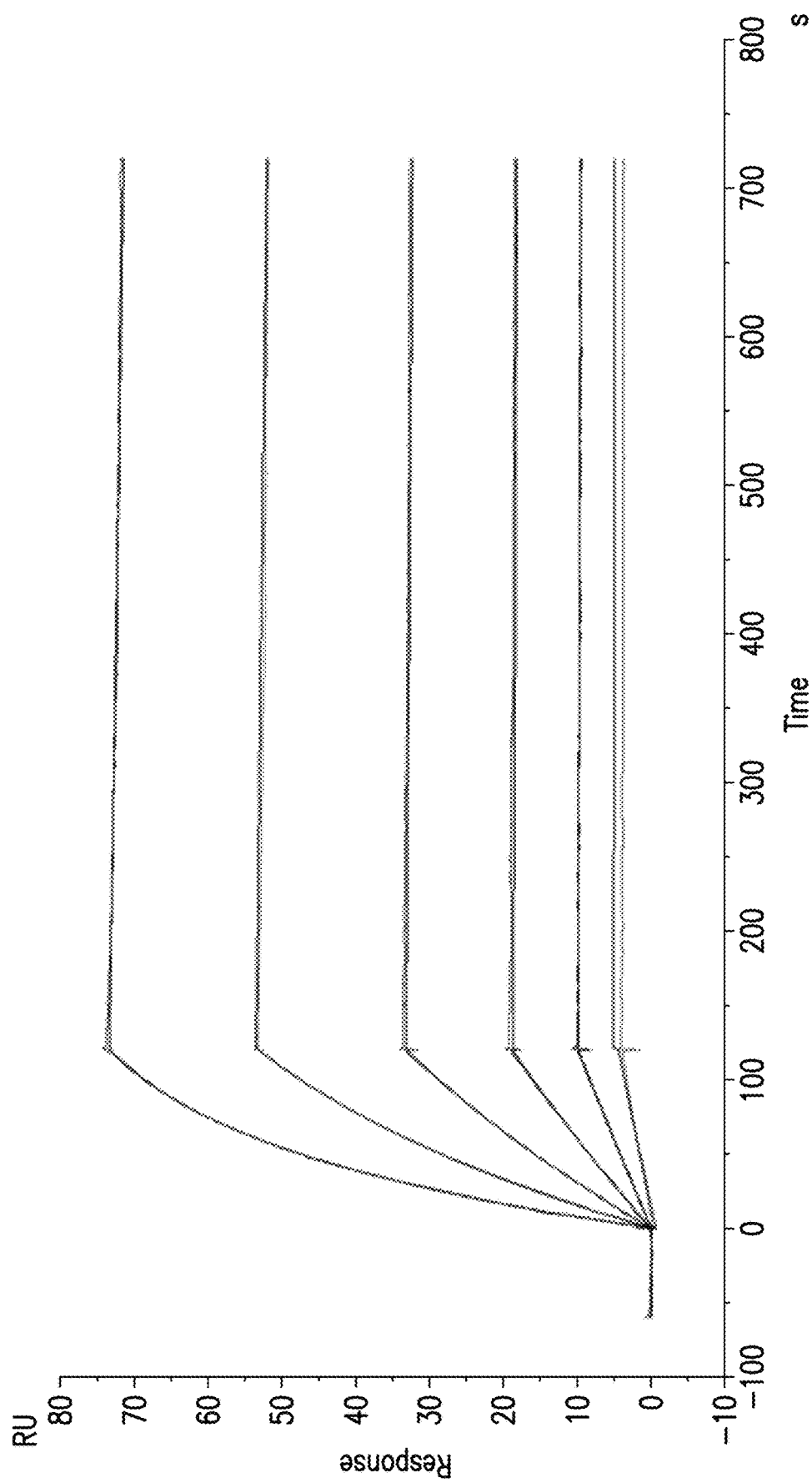
Figure 18G:
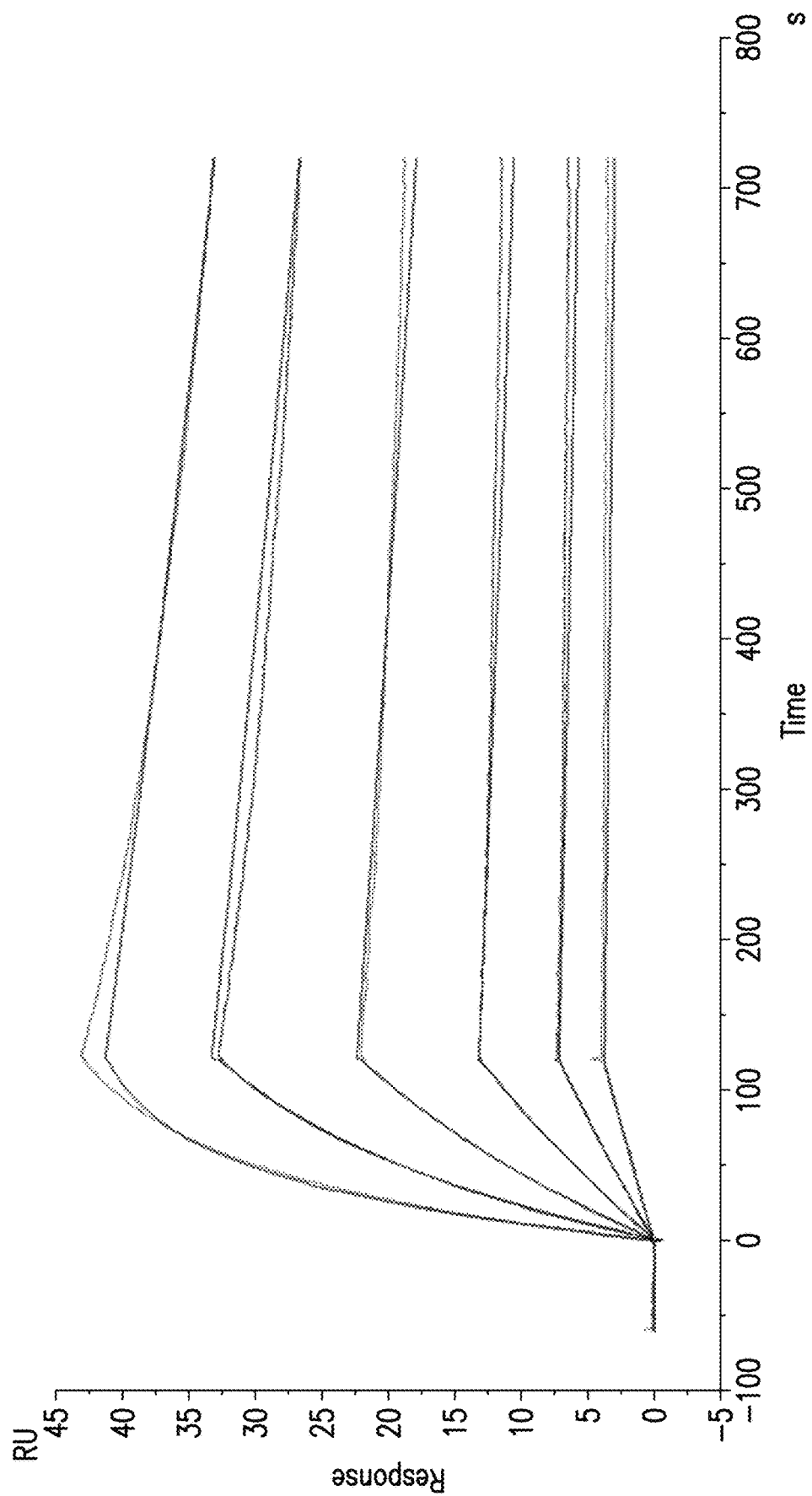
Figure 18H:
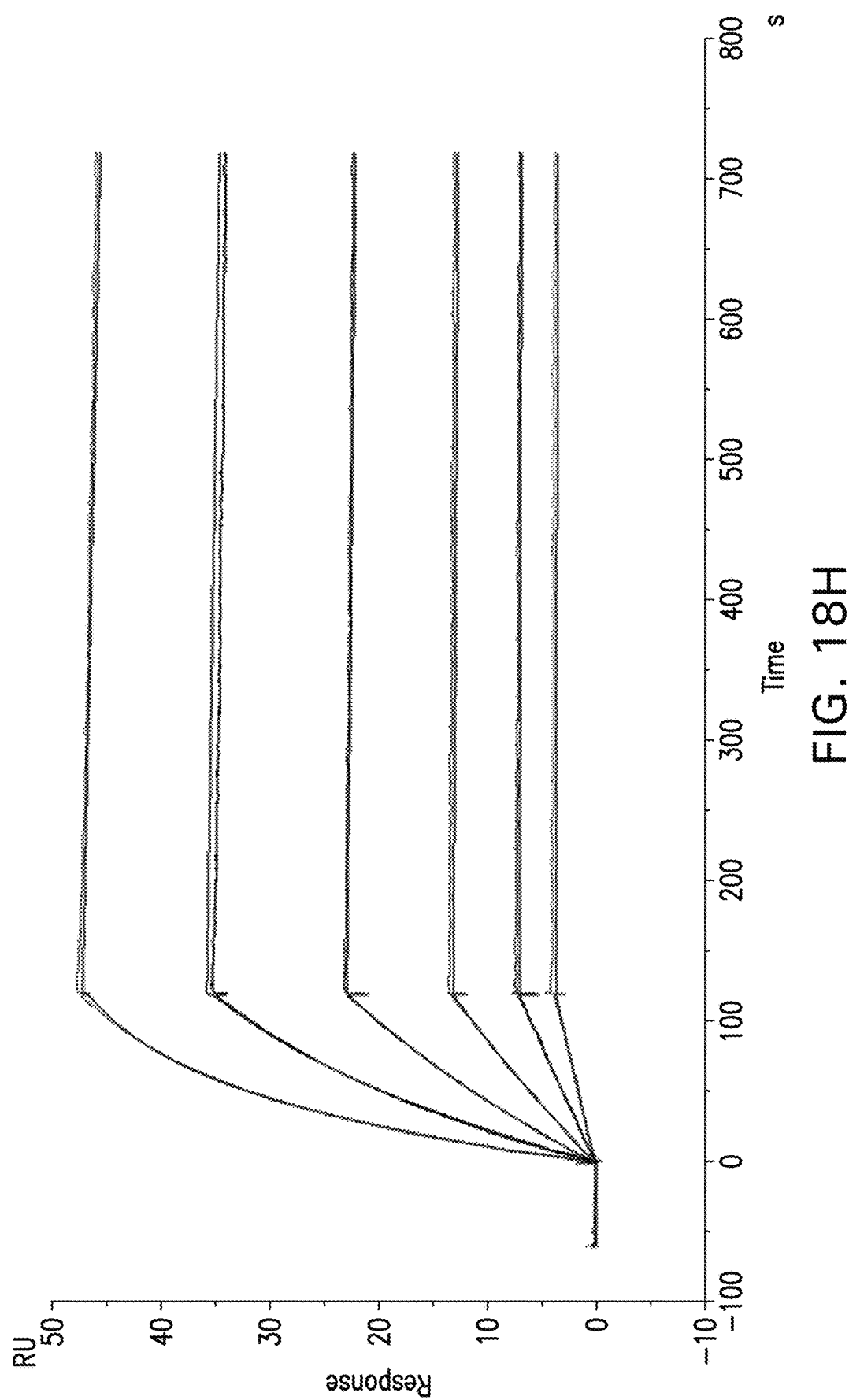

The ability of caninized SC42_101 antibody to block canine NGF from binding to the canine NGF receptors (TrkA and p75) was measured in an SPR assay on a Biacore T200. The format of the assay was to capture the NGF receptor on a sensor chip and flow over either canine NGF only, NGF mixed with caninized SC42_101 antibody, or caninized SC42_101 antibody only. The receptor blocking methods are identical to those described for canine 2166 chimeric antibody in Example 1. The sensorgrams (FIGS. 11, 12, 13, 14) represent the NGF only condition and the caninized SC42_101 antibody-NGF mixture for both the p75-Fc and TrkA-Fc receptors. Under these binding conditions, the binding kinetics for canine NGF only to canine p75 in a dimer format were $k_a$ (1/Ms)=3.8E+7, $k_d$ (1/s)=0.1, and $K_D$=2.7E-9 (FIG. 11). The binding kinetics for canine NGF only to canine TrkA in a dimer format were $k_a$ (1/Ms)=2.4E+7, $k_d$ (1/s)=1.6E-4, and $K_D$=6.6E-12 (FIG. 12). No binding to the canine NGF receptors was observed with the caninized SC42_101 antibody only condition (data not shown). As evidenced by the sensorgrams (FIGS. 13 and 14), caninized SC42_101 antibody effectively blocks canine NGF binding to canine TrkA and p75.

Example 3

Felinization of rat 2166 Antibody

A feline antibody database was generated by performing NGS (next generation sequencing) on feline PBMCs (peripheral blood mononuclear cells). This database contains the sequences from $7.5 \times 10^6$ $V_H$ domains, $1.3 \times 10^6$ VK domains and $3.8 \times 10^6$ $V_L$ domains. The HCDR 1, 2 and LCDR 1, 2, 3 sequences from the 2166 parental antibody were used in an algorithm to identify the closest feline CDR sequences and their linked framework sequences in the feline antibody database. These linked framework sequences were included in the scFv phage display library along with the closest framework germline sequences and the linked framework sequences with 1 to 3 residues reverted back to the closest germline. A proprietary algorithm was used to identify a set of CDR sequences that are similar to the original 2166 CDRs and closer in identity to the germline and expressed CDR sequences. These CDRs and framework sequences were used to generate a scFv antibody phage display library with a theoretical complexity of $3 \times 10^{12}$. The processed form of feline NGF (XP_004001166.1) is identical to the processed form of canine NGF (NP_001181879.1) so for the felininization studies, canine NGF tagged at the C-terminus with the Flag tag (DYKDDDDK) (SEQ ID NO:221) described in Example 1 was used.

Antibody phage selections were completed with NGF for four rounds and with each round the stringency was increased by reducing the antigen concentration and increasing the number of washes. Specifically, 96-multi well plates were coated with 200 pmol of NGF for the first round, 100 pmol for the second round and 50 pmol for the third and fourth rounds. The number of washes with PBS-tween 20 (0.01%) after the selection were six for the first round, seven for the second round, eight for the third round and nine for the fourth round. The output scFv clones from the third and fourth rounds were sequenced and unique clones were reformatted into IgGs and screened for binding to NGF by SPR. The variable domains of clone 101 are shown in FIG. 15 with the CDR regions underlined. The affinity of felinized clone 101 for NGF was determined by SPR. The format of this assay was to immobilize goat anti-cat IgG (30 µg/ml) on a series S CM5 biosensor using EDC/NHS and quenching the remaining sites with ethanolamine. Captured felinized clone 101 (1 µg/ml) onto the goat anti-cat IgG sensor chip. Using single cycle kinetics, five concentrations of NGF were captured. The binding kinetics for felinized clone 101 for NGF were $k_a$ (1/Ms)=3.8E+5, $k_d$ (1/s)=3E-3, and $K_D$=7.8E-9.

Example 4

Affinity maturation of felinized clone 101 using site-specific mutagenesis of the CDRs.

In the first affinity maturation approach, the heavy variable domain and $C_H1$ domain of feline clone 101 (Table 3) were subcloned in the GenScript FASEBA plasmid. The construct included at the C-terminus of the heavy chain (VH-CH1) a single-domain antibody against serum albumin (SASA) tag (see, e.g. US 2013/0129727A1) which has low pM affinity for albumin, and further downstream a His-tag for purification. The light chain variable domain was subcloned with feline $C_\kappa$ (Table 3) into a proprietary E. coli expression vector. Both the heavy chain and light chain had the PelB (pectate lyase B) signal peptide at the N-terminus to facilitate secretion of the Fab when expressed in TG1 E. coli. The expression of the variable domains was regulated by the Lac promoter.

TABLE 3

Sequences

```
clone    DVQLVESGGD LVKPGGSLRL TCVASGLSLT SSSMSWVRQA PGKGLQWVST
101      IYSNGGTYYT DSVKGRFTIS KDNAENTLYL QMNNLKTEDT ATYYCASIYY
VH-CH1   YDADYLHWYF DFWGQGALVT VSSASTTAPS VFPLAPSCGT TSGATVALAC
(IgG1)   LVLGYFPEPV TVSWNSGALT SGVHTFPAVL QASGLYSLSS MVTVPSSRWL
         SDTFTCNVAH PPSNTKVDKT V (SEQ ID NO: 182)

clone 1  EIQMTQSPTS LSASVGDRVT ITCRASEGIS NNLSWYQQTP GKAPKLLIYA
VL-Cκ1   TSNLHSGVPS RFSGSGSGTD FTLTISSLQP EDFATYYCQQ GYKWPLTFGG
         GTKLEITRSD AQPSVELFQP SLDELHTGSA SIVCILNDFY PKEVNVKWKV
         DGVVQNKGIQ ESTTEQNSKD STYSLSSTLT MSSTEYQSHE KFSCEVTHKS
         LASTLVKSEN RSECQRE (SEQ ID NO: 183)
```

A variant library was generated for each CDR position in the heavy and light chains using the GenScript proprietary Precision Mutant Library (PML) which utilizes semiconductor-based oligonucleotide synthesis technology. In generating the mutants, the CDRs were defined using a combination of Kabat and IMGT methodology and the residues selected for each CDR are shown below in Table 4. The residue numbers for the CDRs are shown in parentheses.

TABLE 4

CDR sequences and numbering

| VH | | VL | |
|---|---|---|---|
| CDR1 | GLSLTSSSMS (26-35) (SEQ ID NO: 222) | CDR1 | RASEGISNNLS (24-34) (SEQ ID NO: 225) |
| CDR2 | TIYSNGGTYYTDSVKG (50-65) (SEQ ID NO: 223) | CDR2 | ATSNLHS (50-56) (SEQ ID NO: 226) |
| CDR3 | ASIYYYDADYLHWYFDF (96-112) (SEQ ID NO: 224) | CDR3 | QQGYKWPLT (89-97) (SEQ ID NO: 227) |

The quality of the libraries was verified using NGS (Next Generation Sequencing). Forty-four PML clones were selected from each library for expression in *E. coli* in 96 deep-well plates by inoculating into 2YT medium and inducing with 0.2 mM IPTG overnight at room temperature. The Fab secreted in the medium was analyzed for binding activity by completing an ELISA. In this ELISA, plates were coated with 10 µg/ml of BSA overnight at 4° C., washed 3× with 0.1% tween 20 in PBS, pH 7.4 (PBST), blocked non-specific interactions with 3% non-fat dry milk in PBS (phosphate-buffered saline, pH 7.4) at 37° C. for 1 hour, washed 3× with PBST, added crude Fab supernatant (diluted 1:1 with PBST) incubated at 37° C. for 1 hour, washed 3× with PBST, added 0.15 µg/ml of NGF incubated at 37° C. for 1 hour, washed 3× with PBST, added horseradish peroxidase (HRP) conjugated anti-Flag tag antibody (Flag tag present on NGF) incubated at room temperature for 45 minutes, washed 3× with PBST and detected the HRP conjugate by incubating with TMB substrate for 10 minutes at room temperature and measured absorbance at 450 nm. The top 100 clones with an apparent increase in affinity as measured by ELISA were sequenced to detect the variant in the CDR and 57 unique clones were identified. Mutations from clone 101 for each of the 57 clones are tallied in Table 5.

TABLE 5

Individual mutations at each position compared to clone 101

| | CDR1H | | | | CDR2H | | | | | | | CDR3H | | | | |
|---|---|---|---|---|---|---|---|---|---|---|---|---|---|---|---|---|
| | 28 | 30 | 31 | 35 | 52 | 53 | 55 | 58 | 60 | 62 | 64 | 97 | 99 | 101 | 104 | 112 |
| 101 | S | T | S | S | Y | S | G | Y | T | S | K | S | Y | Y | D | F |
| | H | N | H | V | W | P | R | D | H | D | E | Q | F | H | K | E |
| | | R | | | | | Y | | D | | D | M | | | E | P |
| | | | | | | | | | S | | | N | | | N | H |
| | | | | | | | | | E | | | K | | | Q | N |
| | | | | | | | | | | | | H | | | | |
| | | | | | | | | | | | | T | | | | |

| | CDR1L | | | | CDR2L | | | |
|---|---|---|---|---|---|---|---|---|
| | 24 | 30 | 31 | 34 | 53 | 54 | 55 | 56 |
| 101 | R | S | N | S | N | L | H | S |
| | F | A | Q | G | I | H | M | T |
| | | Q | | A | V | | I | D |
| | | V | | | K | | L | E |
| | | L | | | H | | | N |
| | | P | | | M | | | |
| | | Y | | | L | | | |

Binding of the 57 unique clones were confirmed by an off-rate screening assay in an SPR assay performed on a Biacore T200. For the SPR analyses, bovine serum albumin (BSA) was immobilized to CM5 sensor chip. The sensor chip surface was activated with 50 mmol/L H-Hydroxysuccinimide and 200 mmol/L 1-ethyl-3-(3-dimethylaminopropyl) carbodiimide hydrochloride for 420 s. Afterwards, BSA diluted in 10 mM sodium acetate, pH 4.5 was injected. After the amine coupling reaction, the remaining active coupling sites on the chip surface were blocked with 1 mM ethanolamine hydrochloride. The selected Fab-SASA variants in conditioned medium were captured on the BSA-coated chips. The running buffer was HBS-EP (10 mM HEPES 500 mM NaCl, 3 mM EDTA, 0.05% Tween 20, pH 7.4). After equilibration, antigen was injected for 120 seconds (association phase) followed by the injection of running buffer for 420 sec (dissociation phase). The off-rates of the Fab-SASA clones were obtained from fitting the experimental data locally to a 1:1 interaction model using the Biacore T200 evaluation software. The Fab variants were ranked by their dissociation rate constants (off-rates, kd) shown in Table 6.

TABLE 6

Rank ordering of the Fab variants based on dissociation constants

| Sequence Analysis | ka (1/Ms) | kd (1/s) | KD (M) | Rmax (RU) | Chi$^2$ (RU$^2$) | Ratio WT-kd/ clone-kd |
|---|---|---|---|---|---|---|
| G55R | 1.20E+05 | 1.47E−04 | 1.23E−09 | 19.7 | 0.00634 | 6.41 |
| S30A | 2.77E+05 | 2.92E−04 | 1.05E−09 | 152.2 | 0.618 | 3.23 |
| H55M | 3.33E+05 | 3.12E−04 | 9.35E−10 | 137.7 | 0.712 | 3.02 |
| S30Q | 2.59E+05 | 3.24E−04 | 1.25E−09 | 132.5 | 0.462 | 2.91 |
| D104K | 6.09E+04 | 3.32E−04 | 5.45E−09 | 64.6 | 0.0316 | 2.84 |
| S35V | 3.09E+05 | 3.60E−04 | 1.17E−09 | 106.1 | 0.414 | 2.62 |
| N53I | 2.76E+05 | 3.89E−04 | 1.41E−09 | 118 | 0.347 | 2.42 |
| F112E | 2.84E+05 | 3.99E−04 | 1.41E−09 | 147.2 | 0.488 | 2.36 |
| S97Q | 2.97E+05 | 4.03E−04 | 1.36E−09 | 79.5 | 0.287 | 2.34 |
| N53V | 2.88E+05 | 4.07E−04 | 1.42E−09 | 108.7 | 0.375 | 2.32 |
| H55L | 2.64E+05 | 4.18E−04 | 1.58E−09 | 91.8 | 0.494 | 2.26 |
| G55Y | 2.29E+05 | 4.19E−04 | 1.83E−09 | 17.7 | 0.0131 | 2.25 |
| D104E | 2.37E+05 | 4.26E−04 | 1.80E−09 | 66.4 | 0.126 | 2.21 |
| H55I | 3.34E+05 | 4.36E−04 | 1.31E−09 | 100.7 | 0.67 | 2.16 |
| D104N | 2.39E+05 | 4.46E−04 | 1.87E−09 | 52.8 | 0.0774 | 2.11 |
| S97M | 2.66E+05 | 4.66E−04 | 1.75E−09 | 64.3 | 0.149 | 2.02 |
| Y99F | 3.21E+05 | 4.69E−04 | 1.46E−09 | 100.8 | 0.439 | 2.01 |
| K64E | 1.96E+05 | 4.76E−04 | 2.42E−09 | 50.2 | 0.164 | 1.98 |
| D104Q | 2.20E+05 | 4.78E−04 | 2.17E−09 | 49.6 | 0.056 | 1.97 |
| N31Q | 3.27E+05 | 4.80E−04 | 1.47E−09 | 80.2 | 0.343 | 1.96 |
| S97N | 3.73E+05 | 4.81E−04 | 1.29E−09 | 69.6 | 0.317 | 1.96 |
| S30V | 2.87E+05 | 4.83E−04 | 1.68E−09 | 59.3 | 0.22 | 1.95 |
| Y101H | 3.07E+05 | 4.96E−04 | 1.62E−09 | 61.8 | 0.194 | 1.90 |
| S30L | 2.70E+05 | 5.07E−04 | 1.87E−09 | 92.6 | 0.914 | 1.86 |
| S97K | 3.31E+05 | 5.11E−04 | 1.54E−09 | 62.3 | 0.226 | 1.85 |
| S34G | 4.56E+05 | 5.14E−04 | 1.13E−09 | 65.8 | 0.571 | 1.83 |
| S97H | 2.97E+05 | 5.33E−04 | 1.79E−09 | 72 | 0.198 | 1.77 |
| F112P | 3.98E+05 | 5.52E−04 | 1.39E−09 | 48 | 0.164 | 1.71 |
| K64D | 3.40E+05 | 5.54E−04 | 1.63E−09 | 48.1 | 0.189 | 1.70 |
| S62D | 3.01E+05 | 5.60E−04 | 1.86E−09 | 103.3 | 0.405 | 1.68 |
| L54H | 3.40E+05 | 5.60E−04 | 1.65E−09 | 75.6 | 0.357 | 1.68 |
| T60H | 3.12E+05 | 5.61E−04 | 1.80E−09 | 77.5 | 0.316 | 1.68 |
| Y58D | 3.81E+05 | 5.62E−04 | 1.47E−09 | 108.4 | 0.571 | 1.68 |
| T60D | 2.94E+05 | 5.67E−04 | 1.93E−09 | 90.6 | 0.299 | 1.66 |
| T60S | 3.25E+05 | 5.73E−04 | 1.76E−09 | 80.6 | 0.33 | 1.65 |
| N53K | 2.92E+05 | 5.96E−04 | 2.04E−09 | 60.5 | 0.172 | 1.58 |
| S31H | 3.10E+05 | 6.12E−04 | 1.98E−09 | 66.6 | 0.291 | 1.54 |
| N53H | 3.22E+05 | 6.27E−04 | 1.95E−09 | 69.4 | 0.177 | 1.50 |
| F112H | 3.28E+05 | 6.39E−04 | 1.95E−09 | 81.8 | 0.407 | 1.48 |
| F112N | 3.47E+05 | 6.43E−04 | 1.85E−09 | 72 | 0.316 | 1.47 |
| N53M | 3.46E+05 | 6.48E−04 | 1.87E−09 | 53.7 | 0.312 | 1.46 |
| Y52W | 4.34E+05 | 6.51E−04 | 1.50E−09 | 41.3 | 0.258 | 1.45 |
| R24F | 2.87E+05 | 6.55E−04 | 2.28E−09 | 89.3 | 0.273 | 1.44 |
| N53L | 3.21E+05 | 6.67E−04 | 2.08E−09 | 60 | 0.188 | 1.41 |
| S30P | 2.62E+05 | 6.70E−04 | 2.56E−09 | 75.4 | 0.211 | 1.41 |
| T60E | 2.87E+05 | 6.83E−04 | 2.38E−09 | 77.7 | 0.289 | 1.38 |
| S53P | 3.23E+05 | 6.95E−04 | 2.15E−09 | 56.6 | 0.183 | 1.36 |
| T30N | 3.33E+05 | 7.04E−04 | 2.12E−09 | 71.2 | 0.287 | 1.34 |
| F112E | 2.94E+05 | 7.08E−04 | 2.41E−09 | 64.9 | 0.221 | 1.33 |
| S56T | 3.58E+05 | 7.14E−04 | 1.99E−09 | 65.5 | 0.414 | 1.32 |
| S97T | 3.80E+05 | 7.16E−04 | 1.88E−09 | 51.1 | 0.207 | 1.32 |
| T30R | 3.57E+05 | 7.30E−04 | 2.05E−09 | 61.2 | 0.261 | 1.29 |
| S56D | 3.72E+05 | 7.55E−04 | 2.03E−09 | 49.1 | 0.224 | 1.25 |
| S30Y | 3.55E+05 | 7.82E−04 | 2.20E−09 | 60.5 | 0.4 | 1.21 |
| S34A | 4.50E+05 | 7.83E−04 | 1.74E−09 | 50.4 | 0.361 | 1.20 |

TABLE 6-continued

Rank ordering of the Fab variants based on dissociation constants

| Sequence Analysis | ka (1/Ms) | kd (1/s) | KD (M) | Rmax (RU) | Chi$^2$ (RU$^2$) | Ratio WT-kd/clone-kd |
|---|---|---|---|---|---|---|
| S28H | 3.15E+05 | 8.02E−04 | 2.55E−09 | 79.8 | 0.244 | 1.18 |
| S56E | 3.70E+05 | 8.09E−04 | 2.19E−09 | 54.6 | 0.249 | 1.17 |
| S56N | 3.41E+05 | 9.03E−04 | 2.64E−09 | 50.6 | 0.178 | 1.04 |
| Wild-Type | 3.59E+05 | 9.39E−04 | 2.62E−09 | 59.1 | 0.241 | 1.00 |
| Wild-Type | 3.55E+05 | 9.43E−04 | 2.655E−09 | | | 1.00 |
| Wild-Type | 3.51E+05 | 9.47E−04 | 2.69E−09 | 60.1 | 0.235 | 1.00 |

Fab variants G55R, S30A, S30Q, S35V, N53I, F112E, S97Q, and N53V were selected for combinatorial library construction (Table 7).

TABLE 7

Selected Fab variants for combinatorial library

| | VH | | | | VL | |
|---|---|---|---|---|---|---|
| Position | 35 | 55 | 97 | 112 | 30 | 53 |
| Wild-Type | S | G | S | F | S | N |
| Variant | V | R | Q | E | A | I |
| | | | | | Q | V |

The combinatorial library was constructed in the same Fab-SASA vector described above. The theoretical diversity of the combinatorial library is 2×2×2×2×3×3=144 and the size of the constructed library was 5.6×10$^7$ CFU (colony forming units). The library in-frame rate and diversity were evaluated by DNA sequencing and the results are shown in the tables below.

TABLE 8

Percentage of in-frame Fab-SASA construct in combinatorial library

| | Clones for sequencing | Sequences with stop codons | In-frame rate | Unique clones |
|---|---|---|---|---|
| VH | 47 | 3 | 44/47 = 93.6% | 12 |
| VL | 47 | 2 | 45/47 = 95.7% | 9 |

TABLE 9

Diversity of heavy chain variants in combinatorial library

| Chain | Number of clones | S35V | G55R | S97Q | F112E |
|---|---|---|---|---|---|
| VH | 44 | S(30), V(14) | G(10), R(34) | S(36), Q(8) | F(33), E(11) |

TABLE 10

Diversity of light chain variants in combinatorial library

| Chain | Number of clones | S30A/Q | N53I/V |
|---|---|---|---|
| VL | 43 | S(16), A(21), Q(8) | N(13), I(17), V(15) |

From the combinatorial library, 184 clones were randomly selected and the binding by the NGF ELISA was completed. The NGF ELISA was the same method as described above. The top 20 clones in ELISA binding were sequenced and tested in the SPR off-rate assay. Binding results are shown by amino acid combination in Table 11. Table 12 indicates variable domain sequence IDs for the top 20 clones. The pairings of VH and VL indicate substantial compatibility of the VH and VL mutations and interchangeability of the VH and VL domains.

TABLE 11

Affinity matured Fab variants from the combinatorial library

| | VH | | | | VL | | | | | Ratio (kd) | Ratio (KD) | |
|---|---|---|---|---|---|---|---|---|---|---|---|---|
| Antibody ID | 35 S | 55 G | 97 S | 112 F | 30 S | 53 N | ka (1/Ms) | kd (1/s) | KD (M) | WT/clones | WT/clones | Rmax (RU) |
| AHF17591 | V | R | S | E | A | I | 2.68E+05 | 1.00E−06 | 3.73E−12 | 1685.00 | 925.94 | 19.3 |
| AHF17598 | V | R | S | E | A | I | 2.94E+05 | 5.25E−05 | 1.79E−10 | 32.10 | 19.30 | 25.9 |
| AHF17592 | V | R | S | F | S | V | 1.92E+05 | 1.46E−05 | 7.61E−11 | 115.41 | 45.40 | 28.5 |
| AHF17600 | V | R | S | F | S | V | 1.77E+05 | 5.81E−05 | 3.29E−10 | 29.00 | 10.50 | 26.7 |
| AHF17593 | V | R | Q | F | A | V | 1.63E+05 | 1.00E−06 | 6.13E−12 | 1685.00 | 563.17 | 24.4 |
| AHF17594 | V | G | S | F | A | V | 3.53E+05 | 3.28E−04 | 9.31E−10 | 5.14 | 3.71 | 86.1 |
| AHF17595 | V | R | S | E | Q | N | 1.78E+05 | 1.00E−06 | 5.62E−12 | 1685.00 | 614.99 | 41.6 |
| AHF17596 | V | R | S | F | A | V | 2.27E+05 | 1.82E−05 | 8.02E−11 | 92.58 | 43.08 | 31.5 |
| AHF17608 | V | R | S | F | A | V | 2.28E+05 | 1.00E−06 | 4.39E−12 | 1685.00 | 787.74 | 28.8 |
| AHF17599 | V | R | S | F | A | V | 2.12E+05 | 1.00E−06 | 4.72E−12 | 1685.00 | 732.46 | 34.9 |
| AHF17597 | V | R | S | F | Q | I | 1.99E+05 | 1.08E−05 | 5.44E−11 | 156.02 | 63.51 | 37.6 |
| AHF17601 | V | R | Q | E | A | N | 2.91E+05 | 1.00E−06 | 3.44E−12 | 1685.00 | 1005.41 | 42.6 |
| AHF17602 | V | R | S | F | A | N | 2.10E+05 | 1.00E−06 | 4.76E−12 | 1685.00 | 725.55 | 27.9 |

TABLE 11-continued

Affinity matured Fab variants from the combinatorial library

| Antibody ID | VH 35 S | VH 55 G | VH 97 S | VH 112 F | VL 30 S | VL 53 N | ka (1/Ms) | kd (1/s) | KD (M) | Ratio (kd) WT/clones | Ratio (KD) WT/clones | Rmax (RU) |
|---|---|---|---|---|---|---|---|---|---|---|---|---|
| AHF17606 | V | R | S | F | A | N | 1.87E+05 | 2.01E−05 | 1.07E−10 | 83.83 | 32.29 | 46.3 |
| AHF17610 | V | R | S | F | A | N | 1.82E+05 | 1.00E−06 | 5.49E−12 | 1685.00 | 628.81 | 35 |
| AHF17610 | V | R | S | F | A | N | 1.82E+05 | 1.00E−06 | 5.49E−12 | 1685.00 | 628.81 | 35 |
| AHF17603 | V | G | S | E | A | I | 3.68E+05 | 2.45E−04 | 6.64E−10 | 6.88 | 5.20 | 108.7 |
| AHF17604 | V | R | Q | F | Q | I | 1.45E+05 | 4.66E−05 | 3.21E−10 | 36.16 | 10.76 | 27.9 |
| AHF17605 | V | G | Q | F | A | I | 2.53E+05 | 2.07E−04 | 8.20E−10 | 8.14 | 4.21 | 94.2 |
| AHF17607 | V | R | S | E | S | I | 2.26E+05 | 1.00E−06 | 4.42E−12 | 1685.00 | 780.83 | 36.9 |
| AHF17609 | V | R | S | F | A | I | 2.28E+05 | 1.00E−06 | 4.39E−12 | 1685.00 | 787.74 | 35.9 |
| Blank | | | | | | | 1.92E+04 | NA | NA | NA | NA | NA |
| Blank | | | | | | | 1.45E+04 | NA | NA | NA | NA | NA |
| Wild-type | | | | | | | 5.69E+05 | 1.79E−03 | 3.15E−09 | 0.94 | 0.00 | 28.7 |
| Wild-type | | | | | | | 4.19E+05 | 1.58E−03 | 3.78E−09 | 1.07 | 0.00 | 30.2 |
| Wild-type | | | | | | | 4.94E+05 | 1.69E−03 | 3.47E−09 | 1.00 | 0.00 | 29.45 |

TABLE 12

VH and VL variable domain sequences of affinity matured Fab variants

| Antibody ID | VH SEQ ID NO: | 35 S | 55 G | 97 S | 112 F | VL SEQ ID NO: | 30 S | 53 N |
|---|---|---|---|---|---|---|---|---|
| AHF17591 | 184 | V | R | S | E | 198 | A | I |
| AHF17598 | 184 | V | R | S | E | 198 | A | I |
| AHF17592 | 188 | V | R | S | F | 192 | S | V |
| AHF17600 | 188 | V | R | S | F | 192 | S | V |
| AHF17593 | 185 | V | R | Q | F | 193 | A | V |
| AHF17594 | 186 | V | G | S | F | 193 | A | V |
| AHF17595 | 184 | V | R | S | E | 194 | Q | N |
| AHF17596 | 188 | V | R | S | F | 193 | A | V |
| AHF17608 | 188 | V | R | S | F | 193 | A | V |
| AHF17599 | 188 | V | R | S | F | 193 | A | V |
| AHF17597 | 188 | V | R | S | F | 195 | Q | I |
| AHF17601 | 187 | V | R | Q | E | 196 | A | N |
| AHF17602 | 188 | V | R | S | F | 196 | A | N |
| AHF17606 | 188 | V | R | S | F | 196 | A | N |
| AHF17610 | 188 | V | R | S | F | 196 | A | N |
| AHF17610 | 188 | V | R | S | F | 196 | A | N |
| AHF17603 | 189 | V | G | S | E | 198 | A | I |
| AHF17604 | 187 | V | R | Q | F | 195 | Q | I |
| AHF17605 | 190 | V | G | Q | F | 198 | A | I |
| AHF17607 | 184 | V | R | S | E | 197 | S | I |
| AHF17609 | 188 | V | R | S | F | 198 | A | I |

Example 5

Affinity Maturation of Felinized Clone 101 by scFv Phage Display

In the second affinity maturation approach, a scFv phage display library was constructed containing the frameworks of felinized clone 101 and the following sequences for the heavy and light CDR sequences shown in Table 13.

TABLE 13

CDRs of felinized clone 101 and variants in scFv phage display combinatorial library

| HCDR1 | HCDR2 | HCDR3 | LCDR1 | LCDR2 | LCDR3 |
|---|---|---|---|---|---|
| GLSLTSSS (SEQ ID NO: 229) | IYSNGGT (SEQ ID NO: 266) | ASIYYYDADYLHWYFDF (SEQ ID NO: 224) | EGISNN (SEQ ID NO: 332) | ATS | QQGYKWPLT (SEQ ID NO: 227) |
| ------H- (SEQ ID NO: 230) | -W----- (SEQ ID NO: 153) | -N--------------- (SEQ ID NO: 276) | Q----- (SEQ ID NO: 333) | --E | ---W----- (SEQ ID NO: 356) |
| -----TN- (SEQ ID NO: 231) | ---Q--- (SEQ ID NO: 267) | -E--------------- (SEQ ID NO: 277) | N----- (SEQ ID NO: 334) | -S- | --- H- (SEQ ID NO: 357) |
| --E---N- (SEQ ID NO: 232) | --A---- (SEQ ID NO: 268) | -Q--------------- (SEQ ID NO: 278) | K----- (SEQ ID NO: 335) | --N | ---F----- (SEQ ID NO: 358) |
| A------- (SEQ ID NO: 233) | ---E--- (SEQ ID NO: 269) | -D--------------- (SEQ ID NO: 279) | -A---- (SEQ ID NO: 336) | --D | ----R---- (SEQ ID NO: 359) |
| L------- (SEQ ID NO: 234) | ---R--- (SEQ ID NO: 270) | -K--------------- (SEQ ID NO: 280) | --L--- (SEQ ID NO: 337) | --Q | ----E---- (SEQ ID NO: 360) |
| N------- (SEQ ID NO: 235) | ---S--- (SEQ ID NO: 271) | --L-------------- (SEQ ID NO: 281) | --V--- (SEQ ID NO: 338) | --K | ----S---- (SEQ ID NO: 361) |
| --E----- (SEQ ID NO: 236) | LW----- (SEQ ID NO: 272) | ---T------------- (SEQ ID NO: 282) | ---G-- (SEQ ID NO: 339) | -A- | ----Q---- (SEQ ID NO: 362) |
| --G----- (SEQ ID NO: 237) | -W-S--- (SEQ ID NO: 273) | ---W------------- (SEQ ID NO: 283) | ---D-- (SEQ ID NO: 340) | -Q- | -----F--- (SEQ ID NO: 363) |
| --A----- (SEQ ID NO: 238) | -W-E--- (SEQ ID NO: 274) | ---F------------- (SEQ ID NO: 284) | ----S- (SEQ ID NO: 341) | -D- | -----I--- (SEQ ID NO: 364) |

TABLE 13-continued

CDRs of felinized clone 101 and variants in
scFv phage display combinatorial library

| HCDR1 | HCDR2 | HCDR3 | LCDR1 | LCDR2 | LCDR3 |
|---|---|---|---|---|---|
| --D----- (SEQ ID NO: 239) | -W-D--- (SEQ ID NO: 275) | ----H-------- (SEQ ID NO: 285) | ----K- (SEQ ID NO: 342) | -Y- | ------E-- (SEQ ID NO: 365) |
| --T----- (SEQ ID NO: 240) | | ----F-------- (SEQ ID NO: 286) | ----Y- (SEQ ID NO: 343) | -V- | -------M- (SEQ ID NO: 366) |
| ---M---- (SEQ ID NO: 241) | | ------E------ (SEQ ID NO: 287) | -----S (SEQ ID NO: 344) | -L- | ---S----- (SEQ ID NO: 367) |
| ---V---- (SEQ ID NO: 242) | | -------S----- (SEQ ID NO: 288) | -----G (SEQ ID NO: 345) | | ---T----- (SEQ ID NO: 368) |
| ----A--- (SEQ ID NO: 243) | | -------V----- (SEQ ID NO: 289) | -----Q (SEQ ID NO: 346) | | ---H----- (SEQ ID NO: 357) |
| ----S--- (SEQ ID NO: 244) | | --------E---- (SEQ ID NO: 290) | -----E (SEQ ID NO: 347) | | ---G----- (SEQ ID NO: 369) |
| ----V--- (SEQ ID NO: 245) | | ---------H--- (SEQ ID NO: 291) | -----K (SEQ ID NO: 348) | | ---L----- (SEQ ID NO: 370) |
| ----N--- (SEQ ID NO: 246) | | -A----------- (SEQ ID NO: 292) | -----D (SEQ ID NO: 349) | | ---V----- (SEQ ID NO: 371) |
| ----M--- (SEQ ID NO: 247) | | -Y----------- (SEQ ID NO: 293) | -----T (SEQ ID NO: 350) | | ---R----- (SEQ ID NO: 372) |
| -----TH-- (SEQ ID NO: 248) | | -T----------- (SEQ ID NO: 294) | -----L (SEQ ID NO: 351) | | ---D----- (SEQ ID NO: 373) |
| -----H-- (SEQ ID NO: 249) | | -V----------- (SEQ ID NO: 295) | -----A (SEQ ID NO: 352) | | ---K----- (SEQ ID NO: 374) |
| -----G-- (SEQ ID NO: 250) | | -L----------- (SEQ ID NO: 296) | -----H (SEQ ID NO: 353) | | --Y-ST-W- (SEQ ID NO: 375) |
| -----E-- (SEQ ID NO: 251) | | -P----------- (SEQ ID NO: 297) | -----F (SEQ ID NO: 354) | | |
| -----R-- (SEQ ID NO: 252) | | -H----------- (SEQ ID NO: 298) | -----R (SEQ ID NO: 355) | | |
| -----K-- (SEQ ID NO: 253) | | -R----------- (SEQ ID NO: 299) | | | |
| ------I- (SEQ ID NO: 254) | | -I----------- (SEQ ID NO: 300) | | | |
| ------T- (SEQ ID NO: 255) | | -G----------- (SEQ ID NO: 301) | | | |
| ------D- (SEQ ID NO: 256) | | --Y---------- (SEQ ID NO: 302) | | | |
| ------N- (SEQ ID NO: 257) | | S------------ (SEQ ID NO: 303) | | | |
| ------Q- (SEQ ID NO: 258) | | T------------ (SEQ ID NO: 304) | | | |
| ------A- (SEQ ID NO: 259) | | D------------ (SEQ ID NO: 305) | | | |
| Q------- (SEQ ID NO: 260) | | N------------ (SEQ ID NO: 306) | | | |
| ------Y- (SEQ ID NO: 261) | | E------------ (SEQ ID NO: 307) | | | |
| -------A (SEQ ID NO: 262) | | Q------------ (SEQ ID NO: 308) | | | |
| -----A-- (SEQ ID NO: 263) | | K------------ (SEQ ID NO: 309) | | | |
| --Y----- (SEQ ID NO: 264) | | --Y---------M (SEQ ID NO: 310) | | | |
| --M----- (SEQ ID NO: 265) | | --W---------- (SEQ ID NO: 311) | | | |
| | | -D-F--------- (SEQ ID NO: 312) | | | |
| | | -N-W--------- (SEQ ID NO: 313) | | | |
| | | -Q--F-------- (SEQ ID NO: 314) | | | |
| | | ------E-E---- (SEQ ID NO: 315) | | | |
| | | -------SY---- (SEQ ID NO: 316) | | | |
| | | --------Y---- (SEQ ID NO: 317) | | | |
| | | ----------Y-- (SEQ ID NO: 318) | | | |
| | | -----------F-- (SEQ ID NO: 319) | | | |
| | | ---------F--- (SEQ ID NO: 320) | | | |
| | | -------------L--- (SEQ ID NO: 321) | | | |

TABLE 13-continued

CDRs of felinized clone 101 and variants in scFv phage display combinatorial library

| HCDR1 | HCDR2 | HCDR3 | LCDR1 | LCDR2 | LCDR3 |
|---|---|---|---|---|---|
| | | --------------W--- (SEQ ID NO: 322) | | | |
| | | --------------I--- (SEQ ID NO: 323) | | | |
| | | --------------D--- (SEQ ID NO: 324) | | | |
| | | ----------------Q- (SEQ ID NO: 325) | | | |
| | | -----------YF---- (SEQ ID NO: 326) | | | |
| | | ----------------Y (SEQ ID NO: 327) | | | |
| | | ----------------L (SEQ ID NO: 328) | | | |
| | | ----------------M (SEQ ID NO: 329) | | | |
| | | ----------------I (SEQ ID NO: 330) | | | |
| | | ----------------W (SEQ ID NO: 331) | | | |

The library diversity for the heavy chain was 37 (HCDR1)×11 (HCDR2)×57 (HCDR3)=23,199 and for the light chain was 24 (LCDR1)×13 (LCDR2)×22 (LCDR3)=6,864. The library containing the combined heavy and light chains has a diversity of $1.59 \times 10^8$. Antibody phage selections were completed with NGF for five rounds and with each round the stringency was increased by reducing the antigen concentration and increasing the number of washes. Specifically, 96-multi-well plates were coated with 200 pmol of NGF for the first round, 50 pmol of NGF for the second and third rounds, 25 pmol for the fourth round and 10 pmol for the fifth round. The number of washes with PBS, pH 7.4-Tween 20 (0.01%) after the selection step was three after the first round, four after the second round, five after the third round, six after the fourth round and seven after the fifth round. Isolated 760 clonal phage from each of the outputs of the third, fourth and fifth rounds that were screened in an NGF-binding ELISA. The positive clones were sequenced and 140 unique positive clones were reformatted into feline IgGla, expressed in CHO cells and purified with protein A. The SPR was completed by amine coupling the antibody (~5 µg/ml) to the HC30M sensor chip by EDC/NHS activation, followed by ethanolamine HCL quenching. NGF was the analyte diluted in HEPES-buffered saline with 0.01% tween 20 and 0.5 mg/ml BSA. The NGF was run at concentrations of 500 nM, 166 nM, 55 nM, 18 nM, 6.2 nM, 2.0 nM, 0.68 nM, and 0.23 nM. The affinities of the top three affinity-matured clones are shown below in Table 14. The sequences of variable domains of the top three clones (SC-184_76; SC-184_102; SC-184_110) are shown in FIG. 17

TABLE 14

SPR data of top three affinity-matured feline antibodies

| Clone | ka (1/Ms) | kd (1/s) | KD (M) |
|---|---|---|---|
| 101 | 1.10E+05 | 2.20E−04 | 2.10E−09 |
| SC-184_76 | 2.70E+05 | 6.90E−05 | 2.50E−10 |
| SC-184_102 | 2.10E+05 | 6.30E−05 | 6.30E−10 |
| SC-184_110 | 1.60E+05 | 3.60E−05 | 3.60E−10 |

Example 6

SPR and NGF Receptor Blocking Data of Affinity-Matured Feline Antibodies Directed Against Feline NGF Affinity-matured antibodies AHF17602, SC-184_76, SC-184_102, and SC-184_110 along with the latter three clones containing the G55R mutation (SC-184_76-Arg, SC-184_102-Arg, and SC-184_110-Arg) described in the first affinity maturation approach were evaluated for their affinity to NGF using SPR with a Biacore T200 instrument. The variable domain sequences of AHF17602, SC-184_76-Arg, SC-184_102-Arg, and SC-184_110-Arg are shown in FIG. 17. In addition, clone 101 was also evaluated. Antibodies were captured using an anti-feline coupled CM5 chip. NGF binding was then assessed at multiple concentrations starting at 50 nM using PBSP+ running buffer (Cytiva) with a flow rate of 30 µL/min. The length of the association time was 120 s and the dissociation time was run for 600 s. The chip surface was regenerated with 10 mM glycine. Reference-subtracted sensorgrams were fitted to a 1:1 binding model using Biacore T100 Evaluation software. The data is shown in Table 15 below and the sensorgrams in FIG. 18.

TABLE 15

Affinity of feline NGF antibodies

| Clone | ka (1/Ms) | kd (1/s) | KD | Rmax (RU) |
|---|---|---|---|---|
| 101 | 7.84E+05 | 1.38E−03 | 1.75E−09 | 26.3 |
| AHF17602 | 3.94E+05 | 6.32E−05 | 1.61E−10 | 61.4 |
| SC-184_76 | 8.38E+05 | 3.96E−04 | 4.72E−10 | 61.9 |
| SC-184_76-Arg | 5.85E+05 | 9.01E−05 | 1.54E−10 | 73.4 |
| SC-184_102 | 4.71E+05 | 1.98E−04 | 4.20E−10 | 82.1 |
| SC-184_102-Arg | 3.43E+05 | 4.43E−05 | 1.29E−10 | 87.8 |
| SC-184_110 | 4.92E+05 | 3.80E−04 | 7.73E−10 | 43.2 |
| SC-184_110-Arg | 3.87E+05 | 5.48E−05 | 1.42E−10 | 53.2 |

For the NGF receptor blocking experiments the feline TrkA and p75 NGF receptors were generated and used in an SPR experiment with a Biacore T200. The extracellular domain of feline TrkA (XP_023103311) was cloned with an AviTag (GLNDIFEAQKIEWHE (SEQ ID NO: 228)) and 8× His tag (SEQ ID NO:376) at the C-terminus and expressed in HEK293 cells. The recombinant feline TrkA protein was purified from the conditioned medium using nickel chromatography. The extracellular domain of feline p75 (XP_023099534) was cloned with an AviTag (GLNDIFEAQKIEWHE (SEQ ID NO:228)) and 8× His tag (SEQ ID NO:376) at the C-terminus and expressed in HEK293 cells. The recombinant feline p75 protein was purified from the conditioned medium using nickel chromatography. Both receptors were biotinylated at the AviTag site using the BirA biotin protein ligase reaction kit (Avidity). Biotinylated receptors were captured on a Series S CAP chip and Biotin CAPture reagent (Cytiva). Antibodies were titrated in running buffer (1×PBSP+, Cytiva) and pre-incubated with 10 nM NGF (TrkA assay) or 50 nM NGF (p75 assay) at the indicated ratios. Binding was assessed by injecting these samples over the captured receptor for 180 s. The Rmax was used to calculate the inhibition percent by dividing the Rmax of the pre-mixed samples by an average of the NGF-only Rmax samples that were collected throughout the assay. The ability of each antibody to block binding of NGF to feline TrkA and p75 are shown in Table 16.

TABLE 16

Antibody blocking NGF ability to bind to the NGF receptor

|  | TrkA | | p75 | |
| --- | --- | --- | --- | --- |
| Clone | Ab to NGF ratio | % Block | Ab to NGF ratio | % Block |
| 101 | 10 to 1 | 15 | 1 to 1 | 42 |
| 101 | 50 to 1 | 76 | 5 to 1 | 87 |
| SC-184_76-Arg | 10 to 1 | 99 | 1 to 1 | 100 |
| SC-184_76-Arg | 50 to 1 | 100 | 5 to 1 | 100 |
| SC-184_110-Arg | 10 to 1 | 100 | 1 to 1 | 100 |
| SC-184_110-Arg | 50 to 1 | 100 | 5 to 1 | 100 |
| AHF17602 | 10 to 1 | 99 | 1 to 1 | 100 |
| AHF17602 | 50 to 1 | 100 | 5 to 1 | 100 |

Example 7

Testing the affinity maturation mutation G55R in the canine clone SC-42_101_006.

The feline clone 101, has significant CDR similarity as the canine clone SC-42_101_006 ($V_H$ domain of SC-42_101; $V_L$ domain of SC-42_006). Affinity-matured feline clone AHF17602 removes a potential NG deamidation site by mutation of the G55R and this potential deamidation site exists in the canine clones as well. Clone SC-42_101_006 was mutated to R55 and both the parental and the R55 variant were transiently expressed in CHO cells and purified by Protein A. The variable domain sequences of are shown in FIG. 1 and FIG. 2. Affinity to NGF was assessed using SPR with a Biacore T200 instrument. Antibodies were captured using a Protein A Series S chip. NGF binding was then assessed at multiple concentrations starting at 50 nM using PBSP+ running buffer (Cytiva) with a flow rate of 30 µL/min. The length of the association time was 120 s and the dissociation time was run for 600 s. The chip surface was regenerated with 10 mM glycine. Reference-subtracted sensorgrams were fitted to a 1:1 binding model using Biacore T200 Evaluation software. The data are shown in Table 17 below.

TABLE 17

Affinity of canine NGF antibodies

| Clone | ka (1/Ms) | kd (1/s) | KD (M) | Rmax (RU) |
| --- | --- | --- | --- | --- |
| SC-42_101_006 | 1.51E+06 | 1.74E−04 | 1.15E−10 | 46.7 |
| SC-42_101_006-Arg | 1.38E+06 | 1.89E−04 | 1.39E−10 | 39 |

The invention is further described by the following numbered paragraphs:

1. A isolated protein that specifically binds to canine NGF, which comprises an antigen binding portion that comprises:
   (a) a heavy chain complementarity determining region 1 (VH-CDR1) comprising the amino acid sequence $X_1X_2X_3X_4X_5X_6X_7X_8$ (SEQ ID NO:146), wherein $X_1$ comprises A, G, or N, $X_2$ comprises L or M, $X_3$ comprises A, D, E, or S, $X_4$ comprises F, I, L, M, or V, $X_5$ comprises N or T, $X_6$ comprises E, S, or T, $X_7$ comprises G, H, N, S, or Q, and $X_8$ comprises A or S;
   (b) a heavy chain complementarity determining region 2 (VH-CDR2) comprising the amino acid sequence $X_1X_2$SNGGT (SEQ ID NO:147), wherein $X_1$ comprises I or L, $X_2$ comprises W or Y;
   (c) a heavy chain complementarity determining region 3 (VH-CDR3) comprising the amino acid sequence A$X_2X_4X_5$Y$X_7X_8X_9$YL$X_{12}X_{13}$Y$X_{15}X_{16}X_{17}$ (SEQ ID NO:148), wherein $X_2$ comprises D, E, K, N, Q, S, or T, $X_4$ comprises W or Y, $X_5$ comprises F, H, W, or Y, $X_7$ comprises D or E, $X_8$ comprises A or S, $X_9$ comprises D or Y, $X_{12}$ comprises H or Y, $X_{13}$ comprises F or W, $X_{15}$ comprises F, I, L, W, or Y, $X_{16}$ comprises D or Q, and $X_{17}$ comprises F, I, L, M, W, or Y;
   (d) a light chain complementarity determining region 1 (VL-CDR1) comprising the amino acid sequence $X_1X_2$I$X_4X_5X_6$ (SEQ ID NO:149), wherein $X_1$ comprises D, E, or K, $X_2$ comprises A, G, or N, $X_4$ comprises G, N, Q or S, $X_5$ comprises N or S, $X_6$ comprises A, G, N, S or T;
   (e) a light chain complementarity determining region 2 (VL-CDR2) comprising the amino acid sequence A$X_2X_3$ (SEQ ID NO:150), wherein $X_2$ comprises A, S, or T, $X_3$ comprises A, D, E, N, Q, S, or T; and
   (f) a light chain complementarity determining region 3 (VL-CDR3) comprising the amino acid sequence Q$X_2$G$X_4X_5X_6$P$X_8$T (SEQ ID NO:151), wherein $X_2$ comprises H or Q, $X_4$ comprises F, H, W, or Y, $X_5$ comprises K or Q, $X_6$ comprises F or W, and $X_8$ comprises L or M.

2. The protein of paragraph 1, which comprises an antigen binding portion that comprises:
   (a) a heavy chain complementarity determining region 1 (VH-CDR1) comprising the amino acid sequence $X_1X_2X_3X_4$T$X_6X_7$S (SEQ ID NO:378), wherein $X_1$ comprises A or G, $X_2$ comprises L or M, $X_3$ comprises E or S, $X_4$ comprises F or L, $X_6$ comprises S or T, and $X_7$ comprises H, N, or S;
   (b) a heavy chain complementarity determining region 2 (VH-CDR2) comprising the amino acid sequence IWSNGGT (SEQ ID NO:153);
   (c) a heavy chain complementarity determining region 3 (VH-CDR3) comprising the amino acid sequence A$X_2$IYYY$X_7$ADYLH$X_{13}$Y$X_{13}$D$X_{17}$ (SEQ ID NO:154) comprises, wherein $X_2$ comprises N, Q, or S, $X_7$ comprises D or E, $X_{13}$ comprises F or W, $X_{15}$ comprises F, I, L, W, or Y, and $X_{17}$ comprises F, I, L, or M;

(d) a light chain complementarity determining region 1 (VL-CDR1) comprising the amino acid sequence $X_1GIX_4NX_6$ (SEQ ID NO:380), wherein $X_1$ comprises D or E, $X_4$ comprises Q or S, $X_6$ comprises G, N, S or T;

(e) a light chain complementarity determining region 2 (VL-CDR2) comprising the amino acid sequence $ATX_3$ (SEQ ID NO:156), wherein $X_3$ comprises D, E, N, Q, or S; and (f) a light chain complementarity determining region 3 (VL-CDR3) comprising the amino acid sequence $QQGX_4X_5X_6PLT$ (SEQ ID NO:157), wherein $X_4$ comprises F, H, or Y, $X_5$ comprises K or Q, and $X_6$ comprises F or W.

3. The protein of paragraph 1 or 2, which comprises no more than two (2) changes per VH-CDR as compared to SEQ ID NO:137 and no more than two (2) changes per VL-CDR as compared to SEQ ID NO:138.

4. The protein of paragraph 1 or 2, which comprises no more than one (1) changes per VH-CDR as compared to SEQ ID NO:137 and no more than one (1) change per VL-CDR as compared to SEQ ID NO: 138.

5. The protein of any one of paragraphs 1 to 4, which comprises a heavy chain framework (FR1H+FR2H+FR3H+FR4H) at least 75%, or at least 80%, or at least 85%, or at least 90%, or at least 93%, or at least 95% identical to SEQ ID NO: 13, SEQ ID NO:31, SEQ ID NO:55, SEQ ID NO:61, SEQ ID NO:69, SEQ ID NO:77, SEQ ID NO: 103, SEQ ID NO: 109, SEQ ID NO: 113, SEQ ID NO: 121, SEQ ID NO: 133, SEQ ID NO: 137, or SEQ ID NO: 141.

6. The protein of any one of paragraphs 1 to 5, which comprises a light chain framework (FR1L+FR2L+FR3L+FR4L) at least 75%, or at least 80%, or at least 85%, or at least 90%, or at least 93%, or at least 95% identical to SEQ ID NO: 14, SEQ ID NO:32, SEQ ID NO:56, SEQ ID NO:62, SEQ ID NO:70, SEQ ID NO:78, SEQ ID NO:104, SEQ ID NO:110, SEQ ID NO: 114, SEQ ID NO: 122, SEQ ID NO: 134, SEQ ID NO: 138, or SEQ ID NO: 142.

7. The protein of any one of paragraphs 1 to 6, which comprises a $V_H$ domain comprising SEQ ID NO:13, SEQ ID NO:31, SEQ ID NO:55, SEQ ID NO:61, SEQ ID NO:69, SEQ ID NO:77, SEQ ID NO: 103, SEQ ID NO: 109, SEQ ID NO: 113, SEQ ID NO: 121, SEQ ID NO: 133, SEQ ID NO: 137, or SEQ ID NO: 141.

8. The protein of any one of paragraphs 1 to 7, which comprises a $V_L$ domain comprising SEQ ID NO:14, SEQ ID NO:32, SEQ ID NO:56, SEQ ID NO:62, SEQ ID NO:70, SEQ ID NO:78, SEQ ID NO:104, SEQ ID NO:110, SEQ ID NO:114, SEQ ID NO:122, SEQ ID NO: 134, SEQ ID NO: 138, or SEQ ID NO: 142.

9. An isolated nucleic acid sequence encoding an anti-NGF antibody or antibody fragment of any one of paragraphs 1 to 8.

10. A vector that comprises the nucleic acid of paragraph 9.

11. A recombinant cell which comprises the nucleic acid of any one of paragraphs 9 or 10.

12. A cell that expresses the protein of any one of paragraphs 1 therapeutically effective amount of the anti-NGF protein of any one of paragraphs 1 to 8 or the nucleic acid of paragraphs 9 or 10.

13. A method of producing the anti-NGF protein of any one of paragraphs 1 to 8, which comprises culturing the host cell of paragraph 11 under conditions that result in production of the anti-NGF protein.

14. A pharmaceutical composition comprising a therapeutically effective amount of the anti-NGF protein of any one of paragraphs 1 to 8.

15. A method of treating pain in a subject which comprises administering to the subject a therapeutically effective amount of the anti-NGF protein of any one of paragraphs 1 to 8.

16. The method of paragraph 15, wherein the pain comprises inflammatory pain, post-operative incision pain, cancer pain, primary or metastatic bone cancer pain, fracture pain, osteoporotic fracture pain, pain resulting from burn, pain from trauma, musculoskeletal pain, rheumatic pain, or osteoporosis pain.

17. The method of paragraph 16, wherein the subject comprises a canine.

18. The method of paragraph 16, wherein the subject comprises a feline.

19. The method of paragraph 16, wherein the subject comprises a human.

20. A method of detecting NGF in a sample comprising incubating a sample comprising NGF in the presence of an anti-NGF protein of any one paragraphs 1 to 8 and detecting the anti-NGF protein bound to NGF in the sample.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

SEQUENCE LISTING

```
Sequence total quantity: 395
SEQ ID NO: 1            moltype = AA  length = 123
FEATURE                 Location/Qualifiers
REGION                  1..123
                        note = Synthetic construct
source                  1..123
                        mol_type = protein
                        organism = synthetic construct
SEQUENCE: 1
QVQLKESGPG LVQPSQTLSL TCTVSGLSLT SNSVSWIRQP PGKGLEWMGV IWSNGGTDYN   60
SAIESRLSIN RDTSKSQVFL KMNSLQPEDT AMYFCASIYY YDADYLHWYF DFWGPGTMVT  120
VSS                                                                123

SEQ ID NO: 2            moltype = AA  length = 107
FEATURE                 Location/Qualifiers
REGION                  1..107
                        note = Synthetic construct
source                  1..107
```

```
                            mol_type = protein
                            organism = synthetic construct
SEQUENCE: 2
DIQMTQSPAS LSASLGETVS IECLASEGIS NSLAWYQLKP GKSPQFLIYA TSSLQDGVPS    60
RFSGSGSGTQ YSLKISGMQP EDEGVYYCQQ GYKFPLTFGS GTKLKIK                 107

SEQ ID NO: 3            moltype = AA  length = 123
FEATURE                 Location/Qualifiers
REGION                  1..123
                        note = Synthetic construct
source                  1..123
                        mol_type = protein
                        organism = synthetic construct
SEQUENCE: 3
EVQLVESGGD LVQPAGSLRL SCVASGLSLN SNSMSWVRQA PEKGLQLVAT IWSNGGTQYT    60
DAVKGRFTIS RDNAKNTVYL QMNSLRAEDT AMYYCATIYY YDADYLHWYF DFWGQGTLVT   120
VSS                                                                 123

SEQ ID NO: 4            moltype = AA  length = 107
FEATURE                 Location/Qualifiers
REGION                  1..107
                        note = Synthetic construct
source                  1..107
                        mol_type = protein
                        organism = synthetic construct
SEQUENCE: 4
EIVMTQSPAS LSLSQEEKVT ITCRASEGIS NNLAWYQQKP GQAPKLLIYA TNSLATGVPS    60
RFSGSGSGTD FSLTISSLEP EDVAVYYCQQ GYKFPLTFGQ GTKVEIK                 107

SEQ ID NO: 5            moltype = AA  length = 123
FEATURE                 Location/Qualifiers
REGION                  1..123
                        note = Synthetic construct
source                  1..123
                        mol_type = protein
                        organism = synthetic construct
SEQUENCE: 5
EVQLVESGGD LVAPSQSLSI TCTVSGLSLT SNAISWVRQP PGRGLEWLGT IWSNGGTSYT    60
DAVKGRFTIS RDNAKNTLYL QMNSLRTEDT ARYYCASIYY YDADYLHWYF DMWGQGTLVT   120
VSS                                                                 123

SEQ ID NO: 6            moltype = AA  length = 107
FEATURE                 Location/Qualifiers
REGION                  1..107
                        note = Synthetic construct
source                  1..107
                        mol_type = protein
                        organism = synthetic construct
SEQUENCE: 6
EIVMTQSPAS LSLSVEEKVT ITCRASEGIS NNLAWYQQKP GQAPKLLIYA TSSLATGVPS    60
RFSGSGSGTD FTLTISSLQP EDFATYYCQQ GWKFPLTFGQ GTKVEIK                 107

SEQ ID NO: 7            moltype = AA  length = 123
FEATURE                 Location/Qualifiers
REGION                  1..123
                        note = Synthetic construct
source                  1..123
                        mol_type = protein
                        organism = synthetic construct
SEQUENCE: 7
EVQLVESGGD LVKPEGSLRL SCVVSGLELT SNSMSWVRQA PGKGLQWVGV LWSNGGTDYT    60
DAVKGRFTIS RDNAKNTLYL QMNSLRTEDT ARYYCASIYY YDADYLHWYF DYWGQGTLVT   120
VSS                                                                 123

SEQ ID NO: 8            moltype = AA  length = 107
FEATURE                 Location/Qualifiers
REGION                  1..107
                        note = Synthetic construct
source                  1..107
                        mol_type = protein
                        organism = synthetic construct
SEQUENCE: 8
EIVMTQSPAS LSLSQEEKVT ITCRASEGIS NNVAWYQQKP GQAPKLLIYA TSELATGVPS    60
RFSGSGSGTD FSLTISSLEP EDVAVYYCQQ GYKFPMTFGQ GTKVEIK                 107

SEQ ID NO: 9            moltype = AA  length = 123
FEATURE                 Location/Qualifiers
REGION                  1..123
                        note = Synthetic construct
```

```
source                  1..123
                        mol_type = protein
                        organism = synthetic construct
SEQUENCE: 9
EVQLVESGGD LVKPEGSLSL SCVVSGLSLT SNAMSWVRQA PGKGLQWVAT IWSNGGTDYT    60
DAVKGRFTIS RDNAKNTLYL QMNSLRTEDT ARYYCASIYY YDADYLHWYY DFWGQGTLVT   120
VSS                                                                 123

SEQ ID NO: 10           moltype = AA  length = 107
FEATURE                 Location/Qualifiers
REGION                  1..107
                        note = Synthetic construct
source                  1..107
                        mol_type = protein
                        organism = synthetic construct
SEQUENCE: 10
EIVMTQSPAS LSLSQEDKVT ITCRASEGIS SSLAWYQQKP GQAPKLLIYA TSQLATGVPS    60
RFSGSGSGTD FSFTISSLEP EDVAVYYCQQ GYKWPLTFGQ GTKVEIK                 107

SEQ ID NO: 11           moltype = AA  length = 123
FEATURE                 Location/Qualifiers
REGION                  1..123
                        note = Synthetic construct
source                  1..123
                        mol_type = protein
                        organism = synthetic construct
SEQUENCE: 11
EVQLVESGGD LVAPSQSLSI TCTVSGLSLT ENSISWVRQP PGRGLEWLGV IWSNGGTSYN    60
SAVKGRFTIS RDNAKNTLYL QMNSLRTEDT AVYYCASIYY YDADYLHWYL DFWGPGTLVT   120
ISS                                                                 123

SEQ ID NO: 12           moltype = AA  length = 107
FEATURE                 Location/Qualifiers
REGION                  1..107
                        note = Synthetic construct
source                  1..107
                        mol_type = protein
                        organism = synthetic construct
SEQUENCE: 12
EIVMTQSPAS LSLSQEDKVT ITCRASEGIN NSLAWYQQKP GQAPKLLIYA TQSLATGVPS    60
RFSGSGSGTD FSLTISSLEP EDVAVYYCQQ GFKFPLTFGQ GTKVEIK                 107

SEQ ID NO: 13           moltype = AA  length = 123
FEATURE                 Location/Qualifiers
REGION                  1..123
                        note = Synthetic construct
source                  1..123
                        mol_type = protein
                        organism = synthetic construct
SEQUENCE: 13
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHWYF DLWGQGTLVT   120
VSS                                                                 123

SEQ ID NO: 14           moltype = AA  length = 107
FEATURE                 Location/Qualifiers
REGION                  1..107
                        note = Synthetic construct
source                  1..107
                        mol_type = protein
                        organism = synthetic construct
SEQUENCE: 14
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKWPLTFGQ GTKVEIK                 107

SEQ ID NO: 15           moltype = AA  length = 123
FEATURE                 Location/Qualifiers
REGION                  1..123
                        note = Synthetic construct
source                  1..123
                        mol_type = protein
                        organism = synthetic construct
SEQUENCE: 15
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHFYF DFWGQGTLVT   120
VSS                                                                 123

SEQ ID NO: 16           moltype = AA  length = 107
FEATURE                 Location/Qualifiers
```

```
REGION                  1..107
                        note = Synthetic construct
source                  1..107
                        mol_type = protein
                        organism = synthetic construct
SEQUENCE: 16
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKWPLTFGQ GTKVEIK                 107

SEQ ID NO: 17           moltype = AA   length = 123
FEATURE                 Location/Qualifiers
REGION                  1..123
                        note = Synthetic construct
source                  1..123
                        mol_type = protein
                        organism = synthetic construct
SEQUENCE: 17
EVQLVESGGE LVKPGGSLRL SCVASGLSLN SNSMSWIRQA PGKGLQWVAT IWSNGGTDYT    60
DAVKGRFTIS RDNVKNSLYL QMNSLRAEDT AVYYCASIYF YDADYLHWYF DFWGQGTLVT   120
VSS                                                                 123

SEQ ID NO: 18           moltype = AA   length = 107
FEATURE                 Location/Qualifiers
REGION                  1..107
                        note = Synthetic construct
source                  1..107
                        mol_type = protein
                        organism = synthetic construct
SEQUENCE: 18
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKWPLTFGQ GTKVEIK                 107

SEQ ID NO: 19           moltype = AA   length = 123
FEATURE                 Location/Qualifiers
REGION                  1..123
                        note = Synthetic construct
source                  1..123
                        mol_type = protein
                        organism = synthetic construct
SEQUENCE: 19
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYF YDADYLHWYF DFWGQGTLVT   120
VSS                                                                 123

SEQ ID NO: 20           moltype = AA   length = 107
FEATURE                 Location/Qualifiers
REGION                  1..107
                        note = Synthetic construct
source                  1..107
                        mol_type = protein
                        organism = synthetic construct
SEQUENCE: 20
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKWPLTFGQ GTKVEIK                 107

SEQ ID NO: 21           moltype = AA   length = 123
FEATURE                 Location/Qualifiers
REGION                  1..123
                        note = Synthetic construct
source                  1..123
                        mol_type = protein
                        organism = synthetic construct
SEQUENCE: 21
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHWYY DFWGQGTLVT   120
VSS                                                                 123

SEQ ID NO: 22           moltype = AA   length = 107
FEATURE                 Location/Qualifiers
REGION                  1..107
                        note = Synthetic construct
source                  1..107
                        mol_type = protein
                        organism = synthetic construct
SEQUENCE: 22
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKWPLTFGQ GTKVEIK                 107

SEQ ID NO: 23           moltype = AA   length = 123
```

```
FEATURE                 Location/Qualifiers
REGION                  1..123
                        note = Synthetic construct
source                  1..123
                        mol_type = protein
                        organism = synthetic construct
SEQUENCE: 23
EVQLVESGGE LVKPGGSLRL SCVASGLALT SNSMSWIRQA PGKGLQWVAT IWSNGGTDYT    60
DAVKGRFTIS RDNVKNSLYL QMNSLRAEDT AVYYCADIYY YDADYLHWYF DFWGQGTLVT   120
VSS                                                                 123

SEQ ID NO: 24           moltype = AA   length = 107
FEATURE                 Location/Qualifiers
REGION                  1..107
                        note = Synthetic construct
source                  1..107
                        mol_type = protein
                        organism = synthetic construct
SEQUENCE: 24
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKWPLTFGQ GTKVEIK                 107

SEQ ID NO: 25           moltype = AA   length = 123
FEATURE                 Location/Qualifiers
REGION                  1..123
                        note = Synthetic construct
source                  1..123
                        mol_type = protein
                        organism = synthetic construct
SEQUENCE: 25
EVQLVESGGE LVKPGGSLRL SCVASGLELT SNSMSWIRQA PGKGLQWVAT IWSNGGTDYT    60
DAVKGRFTIS RDNVKNSLYL QMNSLRAEDT AVYYCASIYY YDADYLHWYY DFWGQGTLVT   120
VSS                                                                 123

SEQ ID NO: 26           moltype = AA   length = 107
FEATURE                 Location/Qualifiers
REGION                  1..107
                        note = Synthetic construct
source                  1..107
                        mol_type = protein
                        organism = synthetic construct
SEQUENCE: 26
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKFPLTFGQ GTKVEIK                 107

SEQ ID NO: 27           moltype = AA   length = 123
FEATURE                 Location/Qualifiers
REGION                  1..123
                        note = Synthetic construct
source                  1..123
                        mol_type = protein
                        organism = synthetic construct
SEQUENCE: 27
EVQLVESGGE LVKPGGSLRL SCVASNLSLT SNSMSWIRQA PGKGLQWVAT IWSNGGTDYT    60
DAVKGRFTIS RDNVKNSLYL QMNSLRAEDT AVYYCANIYY YDADYLHWYF DFWGQGTLVT   120
VSS                                                                 123

SEQ ID NO: 28           moltype = AA   length = 107
FEATURE                 Location/Qualifiers
REGION                  1..107
                        note = Synthetic construct
source                  1..107
                        mol_type = protein
                        organism = synthetic construct
SEQUENCE: 28
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKFPLTFGQ GTKVEIK                 107

SEQ ID NO: 29           moltype = AA   length = 123
FEATURE                 Location/Qualifiers
REGION                  1..123
                        note = Synthetic construct
source                  1..123
                        mol_type = protein
                        organism = synthetic construct
SEQUENCE: 29
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHWYY DFWGQGTLVT   120
VSS                                                                 123
```

```
SEQ ID NO: 30            moltype = AA  length = 107
FEATURE                  Location/Qualifiers
REGION                   1..107
                         note = Synthetic construct
source                   1..107
                         mol_type = protein
                         organism = synthetic construct
SEQUENCE: 30
EIVMTQSPAS LSLSQGEKVT ITCRASEGIS NNLAWYQQKP GQAPKLLIYA TSELATGVPS   60
RFSGSGSGTD FSFTISSLEP EDVATYYCQQ GYKFPLTFGQ GTKVEIK                 107

SEQ ID NO: 31            moltype = AA  length = 123
FEATURE                  Location/Qualifiers
REGION                   1..123
                         note = Synthetic construct
source                   1..123
                         mol_type = protein
                         organism = synthetic construct
SEQUENCE: 31
EVQLVESGGE LVKPGGSLRL SCVASGLSLT TNSMSWIRQA PGKGLQWVAT IWSNGGTDYT   60
DAVKGRFTIS RDNVKNSLYL QMNSLRAEDT AVYYCASIYY YDADYLHWYF DMWGQGTLVT   120
VSS                                                                 123

SEQ ID NO: 32            moltype = AA  length = 107
FEATURE                  Location/Qualifiers
REGION                   1..107
                         note = Synthetic construct
source                   1..107
                         mol_type = protein
                         organism = synthetic construct
SEQUENCE: 32
EIVMTQSPAS LSLSQGEKVT ITCRASEGIS NNLAWYQQKP GQAPKLLIYA TSELATGVPS   60
RFSGSGSGTD FSFTISSLEP EDVATYYCQQ GYKFPLTFGQ GTKVEIK                 107

SEQ ID NO: 33            moltype = AA  length = 123
FEATURE                  Location/Qualifiers
REGION                   1..123
                         note = Synthetic construct
source                   1..123
                         mol_type = protein
                         organism = synthetic construct
SEQUENCE: 33
EVQLVESGGE LVKPGGSLRL SCVASGLSLT SNSMSWIRQA PGKGLQWVAT IWSNGGTDYT   60
DAVKGRFTIS RDNVKNSLYL QMNSLRAEDT AVYYCANIYY YDADYLHWYF DFWGQGTLVT   120
VSS                                                                 123

SEQ ID NO: 34            moltype = AA  length = 107
FEATURE                  Location/Qualifiers
REGION                   1..107
                         note = Synthetic construct
source                   1..107
                         mol_type = protein
                         organism = synthetic construct
SEQUENCE: 34
EIVMTQSPAS LSLSQGEKVT ITCRASEGIS NNLAWYQQKP GQAPKLLIYA TSELATGVPS   60
RFSGSGSGTD FSFTISSLEP EDVATYYCQQ GYKFPLTFGQ GTKVEIK                 107

SEQ ID NO: 35            moltype = AA  length = 123
FEATURE                  Location/Qualifiers
REGION                   1..123
                         note = Synthetic construct
source                   1..123
                         mol_type = protein
                         organism = synthetic construct
SEQUENCE: 35
EVQLVESGGE LVKPGGSLRL SCVASGLALT SNSMSWIRQA PGKGLQWVAT IWSNGGTDYT   60
DAVKGRFTIS RDNVKNSLYL QMNSLRAEDT AVYYCANIYY YDADYLHWYF DFWGQGTLVT   120
VSS                                                                 123

SEQ ID NO: 36            moltype = AA  length = 107
FEATURE                  Location/Qualifiers
REGION                   1..107
                         note = Synthetic construct
source                   1..107
                         mol_type = protein
                         organism = synthetic construct
SEQUENCE: 36
EIVMTQSPAS LSLSQGEKVT ITCRASEGIS NNLAWYQQKP GQAPKLLIYA TSELATGVPS   60
```

```
RFSGSGSGTD FSFTISSLEP EDVATYYCQQ GYKFPLTFGQ GTKVEIK                  107

SEQ ID NO: 37           moltype = AA   length = 123
FEATURE                 Location/Qualifiers
REGION                  1..123
                        note = Synthetic construct
source                  1..123
                        mol_type = protein
                        organism = synthetic construct
SEQUENCE: 37
EVQLVESGGE LVKPGGSLRL SCVASGLALT SNSMSWIRQA PGKGLQWVAT IWSNGGTDYT    60
DAVKGRFTIS RDNVKNSLYL QMNSLRAEDT AVYYCASIYY YDADYLHWYF DIWGQGTLVT    120
VSS                                                                  123

SEQ ID NO: 38           moltype = AA   length = 107
FEATURE                 Location/Qualifiers
REGION                  1..107
                        note = Synthetic construct
source                  1..107
                        mol_type = protein
                        organism = synthetic construct
SEQUENCE: 38
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKFPLTFGQ GTKVEIK                  107

SEQ ID NO: 39           moltype = AA   length = 123
FEATURE                 Location/Qualifiers
REGION                  1..123
                        note = Synthetic construct
source                  1..123
                        mol_type = protein
                        organism = synthetic construct
SEQUENCE: 39
EVQLVESGGE LVKPGGSLRL SCVASNLSLT SNSMSWIRQA PGKGLQWVAT IWSNGGTDYT    60
DAVKGRFTIS RDNVKNSLYL QMNSLRAEDT AVYYCAEIYY YDADYLHWYF DFWGQGTLVT    120
VSS                                                                  123

SEQ ID NO: 40           moltype = AA   length = 107
FEATURE                 Location/Qualifiers
REGION                  1..107
                        note = Synthetic construct
source                  1..107
                        mol_type = protein
                        organism = synthetic construct
SEQUENCE: 40
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKFPLTFGQ GTKVEIK                  107

SEQ ID NO: 41           moltype = AA   length = 123
FEATURE                 Location/Qualifiers
REGION                  1..123
                        note = Synthetic construct
source                  1..123
                        mol_type = protein
                        organism = synthetic construct
SEQUENCE: 41
EVQLVESGGE LVKPGGSLRL SCVASGLSLN SNSMSWIRQA PGKGLQWVAT IWSNGGTDYT    60
DAVKGRFTIS RDNVKNSLYL QMNSLRAEDT AVYYCASIYY YDADYLHWYW DFWGQGTLVT    120
VSS                                                                  123

SEQ ID NO: 42           moltype = AA   length = 107
FEATURE                 Location/Qualifiers
REGION                  1..107
                        note = Synthetic construct
source                  1..107
                        mol_type = protein
                        organism = synthetic construct
SEQUENCE: 42
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKFPLTFGQ GTKVEIK                  107

SEQ ID NO: 43           moltype = AA   length = 123
FEATURE                 Location/Qualifiers
REGION                  1..123
                        note = Synthetic construct
source                  1..123
                        mol_type = protein
                        organism = synthetic construct
SEQUENCE: 43
```

```
EVQLVESGGE LVKPGGSLRL SCVASGLELT SNSMSWIRQA PGKGLQWVAT IWSNGGTDYT    60
DAVKGRFTIS RDNVKNSLYL QMNSLRAEDT AVYYCAQIYY YDADYLHWYF DFWGQGTLVT   120
VSS                                                                123

SEQ ID NO: 44           moltype = AA   length = 107
FEATURE                 Location/Qualifiers
REGION                  1..107
                        note = Synthetic construct
source                  1..107
                        mol_type = protein
                        organism = synthetic construct
SEQUENCE: 44
EIVMTQSPAS LSLSQGEKVT ITCRASEGIS NNLAWYQQKP GQAPKLLIYA TSELATGVPS    60
RFSGSGSGTD FSFTISSLEP EDVATYYCQQ GYKFPLTFGQ GTKVEIK                 107

SEQ ID NO: 45           moltype = AA   length = 123
FEATURE                 Location/Qualifiers
REGION                  1..123
                        note = Synthetic construct
source                  1..123
                        mol_type = protein
                        organism = synthetic construct
SEQUENCE: 45
EVQLVESGGE LVKPGGSLRL SCVASGLSLT SHSMSWIRQA PGKGLQWVAT IWSNGGTDYT    60
DAVKGRFTIS RDNVKNSLYL QMNSLRAEDT AVYYCASIYY YDADYLHWYF DWWGQGTLVT   120
VSS                                                                123

SEQ ID NO: 46           moltype = AA   length = 107
FEATURE                 Location/Qualifiers
REGION                  1..107
                        note = Synthetic construct
source                  1..107
                        mol_type = protein
                        organism = synthetic construct
SEQUENCE: 46
EIVMTQSPAS LSLSQEDKVT ITCRASEGIS NNLAWYQQKP GQAPKLLIYA TSQLATGVPS    60
RFSGSGSGTD FSFTISSLEP EDVATYYCQQ GYKWPLTFGQ GTKVEIK                 107

SEQ ID NO: 47           moltype = AA   length = 123
FEATURE                 Location/Qualifiers
REGION                  1..123
                        note = Synthetic construct
source                  1..123
                        mol_type = protein
                        organism = synthetic construct
SEQUENCE: 47
EVQLVESGGE LVKPGGSLRL SCVASGLSLT TNSMSWIRQA PGKGLQWVAT IWSNGGTDYT    60
DAVKGRFTIS RDNVKNSLYL QMNSLRAEDT AVYYCAQIYY YDADYLHWYF DFWGQGTLVT   120
VSS                                                                123

SEQ ID NO: 48           moltype = AA   length = 107
FEATURE                 Location/Qualifiers
REGION                  1..107
                        note = Synthetic construct
source                  1..107
                        mol_type = protein
                        organism = synthetic construct
SEQUENCE: 48
EIVMTQSPAS LSLSQEDKVT ITCRASEGIS NNLAWYQQKP GQAPKLLIYA TSQLATGVPS    60
RFSGSGSGTD FSFTISSLEP EDVATYYCQQ GYKWPLTFGQ GTKVEIK                 107

SEQ ID NO: 49           moltype = AA   length = 123
FEATURE                 Location/Qualifiers
REGION                  1..123
                        note = Synthetic construct
source                  1..123
                        mol_type = protein
                        organism = synthetic construct
SEQUENCE: 49
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHWYY DFWGQGTLVT   120
VSS                                                                123

SEQ ID NO: 50           moltype = AA   length = 107
FEATURE                 Location/Qualifiers
REGION                  1..107
                        note = Synthetic construct
source                  1..107
                        mol_type = protein
```

```
                        organism = synthetic construct
SEQUENCE: 50
EIVMTQSPAS LSLSQEDKVT ITCRASEGIS NNLAWYQQKP GQAPKLLIYA TSQLATGVPS    60
RFSGSGSGTD FSFTISSLEP EDVATYYCQQ GYKWPLTFGQ GTKVEIK                 107

SEQ ID NO: 51           moltype = AA   length = 123
FEATURE                 Location/Qualifiers
REGION                  1..123
                        note = Synthetic construct
source                  1..123
                        mol_type = protein
                        organism = synthetic construct
SEQUENCE: 51
EVQLVESGGE LVKPGGSLRL SCVASGLALT SNSMSWIRQA PGKGLQWVAT IWSNGGTDYT    60
DAVKGRFTIS RDNVKNSLYL QMNSLRAEDT AVYYCADIYY YDADYLHWYF DFWGQGTLVT   120
VSS                                                                 123

SEQ ID NO: 52           moltype = AA   length = 107
FEATURE                 Location/Qualifiers
REGION                  1..107
                        note = Synthetic construct
source                  1..107
                        mol_type = protein
                        organism = synthetic construct
SEQUENCE: 52
EIVMTQSPAS LSLSQEDKVT ITCRASEGIS NNLAWYQQKP GQAPKLLIYA TSQLATGVPS    60
RFSGSGSGTD FSFTISSLEP EDVATYYCQQ GYKWPLTFGQ GTKVEIK                 107

SEQ ID NO: 53           moltype = AA   length = 123
FEATURE                 Location/Qualifiers
REGION                  1..123
                        note = Synthetic construct
source                  1..123
                        mol_type = protein
                        organism = synthetic construct
SEQUENCE: 53
EVQLVESGGE LVKPGGSLRL SCVASGLALT SNSMSWIRQA PGKGLQWVAT IWSNGGTDYT    60
DAVKGRFTIS RDNVKNSLYL QMNSLRAEDT AVYYCANIYY YDADYLHWYF DFWGQGTLVT   120
VSS                                                                 123

SEQ ID NO: 54           moltype = AA   length = 107
FEATURE                 Location/Qualifiers
REGION                  1..107
                        note = Synthetic construct
source                  1..107
                        mol_type = protein
                        organism = synthetic construct
SEQUENCE: 54
EIVMTQSPAS LSLSQEDKVT ITCRASEGIS NNLAWYQQKP GQAPKLLIYA TSQLATGVPS    60
RFSGSGSGTD FSFTISSLEP EDVATYYCQQ GYKWPLTFGQ GTKVEIK                 107

SEQ ID NO: 55           moltype = AA   length = 123
FEATURE                 Location/Qualifiers
REGION                  1..123
                        note = Synthetic construct
source                  1..123
                        mol_type = protein
                        organism = synthetic construct
SEQUENCE: 55
EVQLVESGGE LVKPGGSLRL SCVASGLELT SNSMSWIRQA PGKGLQWVAT IWSNGGTDYT    60
DAVKGRFTIS RDNVKNSLYL QMNSLRAEDT AVYYCASIYY YDADYLHWYW DFWGQGTLVT   120
VSS                                                                 123

SEQ ID NO: 56           moltype = AA   length = 107
FEATURE                 Location/Qualifiers
REGION                  1..107
                        note = Synthetic construct
source                  1..107
                        mol_type = protein
                        organism = synthetic construct
SEQUENCE: 56
EIVMTQSPAS LSLSQEDKVT ITCRASEGIS NNLAWYQQKP GQAPKLLIYA TSQLATGVPS    60
RFSGSGSGTD FSFTISSLEP EDVATYYCQQ GYKWPLTFGQ GTKVEIK                 107

SEQ ID NO: 57           moltype = AA   length = 123
FEATURE                 Location/Qualifiers
REGION                  1..123
                        note = Synthetic construct
source                  1..123
```

```
                           mol_type = protein
                           organism = synthetic construct
SEQUENCE: 57
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHFYF DFWGQGTLVT   120
VSS                                                                123

SEQ ID NO: 58          moltype = AA  length = 107
FEATURE                Location/Qualifiers
REGION                 1..107
                       note = Synthetic construct
source                 1..107
                       mol_type = protein
                       organism = synthetic construct
SEQUENCE: 58
EIVMTQSPAS LSLSQEDKVT ITCRASEGIS NNLAWYQQKP GQAPKLLIYA TDSLATGVPS    60
RFSGSGSGTD FSFTISSLEP EDVATYYCQQ GYKWPLTFGQ GTKVEIK                107

SEQ ID NO: 59          moltype = AA  length = 123
FEATURE                Location/Qualifiers
REGION                 1..123
                       note = Synthetic construct
source                 1..123
                       mol_type = protein
                       organism = synthetic construct
SEQUENCE: 59
EVQLVESGGE LVKPGGSLRL SCVASNLSLT SNSMSWIRQA PGKGLQWVAT IWSNGGTDYT    60
DAVKGRFTIS RDNVKNSLYL QMNSLRAEDT AVYYCASIYY YEADYLHWYF DFWGQGTLVT   120
VSS                                                                123

SEQ ID NO: 60          moltype = AA  length = 107
FEATURE                Location/Qualifiers
REGION                 1..107
                       note = Synthetic construct
source                 1..107
                       mol_type = protein
                       organism = synthetic construct
SEQUENCE: 60
EIVMTQSPAS LSLSQEDKVT ITCRASEGIS NNLAWYQQKP GQAPKLLIYA TDSLATGVPS    60
RFSGSGSGTD FSFTISSLEP EDVATYYCQQ GYKWPLTFGQ GTKVEIK                107

SEQ ID NO: 61          moltype = AA  length = 123
FEATURE                Location/Qualifiers
REGION                 1..123
                       note = Synthetic construct
source                 1..123
                       mol_type = protein
                       organism = synthetic construct
SEQUENCE: 61
EVQLVESGGE LVKPGGSLRL SCVASGLSLT SHSMSWIRQA PGKGLQWVAT IWSNGGTDYT    60
DAVKGRFTIS RDNVKNSLYL QMNSLRAEDT AVYYCANIYY YDADYLHWYF DFWGQGTLVT   120
VSS                                                                123

SEQ ID NO: 62          moltype = AA  length = 107
FEATURE                Location/Qualifiers
REGION                 1..107
                       note = Synthetic construct
source                 1..107
                       mol_type = protein
                       organism = synthetic construct
SEQUENCE: 62
EIVMTQSPAS LSLSQEDKVT ITCRASEGIS NNLAWYQQKP GQAPKLLIYA TDSLATGVPS    60
RFSGSGSGTD FSFTISSLEP EDVATYYCQQ GYKWPLTFGQ GTKVEIK                107

SEQ ID NO: 63          moltype = AA  length = 123
FEATURE                Location/Qualifiers
REGION                 1..123
                       note = Synthetic construct
source                 1..123
                       mol_type = protein
                       organism = synthetic construct
SEQUENCE: 63
EVQLVESGGE LVKPGGSLRL SCVASGLALT SNSMSWIRQA PGKGLQWVAT IWSNGGTDYT    60
DAVKGRFTIS RDNVKNSLYL QMNSLRAEDT AVYYCASIYY YDADYLHWYF DIWGQGTLVT   120
VSS                                                                123

SEQ ID NO: 64          moltype = AA  length = 107
FEATURE                Location/Qualifiers
REGION                 1..107
```

```
                            note = Synthetic construct
source                      1..107
                            mol_type = protein
                            organism = synthetic construct
SEQUENCE: 64
EIVMTQSPAS LSLSQEDKVT ITCRASEGIS NNLAWYQQKP GQAPKLLIYA TDSLATGVPS    60
RFSGSGSGTD FSFTISSLEP EDVATYYCQQ GYKWPLTFGQ GTKVEIK                 107

SEQ ID NO: 65               moltype = AA   length = 123
FEATURE                     Location/Qualifiers
REGION                      1..123
                            note = Synthetic construct
source                      1..123
                            mol_type = protein
                            organism = synthetic construct
SEQUENCE: 65
EVQLVESGGE LVKPGGSLRL SCVASGLSLT TNSMSWIRQA PGKGLQWVAT IWSNGGTDYT    60
DAVKGRFTIS RDNVKNSLYL QMNSLRAEDT AVYYCASIYY YEADYLHWYF DFWGQGTLVT   120
VSS                                                                 123

SEQ ID NO: 66               moltype = AA   length = 107
FEATURE                     Location/Qualifiers
REGION                      1..107
                            note = Synthetic construct
source                      1..107
                            mol_type = protein
                            organism = synthetic construct
SEQUENCE: 66
EIVMTQSPAS LSLSQEDKVT ITCRASEGIS NNLAWYQQKP GQAPKLLIYA TDSLATGVPS    60
RFSGSGSGTD FSFTISSLEP EDVATYYCQQ GYKWPLTFGQ GTKVEIK                 107

SEQ ID NO: 67               moltype = AA   length = 123
FEATURE                     Location/Qualifiers
REGION                      1..123
                            note = Synthetic construct
source                      1..123
                            mol_type = protein
                            organism = synthetic construct
SEQUENCE: 67
EVQLVESGGE LVKPGGSLRL SCVASGLSLT SHSMSWIRQA PGKGLQWVAT IWSNGGTDYT    60
DAVKGRFTIS RDNVKNSLYL QMNSLRAEDT AVYYCASIYY YDADYLHFYF DFWGQGTLVT   120
VSS                                                                 123

SEQ ID NO: 68               moltype = AA   length = 107
FEATURE                     Location/Qualifiers
REGION                      1..107
                            note = Synthetic construct
source                      1..107
                            mol_type = protein
                            organism = synthetic construct
SEQUENCE: 68
EIVMTQSPAS LSLSQEDKVT ITCRASEGIS NNLAWYQQKP GQAPKLLIYA TDSLATGVPS    60
RFSGSGSGTD FSFTISSLEP EDVATYYCQQ GYKWPLTFGQ GTKVEIK                 107

SEQ ID NO: 69               moltype = AA   length = 123
FEATURE                     Location/Qualifiers
REGION                      1..123
                            note = Synthetic construct
source                      1..123
                            mol_type = protein
                            organism = synthetic construct
SEQUENCE: 69
EVQLVESGGE LVKPGGSLRL SCVASGLELT SNSMSWIRQA PGKGLQWVAT IWSNGGTDYT    60
DAVKGRFTIS RDNVKNSLYL QMNSLRAEDT AVYYCAQIYY YDADYLHWYF DFWGQGTLVT   120
VSS                                                                 123

SEQ ID NO: 70               moltype = AA   length = 107
FEATURE                     Location/Qualifiers
REGION                      1..107
                            note = Synthetic construct
source                      1..107
                            mol_type = protein
                            organism = synthetic construct
SEQUENCE: 70
EIVMTQSPAS LSASQEEKVT ITCRASEGIS NNLAWYQQKP GQAPKLLIYA TSELATGVPS    60
RFSGSGSGTD FSFTISSLQP EDVAVYYCQQ GYKWPLTFGQ GTKVEIK                 107

SEQ ID NO: 71               moltype = AA   length = 123
FEATURE                     Location/Qualifiers
```

| | | |
|---|---|---|
| REGION | 1..123 | |
| | note = Synthetic construct | |
| source | 1..123 | |
| | mol_type = protein | |
| | organism = synthetic construct | |

SEQUENCE: 71
EVQLVESGGE LVKPGGSLRL SCVASGLSLN SNSMSWIRQA PGKGLQWVAT IWSNGGTDYT   60
DAVKGRFTIS RDNVKNSLYL QMNSLRAEDT AVYYCASIYY YDADYLHWYF DLWGQGTLVT  120
VSS                                                              123

| | | |
|---|---|---|
| SEQ ID NO: 72 | moltype = AA   length = 107 | |
| FEATURE | Location/Qualifiers | |
| REGION | 1..107 | |
| | note = Synthetic construct | |
| source | 1..107 | |
| | mol_type = protein | |
| | organism = synthetic construct | |

SEQUENCE: 72
EIVMTQSPAS LSASQEEKVT ITCRASEGIS NNLAWYQQKP GQAPKLLIYA TSELATGVPS   60
RFSGSGSGTD FSFTISSLQP EDVAVYYCQQ GYKWPLTFGQ GTKVEIK              107

| | | |
|---|---|---|
| SEQ ID NO: 73 | moltype = AA   length = 123 | |
| FEATURE | Location/Qualifiers | |
| REGION | 1..123 | |
| | note = Synthetic construct | |
| source | 1..123 | |
| | mol_type = protein | |
| | organism = synthetic construct | |

SEQUENCE: 73
EVQLVESGGE LVKPGGSLRL SCVASGLSLT TNSMSWIRQA PGKGLQWVAT IWSNGGTDYT   60
DAVKGRFTIS RDNVKNSLYL QMNSLRAEDT AVYYCASIYY YDADYLHWYY DFWGQGTLVT  120
VSS                                                              123

| | | |
|---|---|---|
| SEQ ID NO: 74 | moltype = AA   length = 107 | |
| FEATURE | Location/Qualifiers | |
| REGION | 1..107 | |
| | note = Synthetic construct | |
| source | 1..107 | |
| | mol_type = protein | |
| | organism = synthetic construct | |

SEQUENCE: 74
EIVMTQSPAS LSASQEEKVT ITCRASEGIS NNLAWYQQKP GQAPKLLIYA TSELATGVPS   60
RFSGSGSGTD FSFTISSLQP EDVAVYYCQQ GYKWPLTFGQ GTKVEIK              107

| | | |
|---|---|---|
| SEQ ID NO: 75 | moltype = AA   length = 123 | |
| FEATURE | Location/Qualifiers | |
| REGION | 1..123 | |
| | note = Synthetic construct | |
| source | 1..123 | |
| | mol_type = protein | |
| | organism = synthetic construct | |

SEQUENCE: 75
EVQLVESGGE LVKPGGSLRL SCVASGLSLT SNSMSWIRQA PGKGLQWVAT IWSNGGTDYT   60
DAVKGRFTIS RDNVKNSLYL QMNSLRAEDT AVYYCASIYY YDADYLHWYF DLWGQGTLVT  120
VSS                                                              123

| | | |
|---|---|---|
| SEQ ID NO: 76 | moltype = AA   length = 107 | |
| FEATURE | Location/Qualifiers | |
| REGION | 1..107 | |
| | note = Synthetic construct | |
| source | 1..107 | |
| | mol_type = protein | |
| | organism = synthetic construct | |

SEQUENCE: 76
EIVMTQSPAS LSASQEEKVT ITCRASEGIS NNLAWYQQKP GQAPKLLIYA TSELATGVPS   60
RFSGSGSGTD FSFTISSLQP EDVAVYYCQQ GYKWPLTFGQ GTKVEIK              107

| | | |
|---|---|---|
| SEQ ID NO: 77 | moltype = AA   length = 123 | |
| FEATURE | Location/Qualifiers | |
| REGION | 1..123 | |
| | note = Synthetic construct | |
| source | 1..123 | |
| | mol_type = protein | |
| | organism = synthetic construct | |

SEQUENCE: 77
EVQLVESGGE LVKPGGSLRL SCVASGLSLT SHSMSWIRQA PGKGLQWVAT IWSNGGTDYT   60
DAVKGRFTIS RDNVKNSLYL QMNSLRAEDT AVYYCASIYY YDADYLHWYY DFWGQGTLVT  120
VSS                                                              123

```
SEQ ID NO: 78              moltype = AA  length = 107
FEATURE                    Location/Qualifiers
REGION                     1..107
                           note = Synthetic construct
source                     1..107
                           mol_type = protein
                           organism = synthetic construct
SEQUENCE: 78
EIVMTQSPAS LSASQEEKVT ITCRASEGIS NNLAWYQQKP GQAPKLLIYA TSELATGVPS   60
RFSGSGSGTD FSFTISSLQP EDVAVYYCQQ GYKWPLTFGQ GTKVEIK                107

SEQ ID NO: 79              moltype = AA  length = 123
FEATURE                    Location/Qualifiers
REGION                     1..123
                           note = Synthetic construct
source                     1..123
                           mol_type = protein
                           organism = synthetic construct
SEQUENCE: 79
EVQLVESGGE LVKPGGSLRL SCVASGLSLT SHSMSWIRQA PGKGLQWVAT IWSNGGTDYT   60
DAVKGRFTIS RDNVKNSLYL QMNSLRAEDT AVYYCASIYY YDADYLHFYF DFWGQGTLVT  120
VSS                                                                123

SEQ ID NO: 80              moltype = AA  length = 107
FEATURE                    Location/Qualifiers
REGION                     1..107
                           note = Synthetic construct
source                     1..107
                           mol_type = protein
                           organism = synthetic construct
SEQUENCE: 80
EIVMTQSPAS LSASQEEKVT ITCRASEGIS NNLAWYQQKP GQAPKLLIYA TSELATGVPS   60
RFSGSGSGTD FSFTISSLQP EDVAVYYCQQ GYKWPLTFGQ GTKVEIK                107

SEQ ID NO: 81              moltype = AA  length = 123
FEATURE                    Location/Qualifiers
REGION                     1..123
                           note = Synthetic construct
source                     1..123
                           mol_type = protein
                           organism = synthetic construct
SEQUENCE: 81
EVQLVESGGE LVKPGGSLRL SCVASNLSLT SNSMSWIRQA PGKGLQWVAT IWSNGGTDYT   60
DAVKGRFTIS RDNVKNSLYL QMNSLRAEDT AVYYCANIYY YDADYLHWYF DFWGQGTLVT  120
VSS                                                                123

SEQ ID NO: 82              moltype = AA  length = 107
FEATURE                    Location/Qualifiers
REGION                     1..107
                           note = Synthetic construct
source                     1..107
                           mol_type = protein
                           organism = synthetic construct
SEQUENCE: 82
EIVMTQSPAS LSASQEEKVT ITCRASEGIS NNLAWYQQKP GQAPKLLIYA TSELATGVPS   60
RFSGSGSGTD FSFTISSLQP EDVAVYYCQQ GYKWPLTFGQ GTKVEIK                107

SEQ ID NO: 83              moltype = AA  length = 123
FEATURE                    Location/Qualifiers
REGION                     1..123
                           note = Synthetic construct
source                     1..123
                           mol_type = protein
                           organism = synthetic construct
SEQUENCE: 83
EVQLVESGGE LVKPGGSLRL SCVASGLALT SNSMSWIRQA PGKGLQWVAT IWSNGGTDYT   60
DAVKGRFTIS RDNVKNSLYL QMNSLRAEDT AVYYCASIYY YDADYLHWYF DIWGQGTLVT  120
VSS                                                                123

SEQ ID NO: 84              moltype = AA  length = 107
FEATURE                    Location/Qualifiers
REGION                     1..107
                           note = Synthetic construct
source                     1..107
                           mol_type = protein
                           organism = synthetic construct
SEQUENCE: 84
EIVMTQSPAS LSASQEEKVT ITCRASEGIS NNLAWYQQKP GQAPKLLIYA TDSLATGVPS   60
RFSGSGSGTD FSFTISSLQP EDVAVYYCQQ GYKWPLTFGQ GTKVEIK                107
```

```
SEQ ID NO: 85            moltype = AA   length = 123
FEATURE                  Location/Qualifiers
REGION                   1..123
                         note = Synthetic construct
source                   1..123
                         mol_type = protein
                         organism = synthetic construct
SEQUENCE: 85
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYY YDADYLHWYY DFWGQGTLVT   120
VSS                                                                 123

SEQ ID NO: 86            moltype = AA   length = 107
FEATURE                  Location/Qualifiers
REGION                   1..107
                         note = Synthetic construct
source                   1..107
                         mol_type = protein
                         organism = synthetic construct
SEQUENCE: 86
EIVMTQSPAS LSASQEEKVT ITCRASEGIS NNLAWYQQKP GQAPKLLIYA TDSLATGVPS    60
RFSGSGSGTD FSFTISSLQP EDVAVYYCQQ GYKWPLTFGQ GTKVEIK                 107

SEQ ID NO: 87            moltype = AA   length = 123
FEATURE                  Location/Qualifiers
REGION                   1..123
                         note = Synthetic construct
source                   1..123
                         mol_type = protein
                         organism = synthetic construct
SEQUENCE: 87
EVQLVESGGE LVKPGGSLRL SCVASGLALT SNSMSWIRQA PGKGLQWVAT IWSNGGTDYT    60
DAVKGRFTIS RDNVKNSLYL QMNSLRAEDT AVYYCADIYY YDADYLHWYF DFWGQGTLVT   120
VSS                                                                 123

SEQ ID NO: 88            moltype = AA   length = 107
FEATURE                  Location/Qualifiers
REGION                   1..107
                         note = Synthetic construct
source                   1..107
                         mol_type = protein
                         organism = synthetic construct
SEQUENCE: 88
EIVMTQSPAS LSASQEEKVT ITCRASEGIS NNLAWYQQKP GQAPKLLIYA TDSLATGVPS    60
RFSGSGSGTD FSFTISSLQP EDVAVYYCQQ GYKWPLTFGQ GTKVEIK                 107

SEQ ID NO: 89            moltype = AA   length = 123
FEATURE                  Location/Qualifiers
REGION                   1..123
                         note = Synthetic construct
source                   1..123
                         mol_type = protein
                         organism = synthetic construct
SEQUENCE: 89
EVQLVESGGE LVKPGGSLRL SCVASGLSLN SNSMSWIRQA PGKGLQWVAT IWSNGGTDYT    60
DAVKGRFTIS RDNVKNSLYL QMNSLRAEDT AVYYCANIYY YDADYLHWYF DFWGQGTLVT   120
VSS                                                                 123

SEQ ID NO: 90            moltype = AA   length = 107
FEATURE                  Location/Qualifiers
REGION                   1..107
                         note = Synthetic construct
source                   1..107
                         mol_type = protein
                         organism = synthetic construct
SEQUENCE: 90
EIVMTQSPAS LSASQEEKVT ITCRASEGIS NNLAWYQQKP GQAPKLLIYA TDSLATGVPS    60
RFSGSGSGTD FSFTISSLQP EDVAVYYCQQ GYKWPLTFGQ GTKVEIK                 107

SEQ ID NO: 91            moltype = AA   length = 123
FEATURE                  Location/Qualifiers
REGION                   1..123
                         note = Synthetic construct
source                   1..123
                         mol_type = protein
                         organism = synthetic construct
SEQUENCE: 91
EVQLVESGGE LVKPGGSLRL SCVASGLSLT SHSMSWIRQA PGKGLQWVAT IWSNGGTDYT    60
```

```
DAVKGRFTIS RDNVKNSLYL QMNSLRAEDT AVYYCAKIYY YDADYLHWYF DFWGQGTLVT    120
VSS                                                                123

SEQ ID NO: 92           moltype = AA   length = 107
FEATURE                 Location/Qualifiers
REGION                  1..107
                        note = Synthetic construct
source                  1..107
                        mol_type = protein
                        organism = synthetic construct
SEQUENCE: 92
EIVMTQSPAS LSASQEEKVT ITCRASEGIS NNLAWYQQKP GQAPKLLIYA TDSLATGVPS    60
RFSGSGSGTD FSFTISSLQP EDVAVYYCQQ GYKWPLTFGQ GTKVEIK                 107

SEQ ID NO: 93           moltype = AA   length = 123
FEATURE                 Location/Qualifiers
REGION                  1..123
                        note = Synthetic construct
source                  1..123
                        mol_type = protein
                        organism = synthetic construct
SEQUENCE: 93
EVQLVESGGE LVKPGGSLRL SCVASGLSLT SHSMSWIRQA PGKGLQWVAT IWSNGGTDYT    60
DAVKGRFTIS RDNVKNSLYL QMNSLRAEDT AVYYCASIYY YDADYLHWYY DFWGQGTLVT    120
VSS                                                                123

SEQ ID NO: 94           moltype = AA   length = 107
FEATURE                 Location/Qualifiers
REGION                  1..107
                        note = Synthetic construct
source                  1..107
                        mol_type = protein
                        organism = synthetic construct
SEQUENCE: 94
EIVMTQSPAS LSASQEEKVT ITCRASEGIS NNLAWYQQKP GQAPKLLIYA TDSLATGVPS    60
RFSGSGSGTD FSFTISSLQP EDVAVYYCQQ GYKWPLTFGQ GTKVEIK                 107

SEQ ID NO: 95           moltype = AA   length = 123
FEATURE                 Location/Qualifiers
REGION                  1..123
                        note = Synthetic construct
source                  1..123
                        mol_type = protein
                        organism = synthetic construct
SEQUENCE: 95
EVQLVESGGE LVKPGGSLRL SCVASGLSLT SHSMSWIRQA PGKGLQWVAT IWSNGGTDYT    60
DAVKGRFTIS RDNVKNSLYL QMNSLRAEDT AVYYCASIYY YEADYLHWYF DFWGQGTLVT    120
VSS                                                                123

SEQ ID NO: 96           moltype = AA   length = 107
FEATURE                 Location/Qualifiers
REGION                  1..107
                        note = Synthetic construct
source                  1..107
                        mol_type = protein
                        organism = synthetic construct
SEQUENCE: 96
EIVMTQSPAS LSLSQEDKVT ITCRASEGIS NNLAWYQQKP GQAPKLLIYA TSELATGVPS    60
RFSGSGSGTD FTLTISSLQP EDFATYYCQQ GYKWPLTFGQ GTKVEIK                 107

SEQ ID NO: 97           moltype = AA   length = 123
FEATURE                 Location/Qualifiers
REGION                  1..123
                        note = Synthetic construct
source                  1..123
                        mol_type = protein
                        organism = synthetic construct
SEQUENCE: 97
EVQLVESGGE LVKPGGSLRL SCVASGLSLT SNSMSWIRQA PGKGLQWVAT IWSNGGTDYT    60
DAVKGRFTIS RDNVKNSLYL QMNSLRAEDT AVYYCASIYF YDADYLHWYF DFWGQGTLVT    120
VSS                                                                123

SEQ ID NO: 98           moltype = AA   length = 107
FEATURE                 Location/Qualifiers
REGION                  1..107
                        note = Synthetic construct
source                  1..107
                        mol_type = protein
                        organism = synthetic construct
```

```
SEQUENCE: 98
EIVMTQSPAS LSLSQEDKVT ITCRASEGIS NNLAWYQQKP GQAPKLLIYA TSELATGVPS   60
RFSGSGSGTD FTLTISSLQP EDFATYYCQQ GYKWPLTFGQ GTKVEIK                107

SEQ ID NO: 99           moltype = AA  length = 123
FEATURE                 Location/Qualifiers
REGION                  1..123
                        note = Synthetic construct
source                  1..123
                        mol_type = protein
                        organism = synthetic construct
SEQUENCE: 99
EVQLVESGGE LVKPGGSLRL SCVASGLSLT SHSMSWIRQA PGKGLQWVAT IWSNGGTDYT   60
DAVKGRFTIS RDNVKNSLYL QMNSLRAEDT AVYYCANIYY YDADYLHWYF DFWGQGTLVT  120
VSS                                                                123

SEQ ID NO: 100          moltype = AA  length = 107
FEATURE                 Location/Qualifiers
REGION                  1..107
                        note = Synthetic construct
source                  1..107
                        mol_type = protein
                        organism = synthetic construct
SEQUENCE: 100
EIVMTQSPAS LSLSQEDKVT ITCRASEGIS NNLAWYQQKP GQAPKLLIYA TSELATGVPS   60
RFSGSGSGTD FTLTISSLQP EDFATYYCQQ GYKWPLTFGQ GTKVEIK                107

SEQ ID NO: 101          moltype = AA  length = 123
FEATURE                 Location/Qualifiers
REGION                  1..123
                        note = Synthetic construct
source                  1..123
                        mol_type = protein
                        organism = synthetic construct
SEQUENCE: 101
EVQLVESGGE LVKPGGSLRL SCVASGLSLT TNSMSWIRQA PGKGLQWVAT IWSNGGTDYT   60
DAVKGRFTIS RDNVKNSLYL QMNSLRAEDT AVYYCASIYY YDADYLHWYF DLWGQGTLVT  120
VSS                                                                123

SEQ ID NO: 102          moltype = AA  length = 107
FEATURE                 Location/Qualifiers
REGION                  1..107
                        note = Synthetic construct
source                  1..107
                        mol_type = protein
                        organism = synthetic construct
SEQUENCE: 102
EIVMTQSPAS LSLSQEDKVT ITCRASEGIS NNLAWYQQKP GQAPKLLIYA TSELATGVPS   60
RFSGSGSGTD FTLTISSLQP EDFATYYCQQ GYKWPLTFGQ GTKVEIK                107

SEQ ID NO: 103          moltype = AA  length = 123
FEATURE                 Location/Qualifiers
REGION                  1..123
                        note = Synthetic construct
source                  1..123
                        mol_type = protein
                        organism = synthetic construct
SEQUENCE: 103
EVQLVESGGE LVKPGGSLRL SCVASGLSLT SNSMSWIRQA PGKGLQWVAT IWSNGGTDYT   60
DAVKGRFTIS RDNVKNSLYL QMNSLRAEDT AVYYCASIYY YDADYLHFYF DFWGQGTLVT  120
VSS                                                                123

SEQ ID NO: 104          moltype = AA  length = 107
FEATURE                 Location/Qualifiers
REGION                  1..107
                        note = Synthetic construct
source                  1..107
                        mol_type = protein
                        organism = synthetic construct
SEQUENCE: 104
EIVMTQSPAS LSLSQEDKVT ITCRASEGIS NNLAWYQQKP GQAPKLLIYA TSELATGVPS   60
RFSGSGSGTD FTLTISSLQP EDFATYYCQQ GYKWPLTFGQ GTKVEIK                107

SEQ ID NO: 105          moltype = AA  length = 123
FEATURE                 Location/Qualifiers
REGION                  1..123
                        note = Synthetic construct
source                  1..123
                        mol_type = protein
```

```
                                -continued
                        organism = synthetic construct
SEQUENCE: 105
EVQLVESGGD LVKPEGSLRL SCVVSGLSLT SGSMSWVRQA PGKGLQWVGV IYSNGGTDYT    60
DAVKGRFTIS RDNAKNTVYL QMNSLRTEDT AVYYCASIYY YDAYYLHWYY DFWGQGTLVT   120
VSS                                                                 123

SEQ ID NO: 106          moltype = AA   length = 107
FEATURE                 Location/Qualifiers
REGION                  1..107
                        note = Synthetic construct
source                  1..107
                        mol_type = protein
                        organism = synthetic construct
SEQUENCE: 106
EIVMTQSPAS LSLSQGEKVT ITCRASEGIS NNLAWYQQKP GQAPKLLIYA TSSMATGVPS    60
RFSGSGSGTD FSFTISSLEP EDVATYYCQQ GYKFPLTFGA GTKVELK                 107

SEQ ID NO: 107          moltype = AA   length = 123
FEATURE                 Location/Qualifiers
REGION                  1..123
                        note = Synthetic construct
source                  1..123
                        mol_type = protein
                        organism = synthetic construct
SEQUENCE: 107
EVQLVESGGD LVQPGGSLRL SCVVSGLDLT SNSMSWVRQA PGKGLQWVTV IWSNGGSDYA    60
DAVKGRFTIS RDNAKNTVYL QMNSLRAEDT AMYYCASIYY YDADYLHWYF QFWGQGTLVT   120
VSS                                                                 123

SEQ ID NO: 108          moltype = AA   length = 107
FEATURE                 Location/Qualifiers
REGION                  1..107
                        note = Synthetic construct
source                  1..107
                        mol_type = protein
                        organism = synthetic construct
SEQUENCE: 108
EIVMTQSPAS LSLSQEEKVT ITCRASEGIS NNLAWYQQKP GQAPKLLIYA ASSLQTGVPS    60
RFSGSGSGTD FSFTISSLEP EDVATYYCQH GYKFPLTFGA GTKVELK                 107

SEQ ID NO: 109          moltype = AA   length = 123
FEATURE                 Location/Qualifiers
REGION                  1..123
                        note = Synthetic construct
source                  1..123
                        mol_type = protein
                        organism = synthetic construct
SEQUENCE: 109
EVQLVESGGD LVKPAGSLRL SCVASALSLT SNSMSWVRQA PGKGLQLVAT IWSNGGTDYT    60
DAVKGRFTIS RDNAKNTVYL QMNSLRAEDT AMYYCASIYY YDADYLHWYW DFWGQGTLVT   120
VSS                                                                 123

SEQ ID NO: 110          moltype = AA   length = 107
FEATURE                 Location/Qualifiers
REGION                  1..107
                        note = Synthetic construct
source                  1..107
                        mol_type = protein
                        organism = synthetic construct
SEQUENCE: 110
EIVMTQSPAS LSASQEEKVT ITCRASEGIQ NSLAWYQQKP GQAPKLLIYA TNSLATGVPS    60
RFSGSGSGTD FTLTISSLQP EDFATYYCQQ GHKFPLTFGA GTKVELK                 107

SEQ ID NO: 111          moltype = AA   length = 123
FEATURE                 Location/Qualifiers
REGION                  1..123
                        note = Synthetic construct
source                  1..123
                        mol_type = protein
                        organism = synthetic construct
SEQUENCE: 111
EVQLVESGGD LVQPAGSLRL SCVASGLSLT SQSMSWVRQA PGKGLQLVAI IWSNGGTDYT    60
DAVKGRFTIS RDNAKNTVYL QMNSLRAEDT AMYYCASIYY YDADYLHWYF DMWGQGTLVT   120
VSS                                                                 123

SEQ ID NO: 112          moltype = AA   length = 107
FEATURE                 Location/Qualifiers
REGION                  1..107
                        note = Synthetic construct
```

```
source                   1..107
                         mol_type = protein
                         organism = synthetic construct
SEQUENCE: 112
EIVMTQSPAS LSLSQEEKVT ITCRASEGIS NALAWYQQKP GKAPKLLIYA TESLATGVPS    60
RFSGSGSGTD FTLTISSLQP EDFATYYCQQ GFKFPLTFGA GTKVELK                 107

SEQ ID NO: 113           moltype = AA  length = 123
FEATURE                  Location/Qualifiers
REGION                   1..123
                         note = Synthetic construct
source                   1..123
                         mol_type = protein
                         organism = synthetic construct
SEQUENCE: 113
EVQLVESGGD LVQPGGSLRL SCVVSGLSLT TNSMSWVRQA PGKGLQWVTT IWSNGGTDYA    60
DAVKGRFTIS RDNAKNTVYL QMNSLRAEDT AMYYCAQIYY YDADYLHWYF DFWGQGTLVT   120
VSS                                                                 123

SEQ ID NO: 114           moltype = AA  length = 107
FEATURE                  Location/Qualifiers
REGION                   1..107
                         note = Synthetic construct
source                   1..107
                         mol_type = protein
                         organism = synthetic construct
SEQUENCE: 114
EIVMTQSPAS LSASQEEKVT ITCRASEGIS NNLAWYQQKP GQAPKLLIYA TESLATGVPS    60
RFSGSGSGTD FSFTISSLQP EDVAVYYCQQ GYKWPLTFGQ GTKVEIK                 107

SEQ ID NO: 115           moltype = AA  length = 123
FEATURE                  Location/Qualifiers
REGION                   1..123
                         note = Synthetic construct
source                   1..123
                         mol_type = protein
                         organism = synthetic construct
SEQUENCE: 115
EVQLVESGGD LVKPGGSLSL SCVASGLSVT SNSMDWVRQA PGKGLQWLST IWSNGGTDYA    60
DAVKGRFTIS RDNAKNTLYL QMNSLRTEDT AVYYCAKIYY YDADYLHWYF DFWGQGTLVT   120
VSS                                                                 123

SEQ ID NO: 116           moltype = AA  length = 107
FEATURE                  Location/Qualifiers
REGION                   1..107
                         note = Synthetic construct
source                   1..107
                         mol_type = protein
                         organism = synthetic construct
SEQUENCE: 116
EIVMTQSPAS LSLSQEDKVT ITCRASEGIG NSLAWYQQKP GQAPKLLIYA TSQLATGVPS    60
RFSGSGSGTD FTLTISSLQP EDFATYYCQQ GHKFPLTFGQ GTKVEIK                 107

SEQ ID NO: 117           moltype = AA  length = 123
FEATURE                  Location/Qualifiers
REGION                   1..123
                         note = Synthetic construct
source                   1..123
                         mol_type = protein
                         organism = synthetic construct
SEQUENCE: 117
EVQLVESGGD LVKPEGSLSL SCVVSGLSLT SSSMSWVRQA PGKGLEWVAT IWSNGGTDYN    60
DAVKGRFTIS RDNAKNTLYL KMNSLRTEDT AVYYCASIYY YDADYLYWYF DFWGQGTLVT   120
VSS                                                                 123

SEQ ID NO: 118           moltype = AA  length = 107
FEATURE                  Location/Qualifiers
REGION                   1..107
                         note = Synthetic construct
source                   1..107
                         mol_type = protein
                         organism = synthetic construct
SEQUENCE: 118
EIVMTQSPAS LSLSQEEKVT ITCRASDGIS NSLAWYQQKP GQAPKLLIYA TQSLARGVPS    60
RFSGSGSGTD FSLTISSLEP EDVAVYYCQQ GYKWPLTFGA GTKVELK                 107

SEQ ID NO: 119           moltype = AA  length = 123
FEATURE                  Location/Qualifiers
REGION                   1..123
```

```
                            note = Synthetic construct
source                      1..123
                            mol_type = protein
                            organism = synthetic construct
SEQUENCE: 119
EVQLVESGGD LVKPEGSLRL TCVVSGLSMT SNSMSWVRQA PGKGLQWVAT IWSNGGTDYT    60
DAVKGRFTIS RDNAKNTLYL QMNSLRTEDT ARYYCASIYY YDSDYLHWYF DFWGQGTLVT   120
VSS                                                                 123

SEQ ID NO: 120              moltype = AA  length = 107
FEATURE                     Location/Qualifiers
REGION                      1..107
                            note = Synthetic construct
source                      1..107
                            mol_type = protein
                            organism = synthetic construct
SEQUENCE: 120
EIVMTQSPAS LSASQEEKVT ITCRASEAIS NSLAWYQQKP GQAPKLLIYA SSSLATGVPS    60
RFSGSGSGTD FSFTISSLEP EDVATYYCQQ GWKFPLTFGA GTKVELK                 107

SEQ ID NO: 121              moltype = AA  length = 123
FEATURE                     Location/Qualifiers
REGION                      1..123
                            note = Synthetic construct
source                      1..123
                            mol_type = protein
                            organism = synthetic construct
SEQUENCE: 121
EVQLVESGGD LVAPSQSLSI TCTVSGLSLT SHSISWVRQA PGKGLQWVAT IWSNGGTDYT    60
SAVKGRFTIS RDNAKNTVYL QMNSLRTEDT AVYYCASIYY YDADYLHWYW DFWGQGTLVT   120
VSS                                                                 123

SEQ ID NO: 122              moltype = AA  length = 107
FEATURE                     Location/Qualifiers
REGION                      1..107
                            note = Synthetic construct
source                      1..107
                            mol_type = protein
                            organism = synthetic construct
SEQUENCE: 122
EIVMTQSPAS LSLSQEDKVT ITCRASEGIS NGLAWYQQKP GQAPKLLIYA TSELATGVPS    60
RFSGSGSGTD FSFTISSLEP EDVAVYYCQQ GYKWPLTFGQ GTKVEIK                 107

SEQ ID NO: 123              moltype = AA  length = 123
FEATURE                     Location/Qualifiers
REGION                      1..123
                            note = Synthetic construct
source                      1..123
                            mol_type = protein
                            organism = synthetic construct
SEQUENCE: 123
EVQLVESGGD LVKPEGSLRL SCVVSGLSLT SNGMSWVRQA PGKGLEWVAT IWSNGGTDYT    60
DAVKGRFTIS RDNAKNTLYL QMNSLRTEDT AVYYCASIYY YEADYLHWYY DFWGQGTLVT   120
VSS                                                                 123

SEQ ID NO: 124              moltype = AA  length = 107
FEATURE                     Location/Qualifiers
REGION                      1..107
                            note = Synthetic construct
source                      1..107
                            mol_type = protein
                            organism = synthetic construct
SEQUENCE: 124
EIVMTQSPAS LSLSQGEKVT ITCRASEGIS SSLAWYQQKP GQAPKLLIYA TASLATGVPS    60
RFSGSGSGTD FSFTISSLEP EDVATYYCQQ GYKWPLTFGQ GTKVEIK                 107

SEQ ID NO: 125              moltype = AA  length = 123
FEATURE                     Location/Qualifiers
REGION                      1..123
                            note = Synthetic construct
source                      1..123
                            mol_type = protein
                            organism = synthetic construct
SEQUENCE: 125
EVQLVESGGD LVKPEGSLSL SCVVSGLSLT SHSMSWVRQA PGKGLQWVAT IWSNGGTDYT    60
DAVKGRFTIS KDNSKSQVFL KMNSLQTDDT ARYYCASIYY YDADYLHWYI DFWGQGTLVT   120
VSS                                                                 123

SEQ ID NO: 126              moltype = AA  length = 107
```

```
FEATURE                 Location/Qualifiers
REGION                  1..107
                        note = Synthetic construct
source                  1..107
                        mol_type = protein
                        organism = synthetic construct
SEQUENCE: 126
EIVMTQSPAS LSLSQEDKVT ITCRASEGIS NNLAWYQQKP GQAPKLLIYA TSKLATGVPS    60
RFSGSGSGTD FSFTISSLEP EDVATYYCQQ GYKWPLTFGQ GTKVEIK                 107

SEQ ID NO: 127          moltype = AA  length = 123
FEATURE                 Location/Qualifiers
REGION                  1..123
                        note = Synthetic construct
source                  1..123
                        mol_type = protein
                        organism = synthetic construct
SEQUENCE: 127
EVQLVESGGD LVKPEGSLRL SCVVSGLELT SNSMSWVRQA PGKGLQWVGT IWSNGGTDYT    60
DAVKGRFTIS RDNAKNTLYL QMNSLQTEDT AVYYCASIYY YDADYLHWYW DFWGQGTLVT   120
VSS                                                                 123

SEQ ID NO: 128          moltype = AA  length = 107
FEATURE                 Location/Qualifiers
REGION                  1..107
                        note = Synthetic construct
source                  1..107
                        mol_type = protein
                        organism = synthetic construct
SEQUENCE: 128
EIVMTQSPAS LSLSQGEKVT ITCRASDGIS NSLAWYQQKP GQAPKLLIYA TSELATGVPS    60
RFSGSGSGTD FSFTISSLEP EDVATYYCQQ GYKFPLTFGQ GTKVEIK                 107

SEQ ID NO: 129          moltype = AA  length = 123
FEATURE                 Location/Qualifiers
REGION                  1..123
                        note = Synthetic construct
source                  1..123
                        mol_type = protein
                        organism = synthetic construct
SEQUENCE: 129
EVQLVESGGD LVKPGGSLRL SCVASGLSLT SNSMSWVRQA PEKGLQLVAT IWSNGGTDYT    60
DAVKGRFTIS RDNAKNTVYL QMNSLRAEDT GMYYCASIYY YDADYLHWYF DLWGQGTLVT   120
VSS                                                                 123

SEQ ID NO: 130          moltype = AA  length = 107
FEATURE                 Location/Qualifiers
REGION                  1..107
                        note = Synthetic construct
source                  1..107
                        mol_type = protein
                        organism = synthetic construct
SEQUENCE: 130
EIVMTQSPAS LSLSQGEKVT ITCRASEAIS NSLAWYQQKP GQAPKLLIYA TTSLATGVPS    60
RFSGSGSGTD FTLTISSLQP EDFATYYCQQ GYKWPLTFGQ GTKVEIK                 107

SEQ ID NO: 131          moltype = AA  length = 123
FEATURE                 Location/Qualifiers
REGION                  1..123
                        note = Synthetic construct
source                  1..123
                        mol_type = protein
                        organism = synthetic construct
SEQUENCE: 131
EVQLVESGGD LVKPAGSLRL SCVASGLSLT SHSMSWVRQA PGKGLQLVAT IWSNGGTDYT    60
DAVKGRFTIS RDNAKNTVYL QMNSLRAEDT AMYYCASIYY YDADYLHWYW DFWGQGTLVT   120
VSS                                                                 123

SEQ ID NO: 132          moltype = AA  length = 107
FEATURE                 Location/Qualifiers
REGION                  1..107
                        note = Synthetic construct
source                  1..107
                        mol_type = protein
                        organism = synthetic construct
SEQUENCE: 132
EIVMTQSPAS LSLSQGEKVT ITCRASKGIS NSLAWYQQKP GQAPKLLIYA TSELATGVPS    60
RFSGSGSGTD FSFTISSLEP EDVAVYYCQQ GYKFPLTFGQ GTKVEIK                 107
```

```
SEQ ID NO: 133          moltype = AA  length = 123
FEATURE                 Location/Qualifiers
REGION                  1..123
                        note = Synthetic construct
source                  1..123
                        mol_type = protein
                        organism = synthetic construct
SEQUENCE: 133
EVQLVESGGD LVKPAGSLRL SCVASGLSFT SNSMSWVRQA PGKGLQLVAT IWSNGGTDYT    60
DAVKGRFTIS RDNAKNTVYL QMNSLRAEDT AMYYCASIYY YDADYLHWYL DFWGQGTLVT   120
VSS                                                                123

SEQ ID NO: 134          moltype = AA  length = 107
FEATURE                 Location/Qualifiers
REGION                  1..107
                        note = Synthetic construct
source                  1..107
                        mol_type = protein
                        organism = synthetic construct
SEQUENCE: 134
EIVMTQSPAS LSLSQGEKVT ITCRASEGIS NTLAWYQQKP GQAPKLLIYA TESLATGVPS    60
RFSGSGSGTD FTLTISSLQP EDFATYYCQQ GFKFPLTFGQ GTKVEIK                 107

SEQ ID NO: 135          moltype = AA  length = 123
FEATURE                 Location/Qualifiers
REGION                  1..123
                        note = Synthetic construct
source                  1..123
                        mol_type = protein
                        organism = synthetic construct
SEQUENCE: 135
EVQLVESGGD LVKPGGSLSL SCVASGLSLT SHSMDWVRQA PGKGLQWLST IWSNGGTQYA    60
DAVKGRFTIS RDNSKNTLYL QMNSLRAEDT AVYYCASIWY YDADYLHWYF DFWGQGTLVT   120
VSS                                                                123

SEQ ID NO: 136          moltype = AA  length = 107
FEATURE                 Location/Qualifiers
REGION                  1..107
                        note = Synthetic construct
source                  1..107
                        mol_type = protein
                        organism = synthetic construct
SEQUENCE: 136
EIVMTQSPAS LSLSQGEKVT ITCRASENIS NSLAWYQQKP GQAPKLLIYA TSTLATGVPS    60
RFSGSGSGTD FSLTISSLEP EDVATYYCQQ GFKFPLTFGQ GTKVEIK                 107

SEQ ID NO: 137          moltype = AA  length = 123
FEATURE                 Location/Qualifiers
REGION                  1..123
                        note = Synthetic construct
source                  1..123
                        mol_type = protein
                        organism = synthetic construct
SEQUENCE: 137
EVQLVESGGD LVAPSQSLSI TCTVSGMSLT SNSISWVRQP PGRGLEWLGT IWSNGGTDYT    60
DAVKGRFTIS RDNAKNTVYL QMNSLRAEDT AMYYCAQIYY YDADYLHWYF DFWGQGTLVT   120
VSS                                                                123

SEQ ID NO: 138          moltype = AA  length = 107
FEATURE                 Location/Qualifiers
REGION                  1..107
                        note = Synthetic construct
source                  1..107
                        mol_type = protein
                        organism = synthetic construct
SEQUENCE: 138
EIVMTQSPAS LSASQEEKVT ITCRASEGIS NNLAWYQQKP GQAPKLLIHA TSSLQTGVPS    60
RFSGSGSGTD FTLTISSLQP EDFATYYCQQ GYQFPLTFGQ GTKVEIK                 107

SEQ ID NO: 139          moltype = AA  length = 123
FEATURE                 Location/Qualifiers
REGION                  1..123
                        note = Synthetic construct
source                  1..123
                        mol_type = protein
                        organism = synthetic construct
SEQUENCE: 139
EVQLVESGGD LVKPAGSLRL SCVASGLGLT SNSMSWVRQA PEKGLQLVAV IWSNGGTQYA    60
DAVKGRFTIS RDNAKNTVYL QMNSLRAEDT AMYYCAKIYY YDADYLHWYF DFWGQGTLVT   120
```

```
VSS                                                                   123

SEQ ID NO: 140          moltype = AA  length = 107
FEATURE                 Location/Qualifiers
REGION                  1..107
                        note = Synthetic construct
source                  1..107
                        mol_type = protein
                        organism = synthetic construct
SEQUENCE: 140
EIVMTQSPAS LSLSQGEKVT ITCRASEGIS NNLAWYQQKP GQAPKLLIYA TSALATGVPS      60
RFSGSGSGTD FTLTISSLQP EDFATYYCQQ GYKFPLTFGQ GTKVEIK                   107

SEQ ID NO: 141          moltype = AA  length = 123
FEATURE                 Location/Qualifiers
REGION                  1..123
                        note = synthetic construct
source                  1..123
                        mol_type = protein
                        organism = synthetic construct
SEQUENCE: 141
DVQLVESGGD LVKPGGSLRL TCVASGLSLT SSSMSWVRQA PGKGLQWVST IYSNGGTYYT      60
DSVKGRFTIS KDNAENTLYL QMNNLKTEDT ATYYCASIYY YDADYLHWYF DFWGQGALVT     120
VSS                                                                   123

SEQ ID NO: 142          moltype = AA  length = 107
FEATURE                 Location/Qualifiers
REGION                  1..107
                        note = synthetic construct
source                  1..107
                        mol_type = protein
                        organism = synthetic construct
SEQUENCE: 142
EIQMTQSPTS LSASVGDRVT ITCRASEGIS NNLSWYQQTP GKAPKLLIYA TSNLHSGVPS      60
RFSGSGSGTD FTLTISSLQP EDFATYYCQQ GYKWPLTFGG GTKLEIT                   107

SEQ ID NO: 143          moltype = AA  length = 334
FEATURE                 Location/Qualifiers
source                  1..334
                        mol_type = protein
                        organism = Canis lupus
SEQUENCE: 143
ASTTAPSVFP LAPSCGSTSG STVALACLVS GYFPEPVTVS WNSGSLTSGV HTFPSVLQSS      60
GLYSLSSMVT VPSSRWPSET FTCNVAHPAS KTKVDKPVPK RENGRVPRPP DCPKCPAPEM     120
LGGPSVFIFP PKPKDTLLIA RTPEVTCVVV DLDPEDPEVQ ISWFVDGKQM QTAKTQPREE     180
QFNGTYRVVS VLPIGHQDWL KGKQFTCKVN NKALPSPIER TISKARGQAH QPSVYVLPPS     240
REELSKNTVS LTCLIKDFFP PDIDVEWQSN GQQEPESKYR TTPPQLDEDG SYFLYSKLSV     300
DKSRWQRGDT FICAVMHEAL HNHYTQESLS HSPG                                334

SEQ ID NO: 144          moltype = AA  length = 457
FEATURE                 Location/Qualifiers
REGION                  1..457
                        note = synthetic construct
source                  1..457
                        mol_type = protein
                        organism = synthetic construct
SEQUENCE: 144
QVQLKESGPG LVQPSQTLSL TCTVSGLSLT SNSVSWIRQP PGKGLEWMGV IWSNGGTDYN      60
SAIESRLSIN RDTSKSQVFL KMNSLQPEDT AMYFCASIYY YDADYLHWYF DFWGPGTMVT     120
VSSASTTAPS VFPLAPSCGS TSGSTVALAC LVSGYFPEPV TVSWNSGSLT SGVHTFPSVL     180
QSSGLYSLSS MVTVPSSRWP SETFTCNVAH PASKTKVDKP VPKRENGRVP RPPDCPKCPA     240
PEAAGGPSVF IFPPKPKDTL LIARTPEVTC VVVDLDPEDP EVQISWFVDG KQMQTAKTQP     300
REEQFNGTYR VVSVLPIGHQ DWLKGKQFTC KVNNKALPSP IERTISKARG QAHQPSVYVL     360
PPSREELSKN TVSLTCLIKD FFPPDIDVEW QSNGQQEPES KYRTTPPQLD EDGSYFLYSK     420
LSVDKSRWQR GDTFICAVMH EALHNHYTQE SLSHSPG                             457

SEQ ID NO: 145          moltype = AA  length = 217
FEATURE                 Location/Qualifiers
REGION                  1..217
                        note = synthetic construct
source                  1..217
                        mol_type = protein
                        organism = synthetic construct
SEQUENCE: 145
DIQMTQSPAS LSASLGETVS IECLASEGIS NSLAWYQLKP GKSPQFLIYA TSSLQDGVPS      60
RFSGSGSGTQ YSLKISGMQP EDEGVYYCQQ GYKFPLTFGS GTKLKIKRND AQPAVYLFQP     120
SPDQLHTGSA SVVCLLNSFY PKDINVKWKV DGVIQDTGIQ ESVTEQDKDS TYSLSSTLTM     180
SSTEYLSHEL YSCEITHKSL PSTLIKSFQR SECQRVD                             217
```

-continued

| | | |
|---|---|---|
| SEQ ID NO: 146 | moltype = AA  length = 8 | |
| FEATURE | Location/Qualifiers | |
| source | 1..8 | |
| | mol_type = protein | |
| | organism = synthetic construct | |
| VARIANT | 1 | |
| | note = A can be replaced by G or N | |
| VARIANT | 2 | |
| | note = L can be replaced by M | |
| VARIANT | 3 | |
| | note = A can be replaced by D, E, or S | |
| VARIANT | 4 | |
| | note = F can be replaced by I, L, M, or V | |
| VARIANT | 5 | |
| | note = N can be replaced by T | |
| VARIANT | 6 | |
| | note = E can be replaced by S or T | |
| VARIANT | 7 | |
| | note = G can be replaced by H, N, S, or Q | |
| VARIANT | 8 | |
| | note = A can be replaced by S | |
| SEQUENCE: 146 | | |
| ALAFNEGA | | 8 |
| | | |
| SEQ ID NO: 147 | moltype = AA  length = 7 | |
| FEATURE | Location/Qualifiers | |
| REGION | 1..7 | |
| | note = synthetic construct | |
| VARIANT | 2 | |
| | note = W can be replaced by Y | |
| source | 1..7 | |
| | mol_type = protein | |
| | organism = synthetic construct | |
| SEQUENCE: 147 | | |
| JWSNGGT | | 7 |
| | | |
| SEQ ID NO: 148 | moltype = AA  length = 17 | |
| FEATURE | Location/Qualifiers | |
| REGION | 1..17 | |
| | note = synthetic construct | |
| VARIANT | 2 | |
| | note = D can be replaced by E, K, N, Q, S, or T | |
| VARIANT | 4 | |
| | note = W can be replaced by Y | |
| VARIANT | 5 | |
| | note = F can be replaced by H, W, or Y | |
| VARIANT | 7 | |
| | note = D can be replaced by E | |
| VARIANT | 8 | |
| | note = A can be replaced by S | |
| VARIANT | 9 | |
| | note = D can be replaced by Y | |
| VARIANT | 12 | |
| | note = H can be replaced by Y | |
| VARIANT | 13 | |
| | note = F can be replaced by W | |
| VARIANT | 15 | |
| | note = F can be replaced by I, L, W, or Y | |
| VARIANT | 16 | |
| | note = D can be replaced by Q | |
| VARIANT | 17 | |
| | note = F can be replaced by I, L, M, W, or Y | |
| source | 1..17 | |
| | mol_type = protein | |
| | organism = synthetic construct | |
| SEQUENCE: 148 | | |
| ADIWFYDADY LHFYFDF | | 17 |
| | | |
| SEQ ID NO: 149 | moltype = AA  length = 6 | |
| FEATURE | Location/Qualifiers | |
| source | 1..6 | |
| | mol_type = protein | |
| | organism = synthetic construct | |
| VARIANT | 1 | |
| | note = D can be replaced by E or K | |
| VARIANT | 2 | |
| | note = A can be replaced by G or N | |
| VARIANT | 4 | |
| | note = G can be replaced by N, Q or S | |

```
VARIANT                 5
                        note = N can be replaced by S
VARIANT                 6
                        note = A can be replaced by G, N, S or T
SEQUENCE: 149
DAIGNA                                                                         6

SEQ ID NO: 150          moltype =    length =
SEQUENCE: 150
000

SEQ ID NO: 151          moltype = AA   length = 9
FEATURE                 Location/Qualifiers
REGION                  1..9
                        note = synthetic construct
VARIANT                 2
                        note = H can be replaced by Q
VARIANT                 4
                        note = F can be replaced by H, W, or Y
VARIANT                 5
                        note = K can be replaced by Q
VARIANT                 6
                        note = F can be replaced by W
VARIANT                 8
                        note = L can be replaced by M
source                  1..9
                        mol_type = protein
                        organism = synthetic construct
SEQUENCE: 151
QHGFKFPLT                                                                      9

SEQ ID NO: 152          moltype = AA   length = 8
FEATURE                 Location/Qualifiers
source                  1..8
                        mol_type = protein
                        organism = synthetic construct
VARIANT                 1
                        note = A can be replaced by G
VARIANT                 2
                        note = L can be replaced by M
VARIANT                 3
                        note = E can be replaced by S
VARIANT                 4
                        note = F can be replaced by L
VARIANT                 5
                        note = N can be replaced by T
VARIANT                 6
                        note = E can be replaced by S or T
VARIANT                 7
                        note = H can be replaced by N or S
VARIANT                 8
                        note = A can be replaced by S
SEQUENCE: 152
ALEFNEHA                                                                       8

SEQ ID NO: 153          moltype = AA   length = 7
FEATURE                 Location/Qualifiers
source                  1..7
                        mol_type = protein
                        organism = synthetic construct
SEQUENCE: 153
IWSNGGT                                                                        7

SEQ ID NO: 154          moltype = AA   length = 17
FEATURE                 Location/Qualifiers
REGION                  1..17
                        note = synthetic construct
VARIANT                 2
                        note = N can be replaced by Q or S
VARIANT                 7
                        note = D can be replaced by E
VARIANT                 13
                        note = F can be replaced by W
VARIANT                 15
                        note = F can be replaced by I, L, W, or Y
VARIANT                 17
                        note = F can be replaced by I, L, or M
source                  1..17
                        mol_type = protein
```

-continued

```
                           organism = synthetic construct
SEQUENCE: 154
ANIYYYDADY LHFYFDF                                                            17

SEQ ID NO: 155             moltype = AA   length = 6
FEATURE                    Location/Qualifiers
source                     1..6
                           mol_type = protein
                           organism = synthetic construct
VARIANT                    1
                           note = D can be replaced by E
VARIANT                    4
                           note = N can be replaced by Q or S
VARIANT                    5
                           note = N can be replaced by S
VARIANT                    6
                           note = G can be replaced by N, S or T
SEQUENCE: 155
DGINNG                                                                         6

SEQ ID NO: 156             moltype =    length =
SEQUENCE: 156
000

SEQ ID NO: 157             moltype = AA   length = 9
FEATURE                    Location/Qualifiers
source                     1..9
                           mol_type = protein
                           organism = synthetic construct
VARIANT                    4
                           note = F can be replaced by H or Y
VARIANT                    5
                           note = K can be replaced by Q
VARIANT                    6
                           note = F can be replaced by W
SEQUENCE: 157
QQGFKFPLT                                                                      9

SEQ ID NO: 158             moltype = AA   length = 5
FEATURE                    Location/Qualifiers
source                     1..5
                           mol_type = protein
                           organism = synthetic construct
VARIANT                    1
                           note = E can be replaced by S or T
VARIANT                    2
                           note = G can be replaced by H, N, S, or Q
VARIANT                    3
                           note = A can be replaced by S
VARIANT                    4
                           note = I can be replaced by M or V
VARIANT                    5
                           note = D can be replaced by S
SEQUENCE: 158
EGAID                                                                          5

SEQ ID NO: 159             moltype = AA   length = 16
FEATURE                    Location/Qualifiers
REGION                     1..16
                           note = synthetic construct
VARIANT                    1
                           note = V can be replaced by L, M, or T
VARIANT                    3
                           note = W can be replaced by Y
VARIANT                    9
                           note = D can be replaced by Q, or S
VARIANT                    11
                           note = A can be replaced by N, or T
VARIANT                    12
                           note = D can be replaced by S
VARIANT                    14
                           note = I can be replaced by V
VARIANT                    15
                           note = E can be replaced by K
VARIANT                    16
                           note = G can be replaced by S
source                     1..16
                           mol_type = protein
                           organism = synthetic construct
```

```
VARIANT                  6
                         note = G can be replaced by R
SEQUENCE: 159
VJWSNGGTDY ADAIEG                                                                    16

SEQ ID NO: 160           moltype = AA  length = 15
FEATURE                  Location/Qualifiers
REGION                   1..15
                         note = synthetic construct
VARIANT                  2
                         note = W can be replaced by Y
VARIANT                  3
                         note = F can be replaced by H, W, or Y
VARIANT                  5
                         note = D can be replaced by E
VARIANT                  6
                         note = A can be replaced by S
VARIANT                  7
                         note = D can be replaced by Y
VARIANT                  10
                         note = H can be replaced by Y
VARIANT                  11
                         note = F can be replaced by W
VARIANT                  13
                         note = F can be replaced by I, L, W, or Y
VARIANT                  14
                         note = D can be replaced by Q
VARIANT                  15
                         note = F can be replaced by I, L, M, W, or Y
source                   1..15
                         mol_type = protein
                         organism = synthetic construct
SEQUENCE: 160
IWFYDADYLH FYFDF                                                                     15

SEQ ID NO: 161           moltype = AA  length = 11
FEATURE                  Location/Qualifiers
source                   1..11
                         mol_type = protein
                         organism = synthetic construct
VARIANT                  1
                         note = L can be replaced by R
VARIANT                  4
                         note = D can be replaced by E or K
VARIANT                  5
                         note = A can be replaced by G or N
VARIANT                  7
                         note = G can be replaced by N, Q or S
VARIANT                  8
                         note = N can be replaced by S
VARIANT                  9
                         note = A can be replaced by G, N, S or T
VARIANT                  10
                         note = L can be replaced by V
VARIANT                  11
                         note = A can be replaced by N
SEQUENCE: 161
LASDAIGNAL A                                                                         11

SEQ ID NO: 162           moltype = AA  length = 7
FEATURE                  Location/Qualifiers
source                   1..7
                         mol_type = protein
                         organism = synthetic construct
VARIANT                  2
                         note = A can be replaced by S or T
VARIANT                  3
                         note = A can be replaced by D, E, N, Q, S or T
VARIANT                  4
                         note = A can be replaced by E, K, L, N, Q, S, or T
VARIANT                  5
                         note = L can be replaced by M, or N
VARIANT                  6
                         note = A can be replaced by Q
VARIANT                  7
                         note = G can be replaced by D, R, S, or T
SEQUENCE: 162
AAAALAG                                                                              7
```

```
SEQ ID NO: 163          moltype = AA  length = 9
FEATURE                 Location/Qualifiers
source                  1..9
                        mol_type = protein
                        organism = synthetic construct
VARIANT                 1
                        note = H can be replaced by M , Q, or R
VARIANT                 2
                        note = H can be replaced by N, Q, or S
VARIANT                 4
                        note = F can be replaced by H, W, or Y
VARIANT                 5
                        note = K can be replaced by Q
VARIANT                 6
                        note = F can be replaced by W
VARIANT                 8
                        note = L can be replaced by M
SEQUENCE: 163
HHGFKFPLT                                                                    9

SEQ ID NO: 164          moltype = AA  length = 5
FEATURE                 Location/Qualifiers
source                  1..5
                        mol_type = protein
                        organism = synthetic construct
VARIANT                 1
                        note = E can be replaced by S or T
VARIANT                 2
                        note = H can be replaced by N
VARIANT                 3
                        note = A can be replaced by S
VARIANT                 4
                        note = I can be replaced by M
SEQUENCE: 164
EHAIS                                                                        5

SEQ ID NO: 165          moltype = AA  length = 16
FEATURE                 Location/Qualifiers
REGION                  1..16
                        note = synthetic construct
VARIANT                 11
                        note = A can be replaced by T
VARIANT                 12
                        note = D can be replaced by S
source                  1..16
                        mol_type = protein
                        organism = synthetic construct
VARIANT                 6
                        note = G can be replaced by R
SEQUENCE: 165
TIWSNGGTDY ADAVKG                                                           16

SEQ ID NO: 166          moltype = AA  length = 15
FEATURE                 Location/Qualifiers
REGION                  1..15
                        note = synthetic construct
VARIANT                 5
                        note = D can be replaced by E
VARIANT                 10
                        note = H can be replaced by Y
VARIANT                 11
                        note = F can be replaced by W
VARIANT                 13
                        note = F can be replaced by I, L, W, or Y
VARIANT                 15
                        note = F can be replaced by I, L, or M
source                  1..15
                        mol_type = protein
                        organism = synthetic construct
SEQUENCE: 166
IYYYDADYLH FYFDF                                                            15

SEQ ID NO: 167          moltype = AA  length = 11
FEATURE                 Location/Qualifiers
REGION                  1..11
                        note = synthetic construct
VARIANT                 7
                        note = N can be replaced by Q or S
VARIANT                 8
```

```
                        note = N can be replaced by S
VARIANT                 9
                        note = G can be replaced by N, S or T
source                  1..11
                        mol_type = protein
                        organism = synthetic construct
VARIANT                 10
                        note = L can be replaced by V
SEQUENCE: 167
RASEGINNGL A                                                                11

SEQ ID NO: 168          moltype = AA   length = 7
FEATURE                 Location/Qualifiers
source                  1..7
                        mol_type = protein
                        organism = synthetic construct
VARIANT                 3
                        note = A can be replaced by D, E, N, Q, or S
VARIANT                 4
                        note = E can be replaced by K, Q, or S
VARIANT                 6
                        note = A can be replaced by Q
VARIANT                 7
                        note = R can be replaced by T
SEQUENCE: 168
ATAELAR                                                                     7

SEQ ID NO: 169          moltype = AA   length = 9
FEATURE                 Location/Qualifiers
REGION                  1..9
                        note = synthetic construct
VARIANT                 4
                        note = F can be replaced by H, W, or Y
VARIANT                 5
                        note = K can be replaced by Q
VARIANT                 6
                        note = F can be replaced by W
source                  1..9
                        mol_type = protein
                        organism = synthetic construct
SEQUENCE: 169
QQGFKFPLT                                                                   9

SEQ ID NO: 170          moltype = AA   length = 7
FEATURE                 Location/Qualifiers
source                  1..7
                        mol_type = protein
                        organism = synthetic construct
VARIANT                 1
                        note = A can be replaced by G, or N
VARIANT                 2
                        note = L can be replaced by M
VARIANT                 3
                        note = A can be replaced by D, E, or S
VARIANT                 4
                        note = F can be replaced by I, L, M, or V
VARIANT                 5
                        note = N can be replaced by T
VARIANT                 6
                        note = E can be replaced by S, or T
VARIANT                 7
                        note = G can be replaced by H, N, S, or Q
SEQUENCE: 170
ALAFNEG                                                                     7

SEQ ID NO: 171          moltype = AA   length = 5
FEATURE                 Location/Qualifiers
REGION                  1..5
                        note = synthetic construct
VARIANT                 1
                        note = W can be replaced by Y
source                  1..5
                        mol_type = protein
                        organism = synthetic construct
VARIANT                 4
                        note = G can be replaced by R
SEQUENCE: 171
WSNGG                                                                       5
```

```
SEQ ID NO: 172          moltype = AA  length = 15
FEATURE                 Location/Qualifiers
REGION                  1..15
                        note = synthetic construct
VARIANT                 2
                        note = W can be replaced by Y
VARIANT                 3
                        note = F can be replaced by H, W, or Y
VARIANT                 5
                        note = D can be replaced by E
VARIANT                 6
                        note = A can be replaced by S
VARIANT                 7
                        note = D can be replaced by Y
VARIANT                 10
                        note = H can be replaced by Y
VARIANT                 11
                        note = F can be replaced by W
VARIANT                 13
                        note = F can be replaced by I, L, W, or Y
VARIANT                 14
                        note = D can be replaced by Q
VARIANT                 15
                        note = F can be replaced by I, L, M, W, or Y
source                  1..15
                        mol_type = protein
                        organism = synthetic construct
SEQUENCE: 172
IWFYDADYLH FYFDF                                                          15

SEQ ID NO: 173          moltype = AA  length = 7
FEATURE                 Location/Qualifiers
source                  1..7
                        mol_type = protein
                        organism = synthetic construct
VARIANT                 2
                        note = D can be replaced by E, or K
VARIANT                 3
                        note = A can be replaced by G, or N
VARIANT                 5
                        note = G can be replaced by N, Q or S
VARIANT                 6
                        note = N can be replaced by S
VARIANT                 7
                        note = A can be replaced by G, N, S or T
SEQUENCE: 173
SDAIGNA                                                                    7

SEQ ID NO: 174          moltype =     length =
SEQUENCE: 174
000

SEQ ID NO: 175          moltype = AA  length = 6
FEATURE                 Location/Qualifiers
source                  1..6
                        mol_type = protein
                        organism = synthetic construct
VARIANT                 2
                        note = F can be replaced by H, W, or Y
VARIANT                 3
                        note = K can be replaced by Q
VARIANT                 4
                        note = F can be replaced by W
VARIANT                 6
                        note = L can be replaced by M
SEQUENCE: 175
GFKFPL                                                                     6

SEQ ID NO: 176          moltype = AA  length = 7
FEATURE                 Location/Qualifiers
source                  1..7
                        mol_type = protein
                        organism = synthetic construct
VARIANT                 1
                        note = A can be replaced by G, or N
VARIANT                 2
                        note = L can be replaced by M
VARIANT                 3
                        note = A can be replaced by E, or S
```

```
VARIANT                  4
                         note = F can  be replaced by L
VARIANT                  5
                         note = N can be replaced by T
VARIANT                  6
                         note = E can be replaced by S or T
VARIANT                  7
                         note = H can be replaced by N, or S
SEQUENCE: 176
ALAFNEH                                                                  7

SEQ ID NO: 177           moltype = AA  length = 5
FEATURE                  Location/Qualifiers
REGION                   1..5
                         note = synthetic construct
source                   1..5
                         mol_type = protein
                         organism = synthetic construct
VARIANT                  4
                         note = G can be replaced by R
SEQUENCE: 177
WSNGG                                                                    5

SEQ ID NO: 178           moltype = AA  length = 15
FEATURE                  Location/Qualifiers
REGION                   1..15
                         note = synthetic construct
VARIANT                  3
                         note = F can be replaced by Y
VARIANT                  5
                         note = D can be replaced by E
VARIANT                  10
                         note = H can be replaced by Y
VARIANT                  11
                         note = F can be replaced by W
VARIANT                  13
                         note = F can be replaced by I, L, W, or Y
VARIANT                  15
                         note = F can be replaced by I, L, M, W, or Y
source                   1..15
                         mol_type = protein
                         organism = synthetic construct
SEQUENCE: 178
IYFYDADYLH FYFDF                                                         15

SEQ ID NO: 179           moltype = AA  length = 7
FEATURE                  Location/Qualifiers
source                   1..7
                         mol_type = protein
                         organism = synthetic construct
VARIANT                  2
                         note = D can be replaced by E
VARIANT                  5
                         note = N can be replaced by Q, or S
VARIANT                  6
                         note = N can be replaced by S
VARIANT                  7
                         note = G can be replaced by N, S, or T
SEQUENCE: 179
SDGINNG                                                                  7

SEQ ID NO: 180           moltype =   length =
SEQUENCE: 180
000

SEQ ID NO: 181           moltype = AA  length = 6
FEATURE                  Location/Qualifiers
source                   1..6
                         mol_type = protein
                         organism = synthetic construct
VARIANT                  2
                         note = F can be replaced by H, W, or Y
VARIANT                  3
                         note = K can be replaced by Q
VARIANT                  4
                         note = F can be replaced by W
VARIANT                  6
                         note = L can be replaced by M
SEQUENCE: 181
```

```
GFKFPL                                                                           6

SEQ ID NO: 182          moltype = AA  length = 221
FEATURE                 Location/Qualifiers
source                  1..221
                        mol_type = protein
                        organism = synthetic construct
SEQUENCE: 182
DVQLVESGGD LVKPGGSLRL TCVASGLSLT SSSMSWVRQA PGKGLQWVST IYSNGGTYYT   60
DSVKGRFTIS KDNAENTLYL QMNNLKTEDT ATYYCASIYY YDADYLHWYF DFWGQGALVT  120
VSSASTTAPS VFPLAPSCGT TSGATVALAC LVLGYFPEPV TVSWNSGALT SGVHTFPAVL  180
QASGLYSLSS MVTVPSSRWL SDTFTCNVAH PPSNTKVDKT V                      221

SEQ ID NO: 183          moltype = AA  length = 217
FEATURE                 Location/Qualifiers
source                  1..217
                        mol_type = protein
                        organism = synthetic construct
SEQUENCE: 183
EIQMTQSPTS LSASVGDRVT ITCRASEGIS NNLSWYQQTP GKAPKLLIYA TSNLHSGVPS   60
RFSGSGSGTD FTLTISSLQP EDFATYYCQQ GYKWPLTFGG GTKLEITRSD AQPSVFLFQP  120
SLDELHTGSA SIVCILNDFY PKEVNVKWKV DGVVQNKGIQ ESTTEQNSKD STYSLSSTLT  180
MSSSTEYQSHE KFSCEVTHKS LASTLVKSFN RSECQRE                          217

SEQ ID NO: 184          moltype = AA  length = 123
FEATURE                 Location/Qualifiers
source                  1..123
                        mol_type = protein
                        organism = synthetic construct
SEQUENCE: 184
DVQLVESGGD LVKPGGSLRL TCVASGLSLT SSSMVWVRQA PGKGLQWVST IYSNRGTYYT   60
DSVKGRFTIS KDNAENTLYL QMNNLKTEDT ATYYCASIYY YDADYLHWYF DEWGQGALVT  120
VSS                                                                123

SEQ ID NO: 185          moltype = AA  length = 123
FEATURE                 Location/Qualifiers
source                  1..123
                        mol_type = protein
                        organism = synthetic construct
SEQUENCE: 185
DVQLVESGGD LVKPGGSLRL TCVASGLSLT SSSMVWVRQA PGKGLQWVST IYSNRGTYYT   60
DSVKGRFTIS KDNAENTLYL QMNNLKTEDT ATYYCAQIYY YDADYLHWYF DFWGQGALVT  120
VSS                                                                123

SEQ ID NO: 186          moltype = AA  length = 123
FEATURE                 Location/Qualifiers
source                  1..123
                        mol_type = protein
                        organism = synthetic construct
SEQUENCE: 186
DVQLVESGGD LVKPGGSLRL TCVASGLSLT SSSMVWVRQA PGKGLQWVST IYSNGGTYYT   60
DSVKGRFTIS KDNAENTLYL QMNNLKTEDT ATYYCASIYY YDADYLHWYF DFWGQGALVT  120
VSS                                                                123

SEQ ID NO: 187          moltype = AA  length = 123
FEATURE                 Location/Qualifiers
source                  1..123
                        mol_type = protein
                        organism = synthetic construct
SEQUENCE: 187
DVQLVESGGD LVKPGGSLRL TCVASGLSLT SSSMVWVRQA PGKGLQWVST IYSNRGTYYT   60
DSVKGRFTIS KDNAENTLYL QMNNLKTEDT ATYYCAQIYY YDADYLHWYF DEWGQGALVT  120
VSS                                                                123

SEQ ID NO: 188          moltype = AA  length = 123
FEATURE                 Location/Qualifiers
source                  1..123
                        mol_type = protein
                        organism = synthetic construct
SEQUENCE: 188
DVQLVESGGD LVKPGGSLRL TCVASGLSLT SSSMVWVRQA PGKGLQWVST IYSNRGTYYT   60
DSVKGRFTIS KDNAENTLYL QMNNLKTEDT ATYYCASIYY YDADYLHWYF DFWGQGALVT  120
VSS                                                                123

SEQ ID NO: 189          moltype = AA  length = 123
FEATURE                 Location/Qualifiers
source                  1..123
                        mol_type = protein
                        organism = synthetic construct
```

```
SEQUENCE: 189
DVQLVESGGD LVKPGGSLRL TCVASGLSLT SSSMWVWRQA PGKGLQWVST IYSNGGTYYT    60
DSVKGRFTIS KDNAENTLYL QMNNLKTEDT ATYYCASIYY YDADYLHWYF DEWGQGALVT   120
VSS                                                                123

SEQ ID NO: 190          moltype = AA   length = 123
FEATURE                 Location/Qualifiers
source                  1..123
                        mol_type = protein
                        organism = synthetic construct
SEQUENCE: 190
DVQLVESGGD LVKPGGSLRL TCVASGLSLT SSSMWVWRQA PGKGLQWVST IYSNGGTYYT    60
DSVKGRFTIS KDNAENTLYL QMNNLKTEDT ATYYCAQIYY YDADYLHWYF DFWGQGALVT   120
VSS                                                                123

SEQ ID NO: 191          moltype = AA   length = 107
FEATURE                 Location/Qualifiers
source                  1..107
                        mol_type = protein
                        organism = synthetic construct
SEQUENCE: 191
EIQMTQSPTS LSASVGDRVT ITCRASEGIA NNLSWYQQTP GKAPKLLIYA TSILHSGVPS    60
RFSGSGSGTD FTLTISSLQP EDFATYYCQQ GYKWPLTFGG GTKLEIT                107

SEQ ID NO: 192          moltype = AA   length = 107
FEATURE                 Location/Qualifiers
source                  1..107
                        mol_type = protein
                        organism = synthetic construct
SEQUENCE: 192
EIQMTQSPTS LSASVGDRVT ITCRASEGIS NNLSWYQQTP GKAPKLLIYA TSVLHSGVPS    60
RFSGSGSGTD FTLTISSLQP EDFATYYCQQ GYKWPLTFGG GTKLEIT                107

SEQ ID NO: 193          moltype = AA   length = 107
FEATURE                 Location/Qualifiers
source                  1..107
                        mol_type = protein
                        organism = synthetic construct
SEQUENCE: 193
EIQMTQSPTS LSASVGDRVT ITCRASEGIA NNLSWYQQTP GKAPKLLIYA TSVLHSGVPS    60
RFSGSGSGTD FTLTISSLQP EDFATYYCQQ GYKWPLTFGG GTKLEIT                107

SEQ ID NO: 194          moltype = AA   length = 107
FEATURE                 Location/Qualifiers
source                  1..107
                        mol_type = protein
                        organism = synthetic construct
SEQUENCE: 194
EIQMTQSPTS LSASVGDRVT ITCRASEGIQ NNLSWYQQTP GKAPKLLIYA TSNLHSGVPS    60
RFSGSGSGTD FTLTISSLQP EDFATYYCQQ GYKWPLTFGG GTKLEIT                107

SEQ ID NO: 195          moltype = AA   length = 107
FEATURE                 Location/Qualifiers
source                  1..107
                        mol_type = protein
                        organism = synthetic construct
SEQUENCE: 195
EIQMTQSPTS LSASVGDRVT ITCRASEGIQ NNLSWYQQTP GKAPKLLIYA TSILHSGVPS    60
RFSGSGSGTD FTLTISSLQP EDFATYYCQQ GYKWPLTFGG GTKLEIT                107

SEQ ID NO: 196          moltype = AA   length = 107
FEATURE                 Location/Qualifiers
source                  1..107
                        mol_type = protein
                        organism = synthetic construct
SEQUENCE: 196
EIQMTQSPTS LSASVGDRVT ITCRASEGIA NNLSWYQQTP GKAPKLLIYA TSNLHSGVPS    60
RFSGSGSGTD FTLTISSLQP EDFATYYCQQ GYKWPLTFGG GTKLEIT                107

SEQ ID NO: 197          moltype = AA   length = 107
FEATURE                 Location/Qualifiers
source                  1..107
                        mol_type = protein
                        organism = synthetic construct
SEQUENCE: 197
EIQMTQSPTS LSASVGDRVT ITCRASEGIS NNLSWYQQTP GKAPKLLIYA TSILHSGVPS    60
RFSGSGSGTD FTLTISSLQP EDFATYYCQQ GYKWPLTFGG GTKLEIT                107

SEQ ID NO: 198          moltype = AA   length = 123
```

```
FEATURE                 Location/Qualifiers
source                  1..123
                        mol_type = protein
                        organism = synthetic construct
SEQUENCE: 198
DVQLVESGGD LVKPGGSLRL TCVASGLSLT SDSMSWVRQA PGKGLQWVST LWSNGGTYYT    60
DSVKGRFTIS KDNAENTLYL QMNNLKTEDT ATYYCASIYY YEADYLHWYF DFWGQGALVT   120
VSS                                                                 123

SEQ ID NO: 199          moltype = AA   length = 107
FEATURE                 Location/Qualifiers
source                  1..107
                        mol_type = protein
                        organism = synthetic construct
SEQUENCE: 199
EIQMTQSPTS LSASVGDRVT ITCRASEGIA NNLSWYQQTP GKAPKLLIYA TSNLHSGVPS    60
RFSGSGSGTD FTLTISSLQP EDFATYYCQQ GFKWPLTFGG GTKLEIT                 107

SEQ ID NO: 200          moltype = AA   length = 123
FEATURE                 Location/Qualifiers
source                  1..123
                        mol_type = protein
                        organism = synthetic construct
SEQUENCE: 200
DVQLVESGGD LVKPGGSLRL TCVASGLSLT SNSMSWVRQA PGKGLQWVST IWSNGGTYYT    60
DSVKGRFTIS KDNAENTLYL QMNNLKTEDT ATYYCASIYY YEAEYLHWYF DFWGQGALVT   120
VSS                                                                 123

SEQ ID NO: 201          moltype = AA   length = 107
FEATURE                 Location/Qualifiers
source                  1..107
                        mol_type = protein
                        organism = synthetic construct
SEQUENCE: 201
EIQMTQSPTS LSASVGDRVT ITCRASKGIS NNLSWYQQTP GKAPKLLIYA QSNLHSGVPS    60
RFSGSGSGTD FTLTISSLQP EDFATYYCQQ GYKWPLTFGG GTKLEIT                 107

SEQ ID NO: 202          moltype = AA   length = 123
FEATURE                 Location/Qualifiers
source                  1..123
                        mol_type = protein
                        organism = synthetic construct
SEQUENCE: 202
DVQLVESGGD LVKPGGSLRL TCVASGLSLT SASMSWVRQA PGKGLQWVST IYSNGGTYYT    60
DSVKGRFTIS KDNAENTLYL QMNNLKTEDT ATYYCASIYY YEAEYLHWYF DFWGQGALVT   120
VSS                                                                 123

SEQ ID NO: 203          moltype = AA   length = 107
FEATURE                 Location/Qualifiers
source                  1..107
                        mol_type = protein
                        organism = synthetic construct
SEQUENCE: 203
EIQMTQSPTS LSASVGDRVT ITCRASEGIS KNLSWYQQTP GKAPKLLIYA TDNLHSGVPS    60
RFSGSGSGTD FTLTISSLQP EDFATYYCQQ GWKWPLTFGG GTKLEIT                 107

SEQ ID NO: 204          moltype = AA   length = 123
FEATURE                 Location/Qualifiers
source                  1..123
                        mol_type = protein
                        organism = synthetic construct
SEQUENCE: 204
DVQLVESGGD LVKPGGSLRL TCVASGLSLT SDSMSWVRQA PGKGLQWVST LWSNRGTYYT    60
DSVKGRFTIS KDNAENTLYL QMNNLKTEDT ATYYCASIYY YEADYLHWYF DFWGQGALVT   120
VSS                                                                 123

SEQ ID NO: 205          moltype = AA   length = 123
FEATURE                 Location/Qualifiers
source                  1..123
                        mol_type = protein
                        organism = synthetic construct
SEQUENCE: 205
DVQLVESGGD LVKPGGSLRL TCVASGLSLT SNSMSWVRQA PGKGLQWVST IWSNRGTYYT    60
DSVKGRFTIS KDNAENTLYL QMNNLKTEDT ATYYCASIYY YEAEYLHWYF DFWGQGALVT   120
VSS                                                                 123

SEQ ID NO: 206          moltype = AA   length = 123
FEATURE                 Location/Qualifiers
source                  1..123
```

```
                            mol_type = protein
                            organism = synthetic construct
SEQUENCE: 206
DVQLVESGGD LVKPGGSLRL TCVASGLSLT SASMSWVRQA PGKGLQWVST IYSNRGTYYT    60
DSVKGRFTIS KDNAENTLYL QMNNLKTEDT ATYYCASIYY YEAEYLHWYF DFWGQGALVT   120
VSS                                                                 123

SEQ ID NO: 207              moltype = AA  length = 123
FEATURE                     Location/Qualifiers
source                      1..123
                            mol_type = protein
                            organism = synthetic construct
SEQUENCE: 207
EVQLVESGGD LVAPSQSLSI TCTVSGMSLT SNSISWVRQP PGRGLEWLGT IWSNRGTDYT    60
DAVKGRFTIS RDNAKNTVYL QMNSLRAEDT AMYYCAQIYY YDADYLHWYF DFWGQGTLVT   120
VSS                                                                 123

SEQ ID NO: 208              moltype = AA  length = 10
FEATURE                     Location/Qualifiers
source                      1..10
                            mol_type = protein
                            organism = synthetic construct
VARIANT                     1
                            note = A can be replaced by G, L, N, or Q
VARIANT                     3
                            note = A can be replaced by D, E, G, H, I, M, S, T, or Y
VARIANT                     4
                            note = L can be replaced by M or V
VARIANT                     5
                            note = A can be replaced by M, N, R, S, T, or V
VARIANT                     6
                            note = A can be replaced by E, G, H, K, R, S, or T
VARIANT                     7
                            note = A can be replaced by D, H, I, N, Q, S, T, or Y
VARIANT                     8
                            note = A can be replaced by S
VARIANT                     10
                            note = S can be replaced by V
SEQUENCE: 208
ALALAAAAMS                                                           10

SEQ ID NO: 209              moltype = AA  length = 14
FEATURE                     Location/Qualifiers
source                      1..14
                            mol_type = protein
                            organism = synthetic construct
VARIANT                     2
                            note = W can be replaced by Y
VARIANT                     3
                            note = A can be replaced by P or S
VARIANT                     4
                            note = D can be replacd by E, N, Q, R, or S
VARIANT                     5
                            note = G can be replaced by R, or Y
VARIANT                     8
                            note = D can be replaced by Y
VARIANT                     10
                            note = D can be replaced by E, H, S, or T
VARIANT                     12
                            note = D can be replaced by S
VARIANT                     14
                            note = D can be replaced by E, or K
SEQUENCE: 209
JWADGGTDYD DDVD                                                      14

SEQ ID NO: 210              moltype = AA  length = 17
FEATURE                     Location/Qualifiers
source                      1..17
                            mol_type = protein
                            organism = synthetic construct
VARIANT                     1
                            note = A can be replaced by D, E, K, N, Q, S, or T
VARIANT                     2
                            note = A can be replaced by D, E, G, H, I, K, L, M, N, P,
                            Q, R, S, T, V, or Y
VARIANT                     3
                            note = I can be replaced by L, W, or Y
VARIANT                     4
                            note = F can be replaced by T, W, or Y
```

```
VARIANT                     5
                            note = F can be replaced by H, or Y
VARIANT                     6
                            note = H can be replaced by Y
VARIANT                     7
                            note = D can be replaced by E
VARIANT                     8
                            note = A can be replaced by S or V
VARIANT                     9
                            note = D can be replaced by E, H, K, N, Q, or Y
VARIANT                     10
                            note = F can be replaced by H, or Y
VARIANT                     12
                            note = H can be replaced by Y
VARIANT                     13
                            note = F can be replaced by W
VARIANT                     14
                            note = D can be replaced by I, L, W, or Y
VARIANT                     16
                            note = D can be replaced by Q
VARIANT                     17
                            note = E can be replaced by F, H, I, L, M, N, P, W, or Y
SEQUENCE: 210
AAIFFHDADF LHFDFDE                                                              17

SEQ ID NO: 211              moltype = AA   length = 11
FEATURE                     Location/Qualifiers
source                      1..11
                            mol_type = protein
                            organism = synthetic construct
VARIANT                     1
                            note = F can be replaced by R
VARIANT                     4
                            note = E can be replaced by K or N
VARIANT                     5
                            note = A can be replaced by G
VARIANT                     6
                            note = I can be replaced by L or V
VARIANT                     7
                            note = A can be replaced by D, G, L, P, Q, S, V, or Y
VARIANT                     8
                            note = K can be replaced by Q, N, S, or Y
VARIANT                     9
                            note = A can be replaced by D, E, F, G, H, K, L, N, Q, R, S
                             or T
VARIANT                     11
                            note = A can be replaced by G or S
SEQUENCE: 211
FASEAIAKAL A                                                                    11

SEQ ID NO: 212              moltype = AA   length = 7
FEATURE                     Location/Qualifiers
source                      1..7
                            mol_type = protein
                            organism = synthetic construct
VARIANT                     2
                            note = A can be replaced by D, L, Q, S, T, V, or Y
VARIANT                     3
                            note = D can be replaced by E, K, N, Q, or S
VARIANT                     4
                            note = H can be replaced by I, K, L, M, N, or V
VARIANT                     5
                            note = H can be replaced by L
VARIANT                     6
                            note = H can be replaced by I, L, or M
VARIANT                     7
                            note = D can be replaced by E, N, S, or T
SEQUENCE: 212
AADHHHD                                                                         7

SEQ ID NO: 213              moltype = AA   length = 9
FEATURE                     Location/Qualifiers
source                      1..9
                            mol_type = protein
                            organism = synthetic construct
VARIANT                     3
                            note = G can be replaced by Y
VARIANT                     4
                            note = D can be replaced by F, G, H, K, L, R, S, T, V, W,
```

```
                       or Y
VARIANT                5
                       note = E can b replaced by K, Q, R, or S
VARIANT                6
                       note = I can be replaced by F, T, or W
VARIANT                7
                       note = E can be replaced by P
VARIANT                8
                       note = L can be replaced by M or W
SEQUENCE: 213
QQGDEIELT                                                                    9

SEQ ID NO: 214         moltype = AA   length = 10
FEATURE                Location/Qualifiers
source                 1..10
                       mol_type = protein
                       organism = synthetic construct
VARIANT                7
                       note = A can be replaced by D, or N
VARIANT                10
                       note = S can be replaced by V
SEQUENCE: 214
GLSLTSASMS                                                                   10

SEQ ID NO: 215         moltype = AA   length = 7
FEATURE                Location/Qualifiers
source                 1..7
                       mol_type = protein
                       organism = synthetic construct
VARIANT                2
                       note = W can be replaced by Y
VARIANT                5
                       note = G can be replaced by R
SEQUENCE: 215
JWSNGGT                                                                      7

SEQ ID NO: 216         moltype = AA   length = 17
FEATURE                Location/Qualifiers
source                 1..17
                       mol_type = protein
                       organism = synthetic construct
VARIANT                7
                       note = D can be replaced by E
VARIANT                9
                       note = D can be replaced by E
VARIANT                12
                       note = E can be replaced by F
SEQUENCE: 216
ASIYYYDADY LHWYFDE                                                           17

SEQ ID NO: 217         moltype = AA   length = 11
FEATURE                Location/Qualifiers
source                 1..11
                       mol_type = protein
                       organism = synthetic construct
VARIANT                4
                       note = E can be replaced by K
VARIANT                7
                       note = A can be replaced by Q, or S
VARIANT                8
                       note = K can be replaced by N
SEQUENCE: 217
RASEGIAKNL S                                                                 11

SEQ ID NO: 218         moltype = AA   length = 7
FEATURE                Location/Qualifiers
source                 1..7
                       mol_type = protein
                       organism = synthetic construct
VARIANT                2
                       note = Q can be replaced by T
VARIANT                3
                       note = D can be replaced by S
VARIANT                4
                       note = I can be replaced by N, or V
SEQUENCE: 218
AQDILHS                                                                      7

SEQ ID NO: 219         moltype = AA   length = 9
```

```
FEATURE                 Location/Qualifiers
source                  1..9
                        mol_type = protein
                        organism = synthetic construct
VARIANT                 4
                        note = F can be replaced by W, or Y
SEQUENCE: 219
QQGFKWPLT                                                                   9

SEQ ID NO: 220          moltype = AA  length = 8
FEATURE                 Location/Qualifiers
source                  1..8
                        mol_type = protein
                        organism = Canis sp.
SEQUENCE: 220
WSHPQFEK                                                                    8

SEQ ID NO: 221          moltype = AA  length = 8
FEATURE                 Location/Qualifiers
source                  1..8
                        mol_type = protein
                        organism = synthetic construct
SEQUENCE: 221
DYKDDDDK                                                                    8

SEQ ID NO: 222          moltype = AA  length = 10
FEATURE                 Location/Qualifiers
source                  1..10
                        mol_type = protein
                        organism = synthetic construct
SEQUENCE: 222
GLSLTSSSMS                                                                 10

SEQ ID NO: 223          moltype = AA  length = 16
FEATURE                 Location/Qualifiers
source                  1..16
                        mol_type = protein
                        organism = synthetic construct
SEQUENCE: 223
TIYSNGGTYY TDSVKG                                                          16

SEQ ID NO: 224          moltype = AA  length = 17
FEATURE                 Location/Qualifiers
source                  1..17
                        mol_type = protein
                        organism = synthetic construct
SEQUENCE: 224
ASIYYYDADY LHWYFDF                                                         17

SEQ ID NO: 225          moltype = AA  length = 11
FEATURE                 Location/Qualifiers
source                  1..11
                        mol_type = protein
                        organism = synthetic construct
SEQUENCE: 225
RASEGISNNL S                                                               11

SEQ ID NO: 226          moltype = AA  length = 7
FEATURE                 Location/Qualifiers
source                  1..7
                        mol_type = protein
                        organism = synthetic construct
SEQUENCE: 226
ATSNLHS                                                                     7

SEQ ID NO: 227          moltype = AA  length = 9
FEATURE                 Location/Qualifiers
source                  1..9
                        mol_type = protein
                        organism = synthetic construct
SEQUENCE: 227
QQGYKWPLT                                                                   9

SEQ ID NO: 228          moltype = AA  length = 15
FEATURE                 Location/Qualifiers
source                  1..15
                        mol_type = protein
                        organism = synthetic construct
SEQUENCE: 228
```

```
GLNDIFEAQK IEWHE                                                              15

SEQ ID NO: 229             moltype = AA   length = 8
FEATURE                    Location/Qualifiers
source                     1..8
                           mol_type = protein
                           organism = synthetic construct SEQUENCE: 229
GLSLTSSS                                                                       8

SEQ ID NO: 230             moltype = AA   length = 8
FEATURE                    Location/Qualifiers
source                     1..8
                           mol_type = protein
                           organism = synthetic construct SEQUENCE: 230
GLSLTSHS                                                                       8

SEQ ID NO: 231             moltype = AA   length = 8
FEATURE                    Location/Qualifiers
source                     1..8
                           mol_type = protein
                           organism = synthetic construct SEQUENCE: 231
GLSLTTNS                                                                       8

SEQ ID NO: 232             moltype = AA   length = 8
FEATURE                    Location/Qualifiers
source                     1..8
                           mol_type = protein
                           organism = synthetic construct SEQUENCE: 232
GLELTSNS                                                                       8

SEQ ID NO: 233             moltype = AA   length = 8
FEATURE                    Location/Qualifiers
source                     1..8
                           mol_type = protein
                           organism = synthetic construct SEQUENCE: 233
ALSLTSSS                                                                       8

SEQ ID NO: 234             moltype = AA   length = 8
FEATURE                    Location/Qualifiers
source                     1..8
                           mol_type = protein
                           organism = synthetic construct SEQUENCE: 234
LLSLTSSS                                                                       8

SEQ ID NO: 235             moltype = AA   length = 8
FEATURE                    Location/Qualifiers
source                     1..8
                           mol_type = protein
                           organism = synthetic construct SEQUENCE: 235
NLSLTSSS                                                                       8

SEQ ID NO: 236             moltype = AA   length = 8
FEATURE                    Location/Qualifiers
source                     1..8
                           mol_type = protein
                           organism = synthetic construct SEQUENCE: 236
GLELTSSS                                                                       8

SEQ ID NO: 237             moltype = AA   length = 8
FEATURE                    Location/Qualifiers
source                     1..8
                           mol_type = protein
                           organism = synthetic construct SEQUENCE: 237
GLGLTSSS                                                                       8

SEQ ID NO: 238             moltype = AA   length = 8
FEATURE                    Location/Qualifiers
source                     1..8
                           mol_type = protein
                           organism = synthetic construct
```

```
SEQUENCE: 238
GLALTSSS                                                                          8

SEQ ID NO: 239           moltype = AA  length = 8
FEATURE                  Location/Qualifiers
source                   1..8
                         mol_type = protein
                         organism = synthetic construct
SEQUENCE: 239
GLDLTSSS                                                                          8

SEQ ID NO: 240           moltype = AA  length = 8
FEATURE                  Location/Qualifiers
source                   1..8
                         mol_type = protein
                         organism = synthetic construct
SEQUENCE: 240
GLTLTSSS                                                                          8

SEQ ID NO: 241           moltype = AA  length = 8
FEATURE                  Location/Qualifiers
source                   1..8
                         mol_type = protein
                         organism = synthetic construct
SEQUENCE: 241
GLSMTSSS                                                                          8

SEQ ID NO: 242           moltype = AA  length = 8
FEATURE                  Location/Qualifiers
source                   1..8
                         mol_type = protein
                         organism = synthetic construct
SEQUENCE: 242
GLSVTSSS                                                                          8

SEQ ID NO: 243           moltype = AA  length = 8
FEATURE                  Location/Qualifiers
source                   1..8
                         mol_type = protein
                         organism = synthetic construct
SEQUENCE: 243
GLSLASSS                                                                          8

SEQ ID NO: 244           moltype = AA  length = 8
FEATURE                  Location/Qualifiers
source                   1..8
                         mol_type = protein
                         organism = synthetic construct
SEQUENCE: 244
GLSLSSSS                                                                          8

SEQ ID NO: 245           moltype = AA  length = 8
FEATURE                  Location/Qualifiers
source                   1..8
                         mol_type = protein
                         organism = synthetic construct
SEQUENCE: 245
GLSLVSSS                                                                          8

SEQ ID NO: 246           moltype = AA  length = 8
FEATURE                  Location/Qualifiers
source                   1..8
                         mol_type = protein
                         organism = synthetic construct
SEQUENCE: 246
GLSLNSSS                                                                          8

SEQ ID NO: 247           moltype = AA  length = 8
FEATURE                  Location/Qualifiers
source                   1..8
                         mol_type = protein
                         organism = synthetic construct
SEQUENCE: 247
GLSLMSSS                                                                          8

SEQ ID NO: 248           moltype = AA  length = 8
FEATURE                  Location/Qualifiers
source                   1..8
                         mol_type = protein
```

```
                        organism = synthetic construct
SEQUENCE: 248
GLSLTTHS                                                                   8

SEQ ID NO: 249          moltype = AA   length = 8
FEATURE                 Location/Qualifiers
source                  1..8
                        mol_type = protein
                        organism = synthetic construct
SEQUENCE: 249
GLSLTHSS                                                                   8

SEQ ID NO: 250          moltype = AA   length = 8
FEATURE                 Location/Qualifiers
source                  1..8
                        mol_type = protein
                        organism = synthetic construct
SEQUENCE: 250
GLSLTGSS                                                                   8

SEQ ID NO: 251          moltype = AA   length = 8
FEATURE                 Location/Qualifiers
source                  1..8
                        mol_type = protein
                        organism = synthetic construct
SEQUENCE: 251
GLSLTESS                                                                   8

SEQ ID NO: 252          moltype = AA   length = 8
FEATURE                 Location/Qualifiers
source                  1..8
                        mol_type = protein
                        organism = synthetic construct
SEQUENCE: 252
GLSLTRSS                                                                   8

SEQ ID NO: 253          moltype = AA   length = 8
FEATURE                 Location/Qualifiers
source                  1..8
                        mol_type = protein
                        organism = synthetic construct
SEQUENCE: 253
GLSLTKSS                                                                   8

SEQ ID NO: 254          moltype = AA   length = 8
FEATURE                 Location/Qualifiers
source                  1..8
                        mol_type = protein
                        organism = synthetic construct
SEQUENCE: 254
GLSLTSIS                                                                   8

SEQ ID NO: 255          moltype = AA   length = 8
FEATURE                 Location/Qualifiers
source                  1..8
                        mol_type = protein
                        organism = synthetic construct
SEQUENCE: 255
GLSLTSTS                                                                   8

SEQ ID NO: 256          moltype = AA   length = 8
FEATURE                 Location/Qualifiers
source                  1..8
                        mol_type = protein
                        organism = synthetic construct
SEQUENCE: 256
GLSLTSDS                                                                   8

SEQ ID NO: 257          moltype = AA   length = 8
FEATURE                 Location/Qualifiers
source                  1..8
                        mol_type = protein
                        organism = synthetic construct
SEQUENCE: 257
GLSLTSNS                                                                   8

SEQ ID NO: 258          moltype = AA   length = 8
FEATURE                 Location/Qualifiers
source                  1..8
```

```
                        mol_type = protein
                        organism = synthetic construct
SEQUENCE: 258
GLSLTSQS                                                                  8

SEQ ID NO: 259          moltype = AA   length = 8
FEATURE                 Location/Qualifiers
source                  1..8
                        mol_type = protein
                        organism = synthetic construct
SEQUENCE: 259
GLSLTSAS                                                                  8

SEQ ID NO: 260          moltype = AA   length = 8
FEATURE                 Location/Qualifiers
source                  1..8
                        mol_type = protein
                        organism = synthetic construct
SEQUENCE: 260
QLSLTSSS                                                                  8

SEQ ID NO: 261          moltype = AA   length = 8
FEATURE                 Location/Qualifiers
source                  1..8
                        mol_type = protein
                        organism = synthetic construct
SEQUENCE: 261
GLSLTSYS                                                                  8

SEQ ID NO: 262          moltype = AA   length = 8
FEATURE                 Location/Qualifiers
source                  1..8
                        mol_type = protein
                        organism = synthetic construct
SEQUENCE: 262
GLSLTSSA                                                                  8

SEQ ID NO: 263          moltype = AA   length = 8
FEATURE                 Location/Qualifiers
source                  1..8
                        mol_type = protein
                        organism = synthetic construct
SEQUENCE: 263
GLSLTASS                                                                  8

SEQ ID NO: 264          moltype = AA   length = 8
FEATURE                 Location/Qualifiers
source                  1..8
                        mol_type = protein
                        organism = synthetic construct
SEQUENCE: 264
GLYLTSSS                                                                  8

SEQ ID NO: 265          moltype = AA   length = 8
FEATURE                 Location/Qualifiers
source                  1..8
                        mol_type = protein
                        organism = synthetic construct
SEQUENCE: 265
GLMLTSSS                                                                  8

SEQ ID NO: 266          moltype = AA   length = 7
FEATURE                 Location/Qualifiers
source                  1..7
                        mol_type = protein
                        organism = synthetic construct
SEQUENCE: 266
IYSNGGT                                                                   7

SEQ ID NO: 267          moltype = AA   length = 7
FEATURE                 Location/Qualifiers
source                  1..7
                        mol_type = protein
                        organism = synthetic construct
SEQUENCE: 267
IYSQGGT                                                                   7

SEQ ID NO: 268          moltype = AA   length = 7
FEATURE                 Location/Qualifiers
```

```
source                  1..7
                        mol_type = protein
                        organism = synthetic construct
SEQUENCE: 268
IYANGGT                                                                    7

SEQ ID NO: 269          moltype = AA   length = 7
FEATURE                 Location/Qualifiers
source                  1..7
                        mol_type = protein
                        organism = synthetic construct
SEQUENCE: 269
IYSEGGT                                                                    7

SEQ ID NO: 270          moltype = AA   length = 7
FEATURE                 Location/Qualifiers
source                  1..7
                        mol_type = protein
                        organism = synthetic construct
SEQUENCE: 270
IYSRGGT                                                                    7

SEQ ID NO: 271          moltype = AA   length = 7
FEATURE                 Location/Qualifiers
source                  1..7
                        mol_type = protein
                        organism = synthetic construct
SEQUENCE: 271
IYSSGGT                                                                    7

SEQ ID NO: 272          moltype = AA   length = 7
FEATURE                 Location/Qualifiers
source                  1..7
                        mol_type = protein
                        organism = synthetic construct
SEQUENCE: 272
LWSNGGT                                                                    7

SEQ ID NO: 273          moltype = AA   length = 7
FEATURE                 Location/Qualifiers
source                  1..7
                        mol_type = protein
                        organism = synthetic construct
SEQUENCE: 273
IWSSGGT                                                                    7

SEQ ID NO: 274          moltype = AA   length = 7
FEATURE                 Location/Qualifiers
source                  1..7
                        mol_type = protein
                        organism = synthetic construct
SEQUENCE: 274
IWSEGGT                                                                    7

SEQ ID NO: 275          moltype = AA   length = 7
FEATURE                 Location/Qualifiers
source                  1..7
                        mol_type = protein
                        organism = synthetic construct
SEQUENCE: 275
IWSDGGT                                                                    7

SEQ ID NO: 276          moltype = AA   length = 17
FEATURE                 Location/Qualifiers
source                  1..17
                        mol_type = protein
                        organism = synthetic construct
SEQUENCE: 276
ANIYYYDADY LHWYFDF                                                         17

SEQ ID NO: 277          moltype = AA   length = 17
FEATURE                 Location/Qualifiers
source                  1..17
                        mol_type = protein
                        organism = synthetic construct
SEQUENCE: 277
AEIYYYDADY LHWYFDF                                                         17

SEQ ID NO: 278          moltype = AA   length = 17
```

```
FEATURE               Location/Qualifiers
source                1..17
                      mol_type = protein
                      organism = synthetic construct
SEQUENCE: 278
AQIYYYDADY LHWYFDF                                                    17

SEQ ID NO: 279        moltype = AA  length = 17
FEATURE               Location/Qualifiers
source                1..17
                      mol_type = protein
                      organism = synthetic construct
SEQUENCE: 279
ADIYYYDADY LHWYFDF                                                    17

SEQ ID NO: 280        moltype = AA  length = 17
FEATURE               Location/Qualifiers
source                1..17
                      mol_type = protein
                      organism = synthetic construct
SEQUENCE: 280
AKIYYYDADY LHWYFDF                                                    17

SEQ ID NO: 281        moltype = AA  length = 17
FEATURE               Location/Qualifiers
source                1..17
                      mol_type = protein
                      organism = synthetic construct
SEQUENCE: 281
ASLYYYDADY LHWYFDF                                                    17

SEQ ID NO: 282        moltype = AA  length = 17
FEATURE               Location/Qualifiers
source                1..17
                      mol_type = protein
                      organism = synthetic construct
SEQUENCE: 282
ASITYYDADY LHWYFDF                                                    17

SEQ ID NO: 283        moltype = AA  length = 17
FEATURE               Location/Qualifiers
source                1..17
                      mol_type = protein
                      organism = synthetic construct
SEQUENCE: 283
ASIWYYDADY LHWYFDF                                                    17

SEQ ID NO: 284        moltype = AA  length = 17
FEATURE               Location/Qualifiers
source                1..17
                      mol_type = protein
                      organism = synthetic construct
SEQUENCE: 284
ASIFYYDADY LHWYFDF                                                    17

SEQ ID NO: 285        moltype = AA  length = 17
FEATURE               Location/Qualifiers
source                1..17
                      mol_type = protein
                      organism = synthetic construct
SEQUENCE: 285
ASIYHYDADY LHWYFDF                                                    17

SEQ ID NO: 286        moltype = AA  length = 17
FEATURE               Location/Qualifiers
source                1..17
                      mol_type = protein
                      organism = synthetic construct
SEQUENCE: 286
ASIYFYDADY LHWYFDF                                                    17

SEQ ID NO: 287        moltype = AA  length = 17
FEATURE               Location/Qualifiers
source                1..17
                      mol_type = protein
                      organism = synthetic construct
SEQUENCE: 287
ASIYYYEADY LHWYFDF                                                    17
```

| | |
|---|---|
| SEQ ID NO: 288<br>FEATURE<br>source | moltype = AA  length = 17<br>Location/Qualifiers<br>1..17<br>mol_type = protein<br>organism = synthetic construct |

SEQUENCE: 288
ASIYYYDSDY LHWYFDF                                                 17

| | |
|---|---|
| SEQ ID NO: 289<br>FEATURE<br>source | moltype = AA  length = 17<br>Location/Qualifiers<br>1..17<br>mol_type = protein<br>organism = synthetic construct |

SEQUENCE: 289
ASIYYYDVDY LHWYFDF                                                 17

| | |
|---|---|
| SEQ ID NO: 290<br>FEATURE<br>source | moltype = AA  length = 17<br>Location/Qualifiers<br>1..17<br>mol_type = protein<br>organism = synthetic construct |

SEQUENCE: 290
ASIYYYDAEY LHWYFDF                                                 17

| | |
|---|---|
| SEQ ID NO: 291<br>FEATURE<br>source | moltype = AA  length = 17<br>Location/Qualifiers<br>1..17<br>mol_type = protein<br>organism = synthetic construct |

SEQUENCE: 291
ASIYYYDADH LHWYFDF                                                 17

| | |
|---|---|
| SEQ ID NO: 292<br>FEATURE<br>source | moltype = AA  length = 17<br>Location/Qualifiers<br>1..17<br>mol_type = protein<br>organism = synthetic construct |

SEQUENCE: 292
AAIYYYDADY LHWYFDF                                                 17

| | |
|---|---|
| SEQ ID NO: 293<br>FEATURE<br>source | moltype = AA  length = 17<br>Location/Qualifiers<br>1..17<br>mol_type = protein<br>organism = synthetic construct |

SEQUENCE: 293
AYIYYYDADY LHWYFDF                                                 17

| | |
|---|---|
| SEQ ID NO: 294<br>FEATURE<br>source | moltype = AA  length = 17<br>Location/Qualifiers<br>1..17<br>mol_type = protein<br>organism = synthetic construct |

SEQUENCE: 294
ATIYYYDADY LHWYFDF                                                 17

| | |
|---|---|
| SEQ ID NO: 295<br>FEATURE<br>source | moltype = AA  length = 17<br>Location/Qualifiers<br>1..17<br>mol_type = protein<br>organism = synthetic construct |

SEQUENCE: 295
AVIYYYDADY LHWYFDF                                                 17

| | |
|---|---|
| SEQ ID NO: 296<br>FEATURE<br>source | moltype = AA  length = 17<br>Location/Qualifiers<br>1..17<br>mol_type = protein<br>organism = synthetic construct |

SEQUENCE: 296
ALIYYYDADY LHWYFDF                                                 17

| | |
|---|---|
| SEQ ID NO: 297<br>FEATURE<br>source | moltype = AA  length = 17<br>Location/Qualifiers<br>1..17<br>mol_type = protein<br>organism = synthetic construct |

SEQUENCE: 297
APIYYYDADY LHWYFDF                                                 17

```
SEQ ID NO: 298         moltype = AA   length = 17
FEATURE                Location/Qualifiers
source                 1..17
                       mol_type = protein
                       organism = synthetic construct
SEQUENCE: 298
AHIYYYDADY LHWYFDF                                                   17

SEQ ID NO: 299         moltype = AA   length = 17
FEATURE                Location/Qualifiers
source                 1..17
                       mol_type = protein
                       organism = synthetic construct
SEQUENCE: 299
ARIYYYDADY LHWYFDF                                                   17

SEQ ID NO: 300         moltype = AA   length = 17
FEATURE                Location/Qualifiers
source                 1..17
                       mol_type = protein
                       organism = synthetic construct
SEQUENCE: 300
AIIYYYDADY LHWYFDF                                                   17

SEQ ID NO: 301         moltype = AA   length = 17
FEATURE                Location/Qualifiers
source                 1..17
                       mol_type = protein
                       organism = synthetic construct
SEQUENCE: 301
AGIYYYDADY LHWYFDF                                                   17

SEQ ID NO: 302         moltype = AA   length = 17
FEATURE                Location/Qualifiers
source                 1..17
                       mol_type = protein
                       organism = synthetic construct
SEQUENCE: 302
ASYYYYDADY LHWYFDF                                                   17

SEQ ID NO: 303         moltype = AA   length = 17
FEATURE                Location/Qualifiers
source                 1..17
                       mol_type = protein
                       organism = synthetic construct
SEQUENCE: 303
SSIYYYDADY LHWYFDF                                                   17

SEQ ID NO: 304         moltype = AA   length = 17
FEATURE                Location/Qualifiers
source                 1..17
                       mol_type = protein
                       organism = synthetic construct
SEQUENCE: 304
TSIYYYDADY LHWYFDF                                                   17

SEQ ID NO: 305         moltype = AA   length = 17
FEATURE                Location/Qualifiers
source                 1..17
                       mol_type = protein
                       organism = synthetic construct
SEQUENCE: 305
DSIYYYDADY LHWYFDF                                                   17

SEQ ID NO: 306         moltype = AA   length = 17
FEATURE                Location/Qualifiers
source                 1..17
                       mol_type = protein
                       organism = synthetic construct
SEQUENCE: 306
NSIYYYDADY LHWYFDF                                                   17

SEQ ID NO: 307         moltype = AA   length = 17
FEATURE                Location/Qualifiers
source                 1..17
                       mol_type = protein
                       organism = synthetic construct
SEQUENCE: 307
```

```
ESIYYYDADY LHWYFDF                                                    17

SEQ ID NO: 308            moltype = AA  length = 17
FEATURE                   Location/Qualifiers
source                    1..17
                          mol_type = protein
                          organism = synthetic construct SEQUENCE: 308
QSIYYYDADY LHWYFDF                                                    17

SEQ ID NO: 309            moltype = AA  length = 17
FEATURE                   Location/Qualifiers
source                    1..17
                          mol_type = protein
                          organism = synthetic construct SEQUENCE: 309
KSIYYYDADY LHWYFDF                                                    17

SEQ ID NO: 310            moltype = AA  length = 17
FEATURE                   Location/Qualifiers
source                    1..17
                          mol_type = protein
                          organism = synthetic construct SEQUENCE: 310
ASYYYYDADY LHWYFDM                                                    17

SEQ ID NO: 311            moltype = AA  length = 17
FEATURE                   Location/Qualifiers
source                    1..17
                          mol_type = protein
                          organism = synthetic construct SEQUENCE: 311
ASWYYYDADY LHWYFDF                                                    17

SEQ ID NO: 312            moltype = AA  length = 17
FEATURE                   Location/Qualifiers
source                    1..17
                          mol_type = protein
                          organism = synthetic construct SEQUENCE: 312
ADIFYYDADY LHWYFDF                                                    17

SEQ ID NO: 313            moltype = AA  length = 17
FEATURE                   Location/Qualifiers
source                    1..17
                          mol_type = protein
                          organism = synthetic construct SEQUENCE: 313
ANIWYYDADY LHWYFDF                                                    17

SEQ ID NO: 314            moltype = AA  length = 17
FEATURE                   Location/Qualifiers
source                    1..17
                          mol_type = protein
                          organism = synthetic construct SEQUENCE: 314
AQIYFYDADY LHWYFDF                                                    17

SEQ ID NO: 315            moltype = AA  length = 17
FEATURE                   Location/Qualifiers
source                    1..17
                          mol_type = protein
                          organism = synthetic construct SEQUENCE: 315
ASIYYYEAEY LHWYFDF                                                    17

SEQ ID NO: 316            moltype = AA  length = 17
FEATURE                   Location/Qualifiers
source                    1..17
                          mol_type = protein
                          organism = synthetic construct SEQUENCE: 316
ASIYYYDSYY LHWYFDF                                                    17

SEQ ID NO: 317            moltype = AA  length = 17
FEATURE                   Location/Qualifiers
source                    1..17
                          mol_type = protein
                          organism = synthetic construct
```

```
SEQUENCE: 317
ASIYYYDAYY LHWYFDF                                                        17

SEQ ID NO: 318          moltype = AA  length = 17
FEATURE                 Location/Qualifiers
source                  1..17
                        mol_type = protein
                        organism = synthetic construct
SEQUENCE: 318
ASIYYYDADY LYWYFDF                                                        17

SEQ ID NO: 319          moltype = AA  length = 17
FEATURE                 Location/Qualifiers
source                  1..17
                        mol_type = protein
                        organism = synthetic construct
SEQUENCE: 319
ASIYYYDADY LHFYFDF                                                        17

SEQ ID NO: 320          moltype = AA  length = 17
FEATURE                 Location/Qualifiers
source                  1..17
                        mol_type = protein
                        organism = synthetic construct
SEQUENCE: 320
ASIYYYDADF LHWYFDF                                                        17

SEQ ID NO: 321          moltype = AA  length = 17
FEATURE                 Location/Qualifiers
source                  1..17
                        mol_type = protein
                        organism = synthetic construct
SEQUENCE: 321
ASIYYYDADY LHWLFDF                                                        17

SEQ ID NO: 322          moltype = AA  length = 17
FEATURE                 Location/Qualifiers
source                  1..17
                        mol_type = protein
                        organism = synthetic construct
SEQUENCE: 322
ASIYYYDADY LHWWFDF                                                        17

SEQ ID NO: 323          moltype = AA  length = 17
FEATURE                 Location/Qualifiers
source                  1..17
                        mol_type = protein
                        organism = synthetic construct
SEQUENCE: 323
ASIYYYDADY LHWIFDF                                                        17

SEQ ID NO: 324          moltype = AA  length = 17
FEATURE                 Location/Qualifiers
source                  1..17
                        mol_type = protein
                        organism = synthetic construct
SEQUENCE: 324
ASIYYYDADY LHWDFDF                                                        17

SEQ ID NO: 325          moltype = AA  length = 17
FEATURE                 Location/Qualifiers
source                  1..17
                        mol_type = protein
                        organism = synthetic construct
SEQUENCE: 325
ASIYYYDADY LHWYFQF                                                        17

SEQ ID NO: 326          moltype = AA  length = 17
FEATURE                 Location/Qualifiers
source                  1..17
                        mol_type = protein
                        organism = synthetic construct
SEQUENCE: 326
ASIYYYDADY LYFYFDF                                                        17

SEQ ID NO: 327          moltype = AA  length = 17
FEATURE                 Location/Qualifiers
source                  1..17
                        mol_type = protein
```

```
                              organism = synthetic construct
SEQUENCE: 327
ASIYYYDADY LHWYFDY                                                               17

SEQ ID NO: 328          moltype = AA   length = 17
FEATURE                 Location/Qualifiers
source                  1..17
                        mol_type = protein
                        organism = synthetic construct
SEQUENCE: 328
ASIYYYDADY LHWYFDL                                                               17

SEQ ID NO: 329          moltype = AA   length = 17
FEATURE                 Location/Qualifiers
source                  1..17
                        mol_type = protein
                        organism = synthetic construct
SEQUENCE: 329
ASIYYYDADY LHWYFDM                                                               17

SEQ ID NO: 330          moltype = AA   length = 17
FEATURE                 Location/Qualifiers
source                  1..17
                        mol_type = protein
                        organism = synthetic construct
SEQUENCE: 330
ASIYYYDADY LHWYFDI                                                               17

SEQ ID NO: 331          moltype = AA   length = 17
FEATURE                 Location/Qualifiers
source                  1..17
                        mol_type = protein
                        organism = synthetic construct
SEQUENCE: 331
ASIYYYDADY LHWYFDW                                                               17

SEQ ID NO: 332          moltype = AA   length = 6
FEATURE                 Location/Qualifiers
source                  1..6
                        mol_type = protein
                        organism = synthetic construct
SEQUENCE: 332
EGISNN                                                                            6

SEQ ID NO: 333          moltype = AA   length = 6
FEATURE                 Location/Qualifiers
source                  1..6
                        mol_type = protein
                        organism = synthetic construct
SEQUENCE: 333
QGISNN                                                                            6

SEQ ID NO: 334          moltype = AA   length = 6
FEATURE                 Location/Qualifiers
source                  1..6
                        mol_type = protein
                        organism = synthetic construct
SEQUENCE: 334
NGISNN                                                                            6

SEQ ID NO: 335          moltype = AA   length = 6
FEATURE                 Location/Qualifiers
source                  1..6
                        mol_type = protein
                        organism = synthetic construct
SEQUENCE: 335
KGISNN                                                                            6

SEQ ID NO: 336          moltype = AA   length = 6
FEATURE                 Location/Qualifiers
source                  1..6
                        mol_type = protein
                        organism = synthetic construct
SEQUENCE: 336
EAISNN                                                                            6

SEQ ID NO: 337          moltype = AA   length = 6
FEATURE                 Location/Qualifiers
source                  1..6
```

```
                        mol_type = protein
                        organism = synthetic construct
SEQUENCE: 337
EGLSNN                                                                          6

SEQ ID NO: 338          moltype = AA   length = 6
FEATURE                 Location/Qualifiers
source                  1..6
                        mol_type = protein
                        organism = synthetic construct
SEQUENCE: 338
EGVSNN                                                                          6

SEQ ID NO: 339          moltype = AA   length = 6
FEATURE                 Location/Qualifiers
source                  1..6
                        mol_type = protein
                        organism = synthetic construct
SEQUENCE: 339
EGIGNN                                                                          6

SEQ ID NO: 340          moltype = AA   length = 6
FEATURE                 Location/Qualifiers
source                  1..6
                        mol_type = protein
                        organism = synthetic construct
SEQUENCE: 340
EGIDNN                                                                          6

SEQ ID NO: 341          moltype = AA   length = 6
FEATURE                 Location/Qualifiers
source                  1..6
                        mol_type = protein
                        organism = synthetic construct
SEQUENCE: 341
EGISSN                                                                          6

SEQ ID NO: 342          moltype = AA   length = 6
FEATURE                 Location/Qualifiers
source                  1..6
                        mol_type = protein
                        organism = synthetic construct
SEQUENCE: 342
EGISKN                                                                          6

SEQ ID NO: 343          moltype = AA   length = 6
FEATURE                 Location/Qualifiers
source                  1..6
                        mol_type = protein
                        organism = synthetic construct
SEQUENCE: 343
EGISYN                                                                          6

SEQ ID NO: 344          moltype = AA   length = 6
FEATURE                 Location/Qualifiers
source                  1..6
                        mol_type = protein
                        organism = synthetic construct
SEQUENCE: 344
EGISNS                                                                          6

SEQ ID NO: 345          moltype = AA   length = 6
FEATURE                 Location/Qualifiers
source                  1..6
                        mol_type = protein
                        organism = synthetic construct
SEQUENCE: 345
EGISNG                                                                          6

SEQ ID NO: 346          moltype = AA   length = 6
FEATURE                 Location/Qualifiers
source                  1..6
                        mol_type = protein
                        organism = synthetic construct
SEQUENCE: 346
EGISNQ                                                                          6

SEQ ID NO: 347          moltype = AA   length = 6
FEATURE                 Location/Qualifiers
```

```
                        -continued source                  1..6
                        mol_type = protein
                        organism = synthetic construct
SEQUENCE: 347
EGISNE                                                          6

SEQ ID NO: 348          moltype = AA  length = 6
FEATURE                 Location/Qualifiers
source                  1..6
                        mol_type = protein
                        organism = synthetic construct
SEQUENCE: 348
EGISNK                                                          6

SEQ ID NO: 349          moltype = AA  length = 6
FEATURE                 Location/Qualifiers
source                  1..6
                        mol_type = protein
                        organism = synthetic construct
SEQUENCE: 349
EGISND                                                          6

SEQ ID NO: 350          moltype = AA  length = 6
FEATURE                 Location/Qualifiers
source                  1..6
                        mol_type = protein
                        organism = synthetic construct
SEQUENCE: 350
EGISNT                                                          6

SEQ ID NO: 351          moltype = AA  length = 6
FEATURE                 Location/Qualifiers
source                  1..6
                        mol_type = protein
                        organism = synthetic construct
SEQUENCE: 351
EGISNL                                                          6

SEQ ID NO: 352          moltype = AA  length = 6
FEATURE                 Location/Qualifiers
source                  1..6
                        mol_type = protein
                        organism = synthetic construct
SEQUENCE: 352
EGISNA                                                          6

SEQ ID NO: 353          moltype = AA  length = 6
FEATURE                 Location/Qualifiers
source                  1..6
                        mol_type = protein
                        organism = synthetic construct
SEQUENCE: 353
EGISNH                                                          6

SEQ ID NO: 354          moltype = AA  length = 6
FEATURE                 Location/Qualifiers
source                  1..6
                        mol_type = protein
                        organism = synthetic construct
SEQUENCE: 354
EGISNF                                                          6

SEQ ID NO: 355          moltype = AA  length = 6
FEATURE                 Location/Qualifiers
source                  1..6
                        mol_type = protein
                        organism = synthetic construct
SEQUENCE: 355
EGISNR                                                          6

SEQ ID NO: 356          moltype = AA  length = 9
FEATURE                 Location/Qualifiers
source                  1..9
                        mol_type = protein
                        organism = synthetic construct
SEQUENCE: 356
QQGWKWPLT                                                       9

SEQ ID NO: 357          moltype = AA  length = 9
```

| | | |
|---|---|---|
| FEATURE | Location/Qualifiers | |
| source | 1..9 | |
| | mol_type = protein | |
| | organism = synthetic construct | |
| SEQUENCE: 357 | | |
| QQGHKWPLT | | 9 |
| | | |
| SEQ ID NO: 358 | moltype = AA  length = 9 | |
| FEATURE | Location/Qualifiers | |
| source | 1..9 | |
| | mol_type = protein | |
| | organism = synthetic construct | |
| SEQUENCE: 358 | | |
| QQGFKWPLT | | 9 |
| | | |
| SEQ ID NO: 359 | moltype = AA  length = 9 | |
| FEATURE | Location/Qualifiers | |
| source | 1..9 | |
| | mol_type = protein | |
| | organism = synthetic construct | |
| SEQUENCE: 359 | | |
| QQGYRWPLT | | 9 |
| | | |
| SEQ ID NO: 360 | moltype = AA  length = 9 | |
| FEATURE | Location/Qualifiers | |
| source | 1..9 | |
| | mol_type = protein | |
| | organism = synthetic construct | |
| SEQUENCE: 360 | | |
| QQGYEWPLT | | 9 |
| | | |
| SEQ ID NO: 361 | moltype = AA  length = 9 | |
| FEATURE | Location/Qualifiers | |
| source | 1..9 | |
| | mol_type = protein | |
| | organism = synthetic construct | |
| SEQUENCE: 361 | | |
| QQGYSWPLT | | 9 |
| | | |
| SEQ ID NO: 362 | moltype = AA  length = 9 | |
| FEATURE | Location/Qualifiers | |
| source | 1..9 | |
| | mol_type = protein | |
| | organism = synthetic construct | |
| SEQUENCE: 362 | | |
| QQGYQWPLT | | 9 |
| | | |
| SEQ ID NO: 363 | moltype = AA  length = 9 | |
| FEATURE | Location/Qualifiers | |
| source | 1..9 | |
| | mol_type = protein | |
| | organism = synthetic construct | |
| SEQUENCE: 363 | | |
| QQGYKFPLT | | 9 |
| | | |
| SEQ ID NO: 364 | moltype = AA  length = 9 | |
| FEATURE | Location/Qualifiers | |
| source | 1..9 | |
| | mol_type = protein | |
| | organism = synthetic construct | |
| SEQUENCE: 364 | | |
| QQGYKIPLT | | 9 |
| | | |
| SEQ ID NO: 365 | moltype = AA  length = 9 | |
| FEATURE | Location/Qualifiers | |
| source | 1..9 | |
| | mol_type = protein | |
| | organism = synthetic construct | |
| SEQUENCE: 365 | | |
| QQGYKWELT | | 9 |
| | | |
| SEQ ID NO: 366 | moltype = AA  length = 9 | |
| FEATURE | Location/Qualifiers | |
| source | 1..9 | |
| | mol_type = protein | |
| | organism = synthetic construct | |
| SEQUENCE: 366 | | |
| QQGYKWPMT | | 9 |

```
SEQ ID NO: 367          moltype = AA   length = 9
FEATURE                 Location/Qualifiers
source                  1..9
                        mol_type = protein
                        organism = synthetic construct
SEQUENCE: 367
QQGSKWPLT                                                                    9

SEQ ID NO: 368          moltype = AA   length = 9
FEATURE                 Location/Qualifiers
source                  1..9
                        mol_type = protein
                        organism = synthetic construct
SEQUENCE: 368
QQGTKWPLT                                                                    9

SEQ ID NO: 369          moltype = AA   length = 9
FEATURE                 Location/Qualifiers
source                  1..9
                        mol_type = protein
                        organism = synthetic construct
SEQUENCE: 369
QQGGKWPLT                                                                    9

SEQ ID NO: 370          moltype = AA   length = 9
FEATURE                 Location/Qualifiers
source                  1..9
                        mol_type = protein
                        organism = synthetic construct
SEQUENCE: 370
QQGLKWPLT                                                                    9

SEQ ID NO: 371          moltype = AA   length = 9
FEATURE                 Location/Qualifiers
source                  1..9
                        mol_type = protein
                        organism = synthetic construct
SEQUENCE: 371
QQGVKWPLT                                                                    9

SEQ ID NO: 372          moltype = AA   length = 9
FEATURE                 Location/Qualifiers
source                  1..9
                        mol_type = protein
                        organism = synthetic construct
SEQUENCE: 372
QQGRKWPLT                                                                    9

SEQ ID NO: 373          moltype = AA   length = 9
FEATURE                 Location/Qualifiers
source                  1..9
                        mol_type = protein
                        organism = synthetic construct
SEQUENCE: 373
QQGDKWPLT                                                                    9

SEQ ID NO: 374          moltype = AA   length = 9
FEATURE                 Location/Qualifiers
source                  1..9
                        mol_type = protein
                        organism = synthetic construct
SEQUENCE: 374
QQGKKWPLT                                                                    9

SEQ ID NO: 375          moltype = AA   length = 9
FEATURE                 Location/Qualifiers
source                  1..9
                        mol_type = protein
                        organism = synthetic construct
SEQUENCE: 375
QQYYSTPWT                                                                    9

SEQ ID NO: 376          moltype = AA   length = 8
FEATURE                 Location/Qualifiers
source                  1..8
                        mol_type = protein
                        organism = synthetic construct
SEQUENCE: 376
HHHHHHHH                                                                     8
```

```
SEQ ID NO: 377            moltype = AA  length = 8
FEATURE                   Location/Qualifiers
source                    1..8
                          mol_type = protein
                          organism = synthetic construct
SEQUENCE: 377
GGGSGGGS                                                                  8

SEQ ID NO: 378            moltype = AA  length = 8
FEATURE                   Location/Qualifiers
source                    1..8
                          mol_type = protein
                          organism = synthetic construct
VARIANT                   1
                          note = A can be replaced by G
VARIANT                   2
                          note = L can be replaced by M
VARIANT                   3
                          note = E can be replaced by S
VARIANT                   4
                          note = F can be replaced by L
VARIANT                   6
                          note = S can be replaced by T
VARIANT                   7
                          note = H can be replaced by N or S
SEQUENCE: 378
ALEFTSHS                                                                  8

SEQ ID NO: 379            moltype = AA  length = 7
FEATURE                   Location/Qualifiers
source                    1..7
                          mol_type = protein
                          organism = synthetic construct
VARIANT                   5
                          note = G can be replaced by R
SEQUENCE: 379
IWSNGGT                                                                   7

SEQ ID NO: 380            moltype = AA  length = 6
FEATURE                   Location/Qualifiers
source                    1..6
                          mol_type = protein
                          organism = synthetic construct
VARIANT                   1
                          note = D can be replaced by E
VARIANT                   4
                          note = Q can be replaced by S
VARIANT                   6
                          note = G can be replaced by N, S or T
SEQUENCE: 380
DGIQNG                                                                    6

SEQ ID NO: 381            moltype = AA  length = 7
FEATURE                   Location/Qualifiers
source                    1..7
                          mol_type = protein
                          organism = synthetic construct
VARIANT                   5
                          note = G can be replaced by R
SEQUENCE: 381
JWSNGGT                                                                   7

SEQ ID NO: 382            moltype = AA  length = 17
FEATURE                   Location/Qualifiers
source                    1..17
                          mol_type = protein
                          organism = synthetic construct
VARIANT                   2
                          note = N can be replaced by Q, S, or T
VARIANT                   7
                          note = D can be replaced by E
VARIANT                   13
                          note = F can be replaced by W
VARIANT                   15
                          note = F can be replaced by I, L, W, or Y
VARIANT                   17
                          note = F can be replaced by I, L, or M
SEQUENCE: 382
```

ANIYYYDADY LHFYFDF                                                              17

SEQ ID NO: 383          moltype = AA   length = 9
FEATURE                 Location/Qualifiers
source                  1..9
                        mol_type = protein
                        organism = synthetic construct
VARIANT                 4
                        note = F can be replaced by H, W, or Y
VARIANT                 5
                        note = K can be replaced by Q
VARIANT                 6
                        note = F can be replaced by W
VARIANT                 8
                        note = L can be replaced by M
SEQUENCE: 383
QQGFKFPLT                                                                        9

SEQ ID NO: 384          moltype = AA   length = 10
FEATURE                 Location/Qualifiers
source                  1..10
                        mol_type = protein
                        organism = synthetic construct
SEQUENCE: 384
GLSLTSDSMS                                                                      10

SEQ ID NO: 385          moltype = AA   length = 7
FEATURE                 Location/Qualifiers
source                  1..7
                        mol_type = protein
                        organism = synthetic construct
SEQUENCE: 385
LWSNRGT                                                                          7

SEQ ID NO: 386          moltype = AA   length = 11
FEATURE                 Location/Qualifiers
source                  1..11
                        mol_type = protein
                        organism = synthetic construct
SEQUENCE: 386
RASEGIANNL S                                                                    11

SEQ ID NO: 387          moltype = AA   length = 10
FEATURE                 Location/Qualifiers
source                  1..10
                        mol_type = protein
                        organism = synthetic construct
SEQUENCE: 387
GLSLTSNSMS                                                                      10

SEQ ID NO: 388          moltype = AA   length = 7
FEATURE                 Location/Qualifiers
source                  1..7
                        mol_type = protein
                        organism = synthetic construct
SEQUENCE: 388
IWSNRGT                                                                          7

SEQ ID NO: 389          moltype = AA   length = 11
FEATURE                 Location/Qualifiers
source                  1..11
                        mol_type = protein
                        organism = synthetic construct
SEQUENCE: 389
RASKGISNNL S                                                                    11

SEQ ID NO: 390          moltype = AA   length = 10
FEATURE                 Location/Qualifiers
source                  1..10
                        mol_type = protein
                        organism = synthetic construct
SEQUENCE: 390
GLSLTSASMS                                                                      10

SEQ ID NO: 391          moltype = AA   length = 7
FEATURE                 Location/Qualifiers
source                  1..7
                        mol_type = protein
                        organism = synthetic construct

```
SEQUENCE: 391
IYSNRGT                                                                        7

SEQ ID NO: 392          moltype = AA  length = 11
FEATURE                 Location/Qualifiers
source                  1..11
                        mol_type = protein
                        organism = synthetic construct
SEQUENCE: 392
RASEGISKNL S                                                                  11

SEQ ID NO: 393          moltype = AA  length = 10
FEATURE                 Location/Qualifiers
source                  1..10
                        mol_type = protein
                        organism = synthetic construct
SEQUENCE: 393
GLSLTSSSMV                                                                    10

SEQ ID NO: 394          moltype = AA  length = 7
FEATURE                 Location/Qualifiers
source                  1..7
                        mol_type = protein
                        organism = synthetic construct
SEQUENCE: 394
AQSNLHS                                                                        7

SEQ ID NO: 395          moltype = AA  length = 7
FEATURE                 Location/Qualifiers
source                  1..7
                        mol_type = protein
                        organism = synthetic construct
SEQUENCE: 395
ATDNLHS                                                                        7
```

What is claimed is:

1. An antigen binding protein that specifically binds to nerve growth factor (NGF), which comprises:
    a heavy chain variable domain (VH) which comprises:
    a heavy chain complementarity determining region 1 (VH-CDR1) which comprises $GLSLTSX_7SMX_{10}$ (SEQ ID NO:214), wherein $X_7$ comprises A, D, N, or S, and $X_{10}$ comprises S or V;
    a heavy chain complementarity determining region 2 (VH-CDR2) which comprises $X_1X_2SNX_5GT$ (SEQ ID NO:215), wherein $X_1$ comprises I or L, $X_2$ comprises W or Y, and $X_5$ comprises G or R; and
    a heavy chain complementarity determining region 3 (VH-CDR3) which comprises $ASIYYYX_7AX_9YLHWYFDX_{17}$ (SEQ ID NO:216), wherein $X_7$ comprises D or E, $X_9$ comprises D or E, and $X_{17}$ comprises E or F; and
    a light chain variable domain (VL), which comprises:
    a light chain complementarity determining region 1 (VL-CDR1) which comprises $RASX_4GIX_7X_8NLS$ (SEQ ID NO:217), wherein $X_4$ comprises E or K, $X_7$ comprises A, Q, or S, and $X_8$ comprises K or N;
    a light chain complementarity determining region 2 (VL-CDR2) which comprises $AX_2X_3X_4LHS$ (SEQ ID NO:218), wherein $X_2$ comprises Q or T, $X_3$ comprises D or S, and $X_4$ comprises I, N, or V; and
    a light chain complementarity determining region 3 (VL-CDR3) which comprises $QQGX_4KWPLT$ (SEQ ID NO:219), wherein $X_4$ comprises F, W, or Y.

2. The antigen binding protein of claim 1, which comprises no more than two (2) substitutions per VH-CDR as compared to SEQ ID NO:204 and no more than two (2) substitutions per VL-CDR as compared to SEQ ID NO: 199.

3. The antigen binding protein of claim 1, which comprises no more than one (1) substitution per VH-CDR as compared to SEQ ID NO:204 and no more than one (1) substitution per VL-CDR as compared to SEQ ID NO: 199.

4. The antigen binding protein of claim 1, which comprises one or more VH-CDRs of any one of SEQ ID NO: 141, SEQ ID NO: 184, SEQ ID NO: 186, SEQ ID NO: 188, SEQ ID NO: 189, SEQ ID NO: 198, SEQ ID NO:200, SEQ ID NO:202, SEQ ID NO: 204, SEQ ID NO:205, or SEQ ID NO:206 and one or more VL-CDRs of any one of SEQ ID NO: 142, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 199, SEQ ID NO:201, or SEQ ID NO: 203.

5. The antigen binding protein of claim 1, which comprises the VH-CDRs of any one of SEQ ID NO: 141, SEQ ID NO: 184, SEQ ID NO: 186, SEQ ID NO: 188, SEQ ID NO: 189, SEQ ID NO: 198, SEQ ID NO:200, SEQ ID NO:202, SEQ ID NO: 204, SEQ ID NO:205, or SEQ ID NO:206 and the VL-CDRs of any one of SEQ ID NO: 142, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 199, SEQ ID NO:201, or SEQ ID NO:203.

6. The antigen binding protein of claim 1, which comprises the VH-CDRs and VL-CDRs of clone AHF17591, AHF17592, AHF17594, AHF17595, AHF17596, AHF17597, AHF17602, AHF17603, AHF17607, AHF17609, SC-184_76, SC-184_102, SC-184_110, SC-184_76-Arg, SC-184_102-Arg, or SC-184_110-Arg.

7. The antigen binding protein of claim 1, which comprises a heavy chain framework (FR1H+FR2H+FR3H+FR4H) at least 95% identical to the heavy chain framework of SEQ ID NO: 141, SEQ ID NO: 184, SEQ ID NO: 186, SEQ ID NO: 188, SEQ ID NO: 189, SEQ ID NO: 198, SEQ ID NO:200, SEQ ID NO:202, SEQ ID NO:204, SEQ ID NO: 205, or SEQ ID NO:206.

8. The antigen binding protein of claim 1, which comprises a light chain framework (FR1L+FR2L+FR3L+FR4L) at least 95% identical to the light chain framework of SEQ ID NO: 142, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 199, SEQ ID NO: 201, or SEQ ID NO:203.

9. The antigen binding protein of claim 1, which comprises a $V_H$ domain or at least 95% identical to SEQ ID NO:141, SEQ ID NO:184, SEQ ID NO:186, SEQ ID NO:188, SEQ ID NO: 189, SEQ ID NO: 198, SEQ ID NO:200, SEQ ID NO:202, SEQ ID NO: 204, SEQ ID NO:205, or SEQ ID NO:206.

10. The antigen binding protein of claim 1, which comprises a $V_L$ domain at least 95% identical to SEQ ID NO: 142, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 199, SEQ ID NO:201, or SEQ ID NO:203.

11. An isolated nucleic acid sequence encoding an anti-NGF antibody or antibody fragment of claim 1.

12. A vector that comprises the nucleic acid of claim 11.

13. A recombinant cell which comprises the nucleic acid of claim 11.

14. A cell that expresses the antigen binding protein of claim 1.

15. A method of producing the antigen binding protein of claim 1, which comprises culturing a cell that comprises a nucleic acid that encodes the antigen binding protein under conditions that result in production of the antigen binding protein.

16. A pharmaceutical composition comprising a therapeutically effective amount of the anti-NGF protein of claim 1.

17. The antigen binding protein of claim 2, which comprises a heavy chain framework (FR1H+FR2H+FR3H+FR4H) at least 90% identical to the heavy chain framework of SEQ ID NO: 141, SEQ ID NO: 184, SEQ ID NO: 186, SEQ ID NO: 188, SEQ ID NO: 189, SEQ ID NO: 198, SEQ ID NO:200, SEQ ID NO:202, SEQ ID NO: 204, SEQ ID NO:205, or SEQ ID NO:206, and a light chain framework (FR1L+FR2L+FR3L+FR4L) at least 90% identical to the light chain framework of SEQ ID NO: 142, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 199, SEQ ID NO:201, or SEQ ID NO: 203.

18. The antigen binding protein of claim 17, which comprises GLSLTSDSMS (SEQ ID NO:384) at VH-CDR1, LWSNRGT (SEQ ID NO:385) at VH-CDR2, ASIYY-YEADYLHWYFDF (SEQ ID NO:287) at VH-CDR3, RASEGIANNLS (SEQ ID NO: 386) at VL-CDR1, ATSNLHS (SEQ ID NO:226) at VL-CDR2, and QQGFKWPLT (SEQ ID NO:358) at VL-CDR3.

19. The antigen binding protein of claim 18, wherein the VH comprises SEQ ID NO:204 and the $V_L$ comprises SEQ ID NO: 199.

20. The antigen binding protein of claim 17, which comprises GLSLTSNSMS (SEQ ID NO:387) at VH-CDR1, IWSNRGT (SEQ ID NO:388) at VH-CDR2, ASIYYYE-AEYLHWYFDF (SEQ ID NO:315) at VH-CDR3, RASK-GISNNLS (SEQ ID NO: 389) at VL-CDR1, AQSNLHS (SEQ ID NO:394) at VL-CDR2, and QQGYKWPLT (SEQ ID NO:227) at VL-CDR3.

21. The antigen binding protein of claim 20, wherein the VH comprises SEQ ID NO:205 and the $V_L$ comprises SEQ ID NO:201.

22. The antigen binding protein of claim 17, which comprises GLSLTSASMS (SEQ ID NO:390) at VH-CDR1, IYSNRGT (SEQ ID NO:391) at VH-CDR2, ASIYYYE-AEYLHWYFDF (SEQ ID NO:315) at VH-CDR3, RASEGISKNLS (SEQ ID NO: 392) at VL-CDR1, ATDNLHS (SEQ ID NO:395) at VL-CDR2, and QQGWKWPLT (SEQ ID NO:356) at VL-CDR3.

23. The antigen binding protein of claim 22, wherein the VH comprises SEQ ID NO:206 and the $V_L$ comprises SEQ ID NO:203.

24. The antigen binding protein of claim 17, which comprises GLSLTSSSMV (SEQ ID NO:393) at VH-CDR1, IYSNRGT (SEQ ID NO:391) at VH-CDR2, ASIYYY-DADYLHWYFDF (SEQ ID NO:224) at VH-CDR3, RASEGIANNLS (SEQ ID NO: 386) at VL-CDR1, ATSNLHS (SEQ ID NO:226) at VL-CDR2, and QQGYKWPLT (SEQ ID NO:227) at VL-CDR3.

25. The antigen binding protein of claim 24, wherein the VH comprises SEQ ID NO:188 and the $V_L$ comprises SEQ ID NO:196.

26. The antigen binding protein of claim 17, which comprises GLSLTSSSMS (SEQ ID NO:222) at VH-CDR1, IYSNGGT (SEQ ID NO:266) at VH-CDR2, ASIYYY-DADYLHWYFDF (SEQ ID NO:224) at VH-CDR3, RASEGISNNLS (SEQ ID NO: 225) at VL-CDR1, ATSNLHS (SEQ ID NO:226) at VL-CDR2, and QQGYKWPLT (SEQ ID NO:227) at VL-CDR3.

27. The antigen binding protein of claim 26, wherein the $V_H$ comprises SEQ ID NO: 141 and the $V_L$ comprises SEQ ID NO: 142.

* * * * *